US009173999B2

(12) United States Patent
Edwards et al.

(10) Patent No.: US 9,173,999 B2
(45) Date of Patent: Nov. 3, 2015

(54) DEVICES AND METHODS FOR DELIVERING MEDICAMENTS FROM A MULTI-CHAMBER CONTAINER

(75) Inventors: Eric S. Edwards, Midlothian, VA (US); Evan T. Edwards, Gordonsville, VA (US); Mark J. Licata, Doswell, VA (US); Paul F. Meyers, Fishers, IN (US); Frank E. Blondino, Henrico, VA (US)

(73) Assignee: kaleo, Inc., Richmond, VA (US)

( * ) Notice: Subject to any disclaimer, the term of this patent is extended or adjusted under 35 U.S.C. 154(b) by 198 days.

(21) Appl. No.: 13/357,936

(22) Filed: Jan. 25, 2012

(65) Prior Publication Data

US 2013/0023822 A1    Jan. 24, 2013

Related U.S. Application Data

(60) Provisional application No. 61/436,301, filed on Jan. 26, 2011.

(51) Int. Cl.
| | |
|---|---|
| *A61M 5/31* | (2006.01) |
| *A61M 5/315* | (2006.01) |
| *A61M 5/20* | (2006.01) |
| *A61M 5/32* | (2006.01) |

(52) U.S. Cl.
CPC ........... *A61M 5/2033* (2013.01); *A61M 5/2066* (2013.01); *A61M 5/3204* (2013.01); *A61M 2005/206* (2013.01); *A61M 2005/208* (2013.01); *A61M 2005/2013* (2013.01); *A61M 2005/2073* (2013.01); *A61M 2005/2086* (2013.01)

(58) Field of Classification Search
USPC ............. 604/82–90, 131–139, 183, 191, 201, 604/207
See application file for complete search history.

(56) References Cited

U.S. PATENT DOCUMENTS

| | | | |
|---|---|---|---|
| 2,960,087 A | 11/1960 | Uytenbogaart | |
| 3,055,362 A | 9/1962 | Uytenbogaart | |
| 3,115,133 A | 12/1963 | Morando | |
| 3,426,448 A | 2/1969 | Sarnoff | |

(Continued)

FOREIGN PATENT DOCUMENTS

| | | |
|---|---|---|
| DE | 20 2009 003 009 | 7/2009 |
| EP | 1043037 A2 | 10/2000 |

(Continued)

OTHER PUBLICATIONS

IPRP for International Patent Application No. PCT/US2012/022698, mailed Jul. 30, 2013.

(Continued)

*Primary Examiner* — Matthew F Desanto
(74) *Attorney, Agent, or Firm* — Cooley LLP

(57) ABSTRACT

An apparatus includes a housing, a medicament container, and a movable assembly. The movable assembly includes a first movable member and a second movable member. The second movable member is configured to move relative to the first movable member to move the movable assembly from a first configuration to a second configuration. A distal end portion of the second movable member is configured to move a plunger disposed within the medicament container in a distal direction when the movable assembly is moved to the second configuration. The movable assembly is configured to move between a first position and a second position to move the medicament container within the housing between a first container position and a second container position.

38 Claims, 105 Drawing Sheets

(56) References Cited

U.S. PATENT DOCUMENTS

| | | |
|---|---|---|
| 3,688,765 A | 9/1972 | Gasaway |
| 3,768,472 A | 10/1973 | Hodosh et al. |
| 3,795,061 A | 3/1974 | Sarnoff et al. |
| 3,945,379 A | 3/1976 | Pritz et al. |
| 4,108,177 A | 8/1978 | Pistor |
| 4,124,024 A | 11/1978 | Schwebel et al. |
| 4,226,235 A | 10/1980 | Sarnoff et al. |
| 4,258,713 A | 3/1981 | Wardlaw |
| 4,360,019 A | 11/1982 | Portner et al. |
| 4,394,863 A | 7/1983 | Bartner |
| 4,424,057 A | 1/1984 | House |
| 4,441,629 A | 4/1984 | Mackal |
| 4,484,910 A | 11/1984 | Sarnoff |
| 4,573,976 A | 3/1986 | Sampson et al. |
| 4,596,556 A | 6/1986 | Morrow et al. |
| 4,610,666 A | 9/1986 | Pizzino |
| 4,617,557 A | 10/1986 | Gordon |
| 4,624,660 A | 11/1986 | Mijers et al. |
| 4,640,686 A | 2/1987 | Dalling et al. |
| 4,643,721 A | 2/1987 | Brunet |
| 4,666,430 A | 5/1987 | Brown et al. |
| 4,673,657 A | 6/1987 | Christian |
| 4,689,042 A | 8/1987 | Sarnoff et al. |
| 4,693,708 A | 9/1987 | Wanderer et al. |
| 4,755,169 A | 7/1988 | Sarnoff et al. |
| 4,781,697 A | 11/1988 | Slaughter |
| 4,782,841 A | 11/1988 | Lopez |
| 4,784,652 A | 11/1988 | Wikström |
| 4,795,433 A | 1/1989 | Sarnoff |
| 4,820,286 A * | 4/1989 | van der Wal ............ 604/89 |
| 4,853,521 A | 8/1989 | Claeys et al. |
| 4,874,381 A | 10/1989 | Vetter |
| 4,874,382 A | 10/1989 | Lindemann et al. |
| 4,894,054 A | 1/1990 | Miskinyar |
| 4,906,235 A | 3/1990 | Roberts |
| 4,915,695 A | 4/1990 | Koobs |
| 4,941,880 A | 7/1990 | Burns |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,042,977 A | 8/1991 | Bechtold et al. |
| 5,062,603 A | 11/1991 | Smith et al. |
| 5,064,413 A | 11/1991 | McKinnon et al. |
| 5,071,353 A | 12/1991 | van der Wal |
| 5,080,649 A | 1/1992 | Vetter |
| 5,085,642 A | 2/1992 | Sarnoff et al. |
| 5,092,843 A | 3/1992 | Monroe et al. |
| 5,104,380 A | 4/1992 | Holman et al. |
| 5,125,898 A | 6/1992 | Kaufhold, Jr. et al. |
| 5,139,490 A | 8/1992 | Vetter et al. |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,271,527 A | 12/1993 | Haber et al. |
| 5,281,198 A | 1/1994 | Haber et al. |
| 5,286,258 A | 2/1994 | Haber et al. |
| 5,298,023 A | 3/1994 | Haber et al. |
| 5,298,024 A | 3/1994 | Richmond |
| 5,312,326 A | 5/1994 | Myers et al. |
| 5,314,412 A | 5/1994 | Rex |
| 5,320,603 A | 6/1994 | Vetter et al. |
| 5,343,519 A | 8/1994 | Feldman |
| 5,344,407 A | 9/1994 | Ryan |
| 5,354,284 A | 10/1994 | Haber et al. |
| 5,356,376 A | 10/1994 | Milijasevic et al. |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,383,864 A | 1/1995 | van den Heuvel |
| 5,394,866 A | 3/1995 | Ritson et al. |
| 5,399,163 A | 3/1995 | Peterson et al. |
| 5,417,660 A | 5/1995 | Martin |
| 5,466,217 A | 11/1995 | Myers et al. |
| 5,514,097 A | 5/1996 | Knauer |
| 5,514,135 A | 5/1996 | Earle |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,615,771 A | 4/1997 | Hollister |
| 5,616,132 A | 4/1997 | Newman |
| 5,645,534 A | 7/1997 | Chanoch |
| 5,662,612 A | 9/1997 | Niehoff |
| 5,681,291 A | 10/1997 | Galli |
| 5,692,492 A | 12/1997 | Bruna et al. |
| 5,695,476 A | 12/1997 | Harris |
| 5,697,916 A | 12/1997 | Schraga |
| 5,716,338 A | 2/1998 | Hjertman et al. |
| 5,728,074 A | 3/1998 | Castellano et al. |
| 5,743,886 A | 4/1998 | Lynn et al. |
| 5,772,635 A | 6/1998 | Dastur et al. |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,813,397 A | 9/1998 | Goodman et al. |
| 5,814,020 A | 9/1998 | Gross |
| 5,823,346 A | 10/1998 | Weiner |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,988 A | 12/1998 | Davis |
| 5,852,590 A | 12/1998 | de la Huerga |
| 5,853,292 A | 12/1998 | Eggert et al. |
| 5,858,001 A | 1/1999 | Tsals et al. |
| 5,865,795 A | 2/1999 | Schiff et al. |
| 5,868,713 A | 2/1999 | Klippenstein |
| 5,868,721 A | 2/1999 | Marinacci |
| D407,487 S | 3/1999 | Greubel et al. |
| 5,925,021 A | 7/1999 | Castellano et al. |
| 5,928,195 A | 7/1999 | Malamud |
| 5,941,857 A | 8/1999 | Nguyen et al. |
| 5,964,739 A | 10/1999 | Champ |
| 5,970,457 A | 10/1999 | Brant et al. |
| 5,971,953 A | 10/1999 | Bachynsky |
| 6,015,438 A | 1/2000 | Shaw |
| 6,030,363 A | 2/2000 | Kriesel |
| 6,039,713 A | 3/2000 | Botich et al. |
| 6,045,534 A | 4/2000 | Jacobsen et al. |
| 6,056,728 A * | 5/2000 | von Schuckmann ......... 604/207 |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,083,199 A | 7/2000 | Thorley et al. |
| 6,084,526 A | 7/2000 | Blotky et al. |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,119,684 A | 9/2000 | Nöhl et al. |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,179,812 B1 | 1/2001 | Botich et al. |
| 6,192,891 B1 | 2/2001 | Gravel et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,258,063 B1 | 7/2001 | Haar et al. |

(56) References Cited

U.S. PATENT DOCUMENTS

| | | | |
|---|---|---|---|
| 6,259,654 B1 | 7/2001 | de la Huerga |
| 6,264,629 B1 | 7/2001 | Landau |
| 6,312,412 B1 | 11/2001 | Saied et al. |
| 6,317,630 B1 | 11/2001 | Gross et al. |
| 6,334,070 B1 | 12/2001 | Nova et al. |
| 6,364,866 B1 | 4/2002 | Furr et al. |
| 6,387,078 B1 | 5/2002 | Gillespie, III |
| 6,405,912 B2 | 6/2002 | Giannou |
| 6,406,455 B1 | 6/2002 | Willis et al. |
| 6,411,567 B1 | 6/2002 | Niemiec et al. |
| 6,413,236 B1 | 7/2002 | Van Dyke |
| 6,419,656 B1 | 7/2002 | Vetter et al. |
| 6,425,897 B2 | 7/2002 | Overes et al. |
| 6,428,517 B1 | 8/2002 | Hochman et al. |
| 6,428,528 B2 | 8/2002 | Sadowski |
| 6,475,181 B1 | 11/2002 | Potter et al. |
| 6,478,769 B1 | 11/2002 | Parker |
| 6,478,771 B1 | 11/2002 | Lavi et al. |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Sahar et al. |
| 6,530,904 B1 | 3/2003 | Edwards et al. |
| 6,535,714 B2 | 3/2003 | Melker et al. |
| 6,540,672 B1 | 4/2003 | Simonsen et al. |
| 6,540,675 B2 | 4/2003 | Aceti et al. |
| 6,544,233 B1 | 4/2003 | Fukui et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,565,533 B1 | 5/2003 | Smith et al. |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,595,956 B1 | 7/2003 | Gross et al. |
| 6,599,272 B1 | 7/2003 | Hjertman et al. |
| 6,616,627 B2 | 9/2003 | Willis et al. |
| 6,633,796 B1 | 10/2003 | Pool et al. |
| 6,641,566 B2 | 11/2003 | Douglas et al. |
| 6,645,171 B1 | 11/2003 | Robinson et al. |
| 6,645,181 B1 | 11/2003 | Lavi et al. |
| 6,648,850 B2 | 11/2003 | Landau |
| 6,656,150 B2 | 12/2003 | Hill et al. |
| 6,659,980 B2 | 12/2003 | Moberg et al. |
| 6,676,630 B2 | 1/2004 | Landau et al. |
| 6,679,862 B2 | 1/2004 | Diaz et al. |
| 6,689,093 B2 | 2/2004 | Landau |
| 6,702,778 B2 | 3/2004 | Hill et al. |
| 6,707,763 B2 | 3/2004 | Osberg et al. |
| 6,708,050 B2 | 3/2004 | Carim |
| 6,722,916 B2 | 4/2004 | Buccinna et al. |
| 6,723,077 B2 | 4/2004 | Pickup et al. |
| 6,726,661 B2 | 4/2004 | Munk et al. |
| 6,736,796 B2 | 5/2004 | Shekalim |
| 6,743,635 B2 | 6/2004 | Neel et al. |
| 6,749,437 B2 | 6/2004 | Chan |
| 6,752,781 B2 | 6/2004 | Landau et al. |
| 6,764,469 B2 | 7/2004 | Broselow |
| 6,767,336 B1 | 7/2004 | Kaplan |
| 6,770,052 B2 | 8/2004 | Hill et al. |
| 6,770,056 B2 | 8/2004 | Price et al. |
| 6,783,509 B1 | 8/2004 | Landau et al. |
| 6,786,875 B2 | 9/2004 | Barker et al. |
| 6,786,885 B2 | 9/2004 | Hochman et al. |
| 6,793,646 B1 * | 9/2004 | Giambattista et al. ......... 604/90 |
| 6,803,856 B1 | 10/2004 | Murphy et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,817,987 B2 | 11/2004 | Vetter et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,883,222 B2 | 4/2005 | Landau |
| 6,893,420 B2 | 5/2005 | Arnisolle |
| 6,923,764 B2 | 8/2005 | Aceti et al. |
| 6,936,029 B2 | 8/2005 | Mann et al. |
| 6,936,032 B1 | 8/2005 | Bush, Jr. et al. |
| 6,937,150 B2 | 8/2005 | Medema et al. |
| 6,942,646 B2 | 9/2005 | Langley et al. |
| 6,946,299 B2 | 9/2005 | Neel et al. |
| 6,949,082 B2 | 9/2005 | Langley et al. |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,964,650 B2 | 11/2005 | Alexandre et al. |
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |
| 7,014,470 B2 | 3/2006 | Vann |
| 7,077,835 B2 | 7/2006 | Robinson et al. |
| 7,104,972 B2 | 9/2006 | Moller et al. |
| 7,113,101 B2 | 9/2006 | Petersen et al. |
| 7,116,233 B2 | 10/2006 | Zhurin |
| 7,118,553 B2 | 10/2006 | Scherer |
| 7,126,879 B2 | 10/2006 | Snyder |
| 7,158,011 B2 | 1/2007 | Brue |
| 7,191,916 B2 | 3/2007 | Clifford et al. |
| 7,299,981 B2 | 11/2007 | Hickle et al. |
| 7,416,540 B2 | 8/2008 | Edwards et al. |
| 7,500,963 B2 | 3/2009 | Westbye et al. |
| 7,500,967 B2 | 3/2009 | Thorley et al. |
| 7,503,907 B1 | 3/2009 | Lesch, Jr. |
| 7,544,188 B2 | 6/2009 | Edwards et al. |
| 7,648,482 B2 | 1/2010 | Edwards et al. |
| 7,648,483 B2 | 1/2010 | Edwards et al. |
| 7,678,073 B2 | 3/2010 | Griffiths et al. |
| 7,708,719 B2 | 5/2010 | Wilmot et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,806,866 B2 | 10/2010 | Hornmann et al. |
| 7,850,662 B2 | 12/2010 | Veasey et al. |
| 7,871,393 B2 | 1/2011 | Monroe |
| 7,918,823 B2 | 4/2011 | Edwards et al. |
| 7,918,832 B2 | 4/2011 | Veasey et al. |
| 7,938,802 B2 | 5/2011 | Bicknell et al. |
| 7,947,017 B2 | 5/2011 | Edwards et al. |
| 8,016,788 B2 | 9/2011 | Edwards et al. |
| 8,021,335 B2 | 9/2011 | Lesch, Jr. |
| 8,162,886 B2 | 4/2012 | Sadowski et al. |
| 8,177,749 B2 | 5/2012 | Slate et al. |
| 8,251,947 B2 | 8/2012 | Kramer et al. |
| 8,276,583 B2 | 10/2012 | Farieta et al. |
| 8,353,878 B2 | 1/2013 | Moller et al. |
| 8,361,035 B2 | 1/2013 | Thorley et al. |
| 8,613,720 B2 | 12/2013 | Bendek et al. |
| 8,708,968 B2 | 4/2014 | Julian et al. |
| 8,734,394 B2 | 5/2014 | Adams et al. |
| 8,945,048 B2 | 2/2015 | Thorley et al. |
| 2002/0016567 A1 | 2/2002 | Hochman et al. |
| 2002/0042596 A1 | 4/2002 | Hartlaub et al. |
| 2002/0074345 A1 | 6/2002 | Schneider et al. |
| 2002/0076679 A1 | 6/2002 | Aman |
| 2002/0090601 A1 | 7/2002 | Strupat et al. |
| 2002/0096543 A1 | 7/2002 | Juselius |
| 2003/0028145 A1 | 2/2003 | Duchon et al. |
| 2003/0040717 A1 | 2/2003 | Saulenas et al. |
| 2003/0105430 A1 | 6/2003 | Lavi et al. |
| 2003/0106824 A1 | 6/2003 | Wilmot et al. |

(56) References Cited

U.S. PATENT DOCUMENTS

| | | |
|---|---|---|
| 2003/0120222 A1 | 6/2003 | Vaillancourt |
| 2003/0135388 A1 | 7/2003 | Martucci et al. |
| 2004/0015125 A1 | 1/2004 | Alexandre et al. |
| 2004/0019326 A1 | 1/2004 | Gilbert et al. |
| 2004/0024361 A1 | 2/2004 | Fago et al. |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0054327 A1 | 3/2004 | Gillespie, III |
| 2004/0092874 A1 | 5/2004 | Mazidji |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0210199 A1 | 10/2004 | Atterbury et al. |
| 2004/0220524 A1 | 11/2004 | Sadowski et al. |
| 2004/0249358 A1 | 12/2004 | McWethy et al. |
| 2004/0267204 A1 | 12/2004 | Brustowicz |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0062603 A1 | 3/2005 | Fuerst et al. |
| 2005/0090781 A1 | 4/2005 | Baba et al. |
| 2005/0090782 A1 | 4/2005 | Marshall et al. |
| 2005/0096588 A1 | 5/2005 | Hagmann et al. |
| 2005/0101912 A1 | 5/2005 | Faust et al. |
| 2005/0134433 A1 | 6/2005 | Sweeney, II |
| 2005/0148931 A1 | 7/2005 | Juhasz |
| 2005/0148945 A1 | 7/2005 | Chen |
| 2005/0159705 A1 | 7/2005 | Crawford et al. |
| 2005/0165360 A1 | 7/2005 | Stamp |
| 2005/0168337 A1 | 8/2005 | Mahoney |
| 2005/0171477 A1* | 8/2005 | Rubin et al. ............... 604/156 |
| 2005/0182358 A1 | 8/2005 | Veit et al. |
| 2005/0183982 A1 | 8/2005 | Giewercer |
| 2005/0186221 A1 | 8/2005 | Reynolds et al. |
| 2005/0197654 A1 | 9/2005 | Edman et al. |
| 2005/0261742 A1 | 11/2005 | Nova et al. |
| 2005/0267403 A1 | 12/2005 | Landau et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0069350 A1 | 3/2006 | Buenger et al. |
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129090 A1 | 6/2006 | Moberg et al. |
| 2006/0189938 A1 | 8/2006 | Hommann et al. |
| 2006/0200077 A1 | 9/2006 | Righi et al. |
| 2006/0235354 A1 | 10/2006 | Kaal et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0074722 A1 | 4/2007 | Giroux et al. |
| 2007/0100288 A1 | 5/2007 | Bozeman et al. |
| 2007/0129686 A1 | 6/2007 | Daily et al. |
| 2007/0129708 A1 | 6/2007 | Edwards et al. |
| 2007/0184847 A1 | 8/2007 | Hansen et al. |
| 2007/0210147 A1 | 9/2007 | Morrone et al. |
| 2007/0213598 A1 | 9/2007 | Howard et al. |
| 2007/0233001 A1 | 10/2007 | Burroughs et al. |
| 2008/0059133 A1 | 3/2008 | Edwards et al. |
| 2008/0103490 A1* | 5/2008 | Edwards et al. ........... 604/890.1 |
| 2008/0111685 A1 | 5/2008 | Olson et al. |
| 2008/0171995 A1 | 7/2008 | Vitullo et al. |
| 2008/0188798 A1 | 8/2008 | Weber |
| 2008/0255513 A1 | 10/2008 | Kaal et al. |
| 2008/0269689 A1 | 10/2008 | Edwards et al. |
| 2009/0093759 A1 | 4/2009 | Judd et al. |
| 2009/0221962 A1 | 9/2009 | Kaal et al. |
| 2009/0240200 A1 | 9/2009 | Heneveld et al. |
| 2010/0160894 A1 | 6/2010 | Julian et al. |
| 2010/0309012 A1 | 12/2010 | Edwards et al. |
| 2010/0318035 A1 | 12/2010 | Edwards et al. |
| 2011/0060274 A1 | 3/2011 | Kuhn |
| 2012/0016296 A1 | 1/2012 | Charles |
| 2012/0046613 A1 | 2/2012 | Plumptre |
| 2012/0056019 A1 | 3/2012 | Renz et al. |
| 2012/0107783 A1 | 5/2012 | Julian et al. |
| 2012/0116318 A1 | 5/2012 | Edwards et al. |
| 2012/0125951 A1 | 5/2012 | Leak et al. |
| 2012/0136316 A1 | 5/2012 | Davies et al. |
| 2012/0172804 A1 | 7/2012 | Plumptre |
| 2012/0172817 A1 | 7/2012 | Bruggemann et al. |
| 2012/0191049 A1 | 7/2012 | Harms et al. |
| 2012/0191066 A1 | 7/2012 | Schabbach et al. |
| 2012/0197210 A1 | 8/2012 | Kuhn et al. |
| 2012/0209200 A1 | 8/2012 | Jones et al. |
| 2012/0220949 A1 | 8/2012 | Davies et al. |
| 2012/0226238 A1 | 9/2012 | Davies et al. |
| 2012/0238960 A1 | 9/2012 | Smith et al. |
| 2012/0253288 A1 | 10/2012 | Dasbach et al. |
| 2012/0259285 A1 | 10/2012 | Schabbach et al. |
| 2012/0271243 A1 | 10/2012 | Plumptre et al. |
| 2012/0283648 A1 | 11/2012 | Veasey et al. |
| 2012/0283651 A1 | 11/2012 | Veasey et al. |
| 2012/0283662 A1 | 11/2012 | MacDonald et al. |
| 2012/0289906 A1 | 11/2012 | Jones et al. |
| 2012/0289929 A1 | 11/2012 | Boyd et al. |
| 2012/0310168 A1 | 12/2012 | Plumptre et al. |
| 2012/0310206 A1 | 12/2012 | Kouyoumjian et al. |
| 2012/0325865 A1 | 12/2012 | Forstreuter et al. |
| 2012/0330244 A1 | 12/2012 | Helmer et al. |
| 2013/0023822 A1 | 1/2013 | Edwards et al. |
| 2013/0023825 A1 | 1/2013 | Edwards et al. |
| 2013/0060231 A1 | 3/2013 | Adlon et al. |
| 2013/0060232 A1 | 3/2013 | Adlon et al. |
| 2013/0066274 A1 | 3/2013 | O'Connor et al. |
| 2013/0102973 A1 | 4/2013 | Thorley et al. |
| 2013/0110050 A1 | 5/2013 | Boyd et al. |
| 2013/0218074 A1 | 8/2013 | Holmqvist et al. |
| 2013/0226084 A1 | 8/2013 | Samandi et al. |
| 2013/0237932 A1 | 9/2013 | Thueer et al. |
| 2013/0266919 A1 | 10/2013 | Baker et al. |
| 2014/0142544 A1 | 5/2014 | Atterbury et al. |
| 2014/0276414 A1 | 9/2014 | Baker et al. |

FOREIGN PATENT DOCUMENTS

| | | |
|---|---|---|
| EP | 1287840 A1 | 5/2003 |
| EP | 1462134 A1 | 9/2004 |
| EP | 1 518 575 A1 | 3/2005 |
| EP | 1712178 A2 | 10/2006 |
| EP | 1095668 131 | 4/2007 |
| FR | 2 506 161 | 11/1982 |
| FR | 2 509 615 | 1/1983 |
| GB | 2195544 A1 | 4/1988 |
| JP | 55-75335 | 8/2014 |
| MX | PA04009276 | 1/2005 |
| WO | WO 91/04760 A1 | 4/1991 |
| WO | WO 92/18176 | 10/1992 |
| WO | WO 93/02720 | 2/1993 |
| WO | WO 95/26009 | 9/1995 |
| WO | WO 95/35126 | 12/1995 |
| WO | WO 97/30742 | 8/1997 |
| WO | WO 99/07425 | 2/1999 |
| WO | WO 99/43283 | 9/1999 |
| WO | WO 01/24690 A2 | 4/2001 |
| WO | WO 01/26020 A1 | 4/2001 |
| WO | WO 01/41849 A3 | 6/2001 |
| WO | WO 01/88828 | 11/2001 |
| WO | WO 01/93926 A2 | 12/2001 |
| WO | WO 02/24257 A1 | 3/2002 |
| WO | WO 02/051471 A1 | 7/2002 |
| WO | WO 03/057283 A1 | 7/2003 |
| WO | WO 03/095001 A1 | 11/2003 |
| WO | WO 03/097133 A1 | 11/2003 |
| WO | WO 2004/041330 A2 | 5/2004 |
| WO | WO 2004/054644 | 7/2004 |
| WO | WO 2005/050526 A2 | 6/2005 |
| WO | WO 2005/077441 A2 | 8/2005 |
| WO | WO 2006/045525 A1 | 5/2006 |
| WO | WO 2006/085175 A1 | 8/2006 |

(56) References Cited

FOREIGN PATENT DOCUMENTS

| WO | WO 2006/085204 A1 | | 8/2006 |
|---|---|---|---|
| WO | WO 2006/109778 A1 | | 10/2006 |
| WO | WO2006/125692 | | 11/2006 |
| WO | WO 2007/075839 | | 7/2007 |
| WO | WO 2007/088444 A1 | | 8/2007 |
| WO | WO 2008/005315 | | 1/2008 |
| WO | WO 2008/082704 A2 | | 7/2008 |
| WO | WO 2008/148864 | | 12/2008 |
| WO | WO 2010 033806 | * | 3/2010 |
| WO | WO 2013/044172 A1 | | 3/2013 |
| WO | WO 2013/086292 | | 6/2013 |
| WO | WO 2013/119591 | | 8/2013 |

OTHER PUBLICATIONS

International Search Report and Written Opinion for International Patent Application No. PCT/US2012/022698, mailed May 25, 2012.
International Search Report and Written Opinion for International Application No. PCT/US2012/022698, mailed May 25, 2012.
Office Action for U.S. Appl. No. 13/053,451, mailed Nov. 15, 2012.
English Translation of Office Action for Japanese Patent Application No. 2011-257810, mailed Mar. 13, 2013.
"Solutions for Medical Devices," 3M Brochure, ©3M 2006 80-6201-3490-0.
Merle Tingelstad, "Revolutionary Medical Technology Increases Demand for Flexible Interconnects," [online] May 15, 2006 [retrieved on Nov. 15, 2006] Retrieved from the Internet <URL: http://www.ecnmag.com/index.asp?layout=articlePrint&ArticleID=CA6332947 >.
"Flexible circuits / Flex circuits / Flexible Technology Ltd.," Flexible Technology Limited [online] [retrieved on Aug. 28, 2006] Retrieved from the Internet <URL: http://www.flexibletechnology.com/ >.
"Flexible circuits capabilities of Flexible Technology Limited," Our Flexible Circuits Capabilities [online] [retrieved on Aug. 28, 2006] Retrieved from the Internet <URL: http://www.flexibletechnology.com/Flexible circuits Capability.htm >.
"Flex Circuits/flexible circuits design guide," [online] [retrieved on Aug. 28, 2006] Retrieved from the Internet <URL: http://flexiblecircuit.co.uk/Flex Circuits Design Guide.htm >.
"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html >.
"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/product catalogue. asp >.
"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1 >.
Roger Allan, "Medical Electronics: Technology Advances Will Revolutionize Healthcare," Sep. 30, 2002 [online] [retrieved on Nov. 28, 2006] Retrieved from the Internet <URL: http://www.elecdesign.com/Articles/Index.cfm?AD=1&ArticleID=2041>.

RFID Gazette, "Smart Labels in Healthcare," Sep. 29, 2005 [online] [retrieved on Nov. 28, 2006] Retrieved from the Internet <URL: http://www.rfidagazeete.org/2005/09/smart labels in.html >.
"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8.
Dr. Oliver Scholz, "Drug depot in a tooth," [online] [retrieved on Feb. 6, 2007] Retrieved from the Internet <URL: http://www.fraunhofer.de/fhg/EN/press/pi/2007/02Mediendienst22007Thema2.jsp?print=true.
Heartsine Technology, samaritan™ Pad Accessories [online] [retrieved on Jun. 1, 2007] Retrieved from the Internet <URL: http://www.heartsine.com/aboutsam-accessories.htm>.
CliniSense Corporation, "Drug delivery devices a potentially harsh environment for drugs," Stability [online] [retrieved on Jun. 1, 2007] Retrieved from the Internet <URL: http://www.clinisense.com/devices.htm>.
CliniSense Corporation, "LifeTrack Technology a new method to detect improper storage." Stability [online] [retrieved on Jun. 1, 2007] Retrieved from the Internet <URL: http://www.clinisense.com/tech.htm>.
AED Professionals™ Brochure [online] [retrieved on Jun. 1, 2007] Retrieved from the Internet <URL: http://www.aedprofessionals.com/>.
Daniel Ruppar, "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-online.com/drugdelivery/200702/templates/pageviewer_print?pg=44&pm=8>.
Search Report and Written Opinion for International Patent Application No. PCT/US06/03415 mailed Jul. 13, 2006, 10 pages.
Search Report and Written Opinion for International Patent Application No. PCT/US07/84891 mailed Sep. 15, 2008, 7 pages.
Search Report and Written Opinion for International Patent Application No. PCT/US07/007626 mailed Sep. 29, 2008.
Examination Report for British Patent Application No. GB 0708523.6, mailed Dec. 8, 2008.
Examination Report for British Patent Application No. GB 0822532.8, mailed Jan. 21, 2009.
Office Action for U.S. Appl. No. 11/562,061, mailed Feb. 3, 2009.
Examination Report for British Patent Application No. GB 0822532.8, mailed May 21, 2009.
Office Action for Japanese Patent Application No. JP2007-553358, mailed Feb. 24, 2010.
Examination Report for New Zealand Patent Application No. NZ 589864, mailed Dec. 14, 2010.
Search and Examination Report for British Patent Application No. 1105021.8, mailed May 18, 2011.
Office Action for U.S. Appl. No. 11/692,359, mailed Jul. 18, 2011.
Examination Report for Australian Patent Application No. 2012211320, mailed Jan. 28, 2014.
Supplementary Search Report for European Patent Application No. 12739882.4, mailed Aug. 5, 2014.
Chinese Office Action mailed Dec. 2, 2014 for Chinese Application No. 201280015406.6.

* cited by examiner

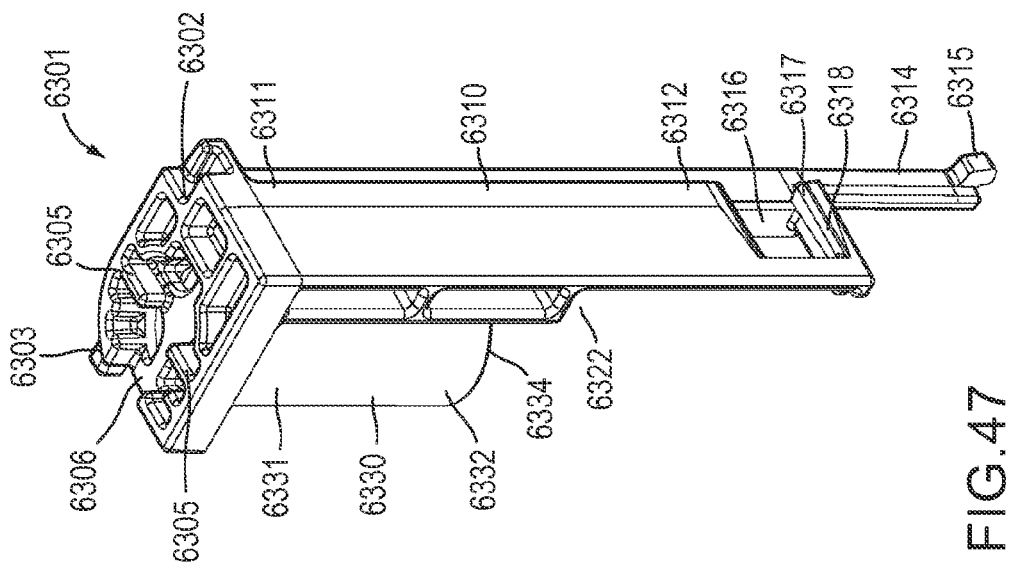
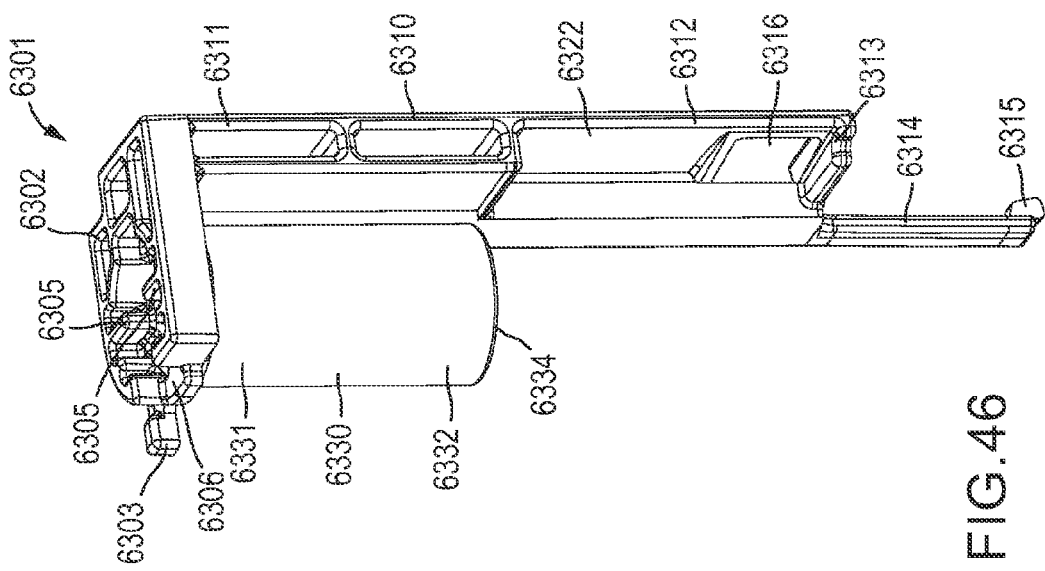

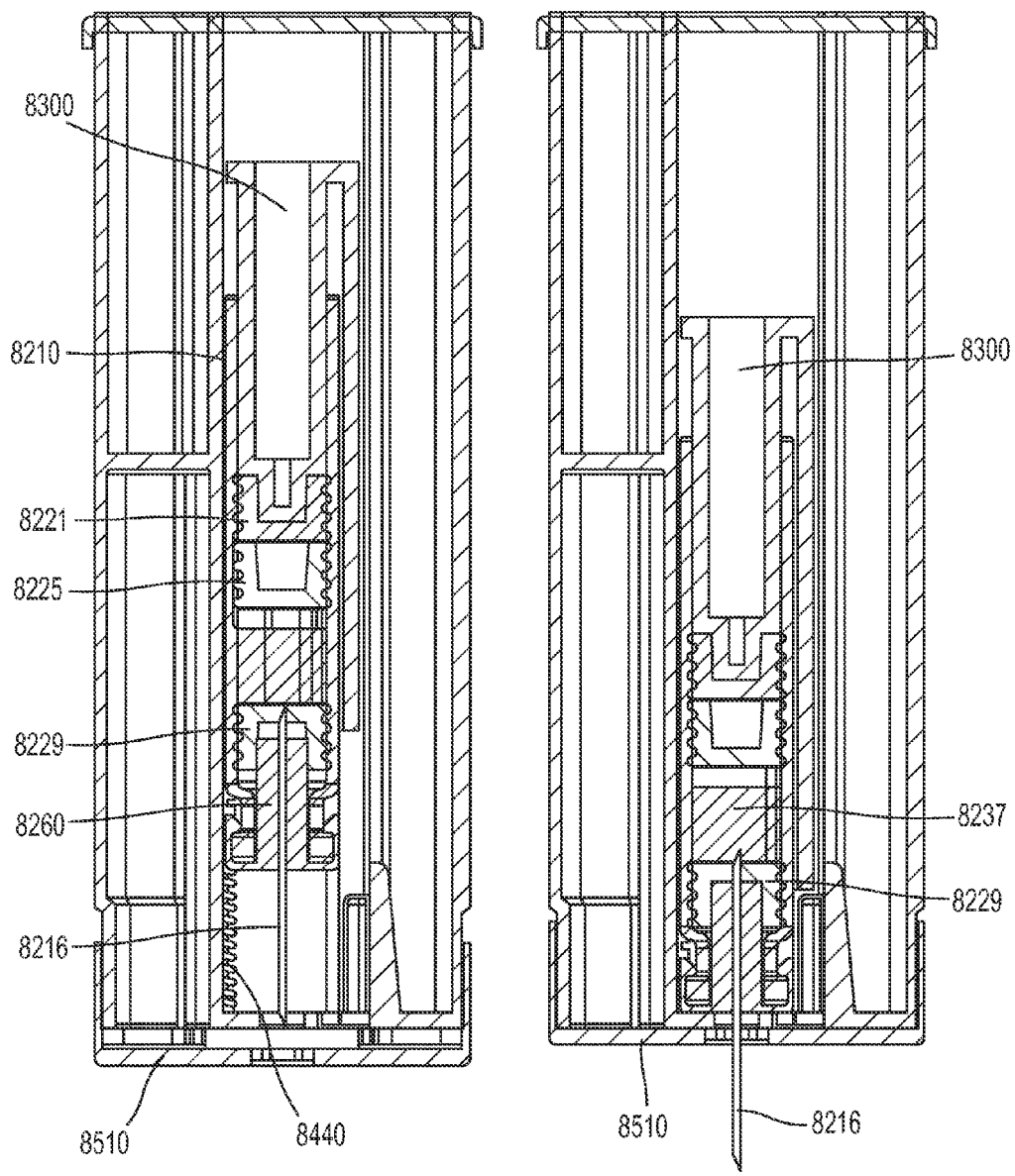

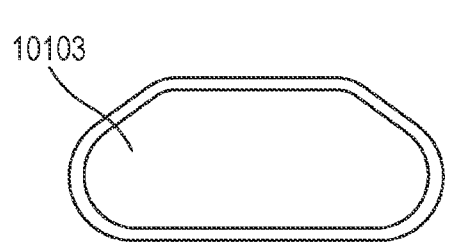
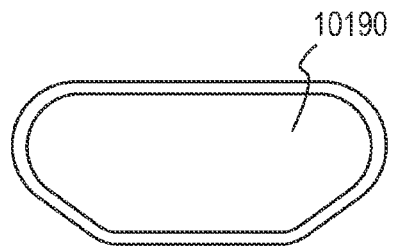
FIG.122    FIG.123
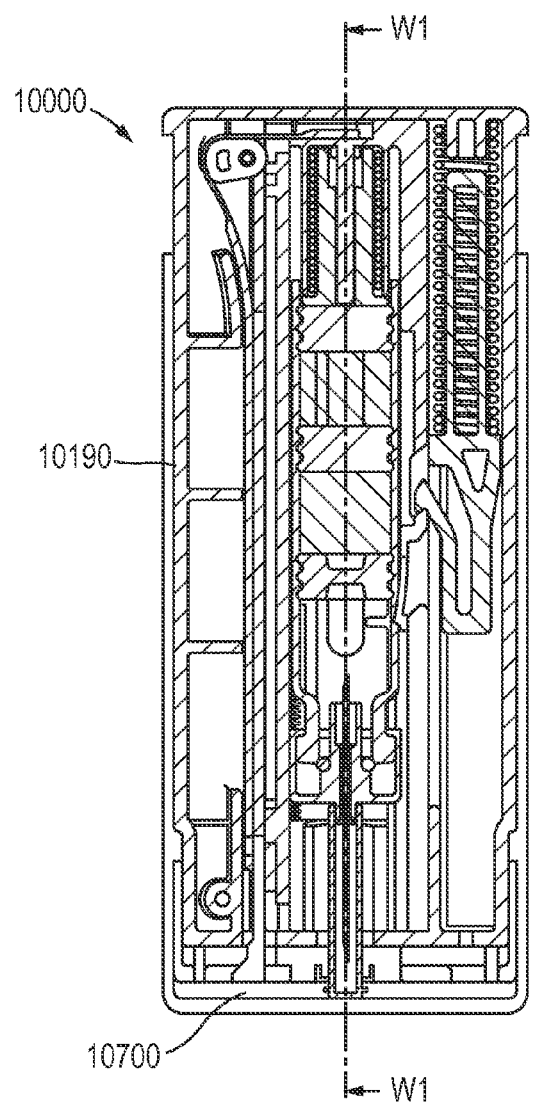
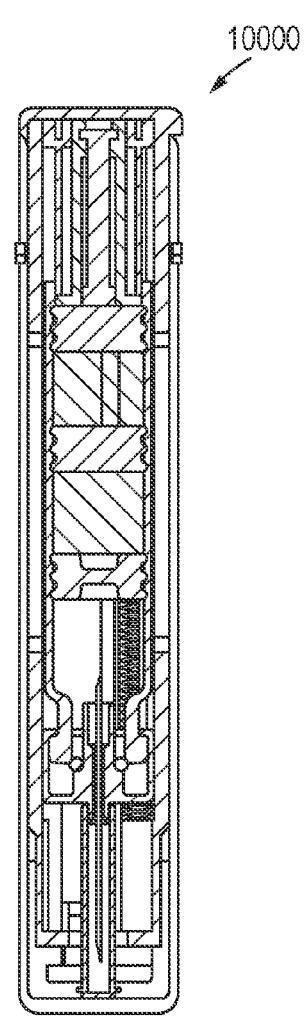
FIG.124    FIG.125

DEVICES AND METHODS FOR DELIVERING MEDICAMENTS FROM A MULTI-CHAMBER CONTAINER

CROSS-REFERENCE TO RELATED APPLICATIONS

This application claims priority to U.S. Provisional Application Ser. No. 61/436,301, entitled "Devices and Methods for Delivering Lyophilized Medicaments," filed Jan. 26, 2011, which is incorporated herein by reference in its entirety.

BACKGROUND

The embodiments described herein relate generally to an injector, and more particularly to a medicament delivery device for mixing a medicament and delivering the medicament into a body of a patient.

Exposure to certain substances, such as, for example, peanuts, shellfish, bee venom, certain drugs, toxins, and the like, can cause allergic reactions in some individuals. Such allergic reactions can, at times, lead to anaphylactic shock, which can cause a sharp drop in blood pressure, hives, and/or severe airway constriction. Accordingly, responding rapidly to mitigate the effects from such exposures can prevent injury and/or death. For example, in certain situations, an injection of epinephrine (i.e., adrenaline) can provide substantial and/or complete relief from the allergic reaction. In other situations, for example, an injection of an antidote to a toxin can greatly reduce and/or eliminate the harm potentially caused by the exposure. Similarly, an injection of glucagon can reduce and/or eliminate the harm potentially caused by reduced blood glucose levels in individuals who suffer from diabetes.

Because emergency medical facilities are not always available when an individual is suffering from a medical condition, some individuals carry an auto-injector to rapidly self-administer a medicament in response to such medical conditions. Some known auto-injectors include a vial containing a liquid medicament and a spring loaded needle to automatically penetrate the user's skin and inject the medicament. The storage of certain medicaments in a liquid form, however, can result in a shorter shelf life and/or an unstable medicament. Accordingly, some known auto-injectors include a vial containing a first medicament that is separated from a second medicament. Such auto-injectors are often referred to as "wet/dry" auto-injectors, because one medicament is often a liquid (e.g., water or another diluent) and the other medicament can be substantially solid or dry (e.g., glucagon powder). In use, the first medicament and the second medicament must be mixed prior to injection.

Some known wet/dry injectors, however, require that the user manually actuate a mixing mechanism prior to injection (e.g., by twisting a portion of the device to complete the mixing step). Such configurations can, however, result in incomplete mixing and/or an injection occurring without mixing. In addition, the operation of some known wet/dry delivery systems includes manually inserting the needle into the skin prior to activation and subsequent medicament delivery. The operation of such configurations may also include separately attaching a needle to prepare the device for injection, resulting in a delay in delivery of the medicament. Moreover, such configurations can be complicated, making them difficult for a user to operate during an emergency situation or by an individual without medical training.

Some known wet/dry injectors employ a single mechanism to automatically mix and inject the medicaments contained therein. Because the mixing operation is not independent from the injection operation in such configurations, however, the medicament can be injected prior to the completion of the mixing operation and/or prior to the injector being properly positioned for the injection operation.

Thus, a need exists for an improved auto-injector that can separately store two or more medicaments and that can mix and inject the medicaments in distinct operations. A need also exists for improved methods of filling medicament containers used in such devices.

SUMMARY

Medicament delivery devices for mixing a medicament and delivering the medicament are described herein. In some embodiments, an apparatus includes a housing, a medicament container, and a movable assembly. The movable assembly includes a first movable member and a second movable member. The second movable member is configured to move relative to the first movable member to move the movable assembly from a first configuration to a second configuration. A distal end portion of the second movable member is configured to move a plunger disposed within the medicament container in a distal direction when the movable assembly is moved to the second configuration. The movable assembly is configured to move between a first position and a second position to move the medicament container within the housing between a first container position and a second container position.

BRIEF DESCRIPTION OF THE DRAWINGS

FIGS. 46-48 illustrate a first movable member included in the movable assembly illustrated in FIG. 45.

FIGS. 106-111 are cross-sectional views illustrating the operation of a medical injector according to an embodiment.

FIG. 122 is a top view of the medical injector illustrated in FIG. 118.

FIG. 123 is a bottom view of the medical injector illustrated in FIG. 118.

FIG. 124 is a cross-sectional view of the medical injector illustrated in FIG. 118.

FIG. 125 is a cross-sectional view of the medical injector illustrated in FIG. 124 taken along the line W1-W1 in FIG. 124.

DETAILED DESCRIPTION

Figure 1:
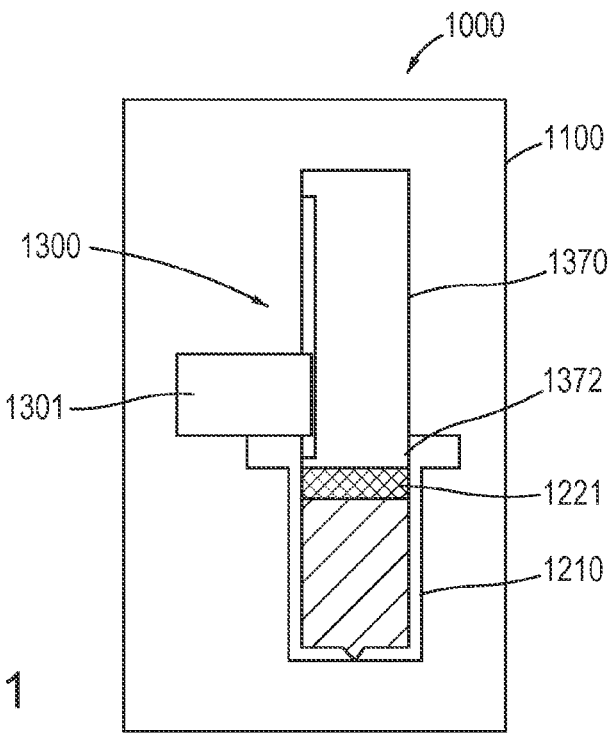
FIGS. 1-4 are schematic illustrations of a medicament delivery device according to an embodiment, in a first, second, third, and fourth configuration, respectively.

Medicament delivery devices for mixing and/or delivering a medicament are described herein. In some embodiments, an apparatus includes a housing, a medicament container, and a movable assembly. The movable assembly includes a first movable member and a second movable member. The second movable member is configured to move relative to the first movable member to change the movable assembly from a first configuration to a second configuration. A distal end portion of the second movable member is configured to move a plunger disposed within the medicament container in a distal direction when the movable assembly is changed to the second configuration. The movable assembly is configured to move between a first position and a second position to move the medicament container within the housing between a first container position and a second container position.

In some embodiments, a medicament delivery device includes a housing, a medicament container, and a movable assembly. The movable assembly is configured to increase in length when moved from a first configuration to a second configuration to move a plunger disposed within the medicament container a first distance. The movable assembly is configured to move between a first position and a second position within the housing to move the plunger a second distance.

In some embodiments, a medicament delivery device includes a housing, a medicament container, a movable member, and a release member. The movable member is configured to move a plunger disposed within the medicament container. The release member includes a first end portion and a second end portion. The second end portion is configured to move between a first position and a second position. In the first position, the second end portion of the release member is configured to limit the movement of the movable member. The second end portion is configured such that when the first end portion is moved in a first direction, the second end portion is moved in a second direction, substantially different from the first, from the first position to the second position.

In some embodiments, a medicament delivery device includes a housing, a medicament container, a movable member, and a release member. The movable member is configured to move the medicament container within the housing and/or a plunger disposed within the medicament container. The release member includes a first end portion, a second end portion, and a pivot portion. The second end portion is configured to move between a first position and a second position. In the first position the second end portion of the release member is configured to limit the movement of the movable member. The pivot portion is configured to be coupled to the housing. The first end portion of the release member is offset a first distance from the pivot portion and the second end portion of the release member is offset from the pivot portion by a second distance, different than the first. In some embodiments, for example, the first end portion and the second end portion are configured, relative to the pivot portion, to produce a mechanical advantage that is related to the difference between the first distance and the second distance.

As used in this specification and the appended claims, the term "medicament" includes any constituent of a therapeutic substance. A medicament can include such constituents regardless of their state of matter (e.g., solid, liquid or gas). Moreover, a medicament can include the multiple constituents that can be included in a therapeutic substance in a mixed state, in an unmixed state and/or in a partially mixed state. A medicament can include both the active constituents and inert constituents of a therapeutic substance. Accordingly, as used herein, a medicament can include non-active constituents such as, water, colorant or the like.

As used herein, the words "proximal" and "distal" refer to direction closer to and away from, respectively, an operator of the medical device. Thus, for example, the end of the medicament delivery device contacting the patient's body would be the distal end of the medicament delivery device, while the end opposite the distal end would be the proximal end of the medicament delivery device.

FIGS. 1-4 are schematic illustrations of a medicament delivery device 1000 according to an embodiment in a first, second, third and fourth configuration, respectively. The medicament delivery device 1000 includes a housing 1100, a medicament container 1210, and a movable assembly 1300. The housing 1100 can be any suitable size, shape, or configuration and can be made of any suitable material. For example, in some embodiments, the housing 1100 is an assembly of multiple parts formed from a plastic material and defines a substantially rectangular shape when assembled.

The medicament container 1210 is disposed within the housing 1100, and contains (i.e., is filled or partially filled with) a medicament. The medicament container 1210 includes a proximal end portion and a distal end portion that can be coupled to a delivery member, such as a tube, a needle or the like (not shown in FIGS. 1-4). The medicament container 1210 further includes an elastomeric member 1221 (also referred to herein as a "plunger"). The elastomeric member 1221 is formulated to be compatible with the medicament housed within the medicament container 1210. Similarly stated, the elastomeric member 1221 is formulated to minimize any reduction in the efficacy of the medicament that may result from contact (either direct or indirect) between the elastomeric member 1221 and the medicament. For example, in some embodiments, the elastomeric member 1221 can be formulated to minimize any leaching or out-gassing of compositions that may have an undesired effect on the medicament. In some embodiments, the elastomeric member 1221 can be disposed within the medicament container 1210 to seal the proximal end portion of the medicament container 1210. In some embodiments, the elastomeric member 1221 can be formulated to maintain its chemical stability, flexibility and/or sealing properties when in contact (either direct or indirect) with a medicament over a long period of time (e.g., for up to six months, one year, two years, five years or longer). The medicament container 1210 can be any container suitable for storing the medicament.

The movable assembly 1300 includes a first movable member 1301 and a second movable member 1370 and is configured to move between a first configuration and a second configuration. The first movable member 1301 and the second movable member 1370 are movably coupled together such that the second movable member 1370 can move with and/or relative to the first movable member 1301. For example, in some embodiments, the second movable member 1370 can include a channel that receives a protrusion included in the first movable member 1301. In this manner, the protrusion of the first movable member 1301 can move within the channel of the second movable member 1370 such that the second movable member 1370 can move relative to the first movable member 1301 while remaining coupled to the first movable member 1370.

Figure 2:
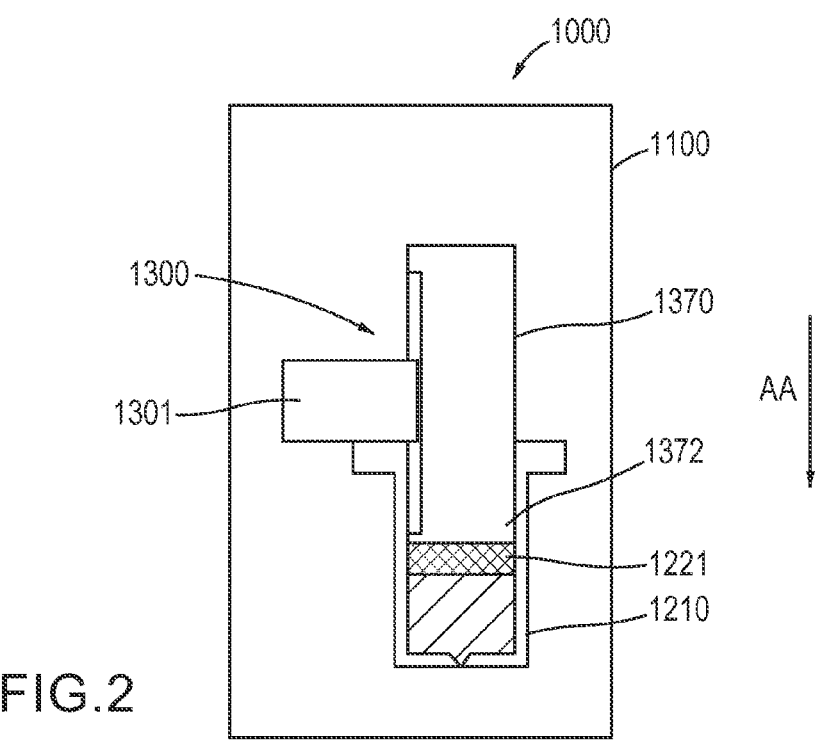

As shown in FIG. 1, the second movable member 1370 includes a distal portion 1372 that engages the plunger 1221 disposed within the medicament container 1210. In some embodiments, the distal end portion 1372 of the second movable member 1370 can be spaced apart from the plunger 1221 when the movable assembly 1300 is in a first configuration (e.g., FIG. 1). The second movable member 1370 can be any suitable mechanism for contacting and/or moving the plunger 1221. For example, in some embodiments, the second movable member 1370 can be a piston that includes a base disposed at the distal end portion 1372 that engages the plunger 1221. The second movable member 1370 can be moved, relative to the first movable member 1301 to move the movable assembly 1300 from the first configuration to a second configuration (FIG. 2). When the second movable member 1370 moves relative to the first movable member 1301, the distal end portion 1372 can move the plunger 1221 in the distal direction within the medicament container 1210, as shown by the arrow AA in FIG. 2. The distal motion of the plunger 1221 can facilitate, for example, a mixing of medicament constituents contained within the medicament container 1210. For example, in some embodiments, the medicament can include a first medicament portion (or constituent) and a second medicament portion (or constituent) configured to mix when pressurized. In some embodiments, the distal movement of the plunger 1221 can facilitate the release of a pressurized gas. In some embodiments, a pressurized gas can be included within the medicament container to separate a first medicament portion (or constituent) from a second medicament portion (or constituent) when the movable assembly 1300 is in the first configuration. Therefore, when the pressurized gas is released, the first medicament portion mixes with the second medicament portion. In yet other embodiments, the distal movement of the plunger 1221 can facilitate the release of gas that is undesirably contained within the medicament prior to delivery of the medicament.

In some embodiments, the second movable member 1370 can be configured to move in the direction AA (e.g., the distal direction) in response to a force exerted by a user (e.g., via direct contact, a pull tab, a slider, and/or the like). In some embodiments, the second movable member 1370 can be configured to move in the direction AA (e.g., the distal direction) in response to a force exerted by an energy storage member (not shown in FIGS. 1-4). In such embodiments, an energy storage member can be any suitable mechanism or device for storing energy. For example, the energy storage member can be a mechanical energy storage member, such as a spring, a device containing compressed gas, a device containing a vapor pressure-based propellant or the like. In other embodiments, the energy storage member can be an electrical energy storage member, such as a battery, a capacitor, a magnetic energy storage member or the like. In yet other embodiments, the energy storage member can be a chemical energy storage member, such as a container containing two substances that, when mixed, react to produce energy. By employing the energy storage member to produce the force rather than relying on a user to manually produce the delivery force, the plunger 1221 can be moved at the desired pressure and/or with the desired force. Moreover, this arrangement reduces the likelihood of partial or improper movement of the plunger 1221 (e.g., that may result if the user is interrupted or otherwise rendered unable to manually produce the force to complete the movement of the second movable member 1370).

Figure 3:
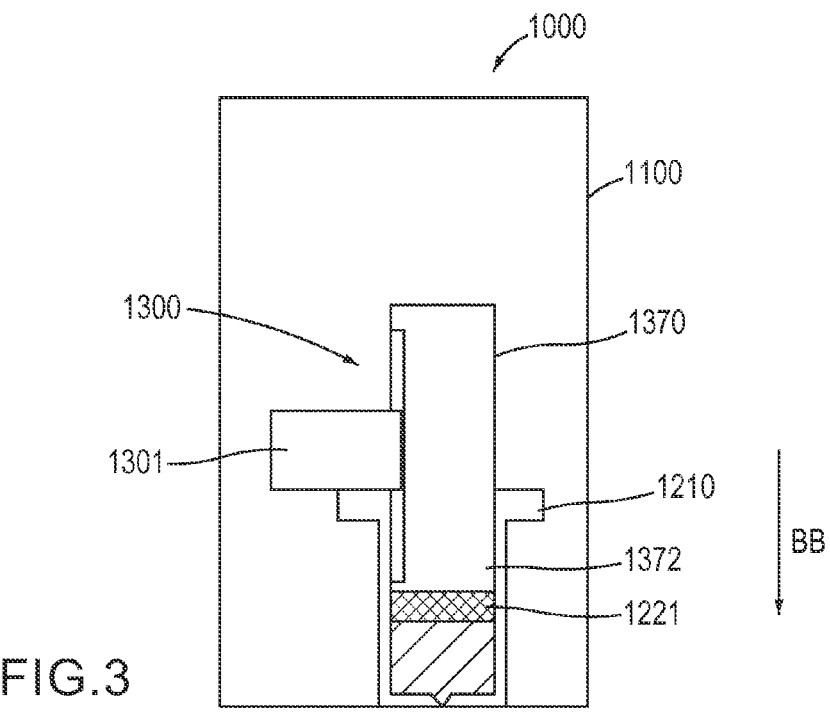
Figure 4:
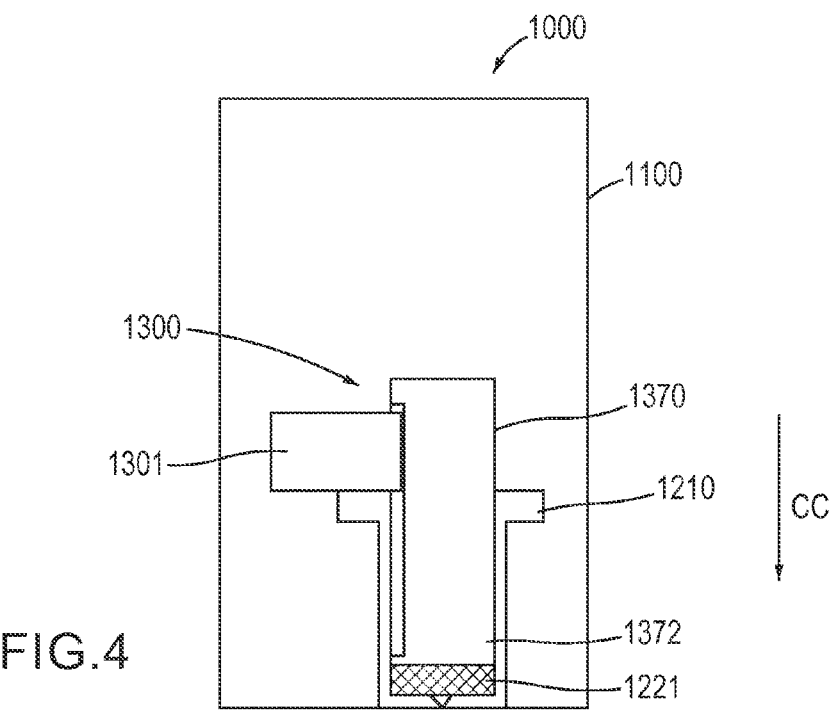

The movable assembly 1300 is configured to move from a first position (e.g., FIG. 1) to a second position (e.g., FIG. 3) within the housing 1100, as shown by the arrow BB in FIG. 3. In some embodiments, the movable assembly 1300 can move in the direction BB (e.g., the distal direction) in response to a portion of the force exerted by the energy storage member (described above). In other embodiments, the movable assembly 1300 can move in the distal direction in response to a second force exerted by the energy storage member. In other embodiments, the movable assembly 1300 can be in contact with or operably coupled to a second energy storage member (different from an energy storage member used to move the second movable member 1370) configured to exert the second force on the movable assembly 1300. In still other embodiments, the movable assembly 1300 can be manually moved to the second position (e.g., as described above).

The distal movement of the movable assembly 1300 is configured to move the medicament container 1210 within the housing 1100 from a first container position (e.g., FIG. 2) to a second container position. In some embodiments, the distal movement (e.g., in the direction of the arrow BB shown in FIG. 3) can facilitate the insertion of a needle, disposed at the distal end portion of the medicament container 1210, into a target location (e.g., the body of a patient). Furthermore, with the medicament container 1210 in the second container position within the housing 1100, the second movable member 1370 can continue to move in the distal direction, as shown by the arrow CC in FIG. 4. In this manner, the second movable member 1370 can move relative to the first movable member 1301 to move the plunger 1221 within the medicament container 1210 such that the medicament disposed therein is delivered to a volume substantially outside the medicament container 1210 (e.g., into the body of the patient via the needle).

Figure 5:
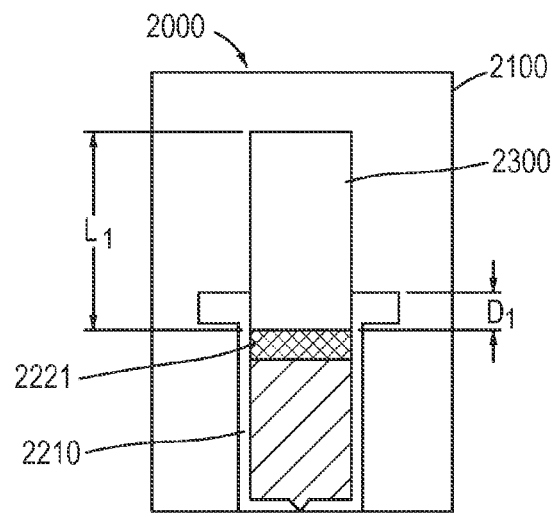
FIGS. 5-7 are schematic illustrations of a medicament delivery device according to an embodiment, in a first, second, and third configuration, respectively.
Figure 6:
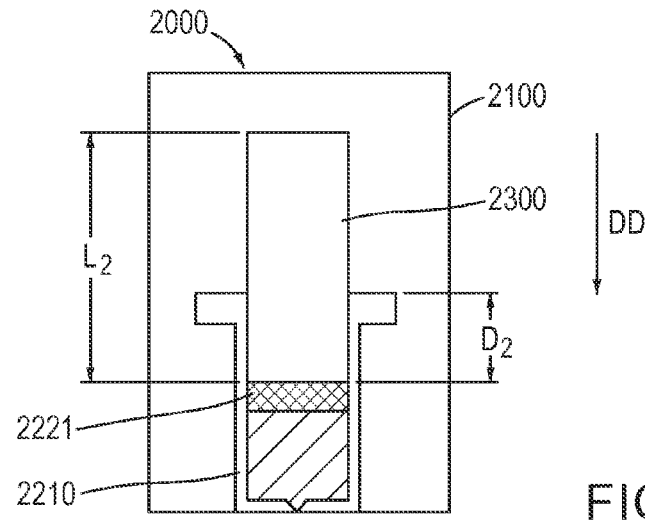
Figure 7:
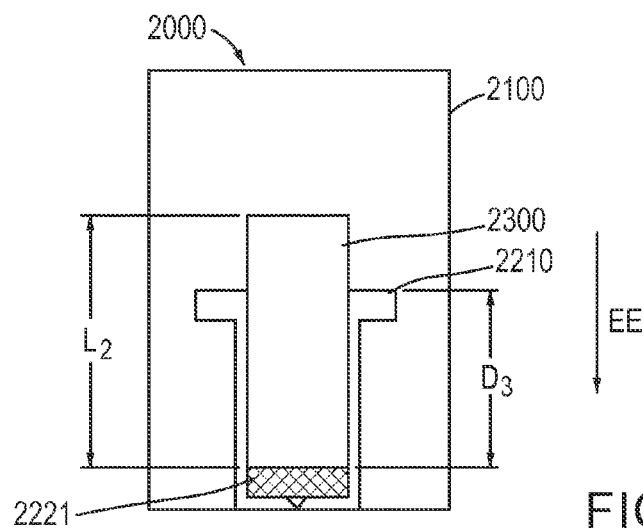

Although the length of the movable assembly 1300, as measured along a longitudinal axis thereof, is substantially constant when the movable assembly 1300 is changed from the first configuration (FIG. 1) to the second configuration (FIG. 2) and/or to the third configuration (FIG. 4), in other embodiments, the length of the movable assembly 1300 can change when the movable assembly 1300 changes between various configurations. Similarly stated, although the overall length of the movable assembly 1300 is the same as the length of the second movable member 1370, and remains the same in the configurations shown in FIGS. 1-4, in other embodiments, the overall length of the movable assembly 1300 can change when the movable assembly 1300 when the movable assembly 1300 changes between various configurations. For example, FIGS. 5-7 are schematic illustrations of a medicament delivery device 2000 according to an embodiment in a first, second, and third configuration, respectively. The medicament delivery device 2000 includes a housing 2100, a medicament container 2210, and a movable assembly 2300. The housing 2100 can be any suitable size, shape, or configuration and can be made of any suitable material. For example, in some embodiments, the housing 2100 is an assembly of multiple parts formed from a plastic material and defines a substantially rectangular shape when assembled.

The medicament container 2210 is disposed within the housing 2100, and contains (i.e., is filled or partially filled with) a medicament. The medicament container 2210 includes a proximal end portion and a distal end portion that is coupled to a delivery member, such as a tube, needle or the like (not shown in FIGS. 5-7). The medicament container 2210 further includes an elastomeric member 2221 (also referred to herein as a "plunger"). The elastomeric member 2221 is formulated to be compatible with the medicament housed within the medicament container 2210. Similarly stated, the elastomeric member 2221 is formulated to minimize any reduction in the efficacy of the medicament that may result from contact (either direct or indirect) between the elastomeric member 2221 and the medicament. For example, in some embodiments, the elastomeric member 2221 can be formulated to minimize any leaching or out-gassing of compositions that may have an undesired effect on the medicament. In some embodiments, the elastomeric member 2221 can be disposed within the medicament container 2210 to seal the proximal end portion of the medicament container 2210. In some embodiments, the elastomeric member 2221 can be formulated to maintain its chemical stability, flexibility and/or sealing properties when in contact (either direct or indirect) with a medicament over a long period of time (e.g., for up to six months, one year, two years, five years or longer). The medicament container 2210 can be any container suitable for storing the medicament.

The movable assembly 2300 can include any number of parts or components, and is configured to move between a first configuration and a second configuration. For example, in some embodiments, the movable assembly 2300 can include at least a first movable member and a second movable member configured to "telescope" to change the length of the movable assembly, as described herein. In other embodiments, the movable assembly 2300 can include a single component that is configured to change lengths. Such single component embodiments can include, for example, an inflatable or expandable member having flexible walls and/or a bellows structure to facilitate a change in length as described herein.

In particular, as shown in FIG. 5, the movable assembly 2300 defines a first length $L_1$ when in the first configuration. Similarly, when the movable assembly 2300 is in the first configuration and first position, the plunger 2221 is disposed within the medicament container 2210 at a first depth $D_1$. As shown in FIG. 6, the distal end portion of the movable assembly 2300 is moved in the direction of the arrow DD when the movable assembly 2300 changes to the second configuration. In this manner, the length $L_1$ of the movable assembly 2300 is increased to a second length $L_2$. Furthermore, when the movable assembly 2300 changes to the second configuration, the plunger 2221 is moved a first distance to a second position within the medicament container 2210 (i.e., such that the plunger 2221 is disposed at a second depth $D_2$, as shown in FIG. 6). In some embodiments, the movable assembly 2300 can be configured to move in the direction DD (e.g., the distal direction) and/or change from the first configuration to the second configuration in response to a force exerted by a user (e.g., via direct contact, a pull tab, a slider, and/or the like). In other embodiments, the movable assembly 2300 can be configured to move in the direction DD and/or change from the first configuration to the second configuration in response to a force exerted by an energy storage member (not shown in FIGS. 5-7). In such embodiments, an energy storage member can be any suitable mechanism for storing energy of the types shown and described herein (e.g., a mechanical energy storage member, a device containing compressed gas, a device containing a vapor pressure-based propellant, an electrical energy storage member, a chemical energy storage member or the like).

The distal motion of the plunger 2221 when the movable assembly is moved to the second configuration can facilitate, for example, a mixing of medicament constituents contained within the medicament container 2210. For example, in some embodiments, the medicament can include a first medicament portion (or constituent) and a second medicament portion (or constituent) configured to mix under a given pressure. In some embodiments, the distal movement of the plunger 2221 can facilitate such mixing. In some embodiments, the distal movement of the plunger 2221 can facilitate the removal (or purging) of air within the medicament and/or medicament container 2210. In such embodiments, the medicament container 2210 can be slightly overfilled such that as the plunger is moved the first distance, the overfilled portion and any undesirable air or gas within the medicament container 2210 and/or needle is expelled before delivery. This arrangement can be used to control the accuracy of a delivery dosage and/or reduce the introduction of an air into the target location. For example, by moving the plunger 2221 the first distance to a known location within the medicament container 2210, the remaining amount of medicament to be delivered (via the subsequent movement of the plunger 2221, as described below) can be accurately controlled.

When the movable assembly 2300 is in the second configuration (e.g., FIG. 6), the movable assembly 2300 can be moved from a first position to a second position within the housing 2100, as shown by the arrow EE in FIG. 7. The distal motion of the movable assembly 2300 (e.g., in the direction of the arrow EE) moves the plunger 2221 within the medicament container 2210 a second distance to place the plunger 2221 at a third depth $D_3$. In this manner, the plunger 2221 is moved within the medicament container 2210 such that the medicament disposed therein is delivered to a volume substantially outside the medicament container 2210 (e.g., into the body of the patient via the needle). Although the medicament container 2210 is shown in FIGS. 5-7 as remaining substantially stationary when the movable assembly 2300 moves, in other embodiments, movement of the movable assembly can cause the medicament container 2210 to move within the housing 2100.

Figure 8:
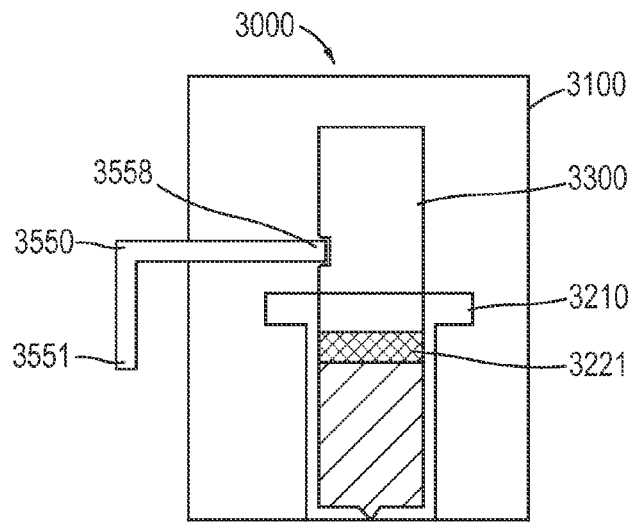
FIGS. 8-10 are schematic illustrations of a medicament delivery device according to an embodiment, in a first, second, and third configuration, respectively.
Figure 9:
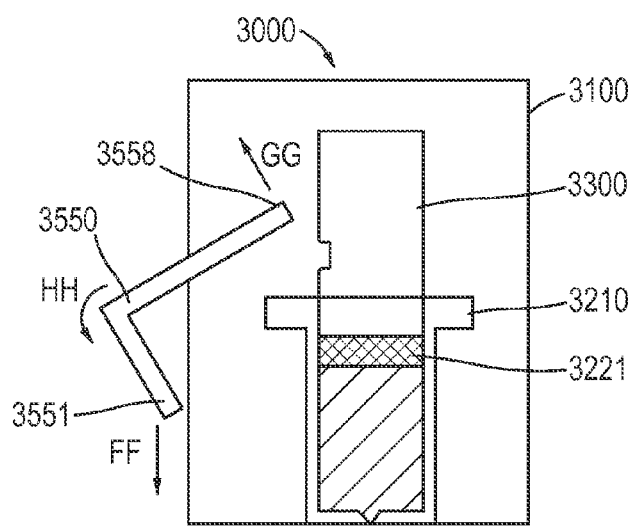
Figure 10:
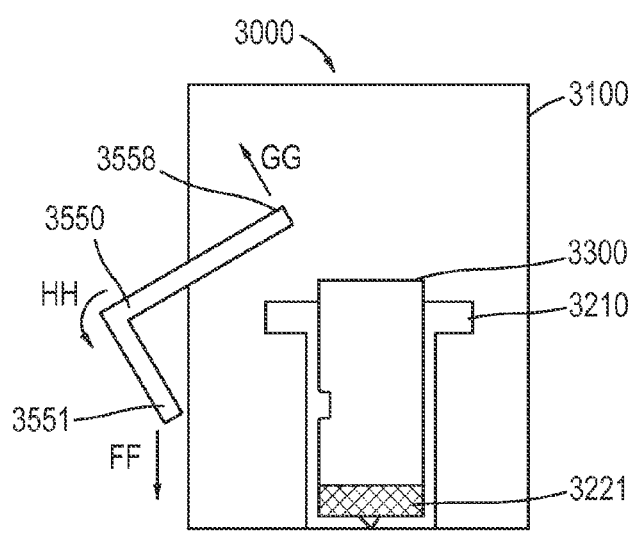

FIGS. 8-10 are schematic illustrations of a medicament delivery device 3000 according to an embodiment in a first, second, and third configuration, respectively. The medicament delivery device 3000 includes a housing 3100, a medicament container 3210, a movable member 3300, and a release member 3550. The housing 3100 can be any suitable size, shape, or configuration and can be made of any suitable material. For example, in some embodiments, the housing 3100 is an assembly of multiple parts formed from a plastic material and defines a substantially rectangular shape when assembled.

The medicament container 3210 is disposed within the housing 3100, and contains (i.e., is filled or partially filled with) a medicament. The medicament container 3210 includes a proximal end portion and a distal end portion that can be coupled to a delivery member, such as a tube, needle or the like (not shown in FIGS. 8-10). The medicament container 3210 further includes an elastomeric member 3221 (also referred to herein as a "plunger"). The elastomeric member 3221 is formulated to be compatible with the medicament housed within the medicament container 3210, as described above.

The movable member 3300 can be any suitable shape, size, or configuration, and is configured to move the plunger 3221 between a first position and a second position, as described herein. For example, in some embodiments, the movable member 3300 can be a piston configured to engage the plunger 3221 and to move the plunger within the medicament container 3210. In some embodiments, the movable member 3300 can be a movable assembly, including any number of parts. For example, in some embodiments, the movable assembly can include a first movable member and a second movable member, such as, for example, the movable assembly 3300 described with respect to FIGS. 5-7.

The release member 3550 includes at least a first end portion 3551 and a retention portion 3558. The release member 3550 can be any suitable size, shape, or configuration and is configured to move between a first position and a second position. As shown in FIG. 8, the retention portion 3558 engages the movable member 3300 when the release member 3550 is the first position. In this manner, the retention portion 3558 is configured to limit the movement of the movable member 3300 when the release member 3550 is in the first position. The release member 3550 can be any suitable mechanism for limiting the movement of the movable member, such as, a lever, a latch, a cable, a rod, and/or the like. For example, as shown in FIGS. 9 and 10, the retention portion 3558 disengages the movable member 3300 when the release member 3550 is moved to the second position. While shown in FIGS. 8-10 as being partially disposed within the housing 3100, in other embodiments, the release member 3550 can be completely disposed within the housing 3100.

As shown in FIG. 9, in use, the first end portion 3551 of the release member 3550 is urged to move in the direction of the arrow FF to the second position to release the movable member 3300. For example, in some embodiments, the first end portion 3551 can be engaged by a portion of the medicament delivery device 3000 such that a distal movement of the portion moves the first end portion 3551 of the release member 3550 in the direction of the arrow FF. In some embodiments, the first end portion 3551 can be coupled to, for example, a safety lock, an arming device, a cover or the like (not shown). In such embodiments, a user can manipulate the safety lock, arming device, or cover as an initial step in operating the medicament delivery device 3000, thereby urging the first end portion 3551 of the release member 3550 to move in the direction FF. In other embodiments, the first end portion 3551 can include, for example, a pull tab, a push button, a slider, and/or the like that can be engaged by the user such that the first end portion 3551 is moved in the direction FF (e.g., the distal direction) when manipulated.

As shown in FIG. 9, the movement of the first end portion 3551 of the release member 3550 can facilitate a pivoting motion of the release member 3550, as shown by the arrow HH in FIG. 9. In this manner, the release member 3550 pivots, rotates, or otherwise reconfigures relative to the housing 3100 such that the retention portion 3558 of the release member 3550 is moved in a second direction as shown by the arrow GG. In this manner, the retention portion 3558 disengages the movable member 3300. By changing the direction of motion of the retention portion 3558, this arrangement can result in more compact delivery devices, placement of the first end portion 3551 of the release member 3550 in an ergonomically desirable position relative to the housing 3100 or the like. In some embodiments, the second direction can be substantially normal to the first direction. In other embodiments, the second direction can be substantially opposite and parallel to the first direction.

In some embodiments, the release member 3550 can be configured such that the first end portion 3551 can be moved in the first direction FF with a first force and the retention end portion 3558 can be moved in the second direction GG with a second force. For example, in some embodiments, the arrangement of the release member 3550 defines a mechanical advantage such that by moving the first end portion 3551 with the first force, the retention portion 3558 moves with the second force, substantially greater than the first force. In other embodiments, the retention portion 3558 moves in the second direction GG with the first force.

With the retention portion 3558 disengaged from the movable member 3300 (e.g., the release member 3550 is in the second configuration), the movable assembly 3300 is urged to move in the distal direction, as shown in FIG. 10. In some embodiments, the movable member 3300 can be configured to move in the distal direction in response to a force exerted by an energy storage member (not shown in FIGS. 8-10). In such embodiments, an energy storage member can be any suitable mechanism for storing energy of the types shown and described herein (e.g., a mechanical energy storage member, a device containing compressed gas, a device containing a vapor pressure-based propellant, an electrical energy storage member, a chemical energy storage member or the like).

Figure 11:
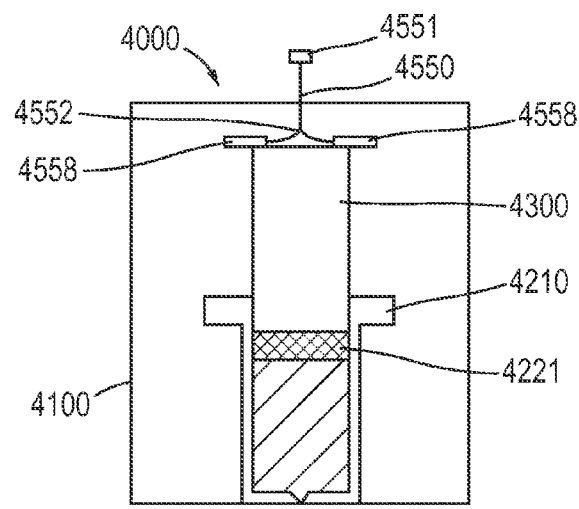
FIGS. 11-13 are schematic illustrations of a medicament delivery device according to an embodiment, in a first, second, and third configuration, respectively.
Figure 12:
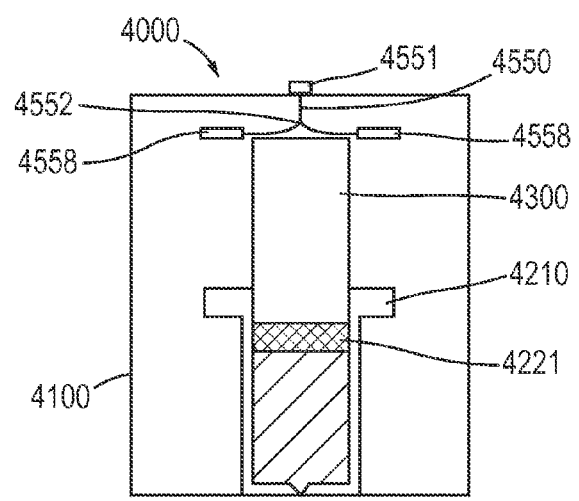
Figure 13:
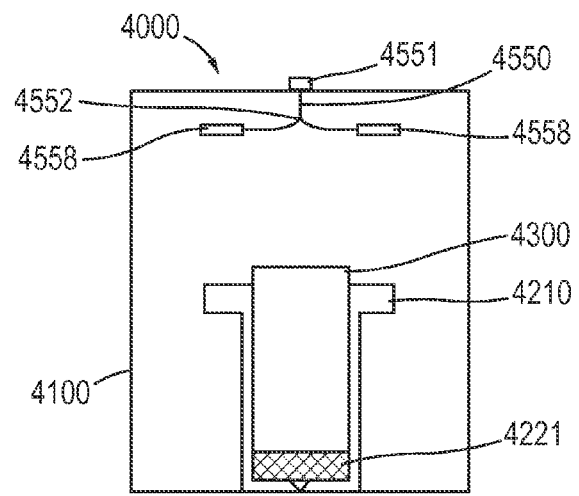

While the release member 3550 is shown in FIGS. 8-10 as being pivotally coupled to the housing 3100, in other embodiments, a release member can move between a first position and a second position in any suitable manner (e.g., translation along any axis, rotation about any axis or combination thereof). For example, FIGS. 11-13 show a medicament delivery device 4000 that includes a housing 4100, a medicament container 4210, a movable member 4300, and a release member 4550. In some embodiments, the housing 4100 and the medicament container 4210 can be substantially similar to the housing 3100 and the medicament container 3210 included in the medicament delivery device 3000.

The release member 4550 includes a first end portion 4551, a second end portion 4552, and retention portions 4558, and is configured to move between a first configuration (FIG. 11) and a second configuration (FIG. 12). As shown in FIG. 11, the retention portions 4558 engage and/or contact the movable member 4300 when the release member 4550 is the first configuration. In this manner, the retention portions 4558 limit the movement of the movable member 4300 when the release member 4550 is in the first configuration. The retention portions 4558 can engage and/or contact the movable member 4300 in any suitable manner. For example, in some embodiments, the movable member 4300 can include a protrusion (not shown in FIG. 11-13) extending from a proximal surface that can be selectively engaged by the retention portions 4558. In other embodiments, the retention portions 4558 can be disposed with a channel defined by the movable member 4300 (not shown).

As shown in FIG. 12, to actuate the medicament delivery device 4000, the first end portion 4551 of the release member 4550 is urged to move in the direction of the arrow II from a first position to a second position. For example, in some embodiments, the first end portion 4551 can be engaged by a portion of the medicament delivery device 4000 such that a movement of the portion moves the first end portion 4551 of the release member 4550 in the direction of the arrow II. In other embodiments, the first end portion 4551 can include, for example, a pull tab, a push button, a slider, and/or the like that can be engaged by the user such that the first end portion 4551 is moved in the direction II (e.g., the distal direction).

The release member 4550 is configured such that the distal movement of the first end portion 4551 moves the retention portions 4558 in a lateral direction relative to the movable member 4300. Said another way, the movement of the first end portion 4551 in a first direction results in movement of the second end portion 4552 in a second direction different from the first direction. Expanding further, the second end portion 4552 of the release member 4550 can be bifurcated such that the distal motion of the first end portion 4551 urges the release member 4550 to separate and/or deform at the second end portion 4552, thereby moving the retention portions 4558 in a direction substantially normal to the direction of motion of the first end portion 4551. In some embodiments, the retention portions 4558 can move within a channel and/or guide portion of the housing 4100 and/or the movable member 4300. In this manner, the distal movement of the first end portion 4551 moves the retention portions 4558 such that the retention portions 4558 disengage the movable member 4300.

When the retention portions 4558 are disengaged from the movable member 4300 (e.g., the release member 4550 is in the second configuration), the movable assembly 4300 is urged to move in the distal direction, as shown by the arrow JJ in FIG. 13. In some embodiments, the movable member 4300 can be configured to move in the distal direction in response to a force exerted by an energy storage member (not shown in FIGS. 11-13). In such embodiments, an energy storage member can be any suitable mechanism. For example, the energy storage member can be any of the energy storage members described above with respect to FIGS. 11-13. Furthermore, the distal movement of the movable member 4300 moves the plunger 4221 in the direction JJ (e.g., the distal direction) within the medicament container 4210. In some embodiments, the distal motion of the plunger 4221 can facilitate a mixing event, such as, for example, the mixing event described above with respect to FIGS. 5-7. In this manner (e.g., with or without a mixing event), the plunger 4221 is moved within the medicament container 4210 such that the medicament disposed therein is delivered to a volume substantially outside the medicament container 4210 (e.g., into the body of the patient via the needle).

While the medicament containers described above include a single plunger, in some embodiments, any of the medicament containers described herein can include any number of plungers and/or can define multiple volumes therein that contain different medicament constituents. For example, as shown in FIGS. 14-17, a medicament delivery device 5000 includes a housing 5100, a medicament container 5210, and a movable assembly 5300. The housing 5100 can be any suitable size, shape, or configuration and can be made of any suitable material. For example, in some embodiments, the housing 5100 is an assembly of multiple parts formed from a plastic material and defines a substantially rectangular shape when assembled.

The medicament container 5210 is disposed within the housing 5100, and includes a first plunger 5221, a second plunger 5225, and a bypass 5220. The medicament container 5210 defines a first volume 5236, and a second volume 5237. Expanding further, the first volume 5236 is defined between a distal end surface of the first plunger 5221, a portion of the medicament container 5120 and a proximal end surface of the second plunger 5225, and can contain a first substance, such as any suitable diluent, as described in further detail herein. Similarly, the second volume 5236 is defined between a distal end surface of the second plunger a distal end portion of the medicament container 5210, and can contain a second substance, such as any suitable medicament (e.g., a lyophilized medicament). In this manner, the diluent contained within the first volume 5236 can be stored separately from with the medicament within the second volume 5237. Upon actuation the diluent can be mixed with the medicament such that the combination of the diluents and the medicament reconstitute the medicament for delivery into, for example, the body of a patient.

The movable assembly 5300 includes a first movable member 5301 and a second movable member 5370, and is configured to move between a first configuration, a second configuration, and a third configuration. The first movable member 5301 and the second movable member 5370 are movably coupled such that the second movable member 5370 can move with and/or relative to the first movable member 5301. As shown, in some embodiments, the second movable member 5370 can substantially surround the first movable member 5301. In some embodiments, the second movable member 5370 can define a substantially annular and/or cylindrical shape such that at least a portion of the first movable member 5301 is disposed therein.

Figure 14:
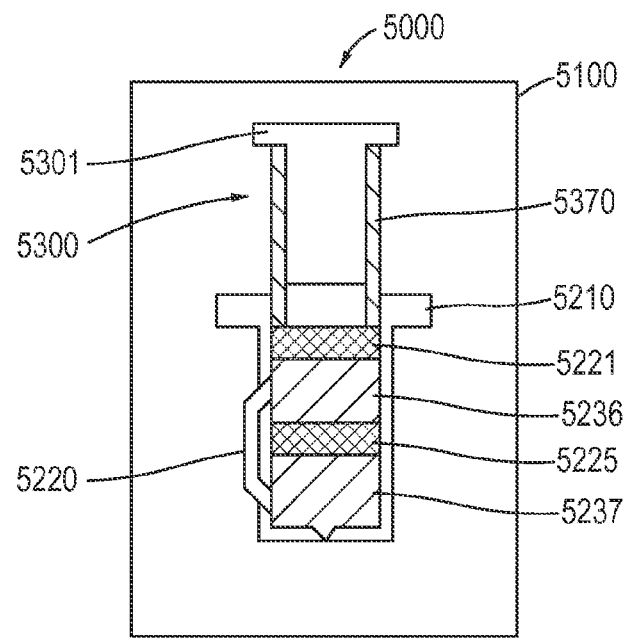
FIGS. 14-17 are schematic illustrations of a medicament delivery device according to an embodiment, in a first, second, third, and fourth configuration, respectively.
Figure 15:
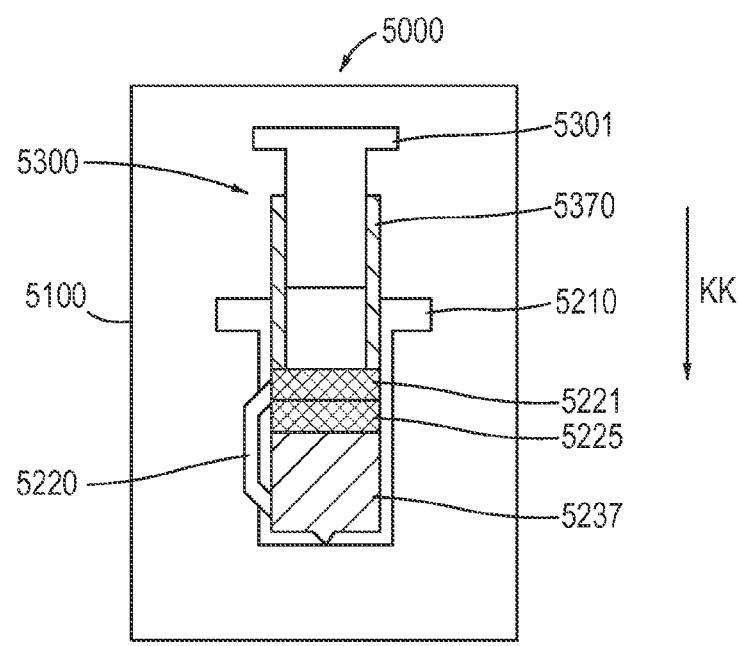

As shown in FIG. 14, the second movable member 5370 engages the first plunger 5221 disposed within the medicament container 5210 and when the movable assembly 5300 is in the first configuration (FIG. 14). In other embodiments, the second movable member 5370 can be spaced apart from the plunger 5221 when the movable assembly 5300 is in the first configuration. The second movable member 5370 can be moved, relative to the first movable member 5301 to move the movable assembly 5300 from the first configuration to the second configuration. For example, in some embodiments, the second movable member 5370 can be moved by a force exerted by an energy storage member (e.g., such as those described herein). When the second movable member 5370 moves relative to the first movable member 5301, a distal end portion of the second movable member 5370 moves the first plunger 5221 in the distal direction within the medicament container 5210, as shown by the arrow KK in FIG. 15. The distal motion of the plunger 5221 can facilitate, for example, a mixing of diluents and the medicament contained within the medicament container 5210. For example, in some embodiments, the distal movement of the first plunger 5221 can cause the second plunger 5225 to move past the bypass 5220 and urge the diluent, contained within the first volume 5236 to move within the bypass 5220 and enter the second volume 5237.

The bypass 5220 can be any suitable bypass (external or internal) configured to define a pathway between the first volume 5236 and the second volume 5237. In some embodiments, the bypass 5220 can include a one way valve such that when a pressure within the first volume 5236 increases (e.g., as induced by the distal movement of the first plunger 5221), the one way valve opens to allow a flow of the diluent through the bypass 5220 to the mixing volume 5237. In other embodiments, the bypass 5220 can include a frangible seal configured to break under the increase pressure. In this manner, when first plunger 5221 is moved, the first volume 5236 is reduced and the distal end surface of the first plunger 5221 can contact the proximal end surface of the second plunger 5255. Accordingly, as the volume defined by the first volume 5236 is reduced, the volume of the second volume 5237 increases. In this manner, the distal end surface of the first plunger 5221 contacts the proximal end surface of the second plunger 5225 at a position within the medicament container 5210 such that the first plunger 5221 of the second plunger 5225 substantially seals an opening of the bypass 5220, thereby preventing potential backflow.

Figure 16:
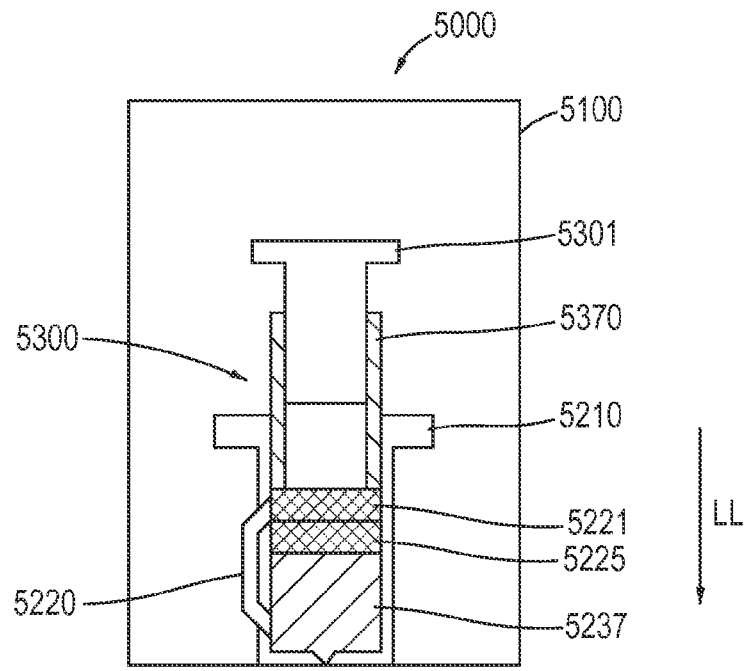
Figure 17:
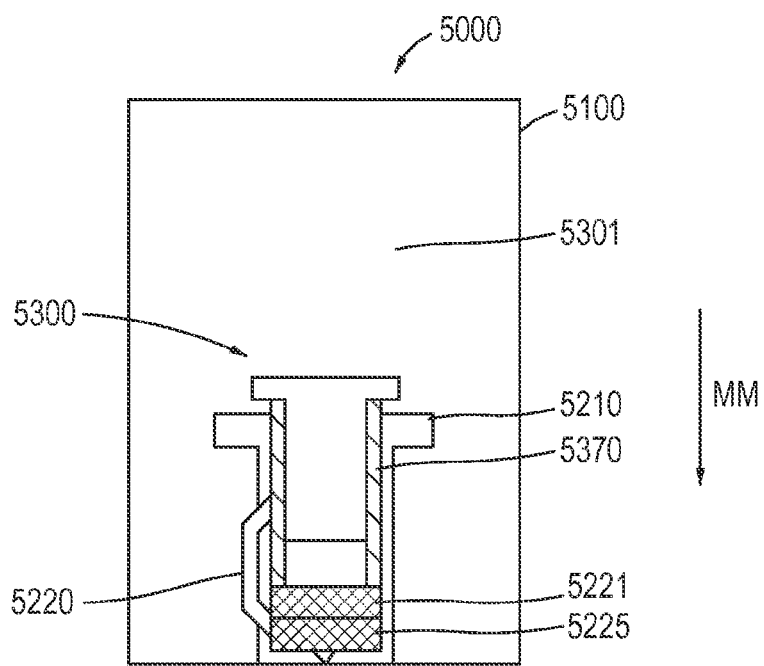

The movable assembly 5300 is configured to move from a first position (e.g., FIG. 14) to a second position within the housing 5100, as shown by the arrow LL in FIG. 16. In some embodiments, the movable assembly 5300 can move in the direction LL (e.g., the distal direction) in response to a portion of a force exerted, for example, by the energy storage member (described above). The distal movement of the movable assembly 5300 moves the medicament container 5210 within the housing 5100 from a first container position (e.g., FIG. 15) to a second container position (e.g., FIG. 16). In some embodiments, the distal movement (e.g., in the direction of the arrow LL shown in FIG. 16) can facilitate the insertion of a needle (not shown in FIGS. 14-17), disposed at the distal end portion of the medicament container 5210, into a target location (e.g., the body of a patient).

When the medicament container 5210 is in the second container position within the housing 5100, the first movable member 5301 moves distally to engage the second movable member 5370. In this manner, the first movable member 5301 and the second movable member 5370 can move together in the distal direction, as shown by the arrow MM in FIG. 17. Thus, the movable assembly 5300 moves in the distal direction and moves the first plunger 5221 and the second plunger 5225 within the medicament container 5210 such that the medicament disposed within the second volume 5237 is delivered to a volume substantially outside the medicament container 5210 (e.g., into the body of the patient via the needle).

Figure 18:
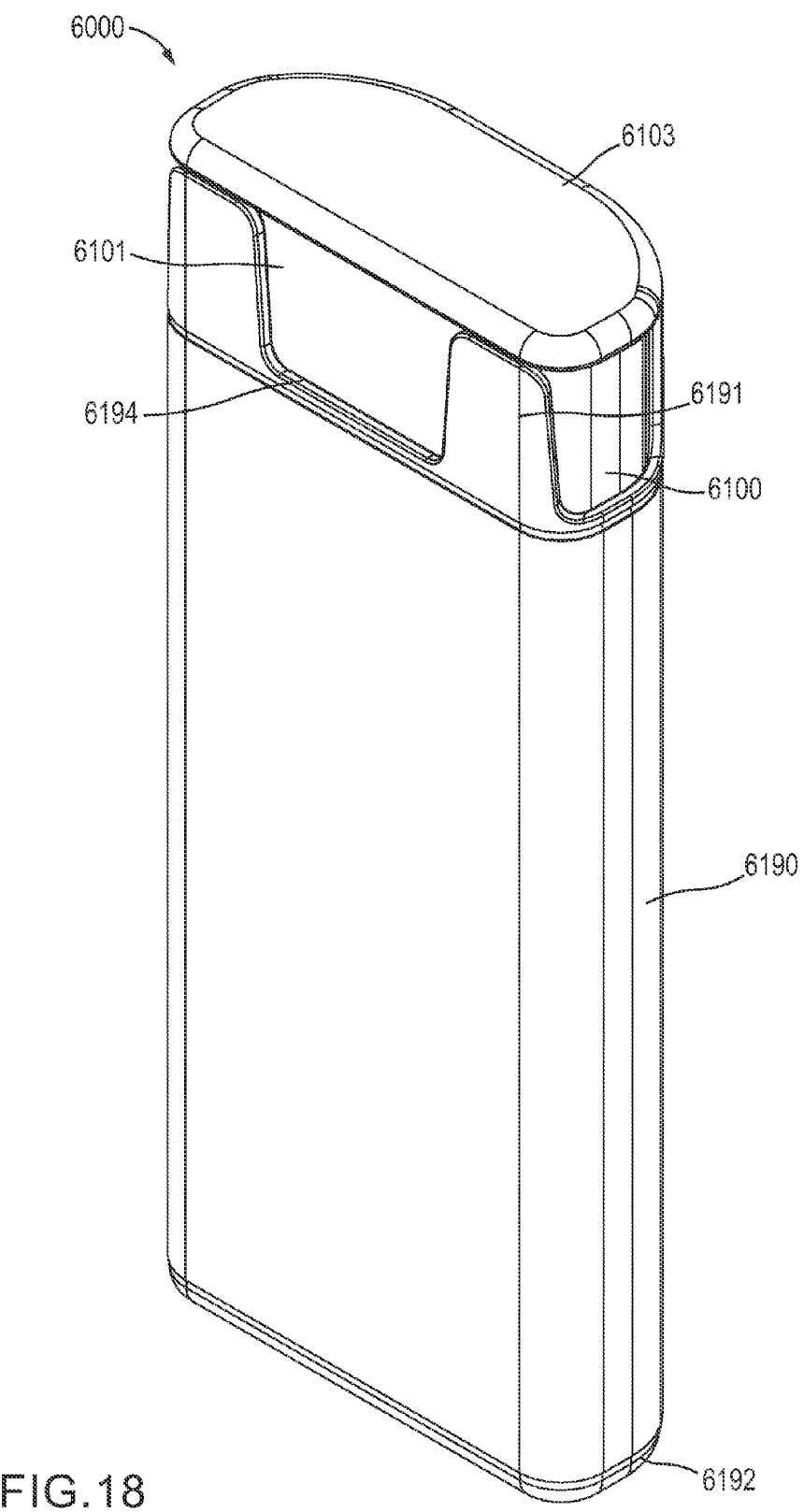
FIGS. 18 and 19 are perspective views of a medical injector according to an embodiment, in a first configuration.
Figure 19:
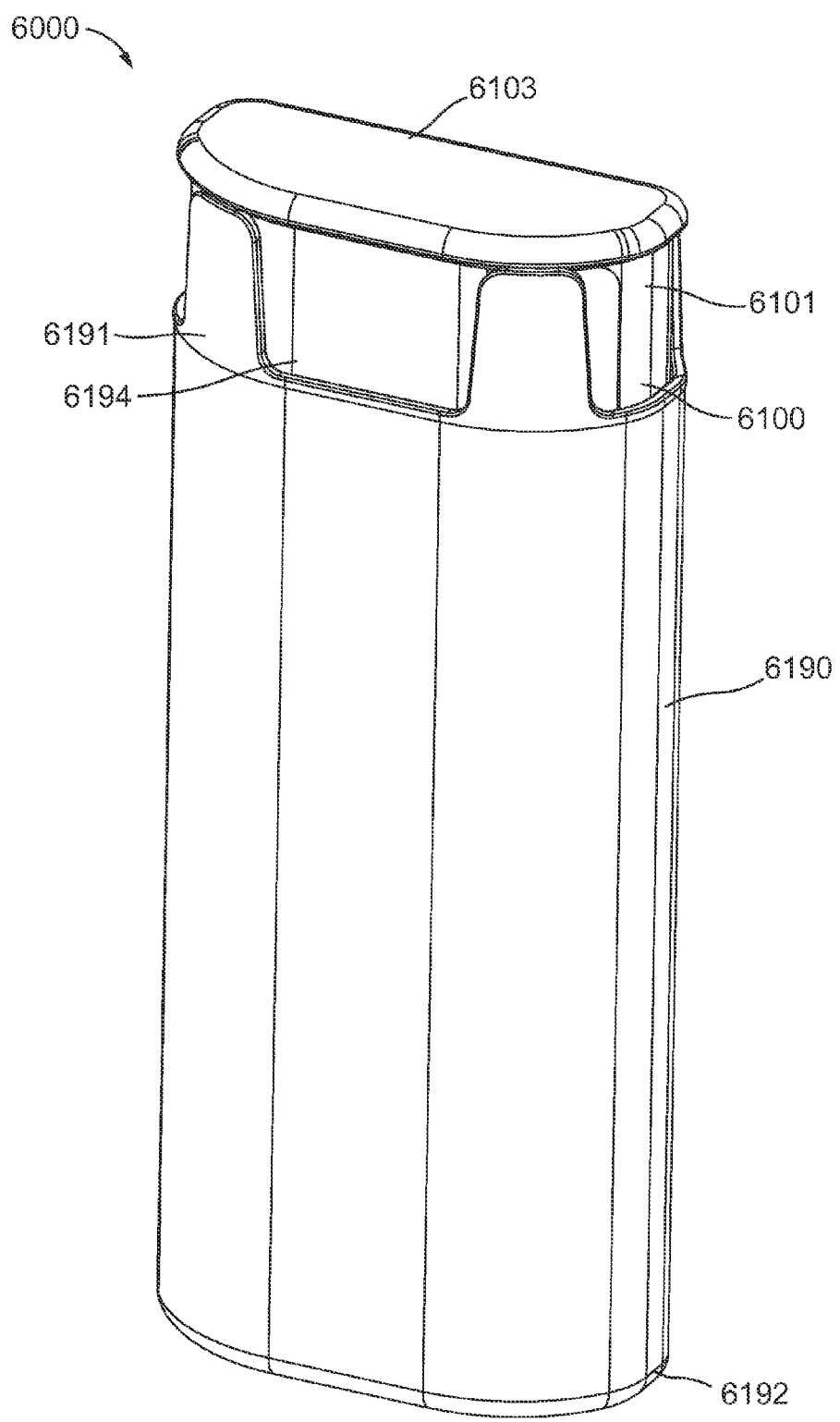
Figure 20:
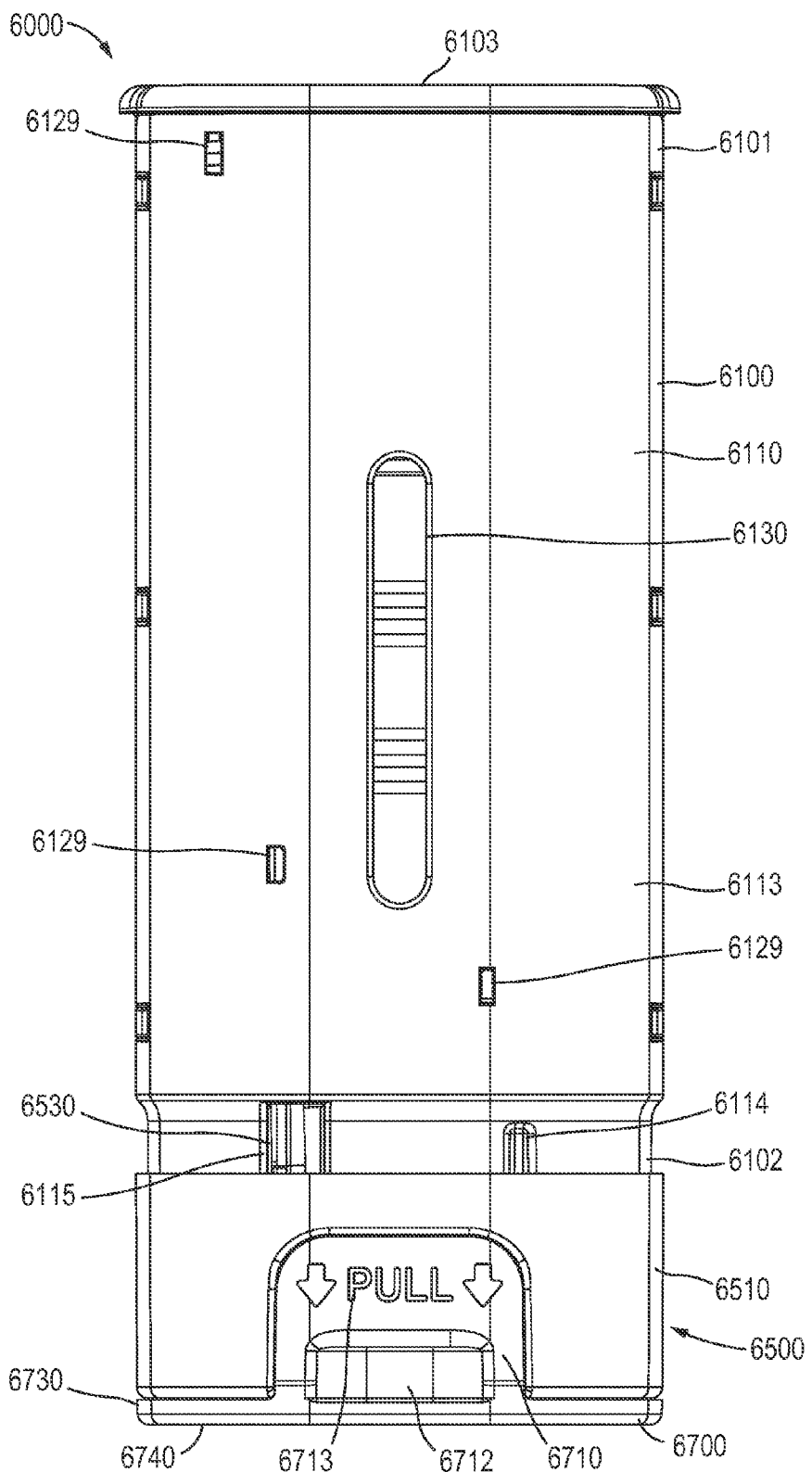
FIG. 20 is a rear view of the medical injector illustrated in FIG. 18 with a cover removed.
Figure 21:
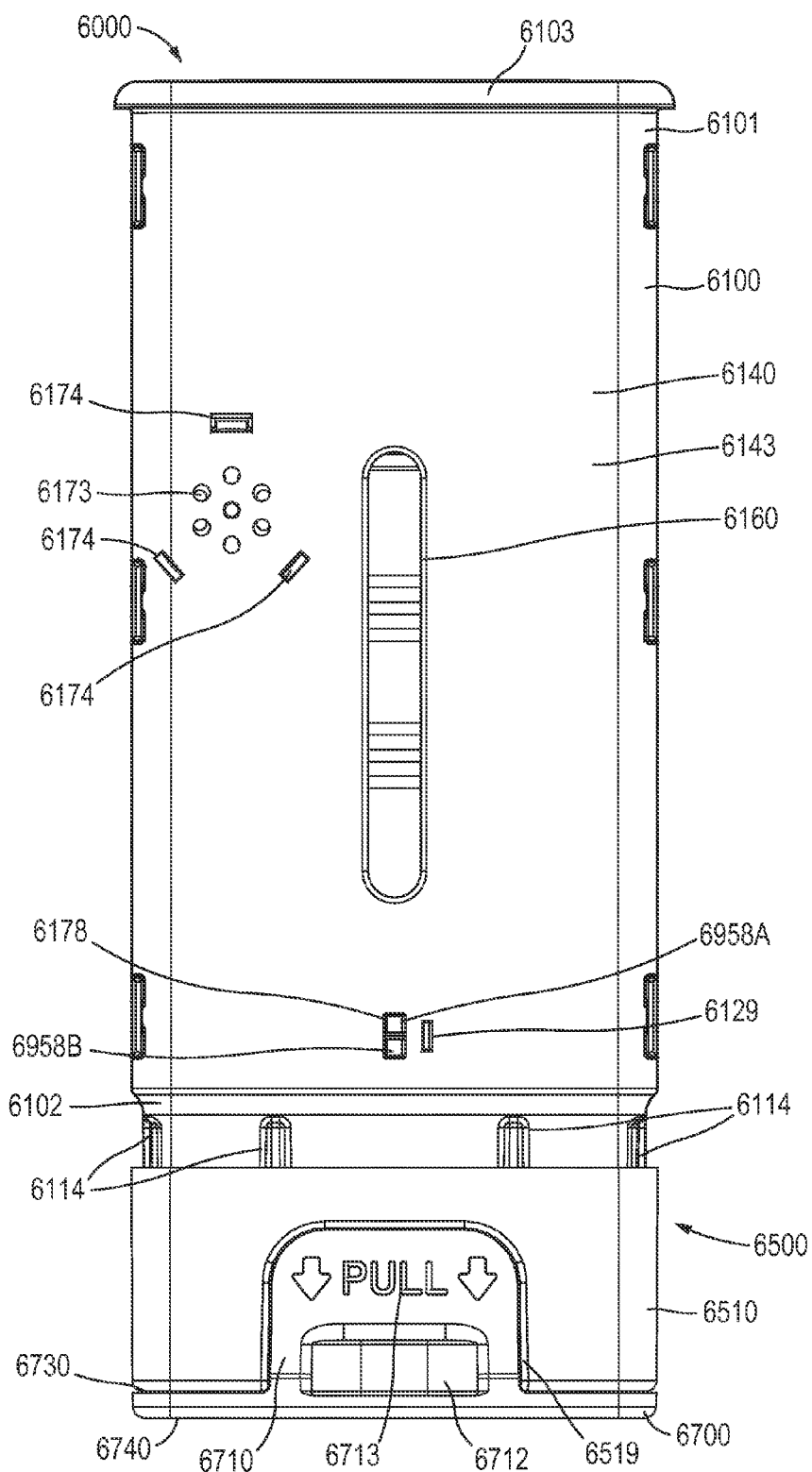
FIG. 21 is a front view of the medical injector illustrated in FIG. 18 with the cover removed.
Figure 22:
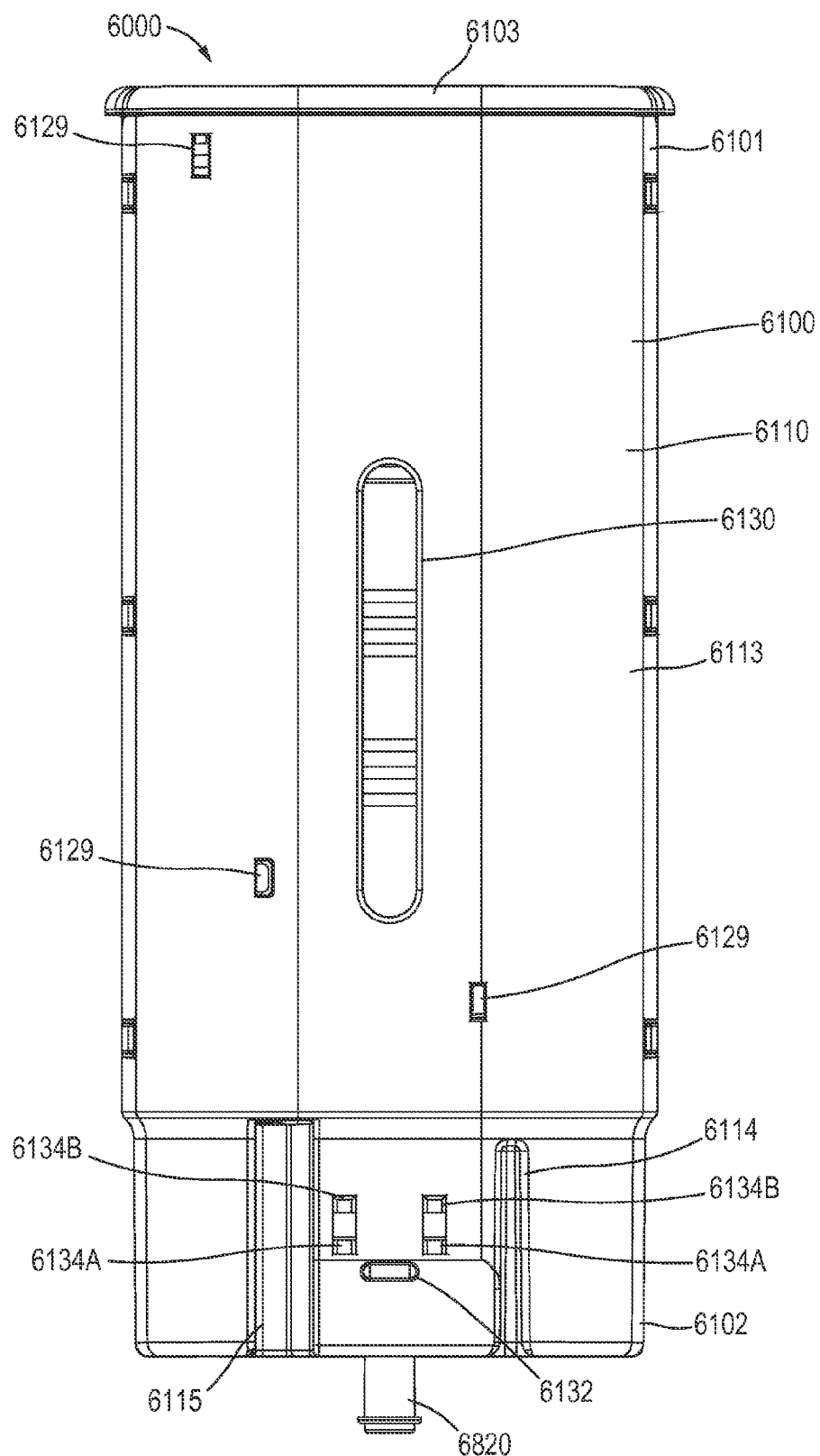
FIG. 22 is a rear view of a portion of the medical injector illustrated in FIG. 18.
Figure 76:
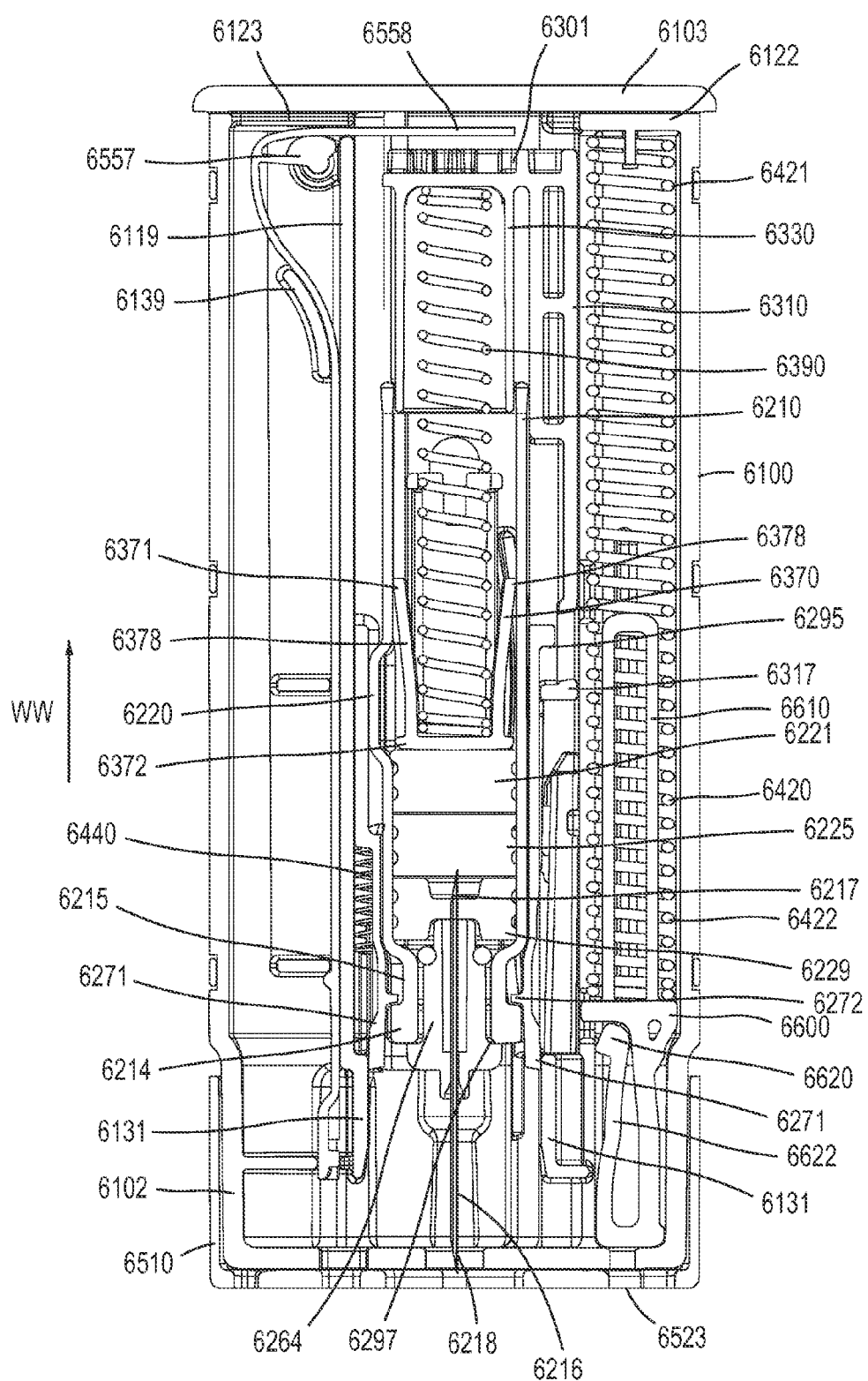
FIG. 76 is a front cross-sectional view of the medical injector illustrated in FIG. 18 in a sixth configuration (i.e., the retraction configuration).

In some embodiments, the medicament delivery device can be a medical injector configured to automatically mix and deliver a medicament contained within a medicament container. For example, FIGS. 18-76 show various views of a medical injector 6000, according to an embodiment in various different configurations (or stages of operation). FIGS. 18-19 are perspective views of the medical injector 6000 in a first configuration (i.e., prior to use). The medical injector 6000 includes a housing 6100 (see e.g., FIGS. 20-27), a system actuator assembly 6500 (see e.g., FIGS. 28-32 and 64-66), a medicament container assembly 6200 containing a medicament 6240 (see e.g., FIGS. 33-44), a movable assembly 6300 (see e.g., FIGS. 45-49), a transfer member 6600 (see e.g., FIG. 50), an electronic circuit system 6900 (see e.g., FIGS. 51-56), a cover 6190 (see e.g., FIGS. 57 and 58), and a safety lock 6700 (see e.g., FIGS. 59-63). A discussion of the components of the medical injector 6000 will be followed by a discussion of the operation of the medical injector 6000.

As shown in FIGS. 20-27, the housing 6100 includes a first housing member 6110 (FIGS. 24 and 25) and a second housing member 6140 (FIGS. 26 and 27) that can couple to form the housing 6100. The housing 6100 has a proximal end portion 6101 and a distal end portion 6102. The housing 6100 defines a first status indicator aperture 6130 (defined by the first housing member 6110) and a second status indicator aperture 6160 (defined by the second housing member 6140). The status indicator apertures 6130, 6160 can allow a patient to monitor the status and/or contents of the medicament container 6210 contained within the housing 6100. For example, by visually inspecting the status indicator aperture 6130 and/or 6160, a patient can determine whether the medicament container 6210 contains a medicament 6240 and/or whether the medicament 6240 has been dispensed.

Figure 24:
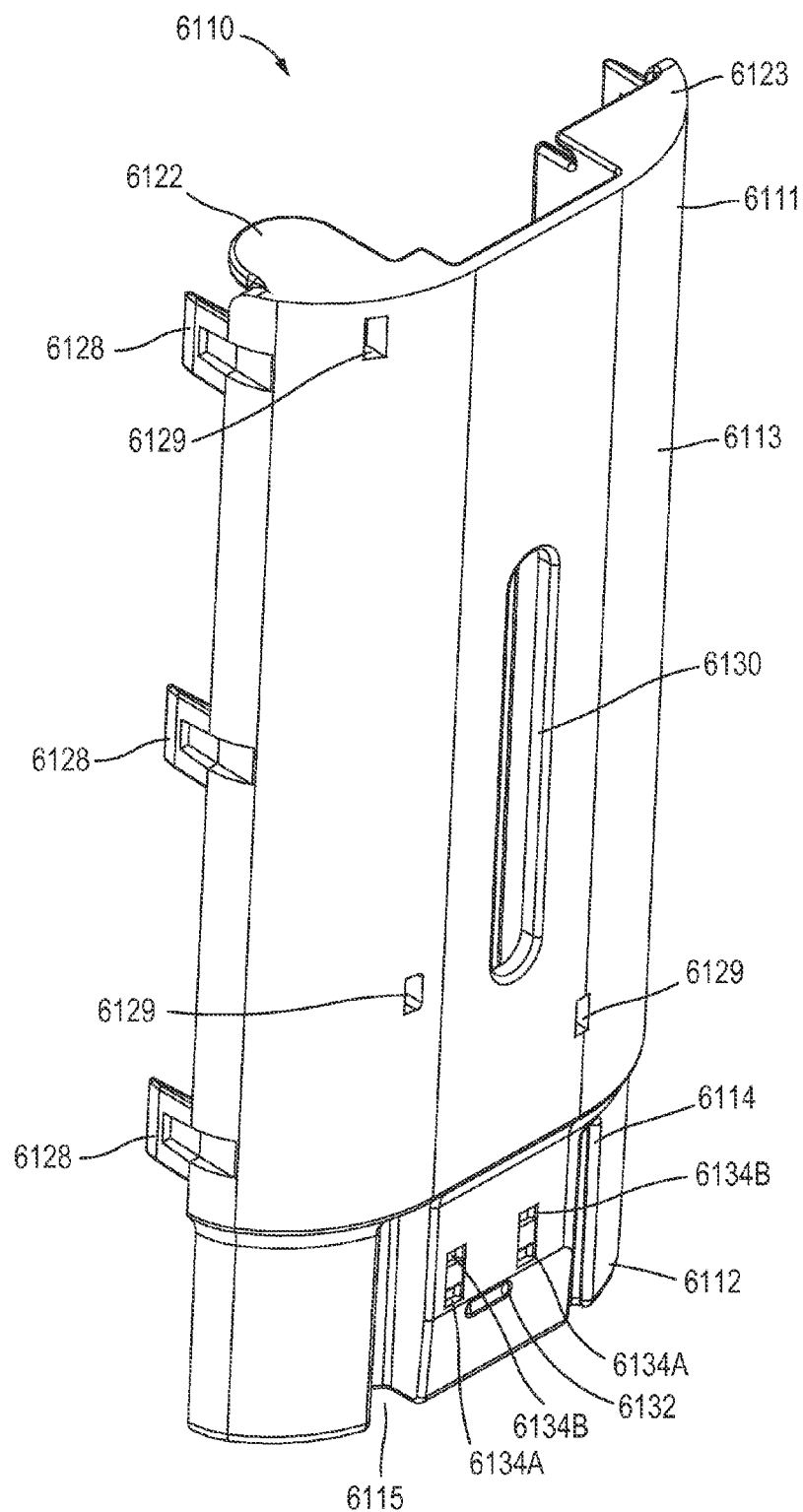
FIG. 24 is a front perspective view of a first portion of the housing of the medical injector illustrated in FIG. 18.
Figure 25:
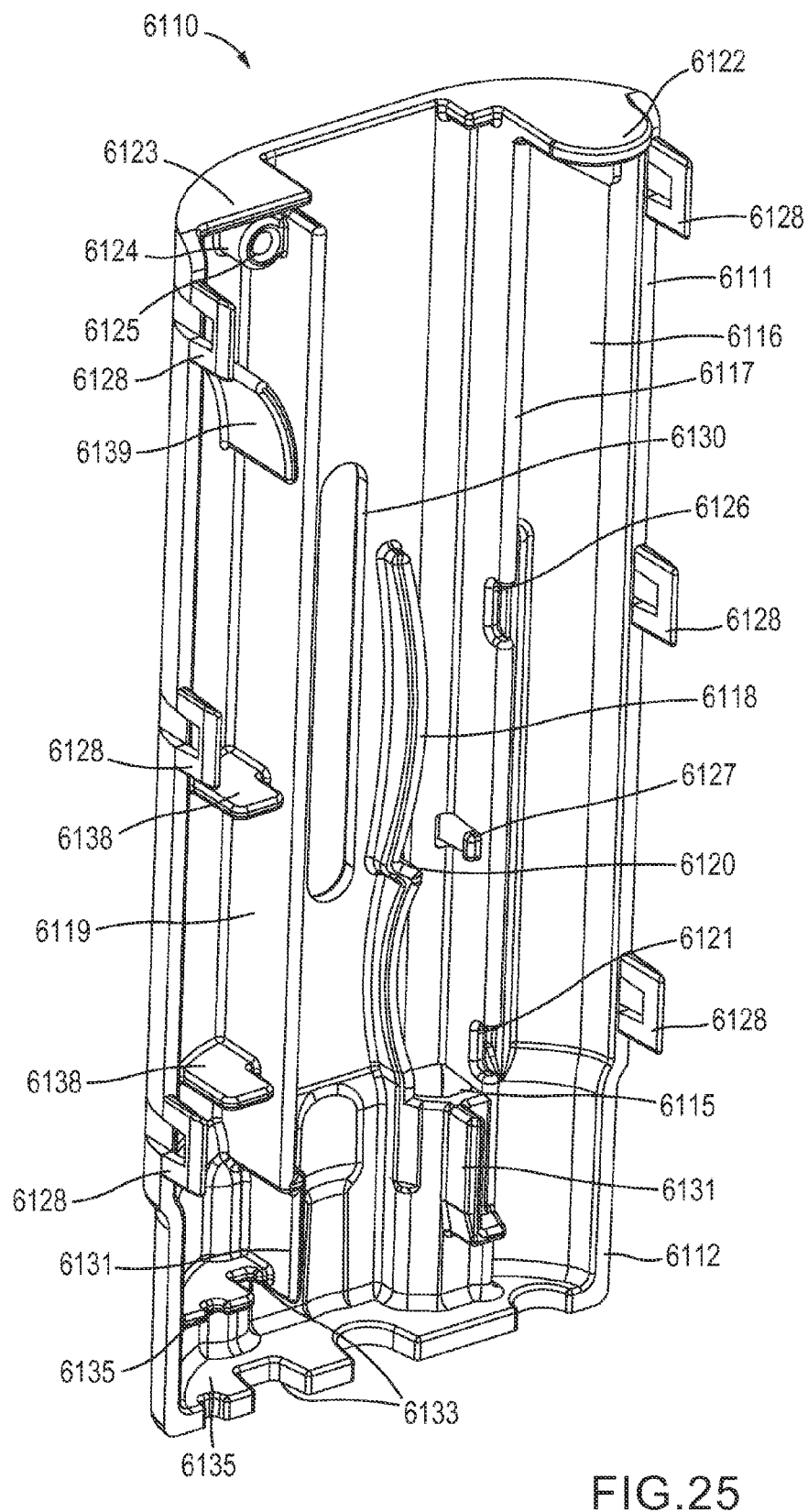
FIG. 25 is a rear perspective view of the first portion of the housing of the medical injector illustrated in FIG. 24.

As shown in FIGS. 24-25, the first housing member 6110 includes an outer surface 6113 and an inner surface 6116, and a proximal end portion 6111 and a distal end portion 6112. The outer surface 6113 defines base retention recesses 6134A and 6134B, an activation rod groove 6115, and a base rail groove 6114, at the distal end portion 6112 of the first housing member 6110. The distal base retention recesses 6134A are configured to receive base connection knobs 6518 of an actuator 6510 (also referred to herein as "base 6510," see e.g., FIG. 66) when the base 6510 is in a first (i.e., pre-actuated) position relative to the housing 6100. The proximal base retention recesses 6134B are configured to receive the base connection knobs 6518 of the base 6510 when the base 6510 is in a second (i.e., actuated) position relative to the housing 6100. The base retention recesses 6134A, 6134B have a tapered proximal sidewall and a non-tapered distal sidewall. This arrangement allows the base retention recesses 6134A, 6134B to receive the base connection knobs 6518 such that the base 6510 can move proximally relative to the housing 6100, but cannot move distally relative to the housing 6100. Said another way, the distal base retention recesses 6134A are configured to prevent the base 6510 from moving in the distal direction when the base 6510 is in the first position and the proximal base retention recesses 6134B are configured to prevent the base 6510 from moving in the distal direction when the base 6510 is in the second position. Similarly stated, the proximal base retention recesses 6134B and the base connection knobs 6518 cooperatively lock the base 6510 to prevent undesirable movement of the base 6510 after the medical injector 6000 is actuated, and to further visually indicate to the user that the medical injector has been actuated.

Figure 66:
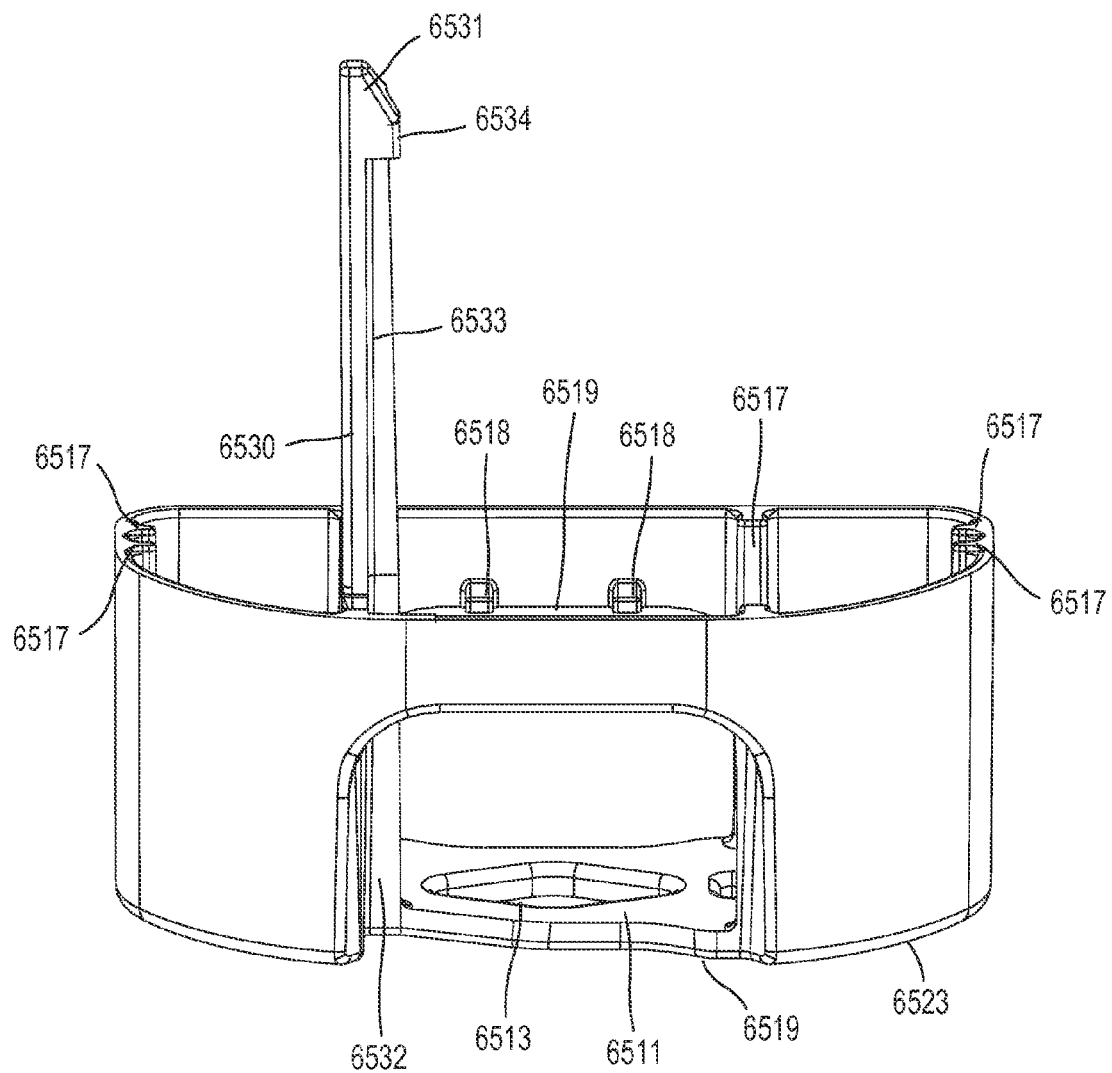
FIG. 66 is a front view of the base included in the medical injector illustrated in FIG. 65.

The activation rod groove 6115 is configured to receive an activator 6530 (also referred to herein as "release member 6530," and/or "rod 6530" see e.g., FIG. 66) of the base 6510. As described in more detail herein, the release member 6530 of the base 6510 is configured to engage a portion of the movable assembly 6300 (also referred to herein as "medicament delivery mechanism 6300") when the base 6510 is moved with respect to the housing 6100 to actuate the medical injector 6000. The base rail groove 6114 is configured to receive a guide member 6517 of the base 6510. The guide member 6517 of the base 6510 and the base rail groove 6114 of the housing 6100 engage each other in a way that allows the guide member 6517 of the base 6510 to slide in a proximal and/or distal direction within the base rail groove 6114 while limiting lateral movement of the guide member 6517 and/or base 6510 with respect to the housing 6100.

The inner surface 6116 of the first housing member 6110 includes a transfer member guide 6117, a movable member guide 6118, a mixing actuator guide 6119, an upper spring plate 6122, an upper mixing actuator plate 6123, and a mixing actuator pivot protrusion 6124 (see e.g., FIG. 25). The transfer member guide 6117 is configured to engage a guide surface 6619 and a guide protrusion 6624 of the transfer member 6600 (see FIG. 50). The guide surface 6619 and the guide protrusion 6624 of the transfer member 6600 and the transfer member guide 6117 of the first housing member 6110 engage each other in a way that allows the guide surface 6619 and the guide protrusion 6624 of the transfer member 6600 to slide in a proximal and/or distal direction along the transfer member guide 6117 while limiting lateral movement of the transfer member 6600 within the housing 6100.

The transfer member guide 6117 defines an upper notch 6126 and a lower notch 6121. The upper notch 6126 defined by the transfer member guide 6117 can receive the guide protrusion 6624 of the transfer member 6600 during assembly of the medical injector 6000. Similarly stated, the guide protrusion 6624 is inserted through the upper notch 6126 and is disposed on an opposite side of the transfer member guide 6117 than the guide surface 6619 of the transfer member 6600. This arrangement allows the transfer member 6600 to move in a proximal and/or distal direction with respect to the housing 6100 but prevents the transfer member 6600 from moving in a lateral direction with respect to the housing 6100. Furthermore, the guide protrusion 6624 can be moved through the upper notch 6126 to disengage the transfer member 6600 from the medicament delivery device 6300 without moving the medicament delivery device 6300. For example, in some embodiments, the medicament 6240 disposed within the medicament container 6210 can expire. In such embodiments, the guide protrusion 6624 can be moved through the upper notch 6126 to disengage from the medicament delivery device 6300, thereby disarming the medical injector 6000 (e.g., rendering the medical injector 6000 incapable of completing an injection event in the designed manner). The lower notch 6121 receives the guide protrusion 6624 to facilitate a retraction event, as described in further detail herein.

Figure 29:
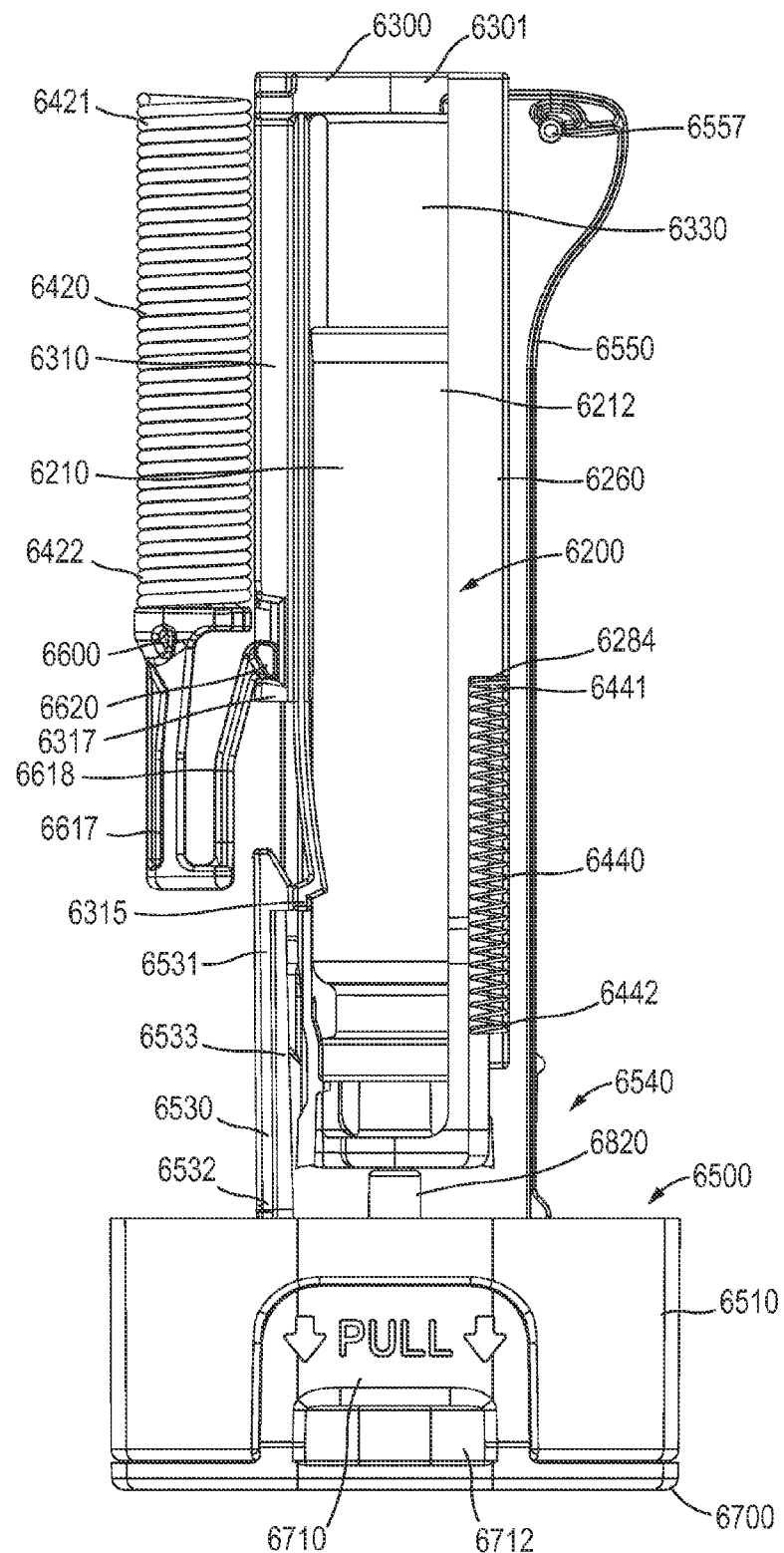
FIG. 29 is a rear view of a medicament delivery mechanism of the medical injector illustrated in FIG. 18.
Figure 30:
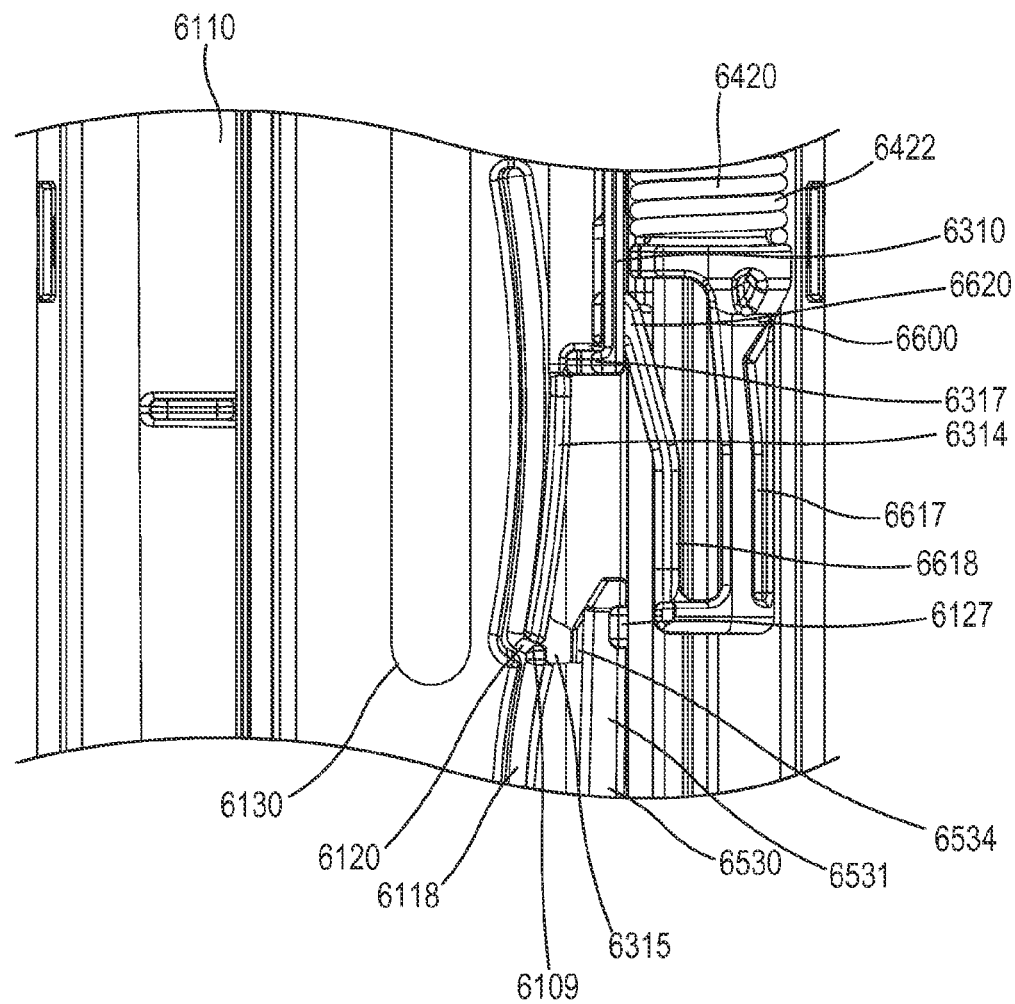
FIG. 30 is an enlarged front view of a portion of the medicament delivery mechanism of the medical injector illustrated in FIG. 29.

Similarly, the movable member guide 6118 is configured to engage a first latch protrusion 6315 included in a first movable member 6301 of the medicament delivery mechanism 6300 (see e.g., FIGS. 29, 30 and 47). As described in more detail below, the movable member guide 6118 defines a latch member notch 6120 that includes an engagement surface 6109 (see FIG. 30) against which the first latch protrusion 6315 of the latch portion 6310 of the first movable member 6301 is disposed when the medical injector 6000 is in the first configuration.

Figure 64:
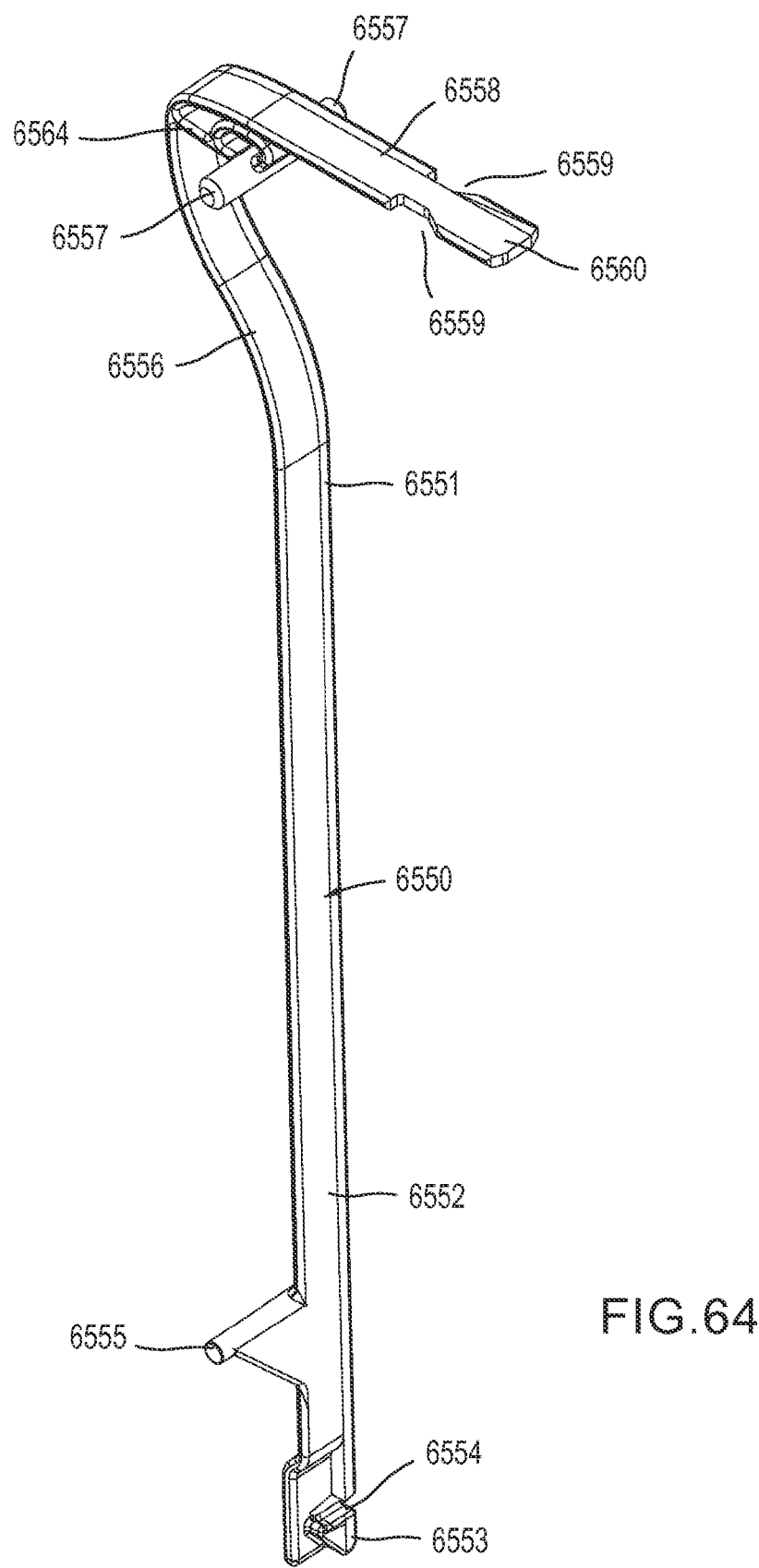
FIG. 64 is a perspective view of a mixing actuator included in the system actuator assembly of the medical injector illustrated in FIG. 18.

The mixing actuator guide 6119 engages a mixing actuator member 6550 included in the system actuation assembly 6500 (see e.g., FIG. 64). Furthermore, the inner surface 6116 of the first housing portion 6110 includes lower retention protrusions 6138 and an upper retention protrusion 6139. The arrangement of the mixing actuator guide 6119 and the upper and lower retention protrusions, 6139 and 6138 respectively, defines a channel or track within which the mixing actuator member 6550 is disposed. Similarly stated, the mixing actuator member 6550 is slidably disposed against and between the mixing actuator guide 6119 and the upper and lower retention protrusions, 6139 and 6138. In this manner, the mixing actuator guide 6119, the lower retention protrusions 6138, and upper retention protrusion 6139 act to guide the mixing actuator member 6550 when the mixing actuator member 6550 is moved within the housing 6100. For example, as described in further detail herein, the mixing actuator member 6550 is disposed in a space defined between the lower retention protrusions 6138 and the mixing actuator guide 6119, thereby limiting the motion of the mixing actuator member to the proximal and distal direction (i.e., limiting lateral movement of the mixing actuator member 6550). Furthermore, the mixing actuator member 6550 can engage and/or slide against the upper retention protrusion 6139 such that the upper retention protrusion 6139 facilitates a deformation of the mixing actuator member 6550 (e.g., the mixing actuator member 6550 deforms, bends, curves, or otherwise reconfigures) when the mixing actuator member 6550 is moved within the housing 6100.

The upper spring plate 6122 is disposed at the proximal end portion 6111 of the first housing member 6110. The upper spring plate 6122 extends from the inner surface 6116 and is configured to contact a proximal end portion 6421 of an energy storage member 6420 (also referred to herein as a "insertion spring 6420" and/or "spring 6420", see FIG. 68). In this manner, when the medical injector 6000 is activated, the upper spring plate 6122 limits proximal movement of the spring 6420 such that the spring 6420 expands distally to move the medicament delivery mechanism 6300 and/or the transfer member 6600 in a distal direction (see e.g., FIG. 73). Similarly stated, the upper spring plate 6122 receives a force from the spring 6420 and applies an equal and opposite reaction force to the proximal end portion 6421 of the spring 6420 such that a distal end portion 6422 of the spring 6420 expands in a distal direction, as described in further detail herein.

The upper mixing actuator plate 6123 is disposed at the proximal end portion 6111 of the first housing member 6110 and extends from the inner surface 6116. The upper mixing actuator plate 6123 is configured to selectively engage the mixing actuator member 6550 of the system actuator assembly 6500 (see FIG. 68). In this manner, the upper mixing actuator plate 6123 is configured to limit the proximal movement of the mixing actuator member 6550, as described in further detail herein. The mixing actuator pivot protrusion 6124 defines an aperture 6125 that receives a pivot protrusion 6557 of the mixing actuator member 6550. In this manner, the mixing actuator member 6550 can pivot about the pivot protrusion 6557 when the mixing actuator member 6550 is moved within the housing 6100.

The inner surface 6116 of the first housing member 6110 further includes carrier engagement protrusions 6131 (see e.g., FIG. 25), and defines actuator grooves 6133 and battery isolation protrusion grooves 6135. The carrier engagement protrusions 6131 selectively engage a set of tabs 6271 included in a carrier 6260 of the medicament container assembly 6200 (see FIG. 71). The actuator grooves 6133 receive a portion of a safety lock actuator 6724 of the safety lock 6700 and the mixing actuator member 6550 of the system actuator assembly 6500. Similarly, the battery isolation protrusion grooves 6135 receive a portion of a battery isolation protrusion 6197 included in the cover 6190 when the medical injector 6000 is in the first configuration.

The first housing member 6110 further includes a set of latches 6128 and a set of openings 6129. The latches 6128 extend from portions of the inner surface 6116 of the first housing member 6110. The first housing member 6110 can include any number of latches 6128 that can have any suitable shape or size. For example, in some embodiments, the latches 6128 vary in size. The latches 6128 are configured to engage portions of the second housing member 6140 to couple the first housing member 6110 to the second housing member 6140, as described in further detail herein.

Figure 26:
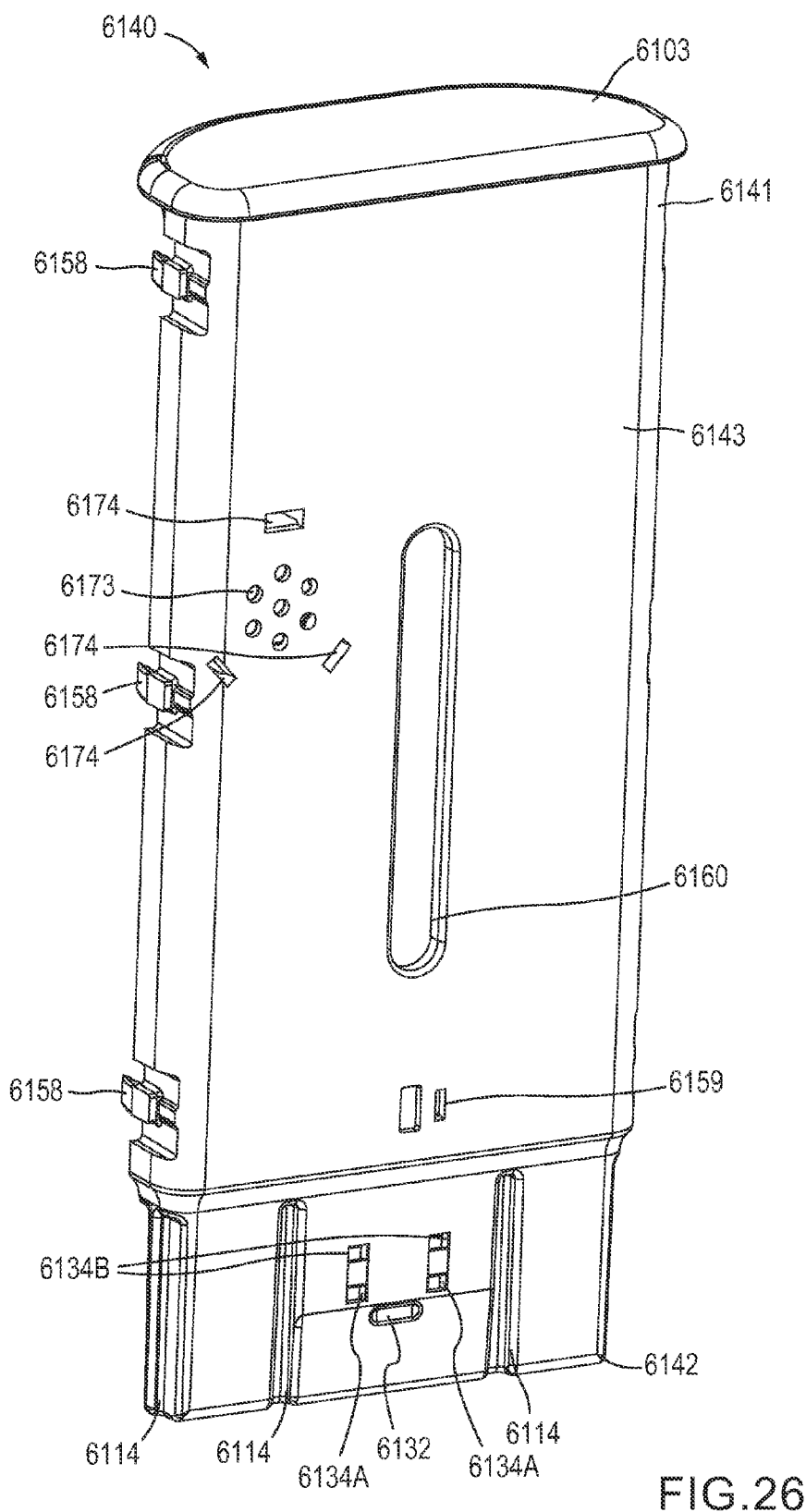
FIG. 26 is a front perspective view of a second portion of the housing of the medical injector illustrated in FIG. 18.
Figure 27:
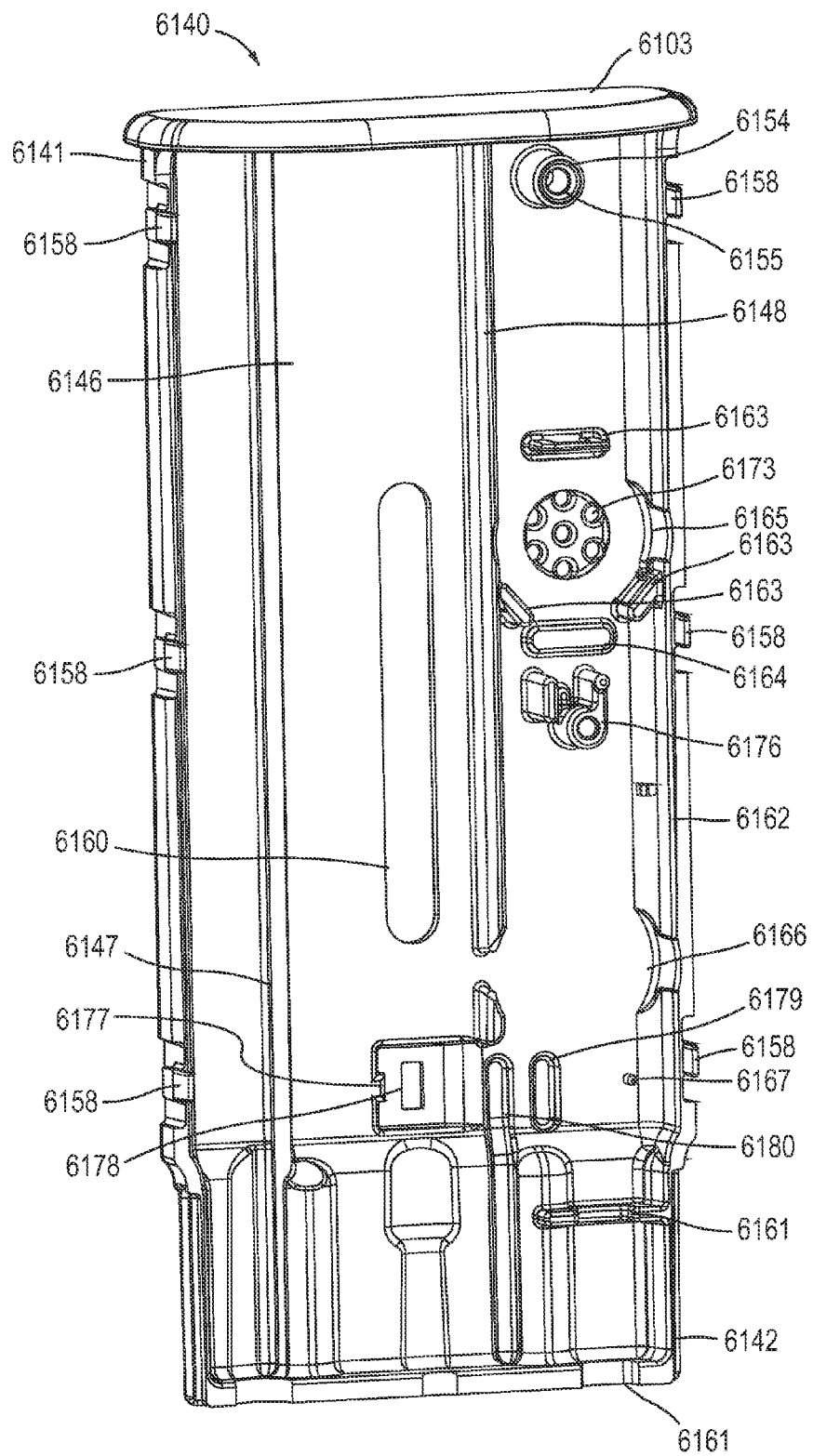
FIG. 27 is a rear perspective view of the second portion of the housing of the medical injector illustrated in FIG. 26.

As shown in FIGS. 26 and 27, the second housing member 6140 includes an outer surface 6143 and an inner surface 6146 and a proximal end portion 6141, a proximal cap 6103, and a distal end portion 6142. The second housing member 6140 further includes a set of tabs 6158 and defines a set of openings 6159. The second housing member 6140 can include any number of tabs 6158 such that the number of tabs 6158 corresponds to the number of latches 6128 of the first housing member 6110. Collectively, the latches 6128 of the first housing member 6110 and the tabs 6158 of the second housing member 6140 couple the first housing member 6110 to the second housing member 6140. Similarly stated, the latches 6128 are configured to engage the tabs 6158 to define a lock fit. Moreover, a surface of each of the latches 6128 is in contact with a surface of the corresponding tab 6158 to define a lock fit such that the first housing member 6110 and the second housing member 6140 collectively define the housing 6100. The openings 6129 of the first housing member 6110 and the openings 6159 of the second housing member 6140 allow access to the internal latches of the second housing member 6140 and the internal tabs of the first housing member 6110, respectively. In this manner, the first housing member 6110 can be decoupled from the second housing member 6140.

The outer surface 6143 defines base retention recesses 6134A and 6134B and base rail grooves 6114, at the distal end portion 6142 of the second housing member 6140. The distal base retention recesses 6134A are configured to receive base connection knobs 6518 of the base 6510 when the base 6510 is in a first (prior to actuation) position relative to the housing 6100. The proximal base retention recesses 6134B are configured to receive the base connection knobs 6518 of the base 6510 when the base 6510 is in a second (actuated) position relative to the housing 6100. The base retention recesses 6134A, 6134B have a tapered proximal sidewall and a non-tapered distal sidewall. This arrangement allows the base retention recesses 6134A, 6134B to receive the base connection knobs 6518 such that the base 6510 can move proximally relative to the housing 6100, but cannot move distally relative to the housing 6100. Said another way, the distal base retention recesses 6134A are configured to prevent the base 6510 from moving distally when the base 6510 is in a first position and the proximal base retention recesses 6134B are configured to prevent the base 6510 from moving distally when the base 6510 is in a second position. Similarly stated, the proximal base retention recesses 6134B and the base connection knobs 6518 cooperatively lock the base 6510 to prevent undesirable movement of the base 6510 after the medical injector 6000 is actuated, and to further visually indicate to the user that the medical injector has been actuated.

The base rail grooves 6114 are configured to receive guide members 6517 of the base 6510. The guide members 6517 of the base 6510 and the base rail grooves 6114 of the second housing member 6140 engage each other in a way that allows the guide members 6517 of the base 6510 to slide in a proximal and/or distal direction within the base rail grooves 6114 while limiting lateral movement of the guide members 6517. This arrangement allows the base 6510 to move in a proximal and/or distal direction with respect to the housing 6100 but prevents the base 6510 from moving in a lateral direction with respect to the housing 6100.

The proximal cap 6103 extends from the proximal end portion 6141 of the second housing member 6140 and encloses the proximal end portion 6101 of the housing 6100 when the first housing member 6110 is coupled to the second housing member 6140.

The inner surface 6146 of the second housing member 6140 includes a transfer member guide 6147 and a movable member guide 6148. The transfer member guide 6147 is configured to engage a second guide surface 6626 of the transfer member 6600 (see FIG. 50). The second guide surface 6626 of the transfer member 6600 and the transfer member guide 6147 of the second housing member 6140 engage each other such that the second guide surface 6626 of the transfer member 6600 slides in a proximal and/or distal direction along a surface of the transfer member groove 6147 while limiting lateral movement of the transfer member 6600. Similarly, the movable member guide 6148 is configured to engage a top portion 6302 of the first movable member 6301 included in the medicament delivery mechanism 6300.

The inner surface 6146 of the second housing member 6140 further includes a mixing actuator pivot protrusion 6154, latches 6163, and a battery clip protrusion 6176. The mixing actuator protrusion 6154 defines and aperture 6155 that receives a pivot protrusion 6557 of the mixing actuator member 6550 (e.g., similar to the pivot protrusion 6124 of the first housing member 6110 described above). The latches 6163 are configured to receive tabs 6957 (see e.g., FIG. 52) included in the electronic circuit system 6900 adjacent the audible output device 6956. The battery clip protrusion 6176 is configured to be coupled to the battery clip 6910. In this manner, the latches 6163 can engage the tabs 6957 of electronic circuit system 6900 and the battery clip 6910 can engage the battery clip protrusion 6176 to collectively couple the electronic circuit system 6900 to the housing 6100. In other embodiments, the electronic circuit system 6900 can be coupled to the housing 6100 by other suitable means such as an adhesive, a clip, a label and/or the like.

The inner surface 6146 of the second housing portion 6140 defines an audible output device recess 6165, a battery recess 6166, multiple sound apertures 6173, an LED aperture 6178, a first actuator groove 6179 and a second actuator groove 6180. A battery 6962 is disposed within the battery recess 6166 when the electronic circuit system 6900 is coupled to the second housing portion 6140. Similarly, an audible output device 6956 is disposed within an audible output device recess 6165 such that a front face of the audible output device 6956 is disposed adjacent the sound apertures 6173. In this manner, the sound apertures 6173 are configured to allow sound produced by the audio output device 6956 to pass from the audio output device 6956 to a region outside of the housing 6100. The LED aperture 6178 is configured to receive LEDs 6958A and 6958B included in the electronic circuit system 6900 such that a user can view the LEDs 6958A, 6958B, which are described in more detail herein.

The inner surface 6146 includes a circuit board retention tab 6177 and a circuit board alignment protrusion 6167. The circuit board retention tab 6177 is configured to engage a portion of a circuit board 6922 included in the electronic circuit system 6900 such that the LEDs 6958A and 6958B are maintained within the LED aperture 6178. With the electronic circuit system 6900 coupled to the second housing portion 6140 (as described above) the circuit board alignment protrusion 6167 can engage the circuit board to ensure alignment of the electronic circuit system 6900 relative to the second housing portion 6140.

The first actuator groove 6179 defined by the inner surface 6146 of the second housing portion 6140 is configured to be disposed adjacent the safety lock actuator groove 6133 defined by the inner surface 6116 of the first housing portion 6110. As described above, the safety lock actuator groove 6133 of the first housing portion 6110 receives the safety lock actuator 6724 of the safety lock 6700 such that the safety lock actuator 6724 can engage the mixing actuator member 6550. In use, the safety lock actuator 6724 moves the mixing actuator member 6550 in the distal direction and a protrusion 6555 of the mixing actuator member 6550 moves in the distal direction within the first actuator groove 6179 to engage a portion of the electronic circuit system 6900, as described in more detail herein. Similarly, the second actuator groove 6180 defined by the inner surface 6146 of the second housing portion 6140 is configured to receive an actuator protrusion 6279 included in the carrier 6260. In use, the carrier 6260 moves in the distal direction such that the actuator protrusion 6279 moves in the distal direction within the second actuator groove 6180 to engage a portion of the electronic circuit system 6900, as further described herein.

Figure 23:
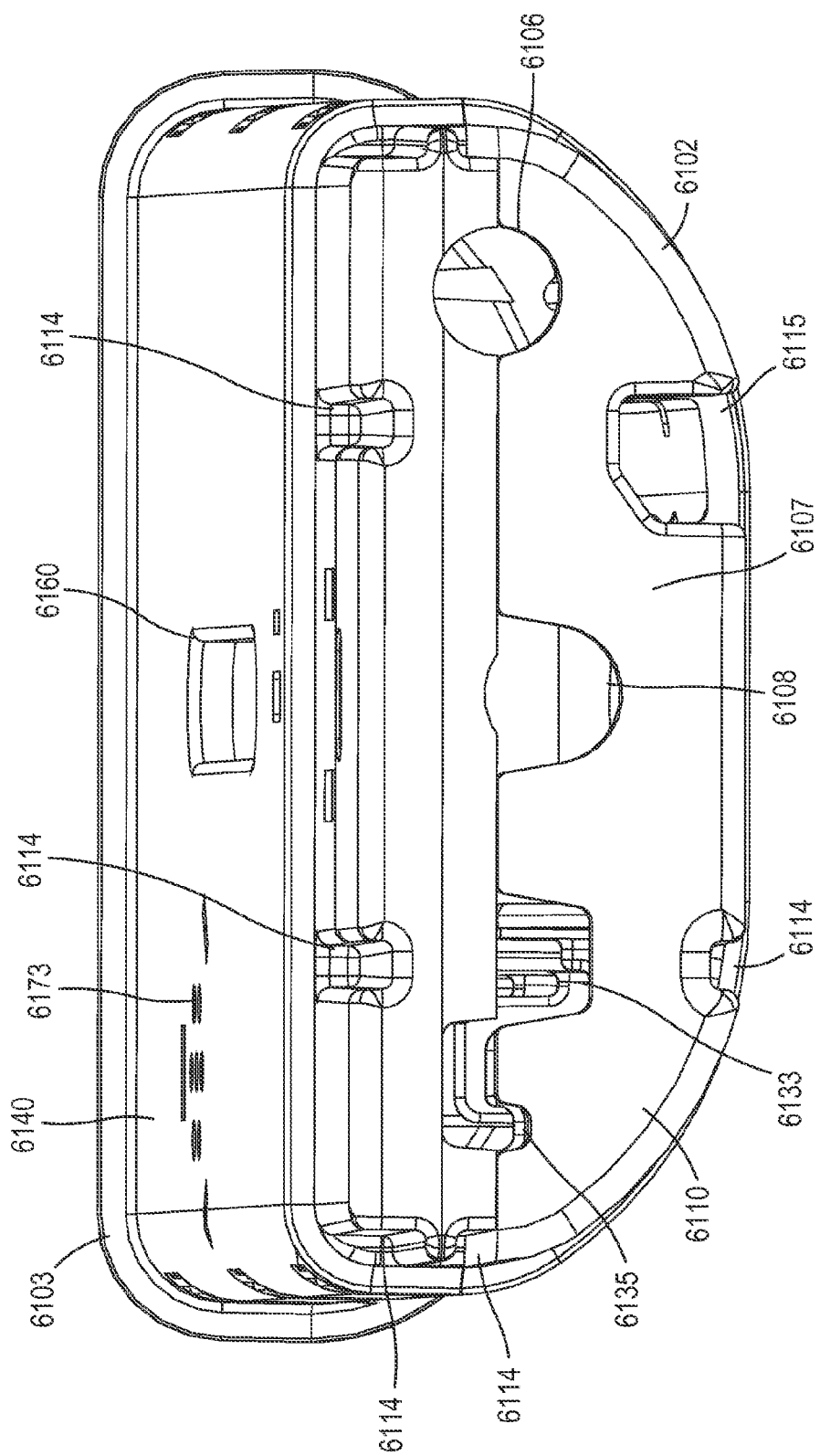
FIG. 23 is a bottom perspective view of a housing of the medical injector illustrated in FIG. 18.

As shown in FIG. 23, when the first housing member 6110 and the second housing member 6140 are assembled, the distal end portion 6102 of the housing 6100 defines a needle aperture 6108 and a transfer member access opening 6106. Similarly stated, the first housing member 6110 and the second housing member 6140 collectively define the needle aperture 6108 and the transfer member access opening 6106. The needle aperture 6108 is configured to allow a needle 6216 (see e.g., FIGS. 73, 74, and 75) to exit the housing 6100 when the medical injector 6000 is actuated, and be retracted back into the housing 6100 upon completion of the injection, as described in further detail herein.

The transfer member access opening 6106 is configured to provide access to the transfer member 6600 when the transfer member 6600 is disposed within the housing 6100. For example, in some embodiments, the transfer member 6600 can be disengaged from the medicament delivery mechanism 6300 without moving the medicament delivery mechanism 6300 in the distal direction. In this manner, the medical injector 6000 can be disabled such that the medicament delivery mechanism 6300 cannot engage the medicament container 6210 to convey a medicament 6240. For example, in some embodiments, a user can disengage the transfer member 6600 from the medicament delivery mechanism 6300, via the transfer member access opening 6106, to safely dispose of an unused medical injector 6000 in which the medicament 6240 has expired. In such embodiments, the user can engage the guide protrusion 6624, via the transfer member access opening 6106, and move the guide protrusion 6624 through the upper notch 6126, as described above. In other embodiments, an operator can manipulate the transfer member within the housing 6100 via the transfer member access opening 6106 during the assembly of the medical injector 6000.

FIGS. 28-50 show the medicament container assembly 6200, the system actuator assembly 6500, the transfer member 6600 and the medicament delivery mechanism 6300 of the medical injector 6000. As shown in FIGS. 28-32, the system actuator assembly 6500 includes the base 6510, a release member 6530, and a mixing actuator assembly 6540. Although the base 6510 and the release member 6530 are shown as being monolithically constructed to form a portion of the system actuator assembly 6500, in other embodiments the system actuator assembly 6500 can include a base that is constructed separately from (and later joined to) a release member. The release member 6530 has a proximal end portion 6531 and a distal end portion 6532. The release member 6530 extends from a proximal surface 6511 of the base 6510.

As shown in FIGS. 29 and 30, the proximal end portion 6531 of the release member 6530 is configured to engage the latch portion 6310 of the medicament delivery mechanism 6300 when the medical injector 6000 is in its first (or storage) configuration. In this manner, the proximal end portion 6531 of the release member 6530 maintains a first latch protrusion 6315 of the latch portion 6310 in contact with the engagement surface 6109 of the latch member notch 6120 of the housing 6100. When the engagement surface 6109 is in contact with the first latch protrusion 6315, the engagement surface 6109 applies a reaction force to the first latch protrusion 6315 in response to the force applied by the spring 6420, which urges the transfer member 6600 and the medicament delivery mechanism 6300 in a distal direction. Similarly stated, when the first latch protrusion 6315 is in contact with the engagement surface 6109, the engagement surface 6109 limits distal movement of the first latch protrusion 6315, and thus, the medicament delivery mechanism 6300. In this manner, when the base 6510 is in a first position (i.e., before actuation of the medical injector 6000), the release member 6530 maintains the first latch protrusion 6315 within the latch member notch 6120 and maintains the medical injector 6000 in the first configuration (e.g., non-actuated configuration). Furthermore, as shown in FIGS. 25 and 30, the first portion 6110 of the housing 6100 includes a retention protrusion 6127 that engages the release member 6530. The retention protrusion contacts the release member 6530 to limit lateral deformation and/or movement of the release member 6530, thereby ensuring that the first latch protrusion is maintained within the latch member notch 6120. Similar stated, the retention protrusion maintains the alignment of the first latch protrusion 6315 and the release member 6530 is maintained.

Figure 31:
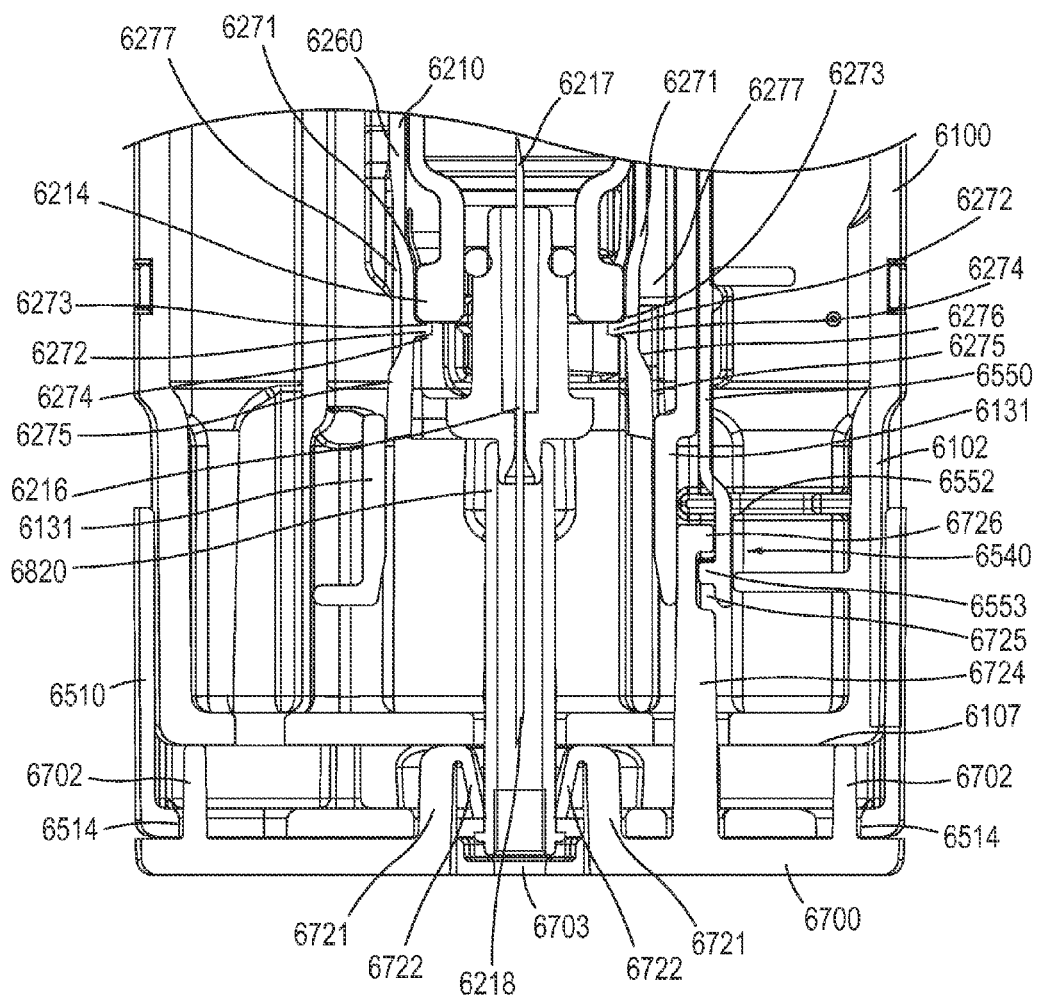
FIG. 31 is an enlarged rear view of a portion of the medicament delivery mechanism of the medical injector illustrated in FIG. 29.

As shown in FIG. 31, when the medical injector 6000 is in its first configuration (i.e., the storage configuration), the safety lock protrusions 6702 are disposed within the safety lock protrusion openings 6514 of the base 6510 (see also FIG. 65), and engage a distal surface 6107 of the housing 6100. In this manner, movement of the safety lock 6700 in the proximal direction is prevented. Therefore, the system actuator assembly 6500 and/or the base 6510 cannot move in the proximal direction to actuate the medicament delivery mechanism 6300. Similarly stated, as shown in FIG. 31, when the medical injector 6000 is in its first configuration (i.e., the storage configuration), the safety lock protrusions 6702 engage the distal surface 6107 of the housing 6100 to limit the proximal movement of the base 6510.

Figure 59:
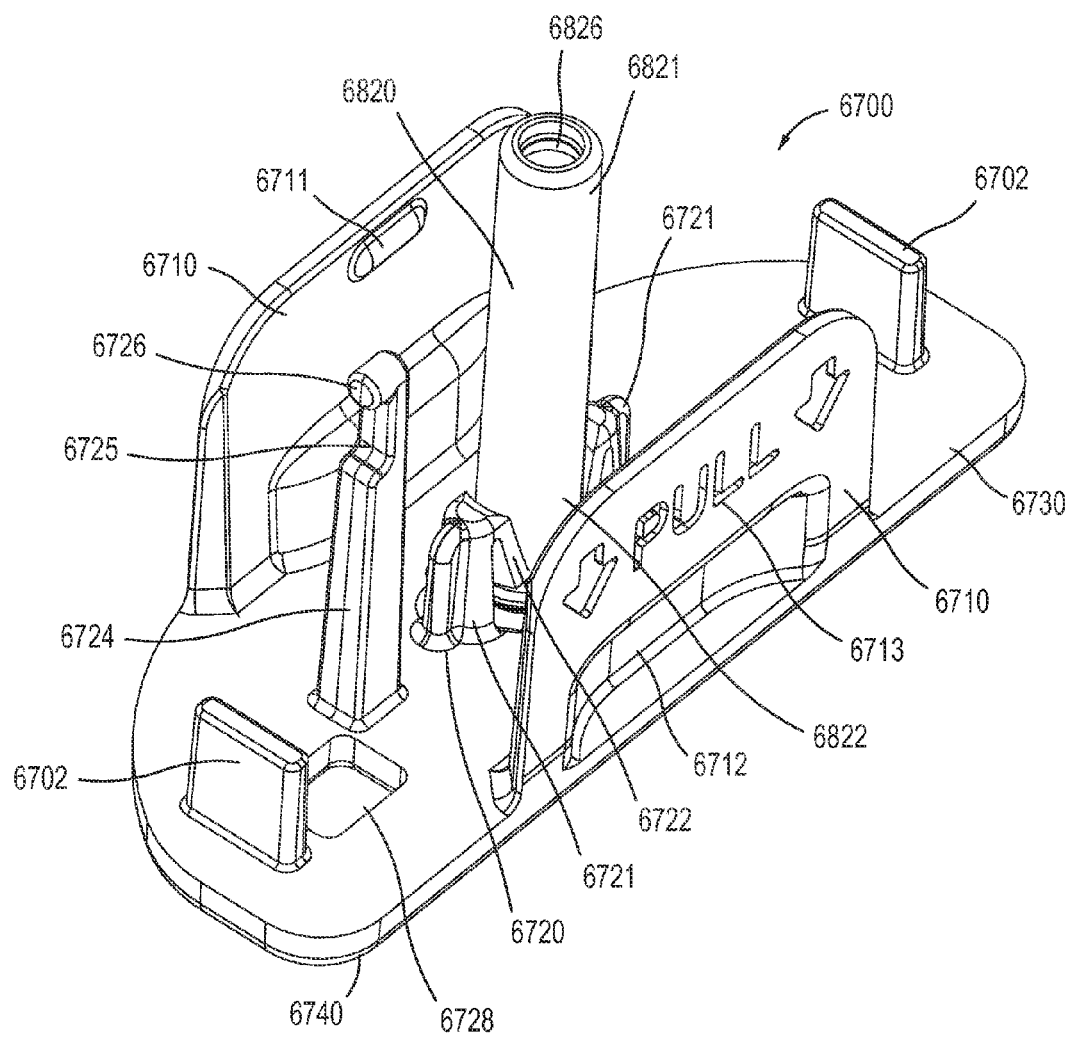
FIG. 59 is a perspective view of a safety lock of the medical injector illustrated in FIG. 18.
Figure 60:
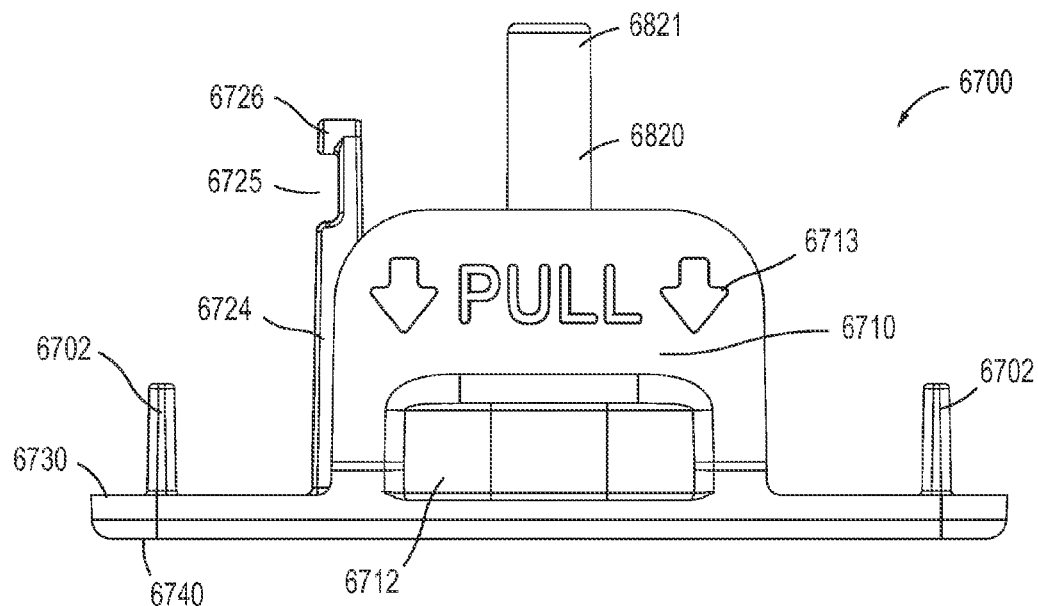
FIG. 60 is a front view of the safety lock of the medical injector illustrated in FIG. 59.
Figure 61:
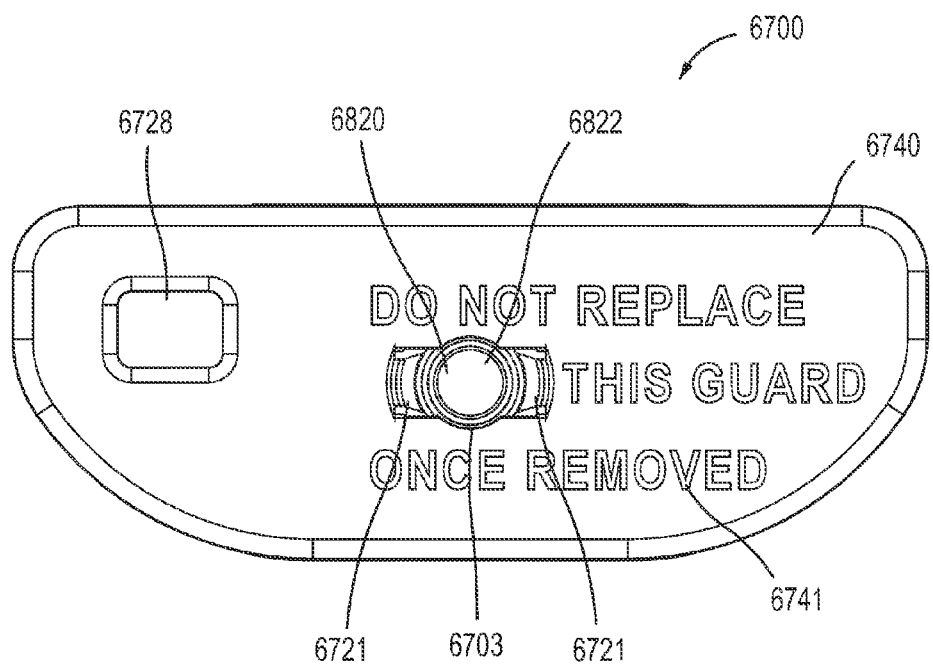
FIG. 61 is a bottom view of the safety lock of the medical injector illustrated in FIG. 59.

The mixing actuator assembly 6540 includes the mixing actuator member 6550 and the safety lock 6700. As shown in FIGS. 31, 59 and 60 the safety lock 6700 includes the safety lock actuator 6724. The safety lock actuator 6724 includes a protrusion 6726 and defines a channel 6725. The channel 6725 receives a catch 6553 included in the mixing actuator member 6550 such that the protrusion 6726 can engage the catch 6553. In this manner, when the safety lock 6700 is moved in the distal direction to be removed from the medical injector 6000, the protrusion 6726 contacts the catch 6553 of the mixing actuator member 6550 such that the removal of the safety lock 6700 moves a distal portion 6552 of the mixing release member 6550 in the distal direction, as described in further detail herein.

Figure 32:
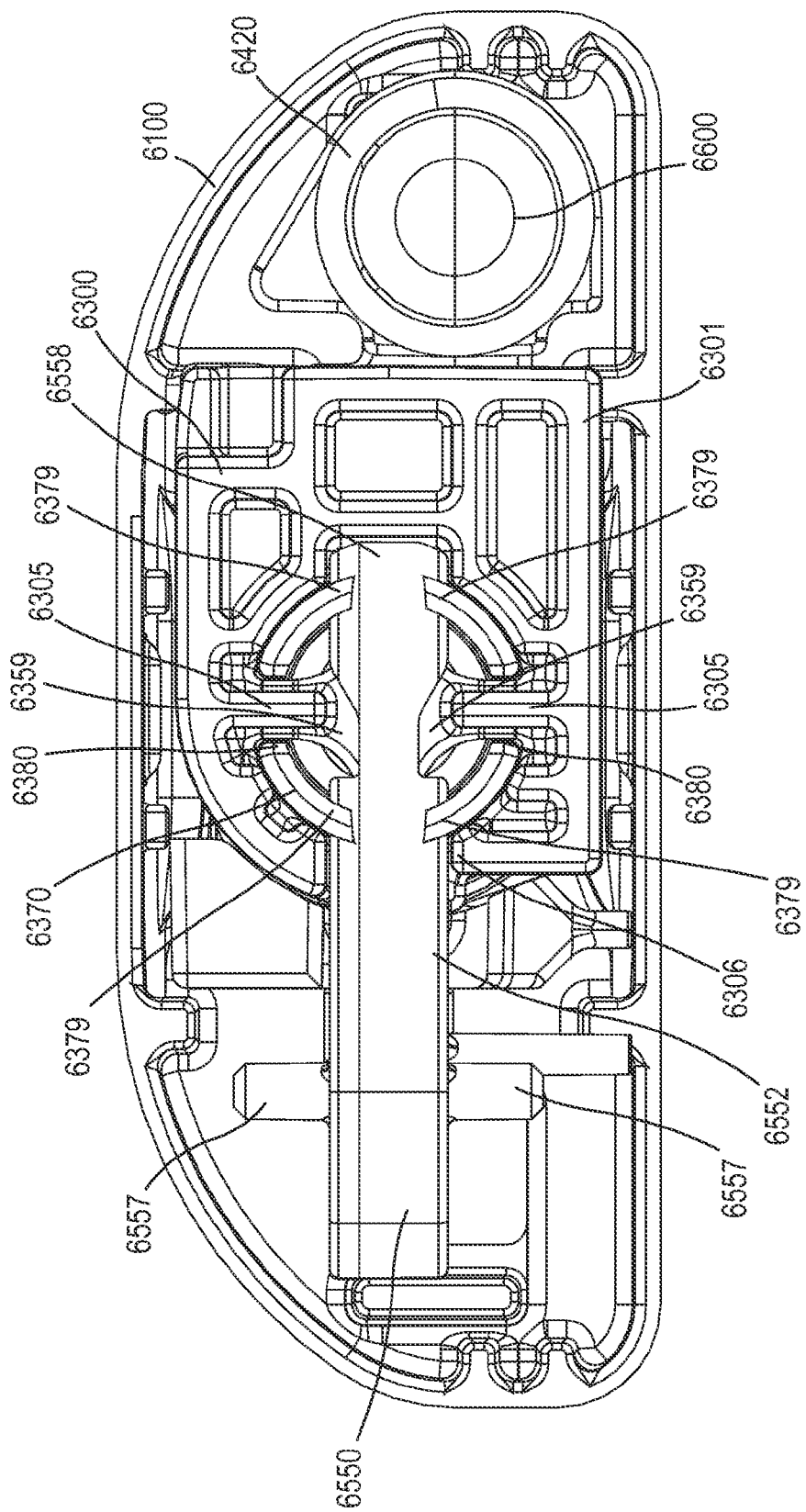
FIG. 32 is a top view of a portion of the medical injector illustrated in FIG. 18.
Figure 70:
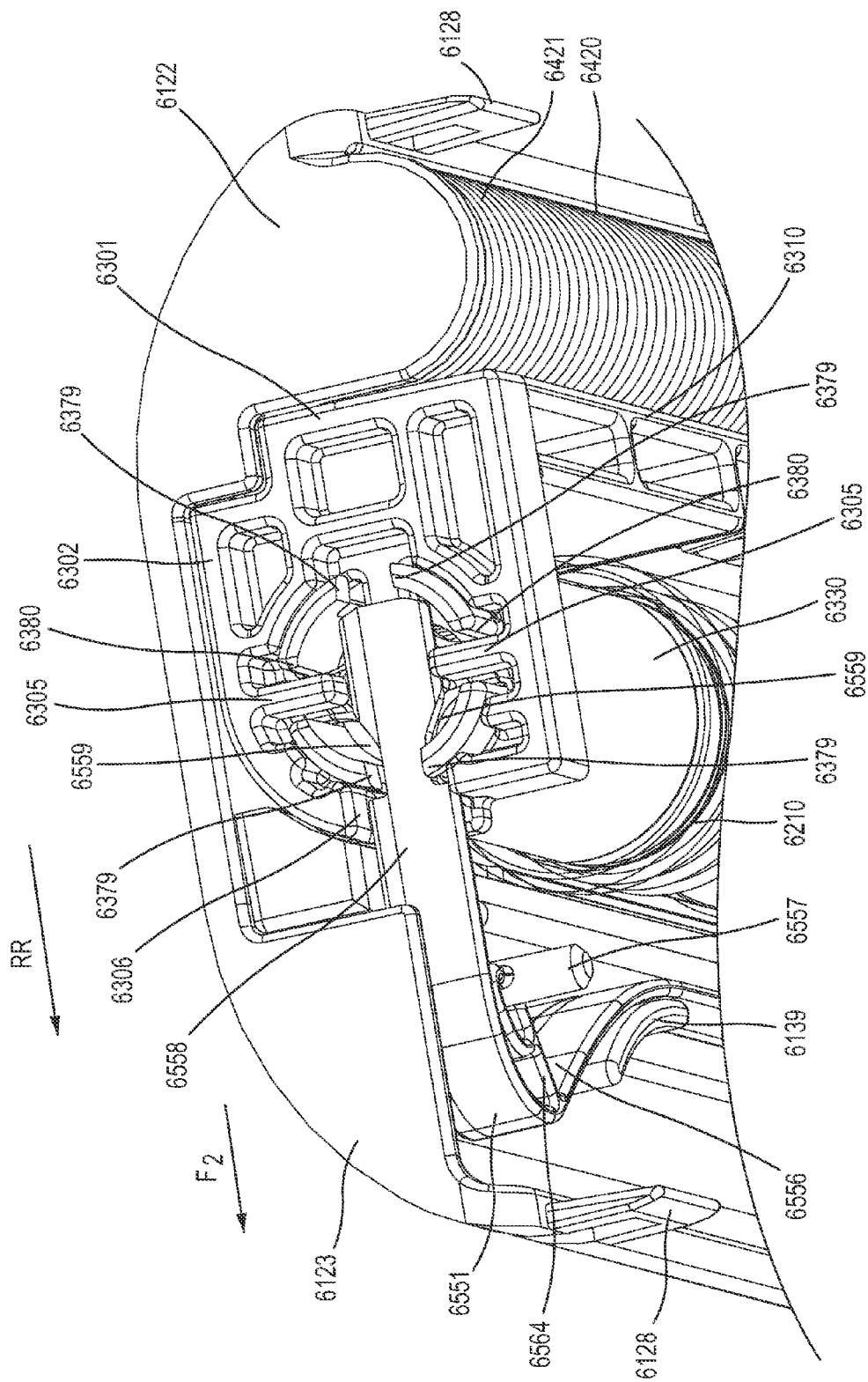
FIG. 70 is a top perspective view of the medical injector illustrated in FIG. 18 in the third configuration.

As shown in FIGS. 32, 64 and 70, the mixing actuator member 6550 includes a proximal end portion 6551 configured to engage the first movable member 6301 and the mixing piston 6370. More specifically, the mixing actuator member 6550 includes a retention portion 6558 movably disposed within an actuator member channel 6306 defined by the first movable member 6301. The retention portion 6558 is configured to move within the actuator member channel 6306 between a first position (e.g., the locked position) and a second position (e.g., the mixing position). As described in more detail herein (see e.g., FIG. 45), the mixing piston 6370 is disposed within the piston portion 6330 of the first movable member 6301 such that a proximal end portion 6371 of the mixing piston 6370 can extend through a proximal end portion 6331 of the piston portion 6330 to engage the mixing actuator 6550. In this manner, when the mixing actuator 6550 is in the first position, a set of retention protrusions 6379 of the mixing piston 6370 can engage the retention portion 6558 of the mixing actuator 6550 such that the medical injector 6000 is maintained in the first configuration. Furthermore, when the safety lock 6700 is moved in the distal direction (e.g., removed from the medical injector 6000), the retention portion 6558 is moved to the second position such that the mixing piston 6370 is actuated to urge a mixing event, as described in further detail herein.

Figure 33:
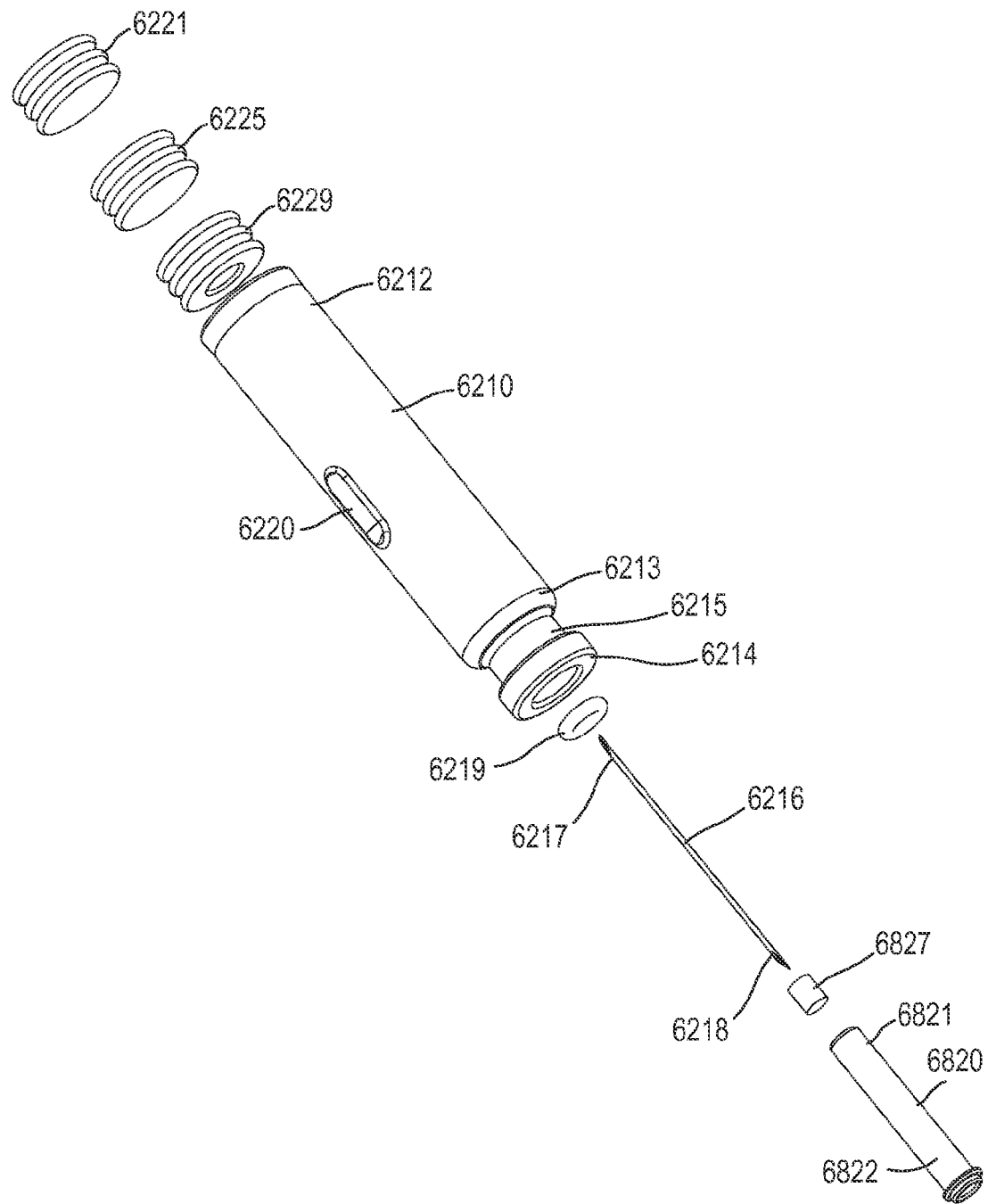
FIG. 33 is an exploded view of a medicament container of the medical injector illustrated in FIG. 18.
Figure 34:
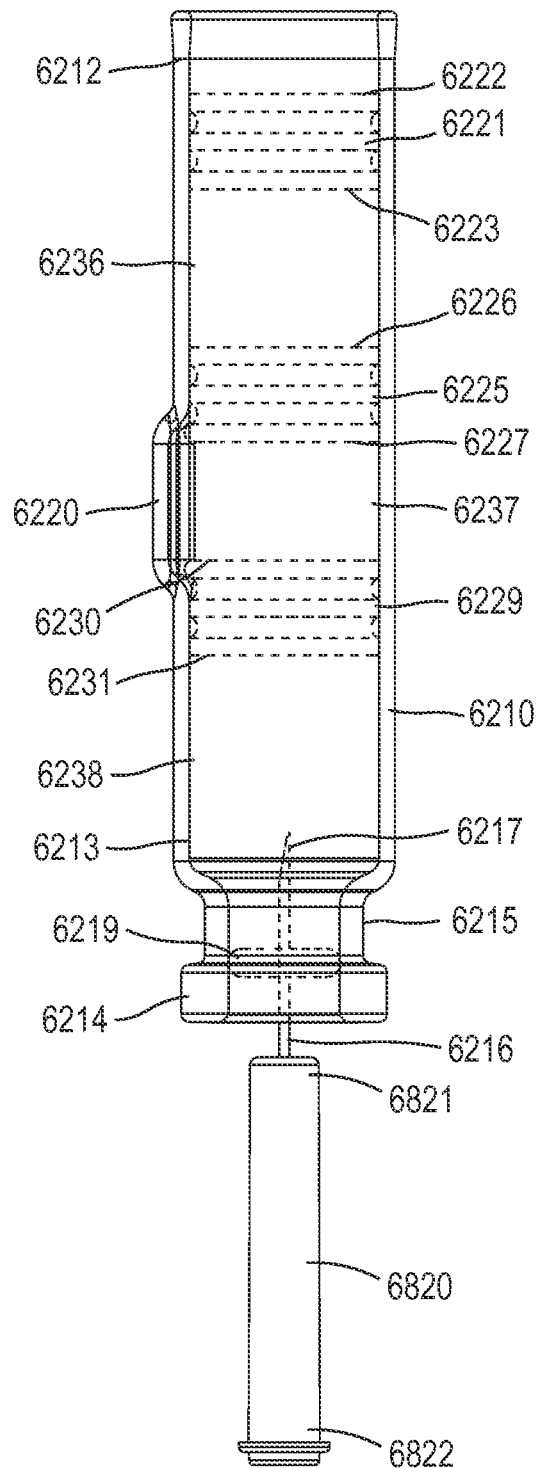
FIG. 34 is a front view of the medicament container shown in FIG. 33.
Figure 35:
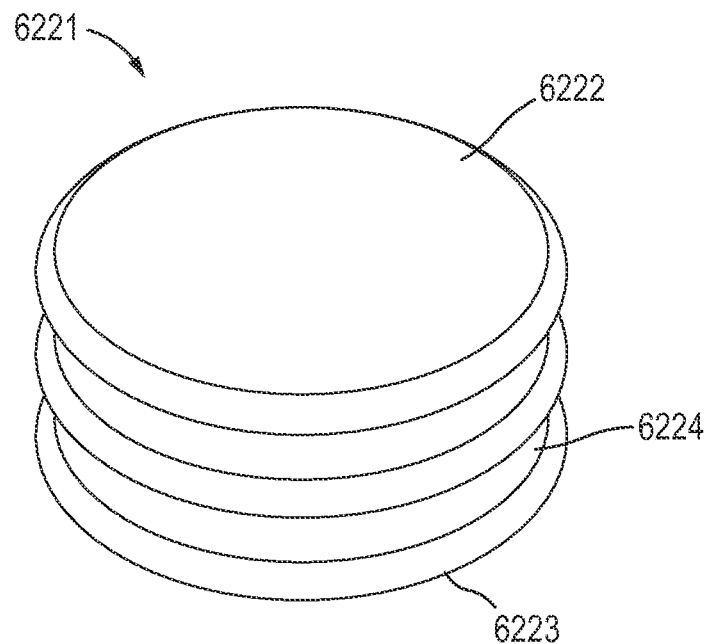
FIGS. 35-38 illustrate an elastomeric member included in the medicament container of FIG. 33.
Figure 36:
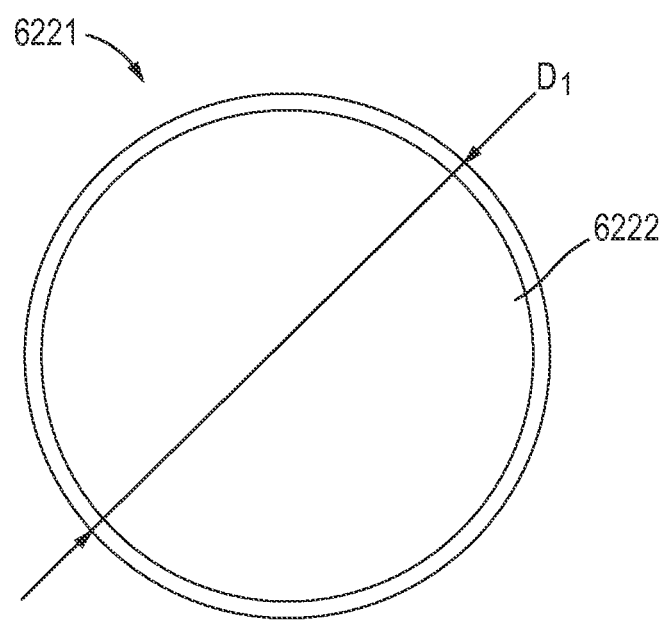
Figure 37:
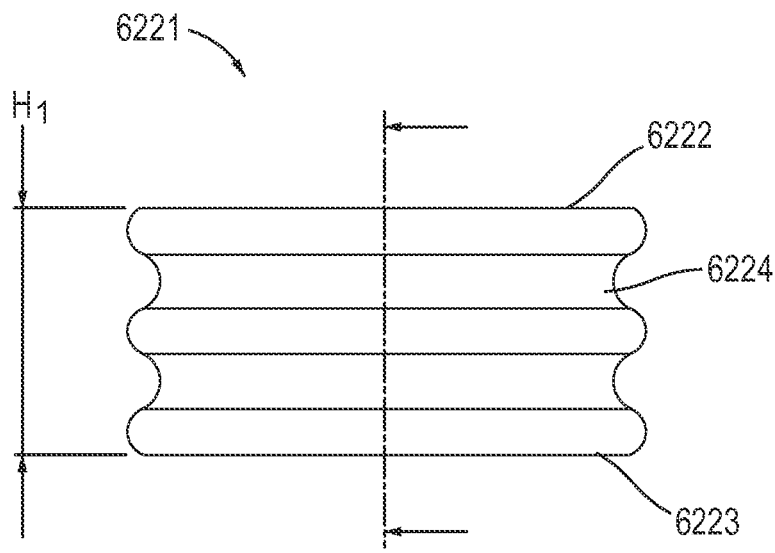
Figure 38:
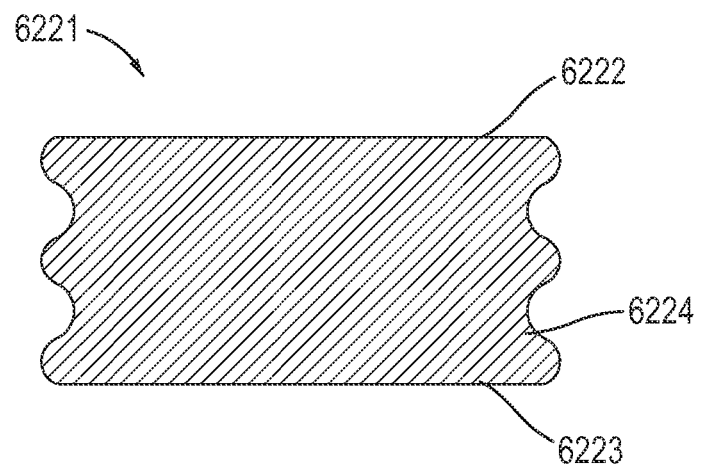
Figure 39:
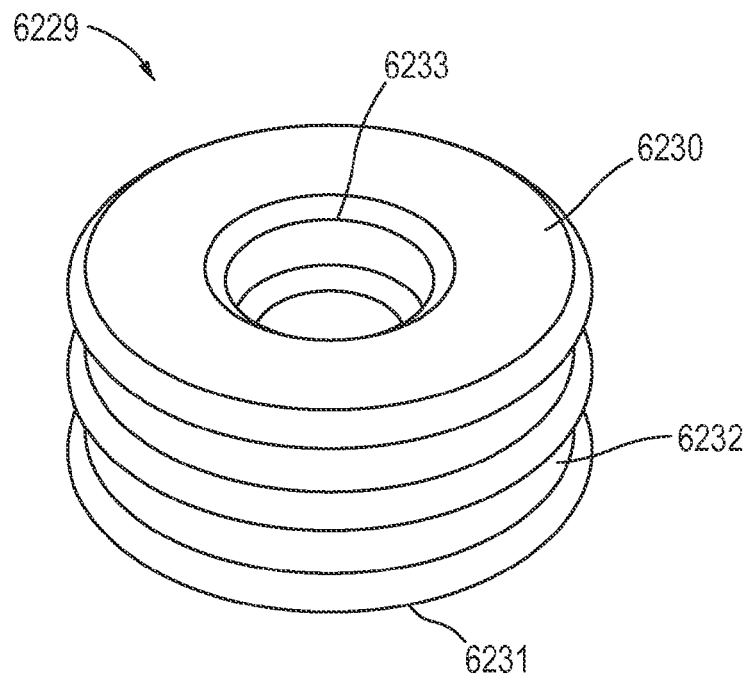
FIGS. 39-42 illustrate an elastomeric member included in the medicament container of FIG. 33.
Figure 40:
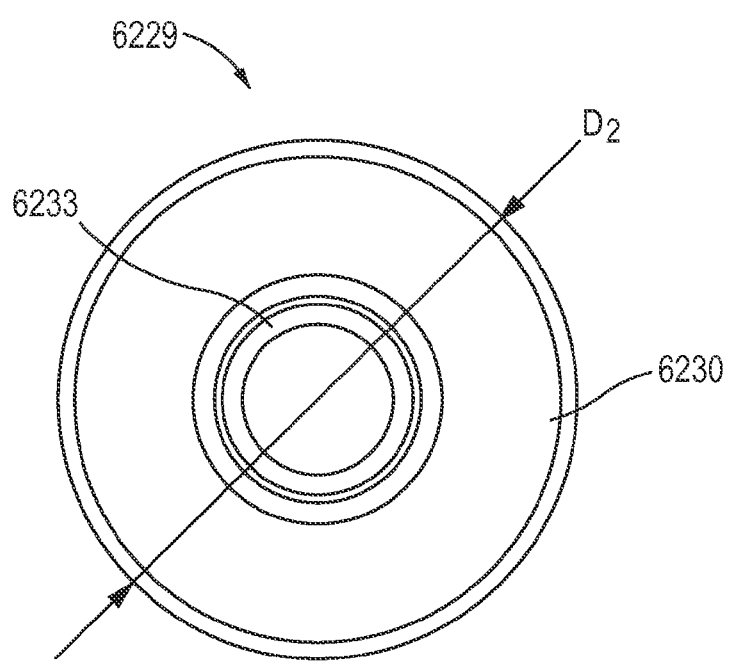
Figure 41:
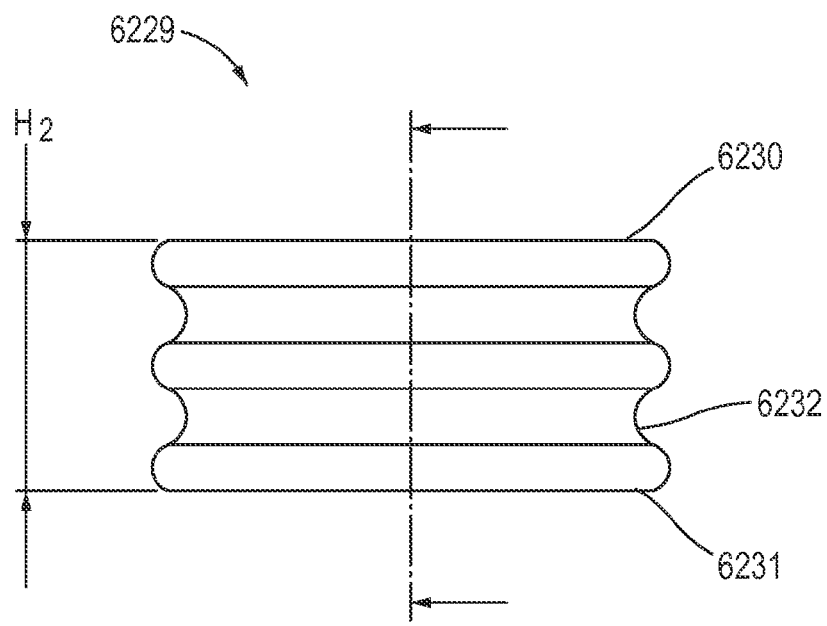
Figure 42:
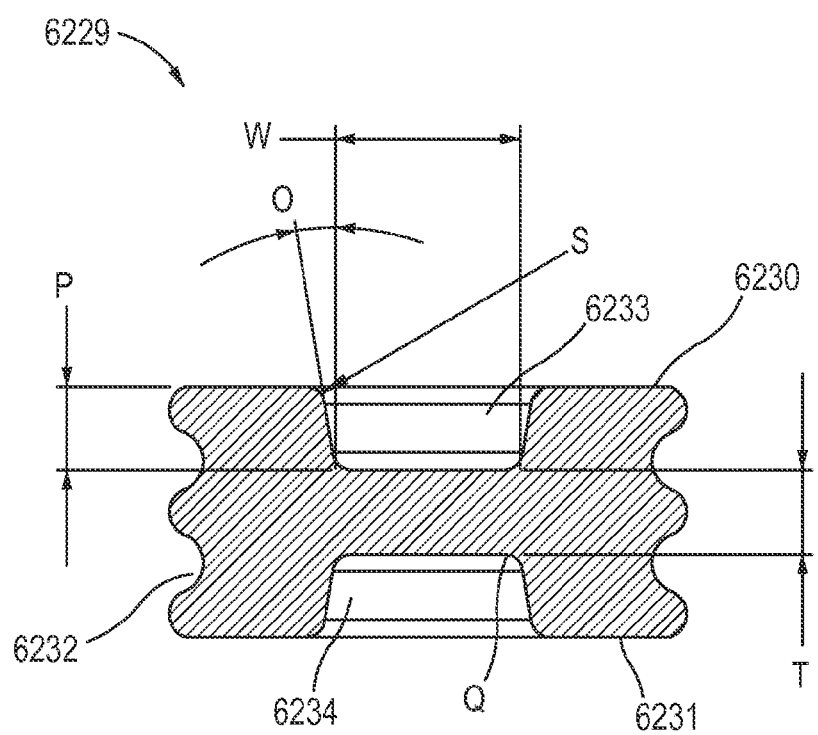

The medicament container assembly 6200 includes a medicament container 6210, the needle 6216, and the carrier 6260. The medicament container 6210 includes a proximal end portion 6212, a distal end portion 6213, and a bypass 6220. The bypass 6220 can be a singular channel bypass or can define multiple channels. Although the bypass 6220 is shown in FIGS. 33 and 34 as an external bypass, in other embodiments, the bypass 6220 can be internal to the medicament container and/or a part of the elastomeric member 6225. Said another way, in some embodiments the bypass can be configured such that the outer diameter of the medicament container 6210 is substantially constant. The bypass 6220 is configured to facilitate the mixing and/or injection of a medicament contained within the medicament container 6210, as described in further detail herein. In particular, the bypass 6220 is configured to place various volumes within the medicament container 6210 in fluid communication with each other.

As shown in FIGS. 33 and 34, the distal end portion 6213 of the medicament container 6210 includes a neck 6215 and a flanged end 6214 configured to engage at least a portion of the carrier 6260 and the needle 6216, as described below. Furthermore, the distal end portion 6213 of the medicament container 6210 includes a sealing member 6219. The sealing member 6219 can be any suitable member, such as, for example, an o-ring. In this manner, the sealing member 6219 is configured to engage an inner surface of the medicament container 6210 and a portion of a needle hub 6264 included in the carrier 6260 (see e.g., FIG. 43) to define a fluidic seal, as described in further detail herein.

The proximal end portion 6212 of the medicament container 6210 receives a first elastomeric member 6221, a second elastomeric member 6225, and a third elastomeric member 6229. In some embodiments, the first elastomeric member 6221, the second elastomeric member 6225, and the third elastomeric member 6229 are placed within the medicament container 6210 during the fill process, as further described herein, to define a diluent volume 6236, a dry medicament volume 6237, and a void volume 6238 (see, e.g., FIG. 34). Said another way, the diluent volume 6236 is a volume disposed within the medicament container 6210 defined between a distal surface 6223 of the first elastomeric member 6221 and a proximal surface 6226 of the second elastomeric member 6225. The dry medicament volume 6237 is a volume disposed within medicament container 6210 defined between a distal surface 6227 of second elastomeric member 6225 and a proximal surface 6230 of third elastomeric member 6229 and the void volume 6238 is a volume disposed within the medicament container 6210 defined between a distal surface 6231 of the third elastomeric member 6229 and the distal end portion 6213 of the medicament container 6210.

As shown in FIG. 34, the diluent volume 6236, the dry medicament volume 6237, and the void volume 6238 are defined by the positions of the first elastomeric member 6221, the second elastomeric member 6225, and the third elastomeric member 6229, relative to and/or within the medicament container 6210. In some embodiments, the diluent volume 6236 can contain a medicament diluent, such as, for example, water. In some embodiments, the dry medicament volume 6237 can contain a lyophilized medicament (e.g., any suitable medicament produced via any suitable lyophilizing process) including any of the formulations and/or compositions described herein.

Figure 28:
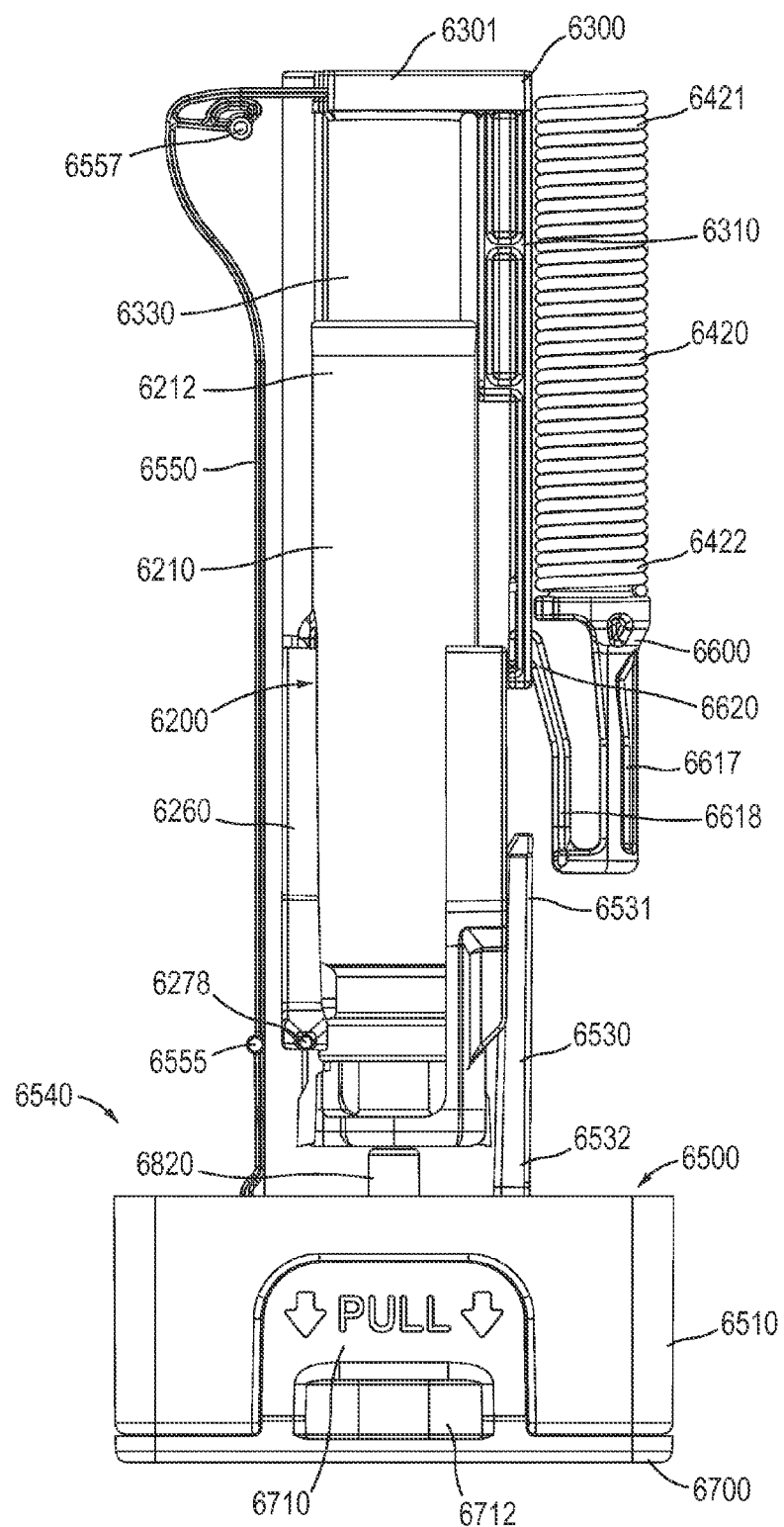
FIG. 28 is a front view of a medicament delivery mechanism of the medical injector illustrated in FIG. 18.

As shown in FIGS. 28 and 29, the proximal end portion 6212 of the medicament container 6210 is coupled to and/or receives a portion of the medicament delivery mechanism 6300 such that medicament delivery mechanism 6300 can move the first elastomeric member 6221, the second elastomeric member 6225, and/or the third elastomeric member 6229 to mix and/or inject the medicament disposed therein. More specifically, the proximal end portion 6212 of the medicament container 6210 can receive a piston portion 6330 of the first movable member 6301 and a second movable member 6370 (also referred to herein as a "mixing piston 6370" and shown, for example, in FIGS. 45 and 49).

The medicament container 6210 can have any suitable size (e.g., length and/or diameter). Moreover, the medicament container 6210, the piston portion 6330, and/or the mixing piston 6370 can be collectively configured such that the piston portion 6330 and/or the mixing piston 6370 travels a desired distance within the medicament container 6210 (i.e., the "stroke") during an injection event. In this manner, the medicament container 6210, the diluent contained within the diluent volume 6236, the lyophilized medicament contained within the dry medicament volume 6237, the void volume 6238, the piston portion 6330, and the mixing piston 6370 can be collectively configured to provide a desired fill volume and delivery volume.

The length of the medicament container 6210 and the length of the piston portion 6330 and/or the mixing piston 6370 can be configured such that the medicament delivery mechanism 6300 can fit in the same housing 6100 regardless of the fill volume, the delivery volume and/or the ratio of the fill volume to the delivery volume. In this manner, the same housing and production tooling can be used to produce devices having various dosages of the medicament. For example, in a first embodiment (e.g., having a fill volume to delivery volume ratio of 0.4), the medicament container has a first length and the second movable member has a first length. In a second embodiment (e.g., having a fill volume to delivery volume ratio of 0.6), the medicament container has a second length shorter than the first length, and the second movable member has a second length longer than the first length. In this manner, the stroke of the device of the second embodiment is longer than that of the device of the first embodiment, thereby allowing a greater dosage. The medicament container of the device of the second embodiment, however, is shorter than the medicament container of the device of the first embodiment, thereby allowing the components of both embodiments to be disposed within the same housing and/or a housing having the same length.

The first elastomeric member 6221, the second elastomeric member 6225, and the third elastomeric member 6229 can be of any design or formulation suitable for contact with the medicament (e.g., the diluent contained in the diluent volume 6236 and/or a lyophilized medicament contained in the dry medicament volume 6237). For example, the elastomeric members 6221, 6225, and 6229 can be formulated to minimize any reduction in the efficacy of the medicament that may result from contact (either direct or indirect) between the elastomeric members 6221, 6225, and 6229 and the medicament. For example, in some embodiments, the first elastomeric member 6221, the second elastomeric member 6225, and the third elastomeric member 6229 can be formulated to minimize any leaching or out-gassing of compositions that may have an undesired effect on the medicament. In other embodiments, the elastomeric members 6221, 6225, and 6229 can be formulated to maintain its chemical stability, flexibility and/or sealing properties when in contact (either direct or indirect) with the medicament over a long period of time (e.g., for up to six months, one year, two years, five years or longer).

As shown in FIGS. 35-38, the first elastomeric member 6221 includes a proximal surface 6222, the distal surface 6223, and a set of grooves 6224. The grooves 6224 can be configured (e.g., have a size and/or shape) to allow expansion of the first elastomeric member 6221 within a medicament container 6210. Furthermore, the first elastomeric member 6221 has a diameter $D_1$ and a height $H_1$. The radius $R_1$ (FIG. 19) can be any suitable radius. For example, in some embodiments, the diameter $D_1$ is directly related to the inner diameter (e.g., diameter of an inner surface) of the walls of the medicament container 6210. In such embodiments, the diameter $D_1$ can be configured to be slightly larger than the inner diameter of the medicament container 6210. In this manner, the sides of the first elastomeric member 6221 can engage the inner surface of the medicament container 6210 to define a fluid seal. Expanding further, with the diameter $D_1$ of the first elastomeric member 6221 slightly larger than the inner radius of the medicament container 6210, the grooves 6224 define a void such that the side of the first elastomeric member 6221 can deform (e.g., be flattened) to occupy a portion of the void when disposed within or moved within the medicament container 6210. Similarly stated, the grooves 6224 allow the sides of the first elastomeric member 6221 to deform such that the diameter $D_1$ can be reduced to be substantially similar to the inner diameter of the medicament container 6210.

The height $H_1$ (FIG. 37) of the first elastomeric member 6221 can be any suitable height. In some embodiments, the height $H_1$ of the first elastomeric member 6221 can be used to control the fill volume and/or the delivery volume. In this manner, the first elastomeric member 6221 can further be configured to control the stroke length of the piston portion 6330 of the first movable member 6301 and/or the mixing piston 6370. In some embodiments, the height $H_1$ of the first elastomeric member 6221 can be such that, in use, the first elastomeric member 6221 does not substantially deform in a longitudinal direction (e.g., proximal and distal direction). Thus, the height $H_1$ of the first elastomeric member 6221 can be such that the first elastomeric member 6221 does not substantially deform when engaged by the first movable member 6301 and/or the second movable member 6370. In some embodiments, the second elastomeric member 6225 can be substantially similar to the first elastomeric member 6221; therefore, the second elastomeric member 6225 is not shown or described in detail herein.

As shown in FIGS. 39-42 the third elastomeric member 6229 includes a proximal surface 6230, a distal surface 6231, a set of grooves 6232, a proximal counter bore 6233, and a distal counter bore 6234. The grooves 6232 can be configured (e.g., have a size and/or shape) to allow expansion of the third elastomeric member 6229 within a medicament container 6210. Furthermore, the third elastomeric member 6229 has a diameter $D_2$, a height $H_2$, and a thickness T. The diameter $D_2$ (FIG. 40) can be any suitable diameter. For example, in some embodiments, the diameter $D_2$ is directly related to the inner diameter (e.g., diameter of an inner surface) of the walls of the medicament container 6210. In such embodiments, the diameter $D_2$ can be configured to be slightly larger than the inner radius of the medicament container 6210. In this manner, the sides of the third elastomeric member 6229 can engage the inner surface of the medicament container 6210 to define a fluid seal. Expanding further, the grooves 6232 allow the sides of the third elastomeric member 6229 to deform such that the diameter $D_2$ can be reduced to be substantially similar to the inner diameter of the medicament container 6210. In some embodiments, the diameter $D_2$ of the third elastomeric member 6229 can be substantially similar to the diameter $D_1$ of the first elastomeric member 6221. Similarly, in some embodiments, the height $H_2$ of the third elastomeric member 6229 can be substantially similar to the height $H_1$ of the first elastomeric member.

Figure 73:
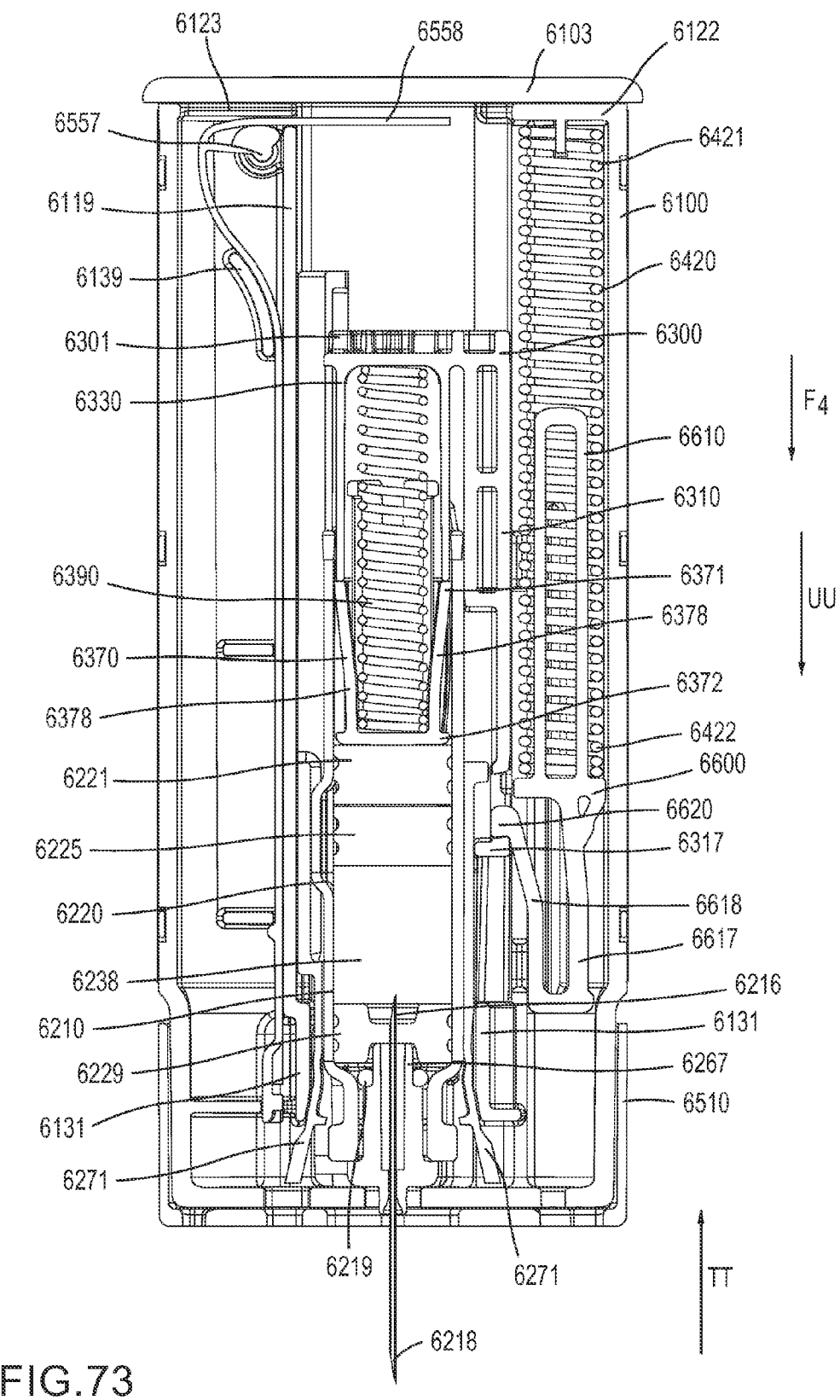
FIG. 73 is a front cross-sectional view of the medical injector illustrated in FIG. 18 in a fourth configuration (i.e., the needle insertion configuration).
Figure 74:
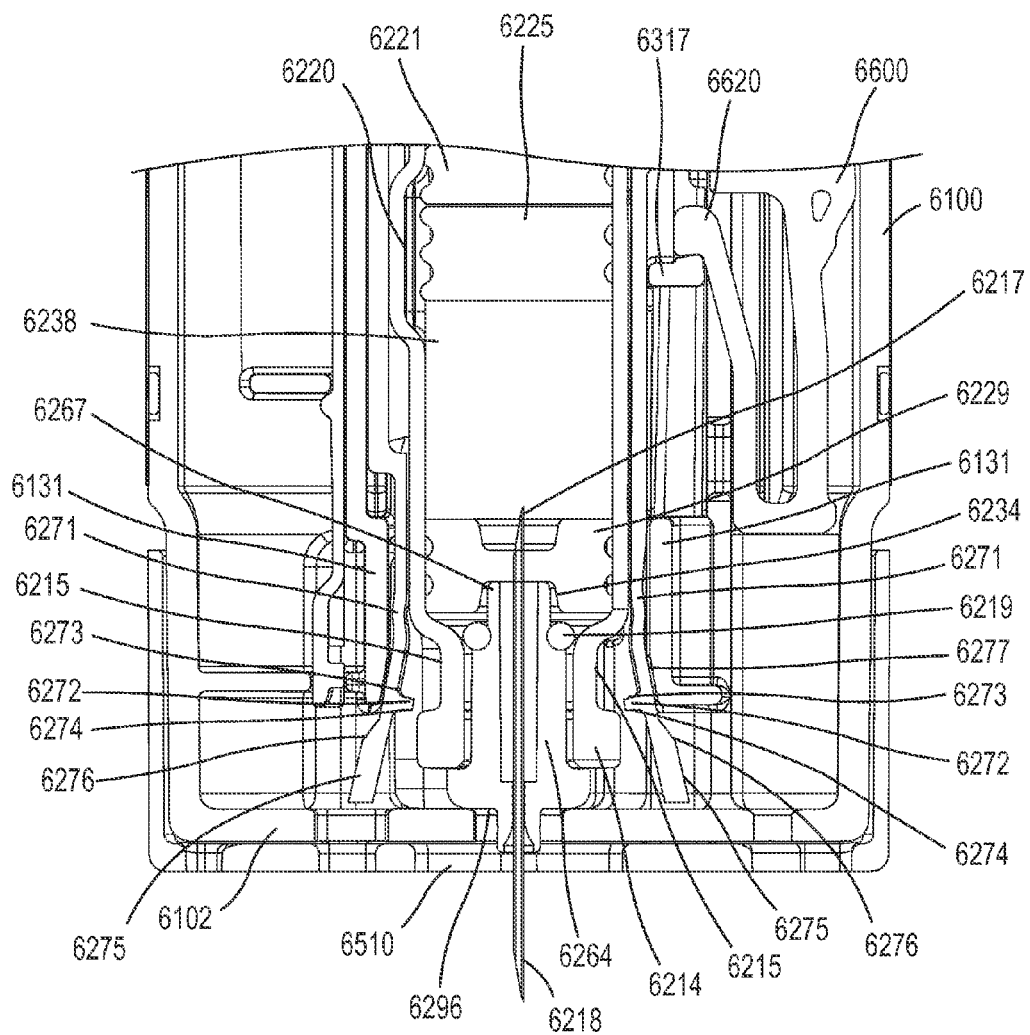
FIG. 74 is an enlarged view of a portion of the cross-section illustrated in FIG. 73.

The proximal counter bore 6233 and the distal counter bore 6234 define a depth P, a width W, an angle O, an external radius S, and an internal radius Q. In use, the third elastomeric member 6229 is configured to engage a portion of the carrier 6260 and the needle 6216. More specifically, the distal counter bore 6234 receives a portion of the needle hub 6264, as shown in FIGS. 73 and 74, described in further detail herein. The width W and depth D of the distal counter bore 6234 can be such that an upper portion 6267 of the needle hub 6264 can be disposed within the distal counter bore 6234 when the medicament container 6210 is moved to a second container position (in which the needle 6216 is placed into fluid communication with the dry medicament volume 6237). Furthermore, the distal counter bore 6234 and the proximal counter bore 6233 reduces the thickness T of the portion of the third elastomeric member 6229 through which the needle 6216 penetrates, as further described herein.

In some embodiments a first elastomeric member, a second elastomeric member, and/or a third elastomeric member of an injector can be similar to first elastomeric member 6221 or third elastomeric member 6229. Said another way, in some embodiments, a medicament container can include three elastomeric members similar to the first elastomeric member 6221. In other embodiments, a medicament container can include three elastomeric members similar to the third elastomeric member 6229. For example, in such embodiments, the first elastomeric member and the second elastomeric member can define a proximal counter bore and a distal counter bore and can be configured to further control the fill volume and/or delivery volume of a diluent and/or lyophilized medicament disposed within the medicament container.

Figure 43:
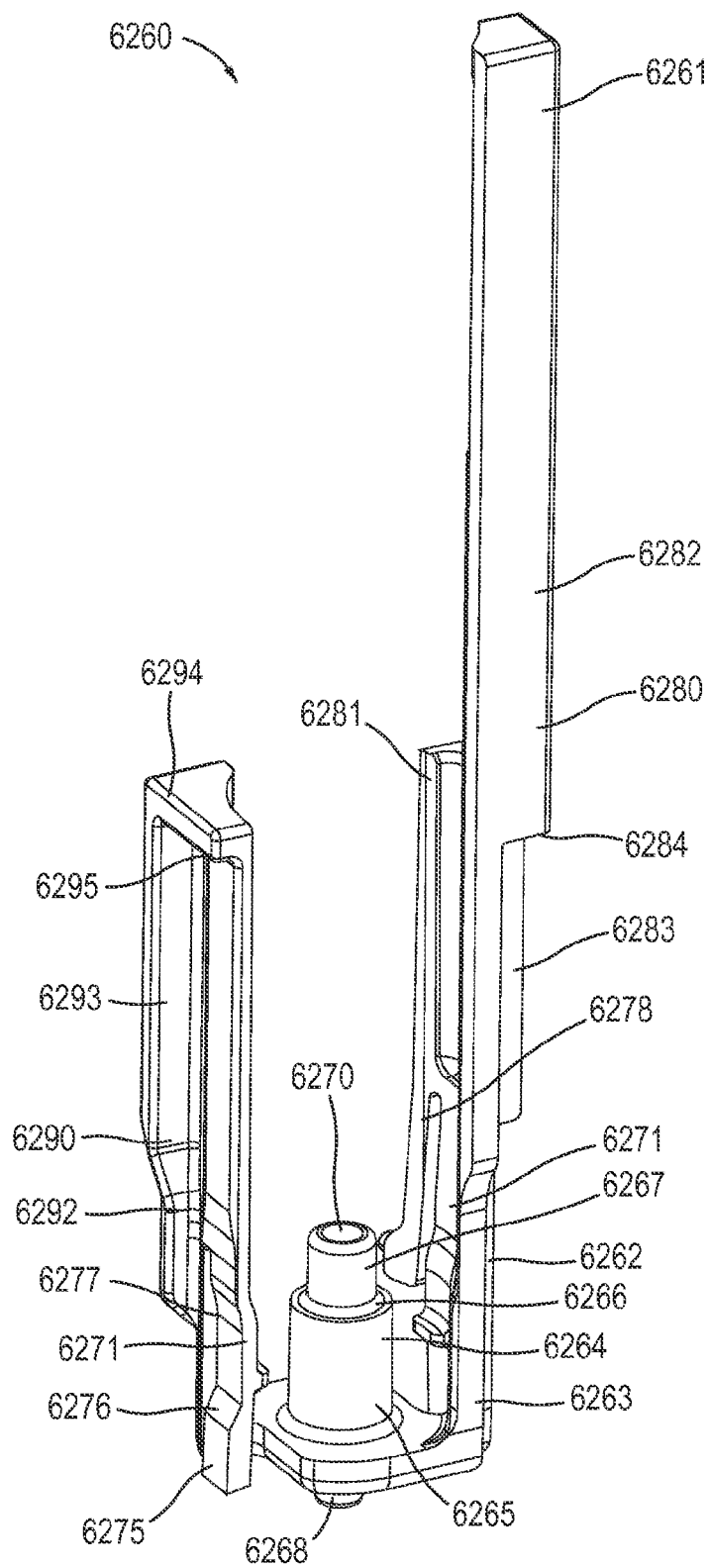
FIGS. 43 and 44 are perspective views of a carrier included in the medical injector illustrated in FIG. 18.
Figure 44:
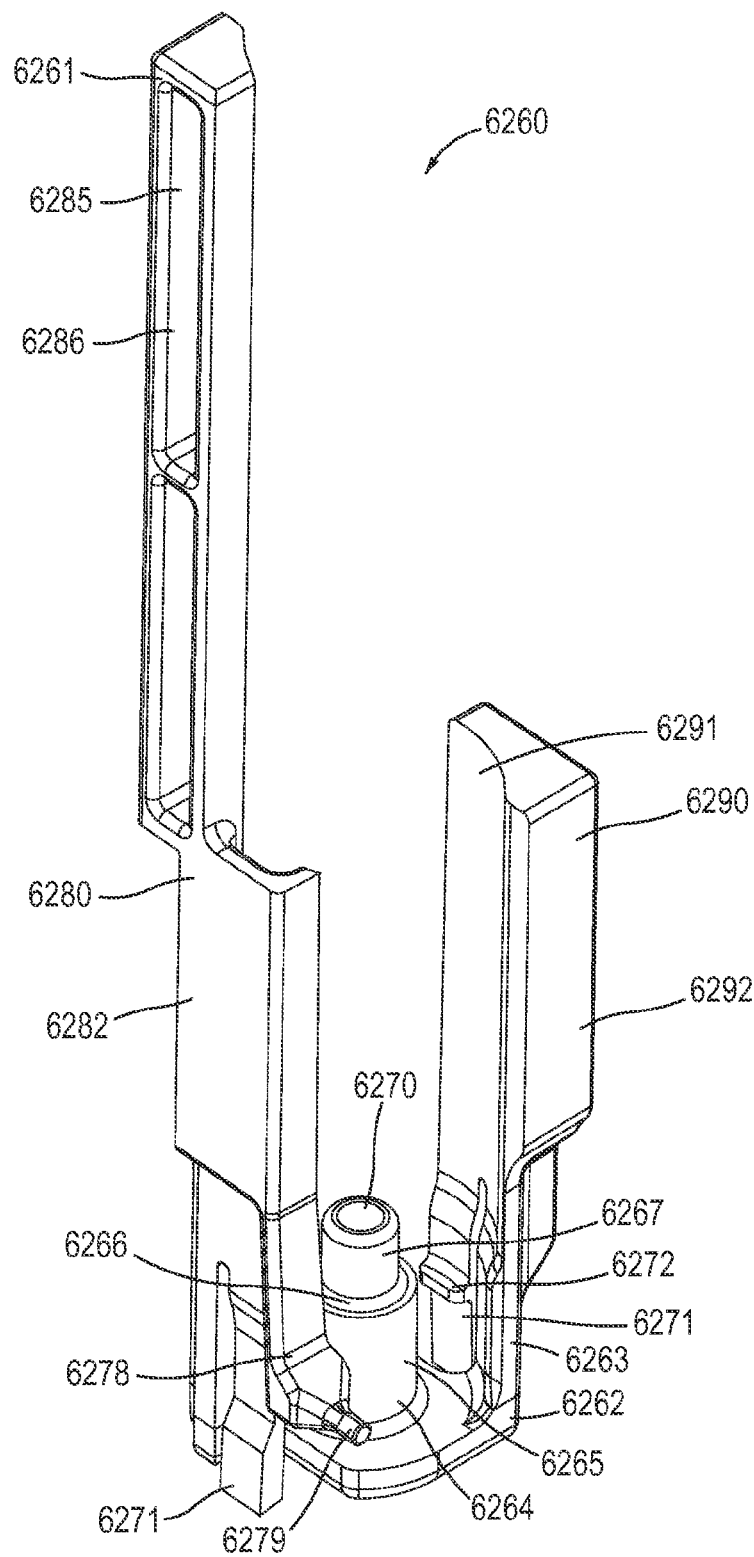

As described above, the medicament container 6210 is configured to engage and/or be coupled to the carrier 6260 (see e.g., FIGS. 28 and 29). Referring to FIGS. 43 and 44, the carrier 6260 includes a proximal end portion 6261, a distal end portion 6262, a needle hub 6264, an electronics engagement portion 6278, a first retention arm 6280, and a second retention arm 6290. The first retention arm 6280 and the second retention arm 6290 extend, in the proximal direction, from a container-mounting portion 6263 disposed at the distal end portion 6262 of the carrier 6260. The container-mounting portion 6263 is configured to selectively engage the flanged end 6214 of the medicament container 6210. More specifically, the carrier 6260 includes the set of tabs 6271 that include a container shoulder 6272. As described above, the set of tabs 6271 are configured to selectively engage the container engagement protrusions 6131 of the housing 6100 (see e.g., FIG. 31). The arrangement of the tabs 6271, the container engagement protrusions 6131, and the container shoulders 6272 are such that the flanged end 6214 of the medicament container 6210 can selectively engage the container shoulder 6272 when moving between the first container position and the second container position, as described in further detail herein.

The needle hub 6264 includes a base portion 6265, an upper portion 6267, and a lower needle port 6268. The base portion 6265 includes a proximal surface 6266 from which the upper portion 6267 extends in the proximal direction. The lower needle port 6268 is configured to extend from the base portion 6265 in the distal direction. The needle hub 6264 defines a needle passageway 6270 that receives a proximal end portion 6217 of the needle 6216 (see e.g., FIG. 31). Expanding further, the needle passageway 6270 can include an inner surface (not shown) that includes any suitable feature to couple the needle 6216 within the needle hub 6264. For example, in some embodiments, the inner surface defining the needle passageway 6270 can include a set of protrusions configured to define a friction fit with the needle 6216. In other embodiments, an adhesive can be applied to the inner surface defining the needle passageway 6270 to couple the needle 6216 to the needle hub 6264. The needle hub 6264 is configured to engage a portion of the medicament container 6210 when the medicament container 6210, as shown in FIG. 31.

The electronics engagement portion 6278 includes an activator protrusion 6279. The electronics engagement portion 6278 extends from a surface of the first retention arm 6280 and is configured to engage the electronic circuit system 6900. More specifically, the activator protrusion 6279 of the electronics engagement portion 6278 is disposed within a second actuation portion 6946 of the electronic circuit system 6900 when the carrier 6260 is in the first position. When the carrier 6260 is moved to the second position (i.e., during the injection event), the activator protrusion 6279 moves in the distal direction to actuate the second actuation portion 6946 of the electronic circuit system 6900 as described in further detail herein.

The first retention arm 6280 includes an inner surface 6281 and an outer surface 6282. The inner surface 6281 engages the medicament container 6210 when the medicament container 6210 is disposed within and/or is coupled to the container-mounting portion 6263. The outer surface 6282 defines a channel 6283 and includes a retraction spring surface 6284. The channel 6283 receives a retraction spring 6440 (FIG. 29) such that a proximal end portion 6441 of the retraction spring 6440 is in contact with the retraction spring surface 6284. The outer surface 6282 further defines a slot 6285. The slot 6285 is configured to receive a guide protrusion 6303 of the first movable member 6301. In this manner, the set of walls 6286 that define the slot 6285 can engage the guide protrusion 6303 of the first movable member 6301 such that the top portion 6302 of the first movable member 6301 is aligned with the carrier 6260 when the first movable member 6301 moves relative to the carrier 6260. Furthermore, during a retraction event, a distal surface of the wall 6286 defining the slot 6285 can engage the guide protrusion 6303 to transfer a portion of a retraction force, exerted by the retraction member 6440, on the first movable member 6301 such that the first movable member 6301 moves in the proximal direction when the carrier 6260 is retracted.

The second retention arm 6290 includes an inner surface 6291 and an outer surface 6292. Similar to the first retention arm 6280, the inner surface 6291 of the second retention arm 6290 engages the medicament container 6210 when the medicament container 6210 is disposed within and/or is coupled to the container-mounting portion 6263. In this manner, the container-mounting portion 6263, the inner surface 6281 of the first retention arm 6280, and the inner surface 6291 of the second retention arm 6290 act to couple the medicament container 6210 to the carrier 6260. The outer surface 6292 defines a channel 6293, and includes a latch 6294. The channel 6293 receives a protrusion 6313 included in the latch portion 6310 of the first movable member 6301. In this manner, the protrusion 6313 can move within the channel during an injection event.

The medicament delivery mechanism 6300 (all or portions of which can also be referred to as a "movable assembly") includes the first movable member 6301, the second movable member 6370 (the mixing piston 6370), and a mixing spring 6390 (see e.g., FIGS. 45-49). The first movable member 6301 includes the top portion 6302, the latch portion 6310, and the piston portion 6330. The top portion 6302 includes the guide protrusion 6303 and the actuator member channel 6306 (for receiving the mixing actuator member 6550), as described above.

The latch portion 6310 includes a proximal end portion 6311 and a distal end portion 6312 (see e.g., FIGS. 46 and 47). The proximal end portion 6311 is disposed at and/or is joined with the top portion 6302 of the first movable member 6301. Similarly stated, the latch portion 6310 is configured to extend from the top portion 6302 of the first movable member 6301 in the distal direction. The distal end portion 6312 of the latch portion 6310 includes a latch arm 6314 having a first latch protrusion 6315, a second latch protrusion 6317, and a protrusion 6313, and defines an opening 6316 and channel 6322. As described above, the first latch protrusion 6315 is configured to engage the release member 6530 of the base 6510 and the engagement surface 6109 of the latch member notch 6120. In particular, as shown in FIG. 30, the release member 6530 urges, bends and/or deforms the latch arm 6314 to maintain the first latch protrusion 6315 within the latch member notch 6120. Thus, the latch arm 6314 can be constructed from a material having sufficient flexibility such that the release member 6530 can urge, bend and/or deform the latch arm 6314 to engage the first latch protrusion 6315 with the latch member notch 6120.

The opening 6316 of the latch portion 6310 is defined between a surface of the distal end portion 6312 of the latch portion 6310 and a proximal surface 6318 of the second latch protrusion 6317 (see e.g., FIG. 47). The opening 6316 is configured to receive the latch 6620 of the transfer member 6600 (see e.g., FIGS. 50 and 29). More particularly, when the medical injector 6000 is in the first configuration (i.e., prior to actuation), the proximal surface 6318 of the second latch protrusion 6317 is in contact with a distal surface 6621 of the latch 6620 of the transfer member 6600. In this manner, the transfer member 6600 can transfer a force produced by the spring 6420 to the latch portion 6310 of the first movable member 6300 to move the medicament delivery mechanism 6300 in the distal direction when the medical injector 6000 is actuated. Similarly stated, this arrangement allows the medicament delivery mechanism 6300 and/or the first movable member 6301 to move with and/or remain coupled to the transfer member 6600 during the insertion and/or injection operation. The channel 6322 receives the second retention arm 6290 of the carrier 6260. In this manner, the second retention arm 6290 can move within the channel 6322 between the first position and the second position. Similarly stated, this arrangement allows at least a portion of the carrier 6260 to move within the first movable member 6301 when the movable member 6301 moves relative to the carrier 6260 (e.g., during an injection event).

Figure 48:
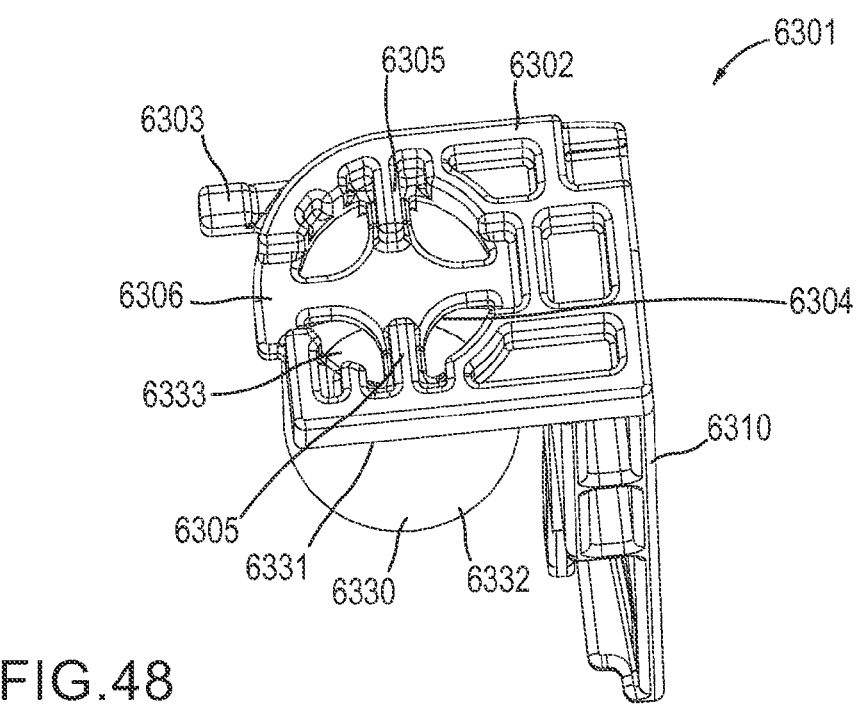

The piston portion 6330 includes a proximal end portion 6331 and a distal end portion 6332 and defines an opening 6333 (see e.g., FIG. 48). More specifically, the proximal end portion 6331 is disposed at and/or joined with a bottom surface 6304 of the top portion 6302 of the first movable member 6301. Expanding further, the piston portion 6330 extends from the bottom surface 6304 of the top portion 6302 and defines an annular shape. Thus, the opening 6333 is defined by the inner walls of the piston portion 6330. The distal end portion 6332 is configured to be disposed at least partially within the proximal end portion 6212 of the medicament container 6210 (see e.g., FIG. 68).

Figure 45:
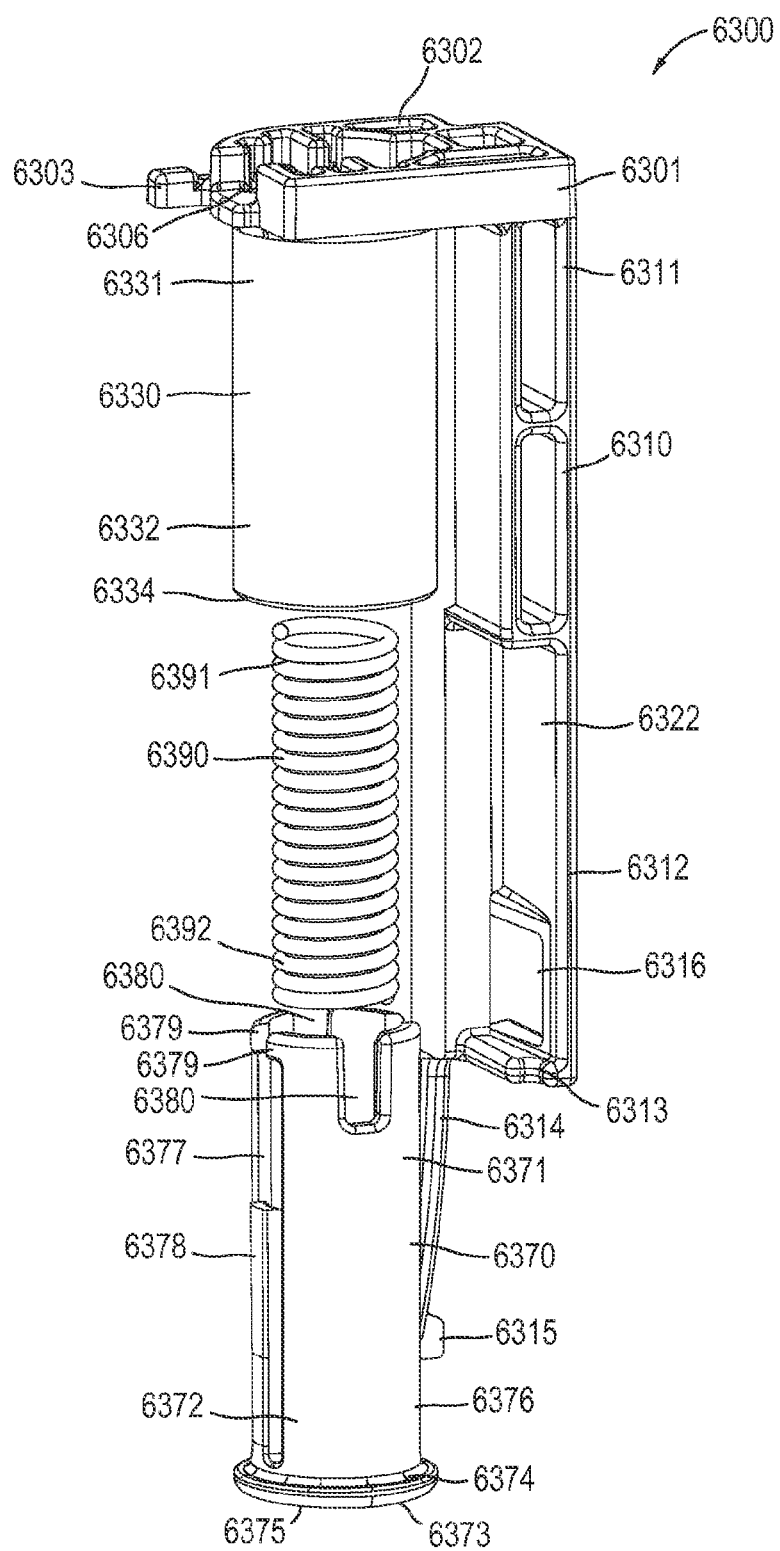
FIG. 45 is a perspective view of a movable assembly of the medical injector illustrated in FIG. 18.

As shown in FIG. 45, the piston portion 6330 is configured to receive at least a portion of the mixing spring 6390 and the mixing piston 6370. More specifically, the medicament delivery mechanism 6300 is configured such that when the medical injector 6000 is in the first configuration (e.g., the storage configuration), the mixing spring 6390 is disposed within the piston portion 6330 and the mixing piston 6370 in a first (e.g., compressed) configuration (see e.g., FIG. 68). Furthermore, the mixing piston 6370 (e.g., the second movable member 6370) is disposed within the piston portion 6330 such that a proximal end portion 6371 of the mixing piston 6370 extends, in the proximal direction, through the piston portion 6330 of the first movable member 6301. Similarly stated, when the mixing piston 6370 is in a first position (the storage position), the proximal end portion 6371 extends through the proximal end portion of the first movable member 6301 such that the mixing piston 6370 can be retained within the piston portion 6330 of the first movable member 6301, as described below.

The mixing piston 6370 includes the proximal end portion 6371 and a distal end portion 6372. The distal end portion 6372 includes a base 6373 with a proximal surface 6374 and a distal surface 6375. The proximal surface 6374 of the base 6373 defines a spring seat that receives a distal end portion 6392 of the mixing spring 6390. The distal surface 6375 of the base 6373 is configured to engage the proximal surface 6222 of the first plunger 6221, as described above. The mixing piston 6370 further includes a set of walls 6376 that extend in the proximal direction from the proximal surface 6374 of the base 6373. The walls 6376 define channels 6377 and include tabs 6378 that selectively engage the piston portion 6330 of the first movable member 6301. The tabs 6378 are configured to move between a first configuration (e.g., a retracted configuration) and a second configuration (e.g., an extended configuration). In some embodiments, the tabs 6378 can define a pre-stress load such that the tabs 6378, without an external force applied, are in the extended configuration. In some embodiments, the tabs 6378 can be maintained in the first configuration by the inner surface of the piston portion 6330. In such embodiments, the tabs 6378 can be moved to the second configuration when the mixing piston 6370 is moved in the distal direction to the second position, as described in further detail herein. As described herein, the tabs 6378 (also referred to as a retention portion or retention members) are configured to contact and/or engage the distal end surface 6334 to limit proximal movement of the mixing piston 6370 relative to the first movable member 6301 (i.e., retraction of the mixing piston 6370 into the piston portion 6330) after the mixing piston 6370 has been actuated. This arrangement prevents retraction of the mixing piston 6370 when the force produced by the spring 6420, which can exceed the force produced by the mixing spring 6390, is applied to the first movable member 6301 via the transfer member 6600.

Figure 49:
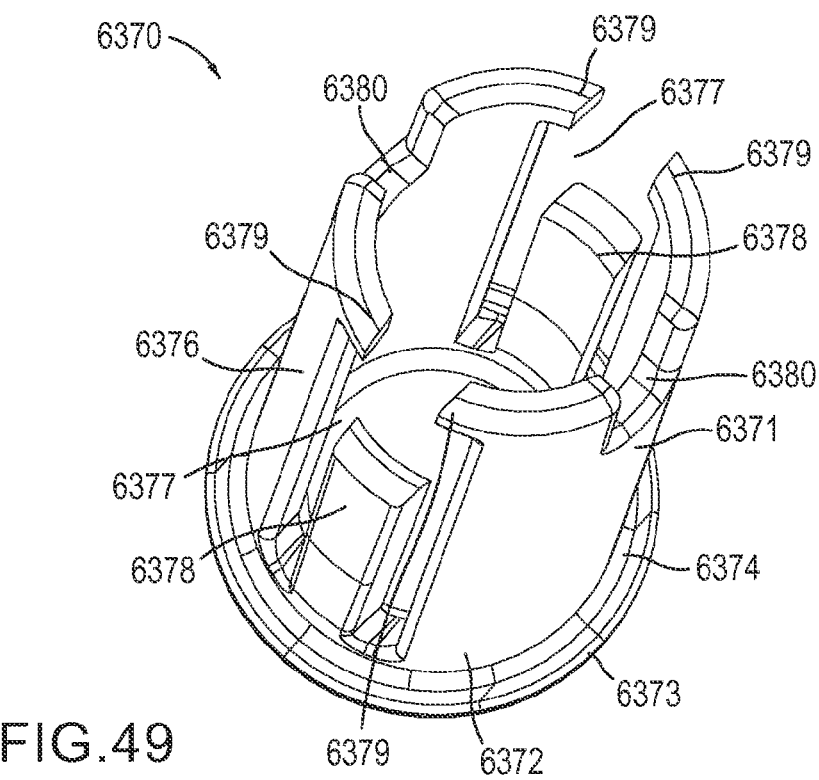
FIG. 49 illustrates a second movable member included in the movable assembly illustrated in FIG. 45.

The proximal end portion 6371 includes retention protrusions (or portions) 6379 and alignment grooves 6380. The retention grooves 6379 extend laterally from a surface of the walls 6376 that define the channels 6377. Similarly stated, as shown in FIG. 49, the retention protrusions 6379 extend into the channels 6377. As described above, the proximal end portion 6371 of the mixing piston 6370 extends through the proximal end portion 6331 of the piston portion 6330. In this manner, the alignment grooves 6380 receive alignment protrusions 6305 included in the top portion 6302 of the first movable member 6301 (see e.g., FIG. 32). Furthermore, when the medical injector 6000 is in the first configuration, the retention protrusions 6379 engage the retention portion 6558 of the mixing actuator member 6550. Thus, when the medical injector 6000 is in the first configuration, the mixing piston 6370 is in a first (e.g., locked) position, in which the movement of the mixing piston 6370 relative to the first movable member 6301 is limited and/or prevented.

The arrangement of the first movable member 6301, the mixing piston 6370, and the mixing actuator member 6550 is such that when the mixing actuator member 6550 is moved to actuate a mixing event, the mixing spring 6390 expands to move the mixing piston 6370 in the distal direction. More particularly, when the retention protrusions 6379 are in contact with the retention portion 6558 of the mixing actuator member 6550, a lock surface 6560 (see e.g., FIG. 64) of the retention portion 6558 applies a reaction force to a distal surface of the retention protrusions 6379 equal to the force exerted by the mixing spring 6390. Therefore, when the mixing actuator member 6550 is moved to the second position (e.g., no longer in contact with the retention protrusions 6379) the reaction force is removed and the mixing spring 6390 expands. Furthermore, the bottom surface 6304 of the top portion 6302 of the first movable member 6301 engages the proximal end portion 6391 of the mixing spring 6390 such that when the mixing spring 6390 expands, the distal end portion 6392 moves in the distal direction. Thus, the expansion of the mixing spring 6390 is such that the mixing spring 6390 exerts a force on the mixing piston 6370 to move the mixing piston 6370 in the distal direction, as further described herein.

Figure 50:
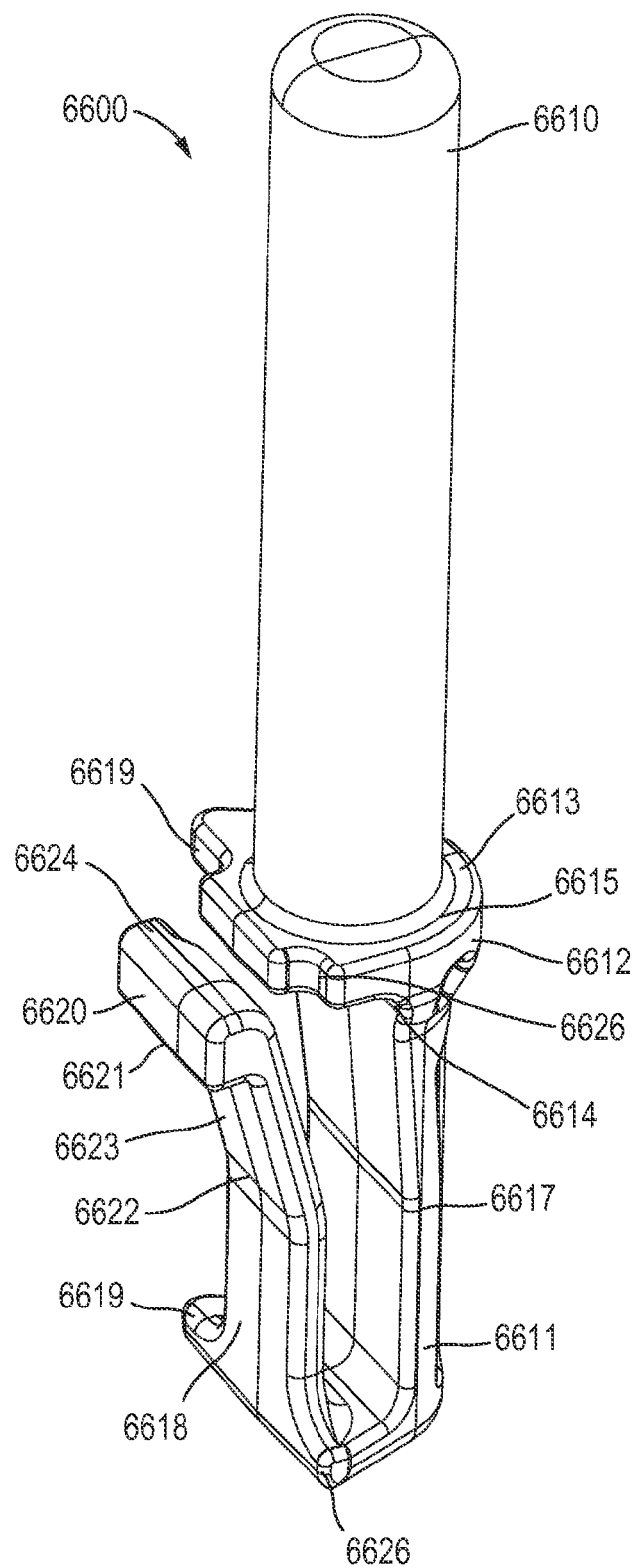
FIG. 50 is a perspective view of a transfer member included in the medical injector illustrated in FIG. 18.
Figure 51:
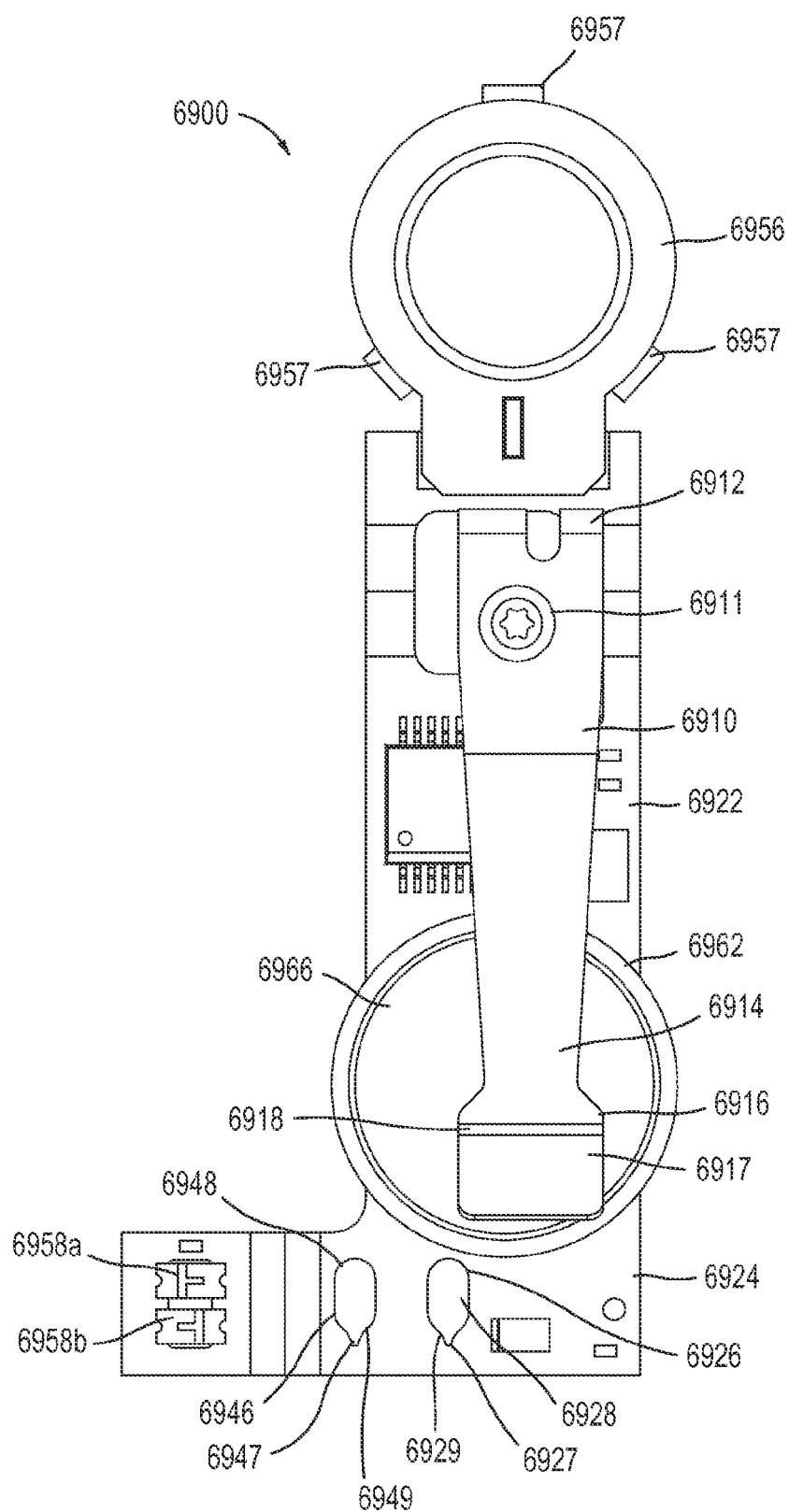
FIG. 51 is a rear view of an electronic circuit system of the medical injector illustrated in FIG. 18.
Figure 52:
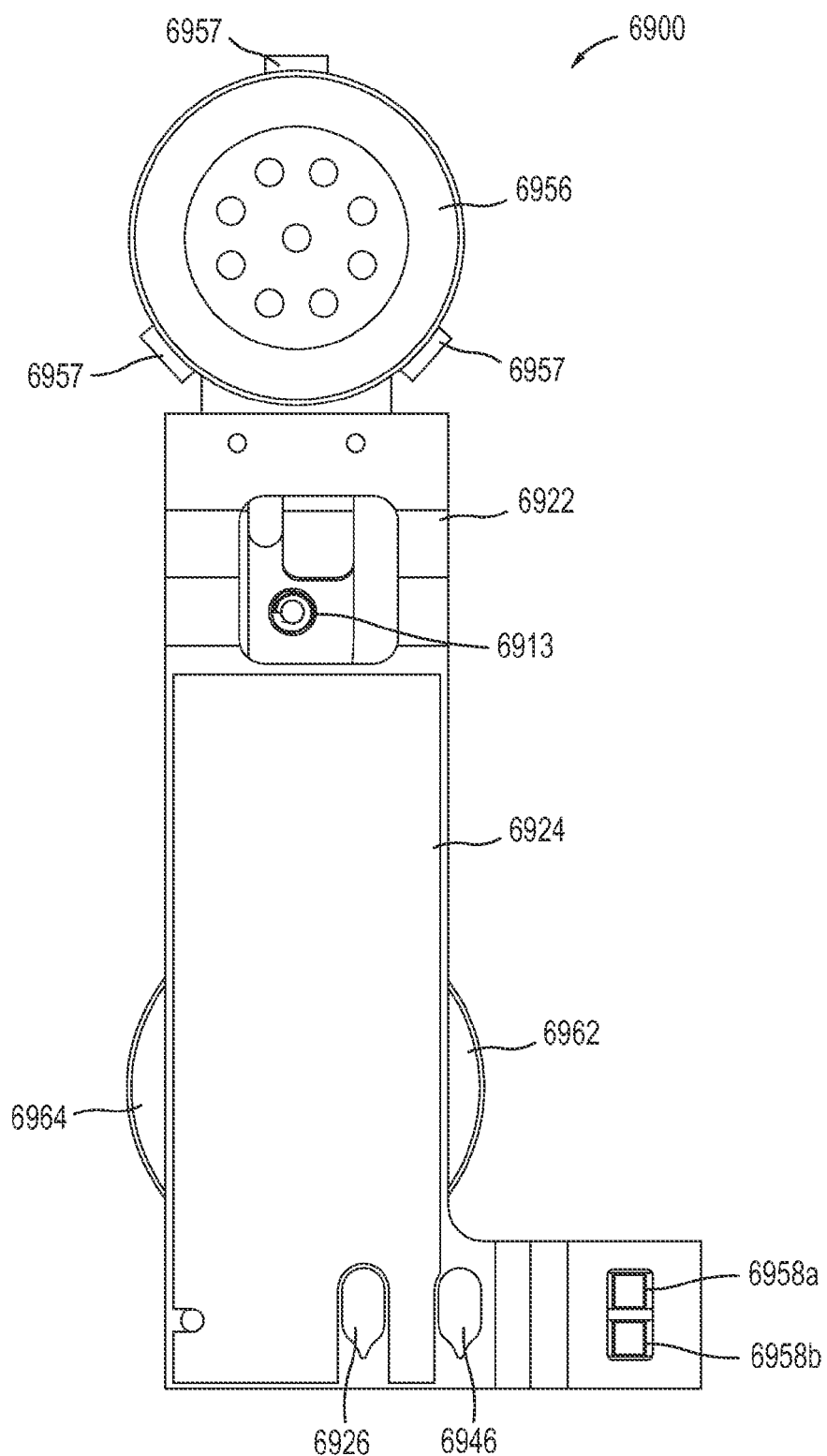
FIG. 52 is a front view of a portion of the electronic circuit system of the medical injector illustrated in FIG. 51.
Figure 53:
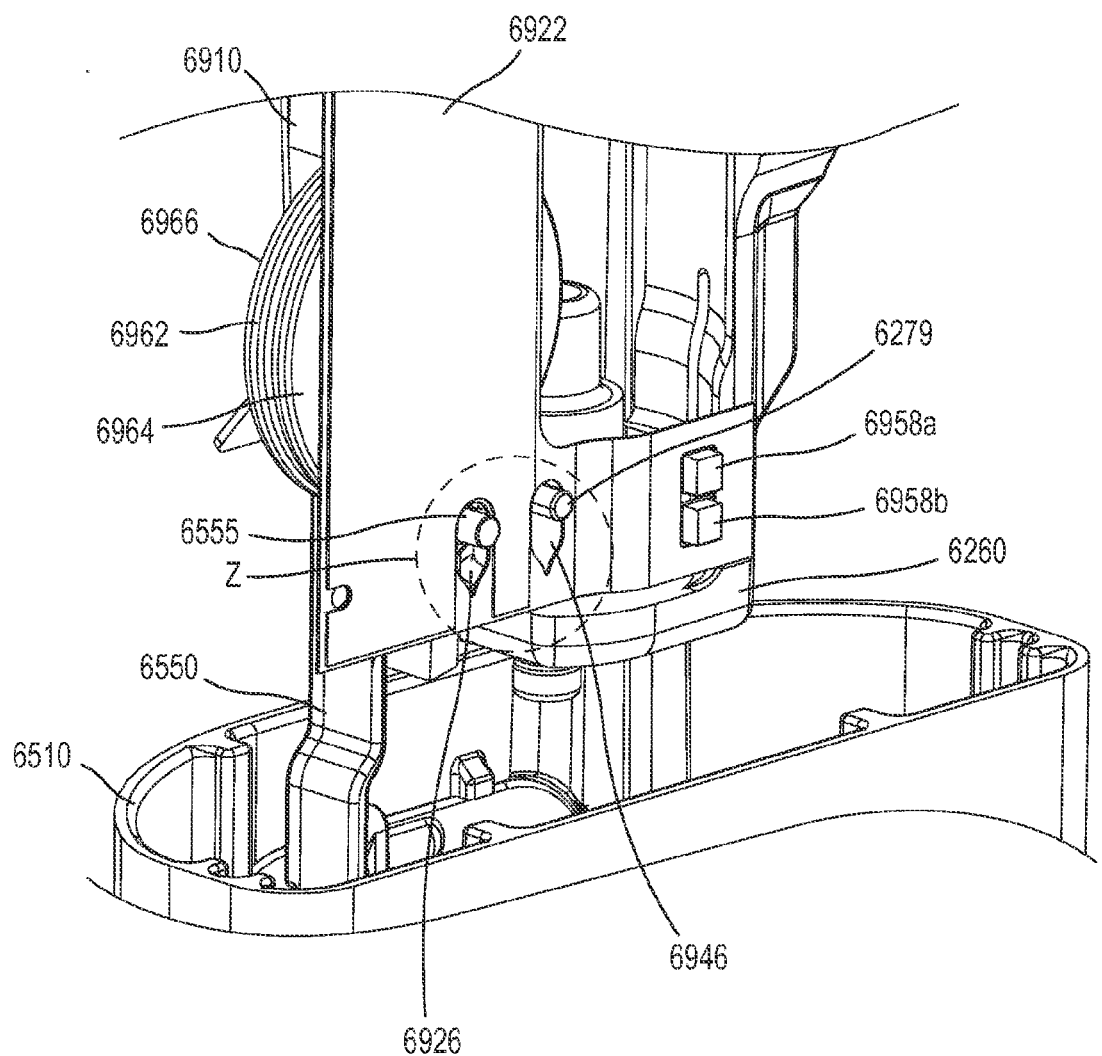
FIG. 53 is a perspective view of a portion of an electronic circuit system of the medical injector illustrated in FIG. 18, in a first configuration.
Figure 54:
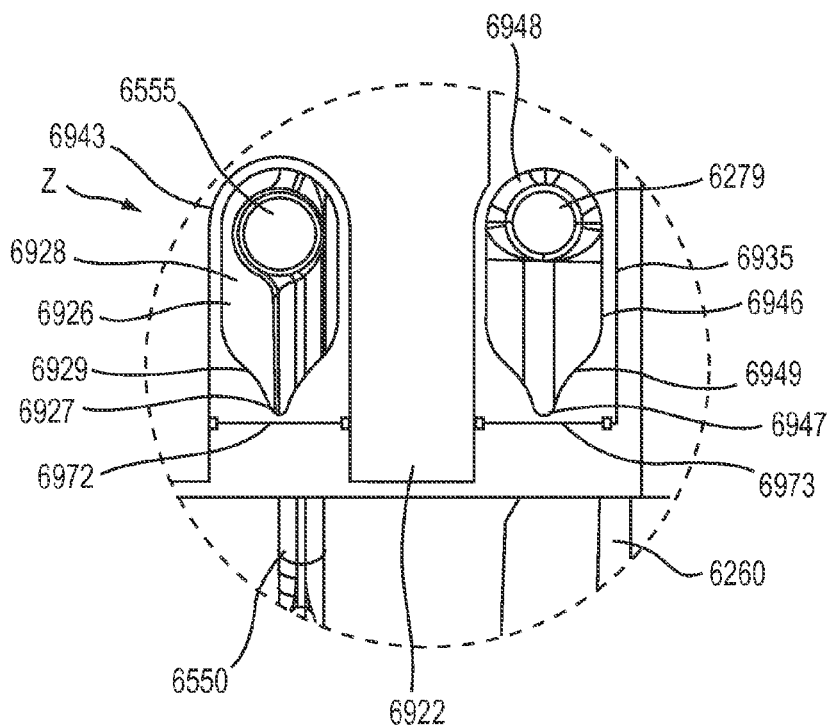
FIGS. 54-56 are front views of a portion of the electronic circuit system of the medical injector labeled as Region Z in FIG. 53 in a first configuration, a second configuration and a third configuration, respectively.
Figure 55:
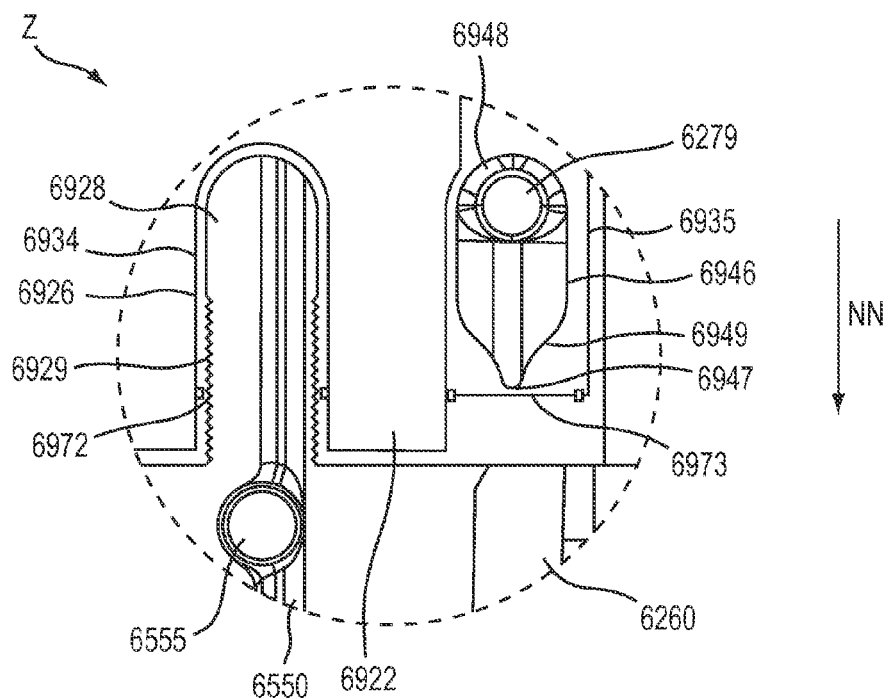
Figure 56:
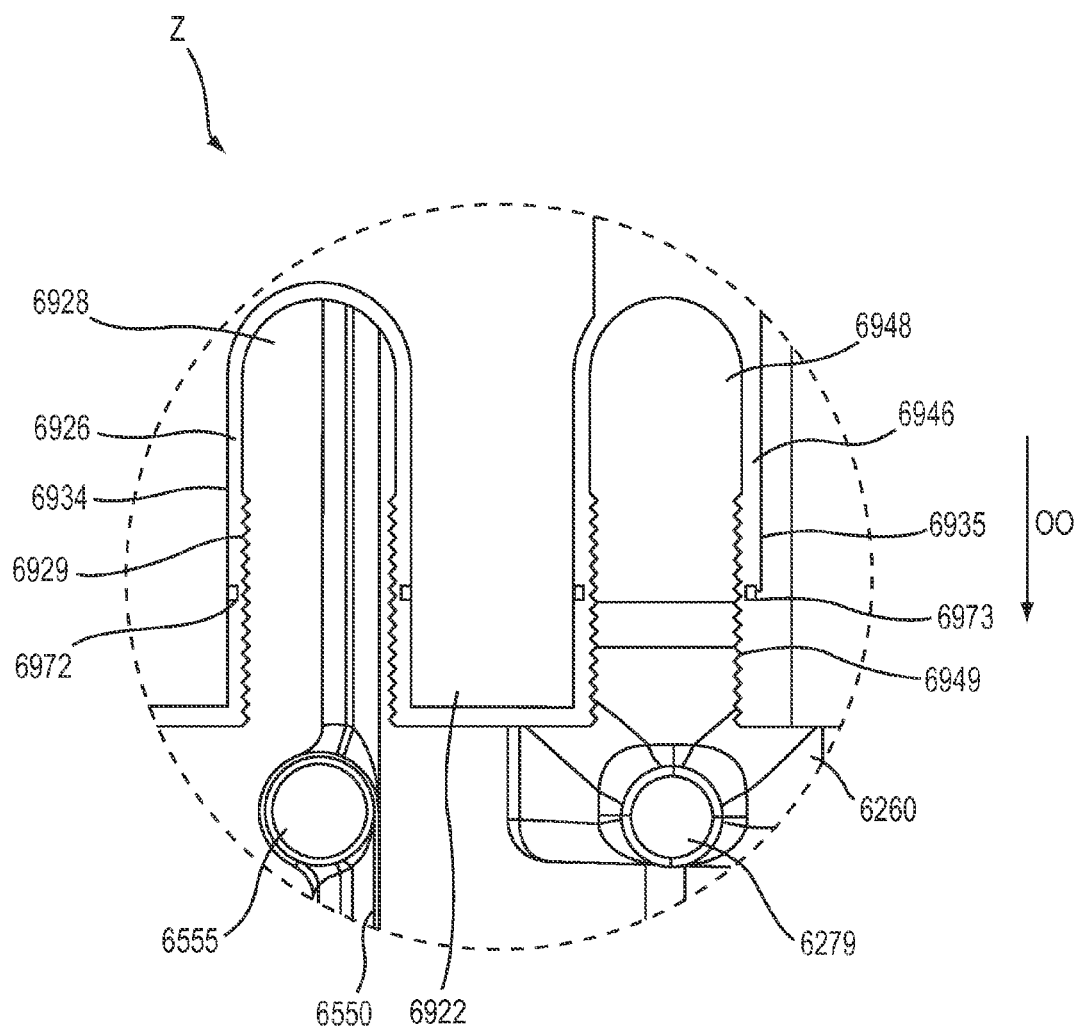

Referring to FIG. 50, the transfer member 6600 includes a proximal end portion 6610 and a distal end portion 6611, and is configured to move between a first configuration (see e.g., FIGS. 50 and 68, in which the transfer member 6600 is engaged to the first movable member 6301) and a second configuration (see e.g., FIG. 76, in which the transfer member 6600 is disengaged from the first movable member 6301). The proximal end portion 6610 is substantially cylindrical and is configured to engage and/or contact the spring 6420. Moreover, the transfer member 6600 includes a ring protrusion 6612 that includes a proximal surface 6613 defining a spring seat 6615. The distal end portion 6422 of the spring 6420 is disposed about the proximal end portion 6610 of the transfer member 6600, and is configured to engage the spring seat 6615 defined by the ring protrusion 6612.

The transfer member 6600 further includes a latch extension 6617 that extends from a distal surface 6614 of the ring protrusion 6612. The latch extension 6617 includes the latch arm 6618 and a bendable portion 6622. The latch arm 6618 includes the first guide surface 6619, the latch 6620, the guide protrusion 6624, and the second guide surface 6626. As described above, the latch extension 6617 extends in a distal direction from the ring protrusion 6612 of the transfer member 6600. The latch arm 6618 is configured to extend from the distal end portion 6611 of the transfer member 6610. Similarly stated, the latch arm 6618 extends from a distal end portion of the latch extension 6617. Moreover, the latch arm 6618 extends from the distal end portion of the latch extension 6617 at a suitable angle such that the latch 6620 is received within the opening 6316 of the first movable member 6301 (see e.g., FIGS. 46 and 47). For example, in some embodiments, the latch arm 6618 extends from the distal end portion of the latch extension 6617 at an acute angle. The first guide surface 6619, the second guide surface 6626, and the guide protrusion 6624 engage the transfer member guide 6117 of the housing 6100, as described above.

The latch 6620 extends from a proximal end portion 6623 of the latch arm 6618. The latch 6620 is configured to engage the second latch protrusion 6317 of the latch portion 6310 of the first movable member 6301. As described above, the distal surface 6621 of the latch 6620 is configured to be in contact with a proximal surface 6318 of the second latch protrusion 6317 when the transfer member 6600 is in the first configuration. In this manner, the transfer member 6600 transfers a force from the actuation of the spring 6420 to the first movable member 6301 and/or the medicament delivery mechanism 6300 to move the medicament delivery mechanism 6300 in the distal direction within the housing 6100. In this manner, the force produced by the spring 6420, which is offset from the medicament delivery mechanism 6300 and/or the medicament container 6210, results in both the insertion of the needle 6216 and injection of the medicament within the medicament container 6210. Although, as described below, the mixing spring 6390 produces a force to mix a diluent and a lyophilized medicament, in other embodiments, a portion of the force produced by the spring 6420 can be used to facilitate the mixing process.

Furthermore, when the transfer member 6600 has moved a desired distance in the distal direction in response to the force produced by the actuation of the spring 6420 (e.g., upon completion of the medicament injection), the guide protrusion 6624 of the latch 6620 aligns with the lower notch 6121 of the housing 6100 (see e.g., FIG. 25) to allow the transfer member 6600 to be moved to the second configuration (see e.g., FIG. 76). Expanding further, when the guide protrusion 6624 is aligned with the lower notch 6121 the guide protrusion 6624 moves through the lower notch 6121 thereby placing transfer member 6600 in the second configuration. In this manner, the latch 6620 can be disengaged from the second latch protrusion 6317. Similarly stated, when the transfer member 6600 is in its second configuration, the late 6620 is disengaged from the first movable member 6301, and the force produced by the spring 6420 is no longer transferred to the medicament delivery mechanism 6300. In particular, the bendable portion 6622 of the latch extension 6617 is configured to bend, relative to the latch extension 6617. In some embodiments, the bendable portion 6622 can define a prestress load such that when the transfer member 6600 is in the first configuration, the bendable portion 6622 is in a bent or deformed position. Thus, when the guide protrusion 6624 is aligned with the lower notch 6121, the bendable portion 6622 of the transfer member 6600 bends (e.g., returns to an undeformed position), thereby placing the transfer member 6600 in its second configuration (see FIG. 76).

When the transfer member 6600 is in its second configuration, the latch 6620 is disengaged from the second latch protrusion 6317 of the first movable member 6301. Said another way, when the guide protrusion 6624 of the latch 6620 is aligned with the lower notch 6121, the bendable portion 6622 of the transfer member 6600 bends (e.g., returns to the undeformed configuration) such that the angle between the latch arm 6618 and the latch extension 6617 is reduced, thus disengaging the transfer member 6600 from the medicament delivery mechanism 6300. Said yet another way, when the transfer member 6600 is in its second configuration, the medicament delivery mechanism 6300 is isolated and/or no longer operably coupled to the spring 6420. In this manner, as described below, the retraction force exerted by the retraction spring 6440 moves the medicament delivery mechanism 6300 and/or the medicament container assembly 6200 proximally within the housing 6100 to retract the needle 6216.

Figure 69:
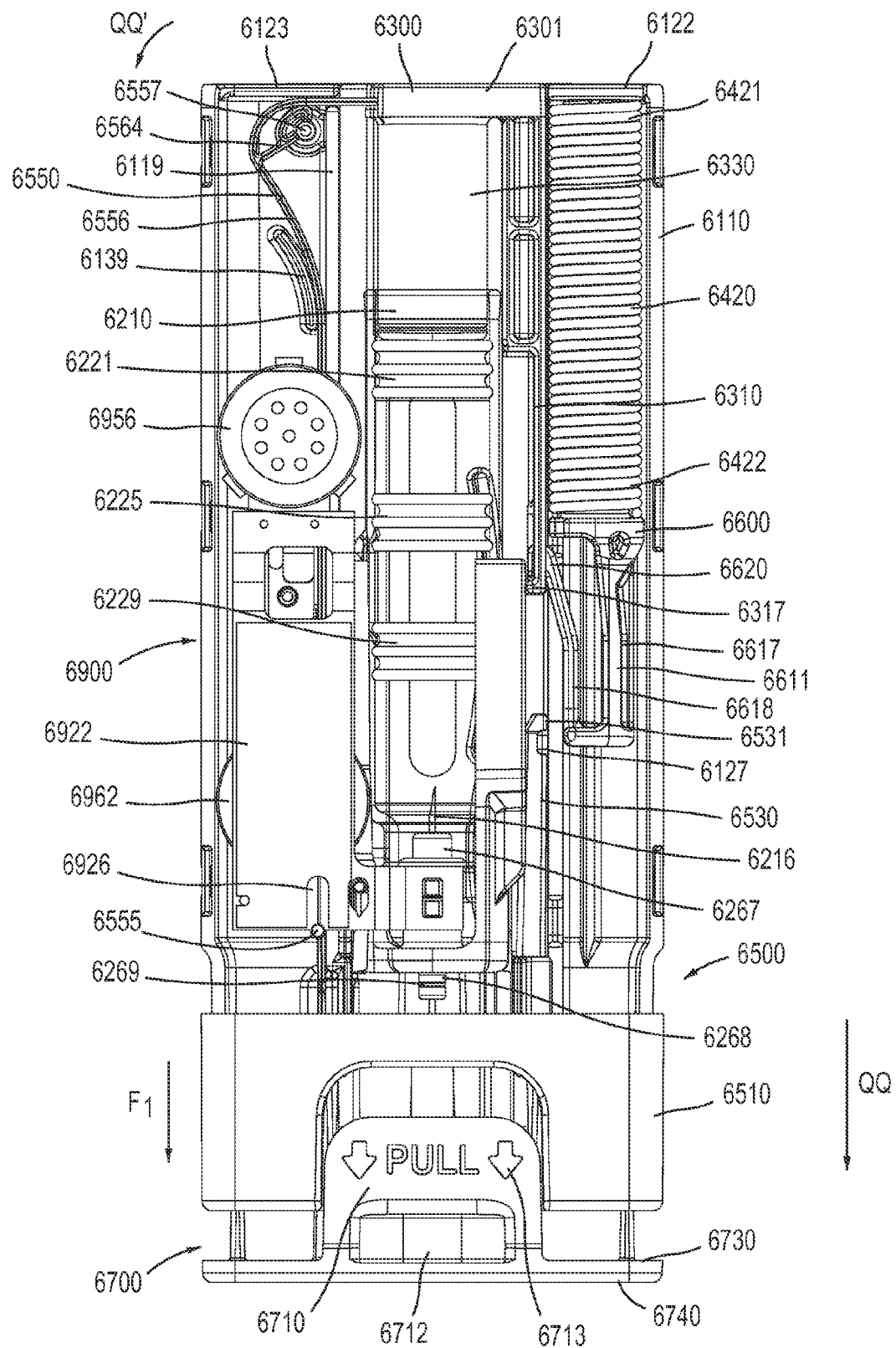
FIG. 69 is a front view of a portion of the medical injector of FIG. 18 just prior to transitioning to a third configuration (i.e., the mixing configuration).

FIGS. 51-56 show the electronic circuit system 6900. The electronic circuit system 6900 of the medical injector 6000 includes a printed circuit board 6922, a battery assembly 6962, an audio output device 6956, two light emitting diodes (LEDs) 6958A, 6958B and a battery clip 6910. The electronic circuit system 6900 is disposed within the housing 6100 (see e.g., FIG. 69). As described herein, the electronic circuit system 6900 is configured to output an electronic output associated with the use of the medical injector 6000.

As described above, the electronic circuit system 6900 is coupled to the second housing member 6140 of the housing 6100. In some embodiments, the electronic circuit system 6900 can be coupled to the housing 6100 by any suitable means such as an adhesive, a clip, a label and/or the like. As described in more detail herein, the battery clip protrusion 6176 of the second housing member 6140 is configured to hold the battery clip 6910 in place. Similarly stated, the battery clip protrusion 6176 of the second housing member 6140 is configured to exert a force on the battery clip 6910 to ensure that electrical contact between the battery assembly 6962 and the battery clip 6910 is maintained when the battery isolation protrusion 6197 of the cover 6190 is removed.

As shown and described above with respect to FIG. 26, the second housing member 6140 defines the sounds apertures 6173, the LED aperture 6178, the first actuator groove 6179, and the second actuator groove 6180. The audible output device 6956 is disposed within the recess 6165 defined by the inner surface 6146 of the second housing member 6140 such that the front face of the audible output device 6956 is disposed adjacent the sound apertures 6173. In this manner, the sound apertures 6173 are configured to allow sound produced by the audio output device 6956 to pass from the audio output device 6956 to a region outside of the housing 6100. Furthermore, the audio output device 6956 includes the tabs 6957 configured to engage the latches 6163 of the second housing member 6140.

The first actuator groove 6179 defined by the second housing member 6140 is disposed adjacent the safety lock actuator groove 6133 defined by the first housing member 6110. In this manner, the first actuator groove 6179 of the second housing member 6140 and the safety lock actuator groove 6133 of the first housing member 6110 collectively receive the protrusion 6555 of the mixing actuator member 6550 (see e.g., FIGS. 53 and 64), which is described in more detail herein. The second actuator groove 6180 of the second housing member 6140 is configured to receive the protrusion 6279 of the electronic engagement portion 6278 included in the carrier 6260 (see e.g., FIGS. 44 and 53), which is described in more detail herein.

The printed circuit board 6922 of the electronic circuit system 6900 includes a substrate 6924, a first actuation portion 6926 and a second actuation portion 6946. The substrate 6924 of the printed circuit board 6922 includes the electrical components for the electronic circuit system 6900 to operate as desired. For example, the electrical components can be resistors, capacitors, inductors, switches, microcontrollers, microprocessors and/or the like. The printed circuit board 6922 may also be constructed of materials other than a flexible substrate such as a FR4 standard board (rigid circuit board).

As shown in FIGS. 53-56, the first actuation portion 6926 includes a first electrical conductor 6934 and defines an opening 6928 having a boundary 6929. The opening 6928 of the first actuation portion 6926 is configured to receive the protrusion 6555 of the mixing actuator member 6550. The boundary 6929 of the opening 6928 has a discontinuous shape, such as, for example, a teardrop shape, that includes a stress concentration riser 6927. The discontinuity and/or the stress concentration riser 6927 of the boundary 6929 can be of any suitable shape to cause the substrate 6924 to deform in a predetermined direction when the protrusion 6555 of the mixing actuator member 6550 is moved relative to the opening 6928, as shown by the arrow NN in FIG. 55.

The opening 6928 is defined adjacent the first electrical conductor 6934 that electronically couples the components included in the electronic circuit system 6900. The first electrical conductor 6934 includes a first switch 6972, which can be, for example a frangible portion of the first electrical conductor 6934. In use, when the safety lock 6700 is moved in the distal direction from the first position to the second position, the protrusion 6726 of the actuator 6724 engages the catch 6553 of the mixing actuator member 6550 and moves the distal end portion 6551 of the mixing actuator member 6550 in the distal direction. In this manner, the protrusion 6555 of the mixing actuator member 6550 moves from a first position (see e.g., FIG. 54) to a second position (see e.g., FIG. 55). The movement of the mixing actuator member 6550 causes the protrusion 6555 to move within the first opening 6928, as indicated by the arrow NN in FIG. 55. The movement of the protrusion 6555 tears the first actuation portion 6926 of the substrate 6924, thereby separating the portion of the first electrical conductor 6934 including the first switch 6972. Said another way, when the safety lock 6700 is moved from its first position to its second position (see e.g., FIG. 69), the mixing actuator member 6550 is actuated and the protrusion 6555 moves the first switch 6972 from a first state (e.g., a state of electrical continuity) to a second state (e.g., a state of electrical discontinuity). Said yet another way, when the safety lock 6700 is moved from its first position to its second position, the mixing actuator member 6550 disrupts the first electrical conductor 6934.

The second actuation portion 6946 includes a second electrical conductor 6935 and defines an opening 6945 having a boundary 6949. As shown in FIGS. 53-56, the opening 6945 of the second actuation portion 6946 is configured to receive the protrusion 6279 of the electronic engagement portion 6278 of the carrier 6260. The boundary 6949 of the opening 6945 has a discontinuous shape that includes a stress concentration riser 6947. The discontinuity and/or the stress concentration riser 6947 of the boundary 6949 can be of any suitable shape to cause the substrate 6924 to deform in a predetermined direction when the protrusion 6279 of the carrier 6260 is moved in a proximal direction relative to the opening 6945, as shown by the arrow OO in FIG. 56.

The second electrical conductor 6935 includes a second switch 6973, which can be, for example, a frangible portion of the second electrical conductor 6935. In use, when the carrier 6260 is moved from its first position to its second position (see e.g., FIG. 73), the protrusion 6555 moves in a distal direction, substantially parallel to a plane defined by a surface of the second actuation portion 6946 of the substrate 6924. The distal movement of the protrusion 6555 tears the second actuation portion 6946 of the substrate 6924, thereby separating the portion of the second electrical conductor 6935 including the second switch 6973. Said another way, when the carrier 6260 is moved from its first position to its second position, the protrusion 6555 moves the second switch 6973 from a first state (e.g., a state of electrical continuity) to a second state (e.g., a state of electrical discontinuity). In some embodiments, other portions the medical injector 6000 can engage the first electrical conductor 6934 or the second electrical conductor 6935 to actuate the electronic circuit system 6900. For example, in some embodiments, a base can include an actuator such that the proximal movement of the base can urge an actuator to move in the proximal direction to actuate the electronic circuit system.

In some embodiments, the safety lock 6700, the mixing actuator member 6550 and/or other portions of the medical injector 6000 can be configured to interact with mechanical and/or optical switches to produce an electronic output in a reversible manner. For example, in some embodiments, the electronic circuit system 6900 can include one or more optical switches configured to change states based on the sensed position of one of the plungers within the medicament container 6210. In some such embodiments, the electronic circuit system 6900 can produce an output when the mixing event has ended based at least in part upon the location of a plunger within the medicament container.

The battery assembly 6962 of the electronic circuit system 6900 includes two batteries stacked on top of one another. In other embodiments, the electronic circuit system can include any number of batteries and/or any suitable type of power source. In some embodiments, for example, the battery assembly can include Lithium batteries such as, for example, CR61616, CR62016s, type AAA or the like. The battery assembly 6962 has a first surface 6964 and a second surface 6966. The first surface 6964 of the battery assembly 6962 can contact an electrical contact (not shown) disposed on the substrate 6924. The second surface 6966 of the battery assembly 6962 is configured to contact a contact portion 6918 of a distal end portion 6916 of a battery clip 6910. When both the electrical contact of the substrate 6924 and the contact portion 6918 of the distal end portion 6916 of the battery clip 6910 contact the battery assembly 6962, the batteries of the battery assembly 6962 are placed in electrical communication with the electronic circuit system 6900. Said another way, when the electrical contact of the substrate 6924 and the contact portion 6918 of the distal end portion 6916 of the battery clip 6910 contact the battery assembly 6962, the battery assembly 6962 is configured to supply power to the electronic circuit system 6900.

The battery clip 6910 (shown in FIG. 51) includes a proximal end portion 6912 and a distal end portion 6916. The proximal end portion 6912 defines a retention aperture (not shown). The retention aperture is configured to receive a screw 6911 to couple the battery clip 6910 to the battery clip protrusion 6176 of the second housing member 6140. In this manner, the battery clip protrusion 6176 maintains the position of the battery clip 6910 with respect to the electronic circuit system housing 6170 and/or the battery assembly 6962.

The distal end portion 6916 of the battery clip 6910 includes a contact portion 6918 and an angled portion 6917. As described above, the contact portion 6918 is configured to contact the second surface 6966 of the battery assembly 6962 to place the battery assembly 6962 in electrical communication with the electronic circuit system 6900. The angled portion 6917 of the distal end portion 6916 of the battery clip 6910 is configured to allow a proximal end portion 6236 of a battery isolation protrusion 6197 (see e.g., FIG. 58) to be disposed between the second surface 6966 of the battery assembly 6962 and the contact portion 6918 of the distal end portion 6916 of the battery clip 6910. When the battery isolation protrusion 6197 is disposed between the second surface 6966 of the battery assembly 6962 and the contact portion 6918 of the distal end portion 6916 of the battery clip 6910, the electrical path between the battery assembly 6962 and the remainder of the electrical circuit system 6900 is disrupted, thereby removing power from the electronic circuit system 6900. The contact portion 6918 of the distal end portion 6916 of the battery clip 6910 is biased such that when the battery isolation protrusion 6197 is removed, the contact portion 6918 will move into contact the second surface 6966 of the battery assembly 6962, thereby restoring electrical communication between the battery assembly 6962 and the electronic circuit system 6900. In some embodiments, the battery isolation protrusion 6197 can be repeatedly removed from between the second surface 6966 of the battery assembly 6962 and the contact portion 6918 of the distal end portion 6916 of the battery clip 6910 and reinserted. Said another way, the battery isolation protrusion 6197 and the battery clip 6910 collectively form a reversible on/off switch.

The audio output device 6956 of the electronic circuit system 6900 is configured to output audible sound to a user in response to use of the medical injector 6000. In some embodiments, the audible output device 6956 can be a speaker. In some embodiments, the audible sound can be, for example, associated with a recorded message and/or a recorded speech. In other embodiments, the audible instructions can be an audible beep, a series of tones and/or or the like.

In some embodiments, the medical injector 6000 can have a network interface device (not shown) configured to operatively connect the electronic circuit system 6900 to a remote device (not shown) and/or a communications network (not shown). In this manner, the electronic circuit system 6900 can send information to and/or receive information from the remote device. The remote device can be, for example, a remote communications network, a computer, a compliance monitoring device, a cell phone, a personal digital assistant (PDA) or the like. Such an arrangement can be used, for example, to download replacement processor-readable code from a central network to the electronic circuit system 6900. In some embodiments, for example, the electronic circuit system 6900 can download information associated with a medical injector 6000, such as an expiration date, a recall notice, updated use instructions or the like. Similarly, in some embodiments, the electronic circuit system 6900 can upload compliance information associated with the use of the medical injector 6000 via the network interface device.

Figure 57:
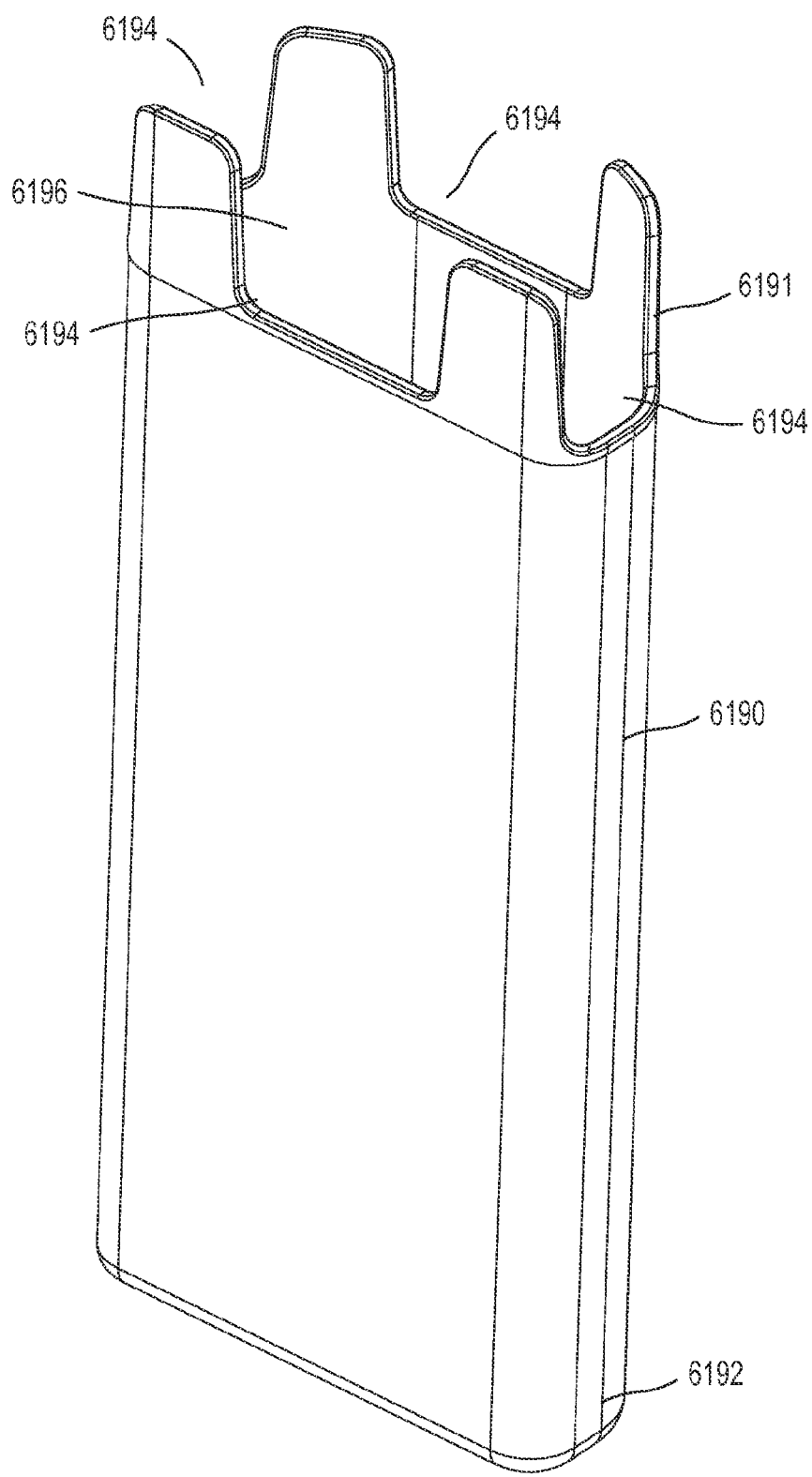
FIGS. 57 and 58 are perspective views of a cover of the medical injector illustrated in FIG. 18.
Figure 58:
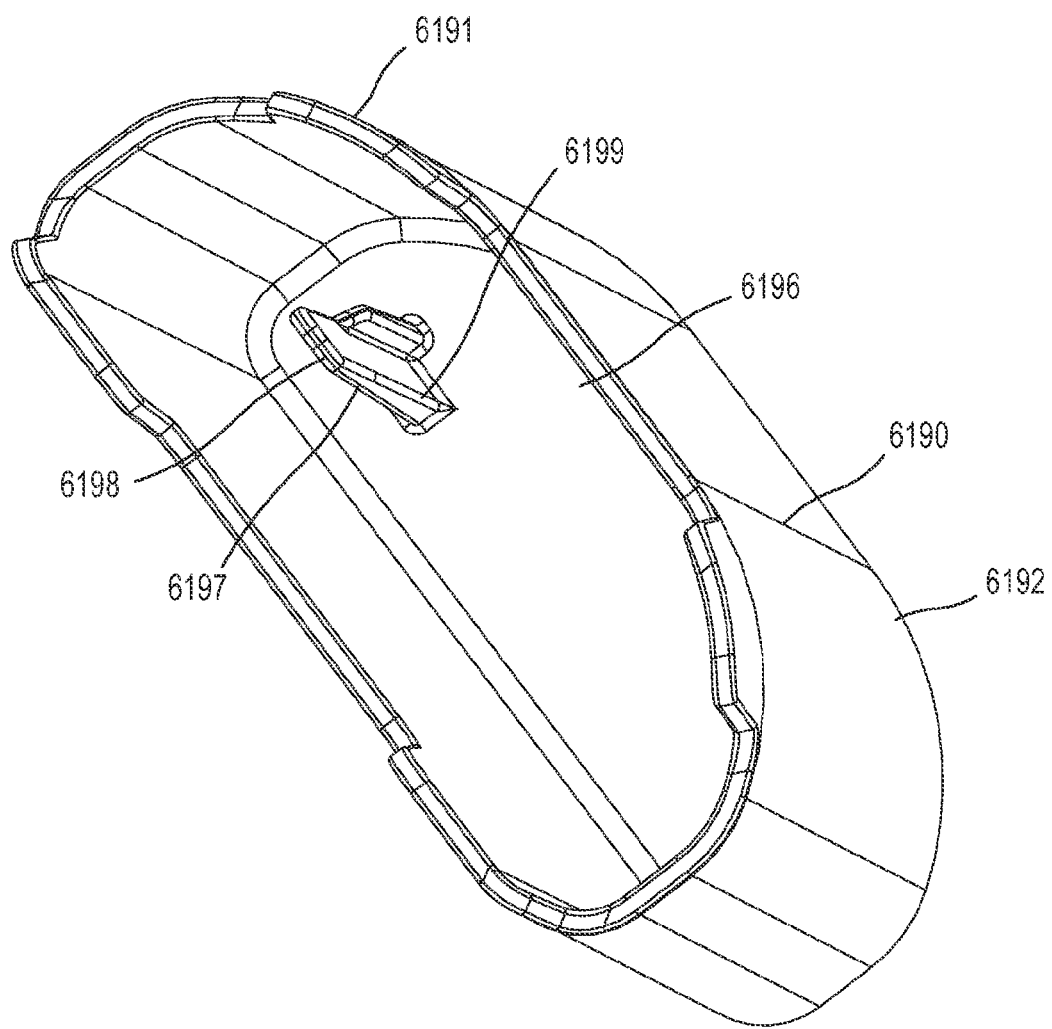

FIGS. 57 and 58 show the cover 6190 of the medical injector 6000. The cover 6190 includes a proximal end portion 6191 and a distal end portion 6192, and defines a cavity 6196. The cavity 6196 of the cover 6190 is configured to receive at least a portion of the housing 6100. Thus, when the portion of the housing 6100 is disposed within the cover 6190, the cover 6190 blocks an optical pathway between the medicament container 6210 and a region outside of the housing 6100. Similarly stated, when the portion of the housing 6100 is disposed within the cover 6190, the cover 6190 is obstructs the first status indicator aperture 6130 and/or the second status indicator aperture 6160 of the housing 6100 to reduce the amount of light transmitted to the medicament within the medicament container 6210. In this manner, the life of the medicament can be extended by the prevention and/or reduction of degradation to the medicament that may be caused by ultra-violet radiation. In some embodiments, for example, when the medicament is not degraded by ultra-violet radiation, the cover 6190 can include status indicator apertures similar to the status indicator aperture 6130 and/or 6160.

As described above, the electronic circuit system 6900 can be actuated when the housing 6100 is at least partially removed from the cover 6190. More particularly, the distal end portion 6192 of the cover 6190 includes the battery isolation protrusion 6197. The battery isolation protrusion 6197 includes a proximal end portion 6198 and a distal end portion 6199. The proximal end portion 6198 of the battery isolation protrusion 6197 is configured to be removably disposed between the second surface 6966 of the battery assembly 6962 and the contact portion 6918 of the distal end portion 6916 of the battery clip 6910, as described above.

The cover 6190 can be any suitable configuration and can include any suitable feature. For example, the cover 6190 includes notches 6194 disposed at the proximal end of the cover 6190. In some embodiments, the notches 6194 can be used to reduce the material needed to manufacture the cover 6190. In some embodiments, the cover 6190 can include openings that can receive inserts (not shown). The inserts can be a flexible inserts and can be configured to increase friction between the cover 6190 and a surface. For example, the inserts can increase the friction between the cover 6190 and a surface on which the medical injector 6000 is placed, to prevent sliding.

FIGS. 59-63 show the safety lock 6700 of the medical injector 6000. The safety lock 6700 of the medical injector 6000 includes a proximal surface 6730, a distal surface 6740 opposite the proximal surface 6730 and a needle sheath 6820. The safety lock 6700 defines a needle sheath aperture 6703 and a battery isolation protrusion aperture 6728. The battery isolation protrusion aperture 6728 is configured to receive the battery isolation protrusion 6197 of the cover 6190 such that the battery isolation protrusion 6197 can be disposed within the housing 6100 and/or in engagement with the electronic circuit system 6900, as described above. Similarly stated, the battery isolation protrusion aperture 6728 of the safety lock 6700 is aligned with the battery isolation protrusion aperture 6135 of the housing 6100, such that the battery isolation protrusion 6197 can be disposed within the housing 6100 when the cover 6190 is disposed about a portion of the housing 6100.

The proximal surface 6730 of the safety lock 6700 includes the safety lock protrusions 6702, the actuator 6724, two opposing pull-tabs 6710, and an engagement portion 6720. As described above, when the safety lock 6700 is in a first (locked) position, the safety lock protrusions 6702 are disposed in the safety lock protrusion opening 6514 defined by the base 6510 and in contact with a distal surface 6107 of the housing 6100 (see e.g., FIGS. 31 and 68). Accordingly, the safety lock protrusions 6702 are configured to prevent the proximal movement of the base 6510 and/or delivery of the medicament.

The actuator 6724 of the safety lock 6700 defines the channel 6725 and includes the protrusion 6726. The actuator 6724 can extend from the proximal surface 6730 of the safety lock 6700 and through a safety lock actuator opening 6524 of the base 6510 (see e.g., FIG. 65). As described above, the channel 6725 receives a catch 6553 of the mixing actuator member 6550 such that the protrusion 6726 can engage the catch 6553. The protrusion 6726 extends in a direction substantially transverse to the actuator 6724 and/or substantially parallel to the proximal surface 6730 of the safety lock 6700. As described above, the protrusion 6726 can engage the catch 6553 to move the mixing actuator member 6550 in the distal direction when the safety lock 6700 is moved distally to remove the needle sheath 6820 and/or prepare the medical injector 6000 for use.

The pull-tabs 6710 of the safety lock 6700 include a grip portion 6712 and indicia 6713. The grip portion 6712 of the pull-tabs 6710 provides an area for the user to grip and/or remove the safety lock 6700 from the rest of the medicament delivery system 6700. The indicia 6713 provide instruction on how to remove the safety lock 6700. The distal end surface 6740 also includes indicia 6741 (see e.g., FIG. 61). In some embodiments, for example, indicia can indicate the direction the user should pull the safety lock 6700 to remove the safety lock 6700. In other embodiments, indicia can indicate the medical injector 6000 is a trainer (e.g., that the medical injector 6000 is devoid of a needle and/or an active medicament).

The engagement portion 6720 of the safety lock 6700 includes engagement members 6721. The engagement members 6721 extend in a proximal direction from the proximal surface 6730. The engagement members 6721 have tabs 6722 that extend from a surface of the engagement members 6721. The tabs 6722 are configured to engage a rib 6825 disposed at a distal end portion 6822 of the needle sheath 6820. In this manner, distal movement of the safety tab 6700 results in distal movement (e.g., removal of) the needle sheath 6820.

Figure 62:
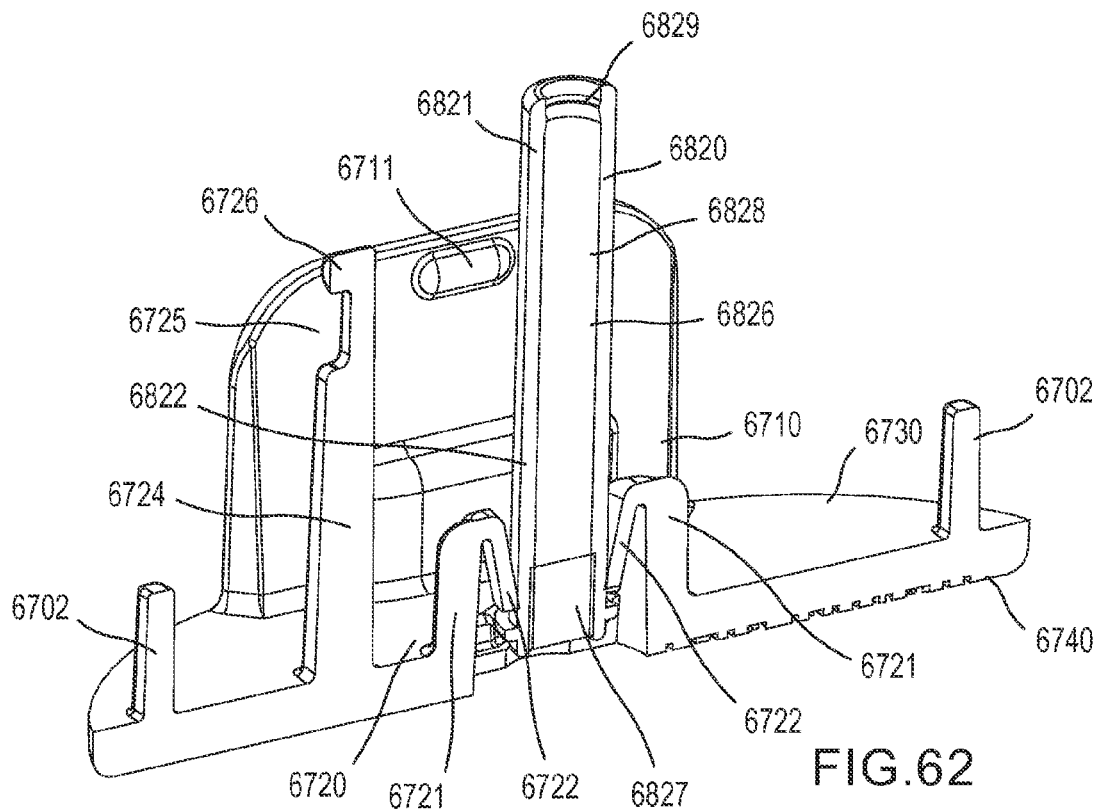
FIG. 62 is a cross-sectional view of the safety lock of the medical injector illustrated in FIG. 59.
Figure 63:
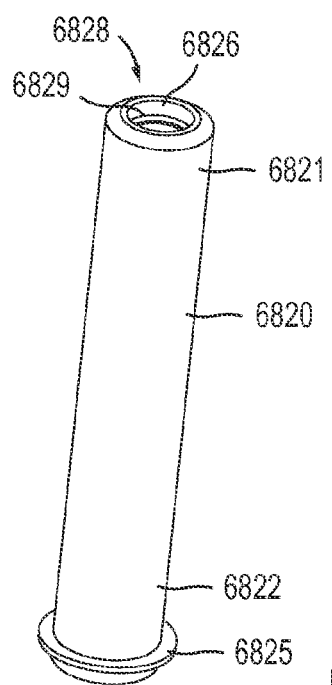
FIG. 63 is a perspective view of a needle sheath of the safety lock of the medical injector illustrated in FIG. 59.

As shown in FIGS. 62 and 63, the needle sheath 68210 includes the distal end portion 6822, a proximal end portion 6821, the rib 6825, and a needle plug 6827. The needle sheath 6820 also defines a bore 6828. The bore 6828 is defined by an inner surface 6826 of the needle sheath 6820 and is configured to receive the needle 6216 and/or a distal end portion of the 6213 of the medicament container 6200. The needle plug 6827 is disposed within the bore 6828 at the distal end portion 6822 of the needle sheath 6820. The needle plug 6827 can be any suitable material configured to engage a proximal end portion 6218 of the needle 6216. For example, in some embodiments, the needle plug can be a cork material or any other suitable porous material (e.g., any suitable Porex™ material) to allow for exposure to ethylene oxide during a sterilization operation.

The inner surface 6826 further define an annular protrusion 6829 disposed at the proximal end portion 6281 of the needle sheath 6820 and is configured to engage an annular notch 6269 defined by the lower needle port 6268 of the carrier 6260. The annular protrusion 6829 defines a friction fit with the annular notch 6269 of the carrier 6260. In this manner, the needle sheath 6820 can be coupled to the carrier 6260 and can protect the user from the needle 6216 and/or can keep the needle 6216 sterile before the user actuates the medical injector 6000.

The distal end portion 6822 of the needle sheath 6820 is configured to be inserted into a space defined between the tabs 6722 of the engagement members 6721 of the safety lock 6700. The tabs 6722 are angled and/or bent towards the distal direction to allow the distal end portion 6822 of the needle sheath 6810 to move between the engagement members 6721 in a distal direction, but not in a proximal direction. Similarly stated, the tabs 6722 include an edge that contacts the rib 6825 of the needle sheath 6820 to prevent the safety lock 6700 from moving in a distal direction relative to the needle sheath 6820. In this manner, the needle sheath 6820 is removed from the needle 6216 when the safety lock 6700 is moved in a distal direction with respect to the housing 6100 (see e.g., FIG. 69).

FIG. 64 shows the mixing actuator member 6550 of the medical injector 6000. The mixing actuator member 6550 includes the proximal end portion 6551, the distal end portion 6552, and the engagement portion 6558. The distal end portion 6552 includes the protrusion 6555 and the catch 6553 having an engagement surface 6554. As described above, the catch 6553 is configured to engage the protrusion 6726 of the actuator 6724 included in the safety lock 6700. In this manner, when the safety lock 6700 is moved in the distal direction, the protrusion 6726 contacts the engagement surface 6554 of the catch 6553 and moves the distal end portion 6552 of the mixing actuator member 6550 in the distal direction. Thus, when the distal end portion 6552 of the mixing actuator member 6550 is moved in the distal direction, the protrusion 6555 is moved in the distal direction to actuate a portion of the electronic circuit system 6900, as described above.

The proximal end portion 6551 defines a curved portion 6556 and includes the pivot protrusions 6557. As described above, the pivot protrusions 6557 are disposed within the pivot protrusion apertures 6125 and 6155 of the housing 6100, such that the mixing actuator member 6550 can pivot about the pivot protrusions 6557 when actuated. Furthermore, the proximal end portion 6551 includes a stiffening arm 6564 configured to facilitate the pivot motion of the mixing actuator member 6550. Expanding further, the stiffening arm 6564 can be configured to transfer and/or amplify of a portion of a force exerted on the catch 6553 by the distal movement of the safety lock 6700 to move the retention portion 6558 in a lateral direction (e.g., a direction substantially perpendicular to the distal direction), as described in further detail herein. More particularly, the stiffening arm 6564 is configured such that the curved portion 6556 of the mixing release member 6550 is spaced apart from the pivot protrusions 6557 by a first distance and the retention portion 6558 is spaced apart from the pivot protrusions 6557 by a second distance, less than the first distance. In this manner the force exerted by the retention portion 6558 during rotation of a portion of the mixing release member 6550 is greater than the force applied to the distal end portion 6552 of the mixing release member 6550.

The retention portion 6558 extends in a substantially normal direction from distal end portion 6552 of the mixing release member 6550. Similarly stated, the retention portion 6558 is substantially perpendicular to a portion of the mixing release member 6550 defined between the proximal end portion 6551 and the distal end portion 6552. The retention portion 6558 includes a lock surface 6560 and defines a set of notches 6559. As described above, the lock surface 6560 can selectively engage the retention protrusions 6379 of the mixing piston 6370 to maintain the mixing piston 6370 in the first (e.g., locked) configuration. The notches 6559 are configured to receive a set of the retention protrusions 6379 when the retention portion 6558 is moved to the second position (e.g., when the safety lock 6700 is removed from the housing 6100).

Figure 65:
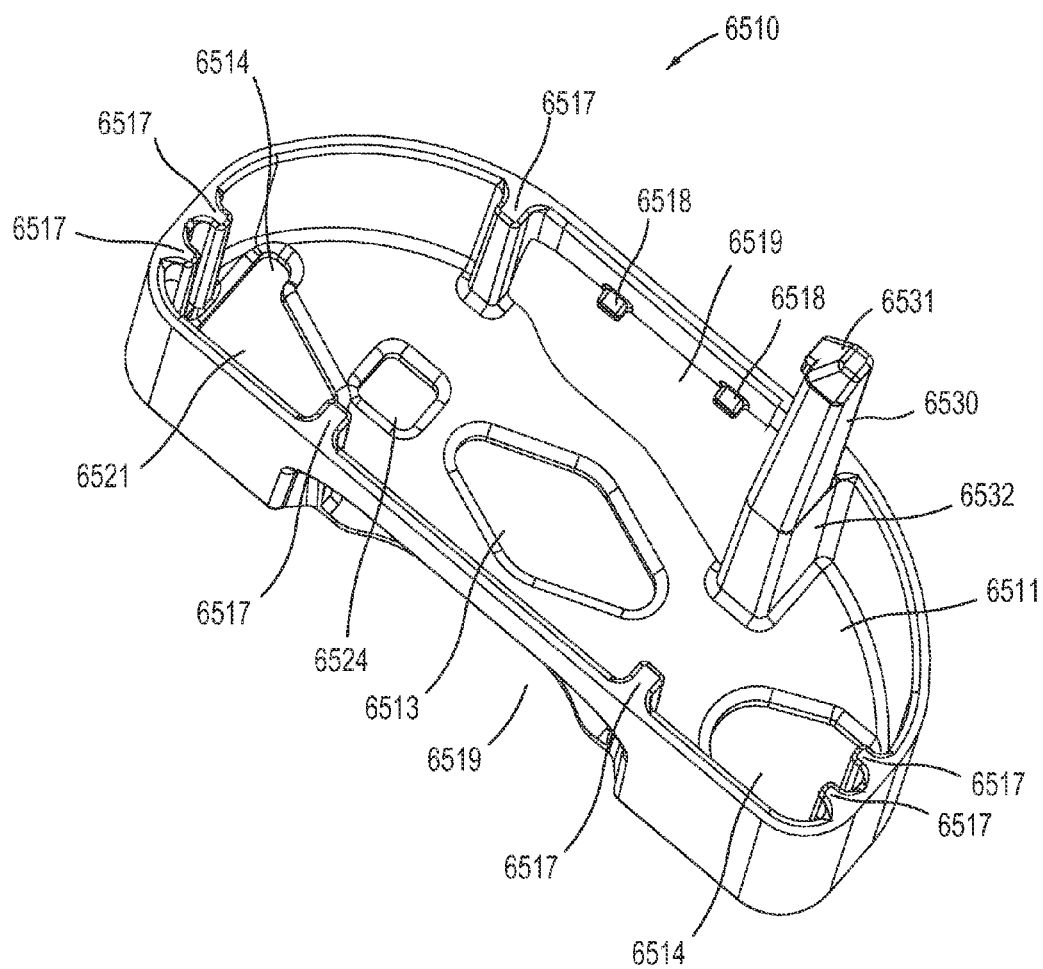
FIG. 65 is a perspective view of a base included in a system actuator assembly of the medical injector illustrated in FIG. 18.

FIGS. 65 and 66 show the base 6510 of the medical injector 6000. The base 6510 includes a proximal surface 6511, a distal surface 6523 and base connection knobs 6518. The base 6510 defines a needle aperture 6513, the safety lock protrusion apertures 6514, the battery isolation protrusion aperture 6521, the safety lock actuator opening 6524, and pull-tab openings 6519. The needle aperture 6513 is configured to receive the needle 6216 when the medical injector 6000 is actuated. The safety lock protrusion apertures 6514 of the base 6510 receive the safety lock protrusions 6702 of the safety lock 6700 when the safety lock 6700 is coupled to the housing 6100 and/or the base 6510. The battery isolation protrusion aperture 6521 of the base 6510 receives the battery isolation protrusion 6197 of the cover 6190. The safety lock actuator opening 6524 receives the actuator 6724 of the safety lock 6700 when the safety lock 6700 is coupled to the housing 6100 and/or the base 6510. The pull-tab openings 6519 are configured to receive the pull-tabs 6710 of the safety lock 6700 when the safety lock 6700 is coupled to the housing 6100 and/or the base 6510.

The proximal surface 6511 of the base 6510 includes and/or is coupled to the release member 6530 and the guide members 6517. The release member 6530 includes a proximal end portion 6531 and a distal end portion 6532 and defines a channel 6533 between a system lock surface 6534 and the distal end portion 6532 (see e.g., FIG. 66). The system lock surface 6534 is disposed at the proximal end portion 6531, and is configured to engage the first latch protrusion 6315 of the medicament delivery mechanism 6300 when the medical injector 6000 is in the first configuration. Moreover, the system lock surface 6534 engages the first latch protrusion 6315 such that the system lock surface 6534 maintains the engagement of the first latch protrusion 6315 and the latch member notch 6120, as described above and shown in FIGS. 29 and 30. Similarly stated, the system lock surface 6534 of the release member 6530 applies a force to the first latch protrusion 6315 to maintain the first latch protrusion 6315 within the latch member notch 6120. In this manner, distal movement of the first movable member 6301 and/or the medicament delivery mechanism 6300 is limited. When the base 6510 is moved in a proximal direction, as described in further detail herein, the system lock surface 6534 moves in the proximal direction to disengage from the first latch protrusion 6315. In response, the first latch protrusion 6315 moves within the channel 6533 of the release member 6530 in a distal direction, as described in further detail herein. Similarly stated, upon actuation of the medicament injector 6000, a portion of the medicament delivery mechanism 6300 moves within the release member 6530.

The guide members 6517 of the base 6510 are configured to engage and/or slide within the base rail grooves 6114 of the housing 6100, as described above. As described above, the base connection knobs 6518 are configured to engage the base retention recesses 6134A, 6134B in a way that allows proximal movement of the base 6510 but limits distal movement of the base 6510 relative to the housing 6100.

Figure 67:
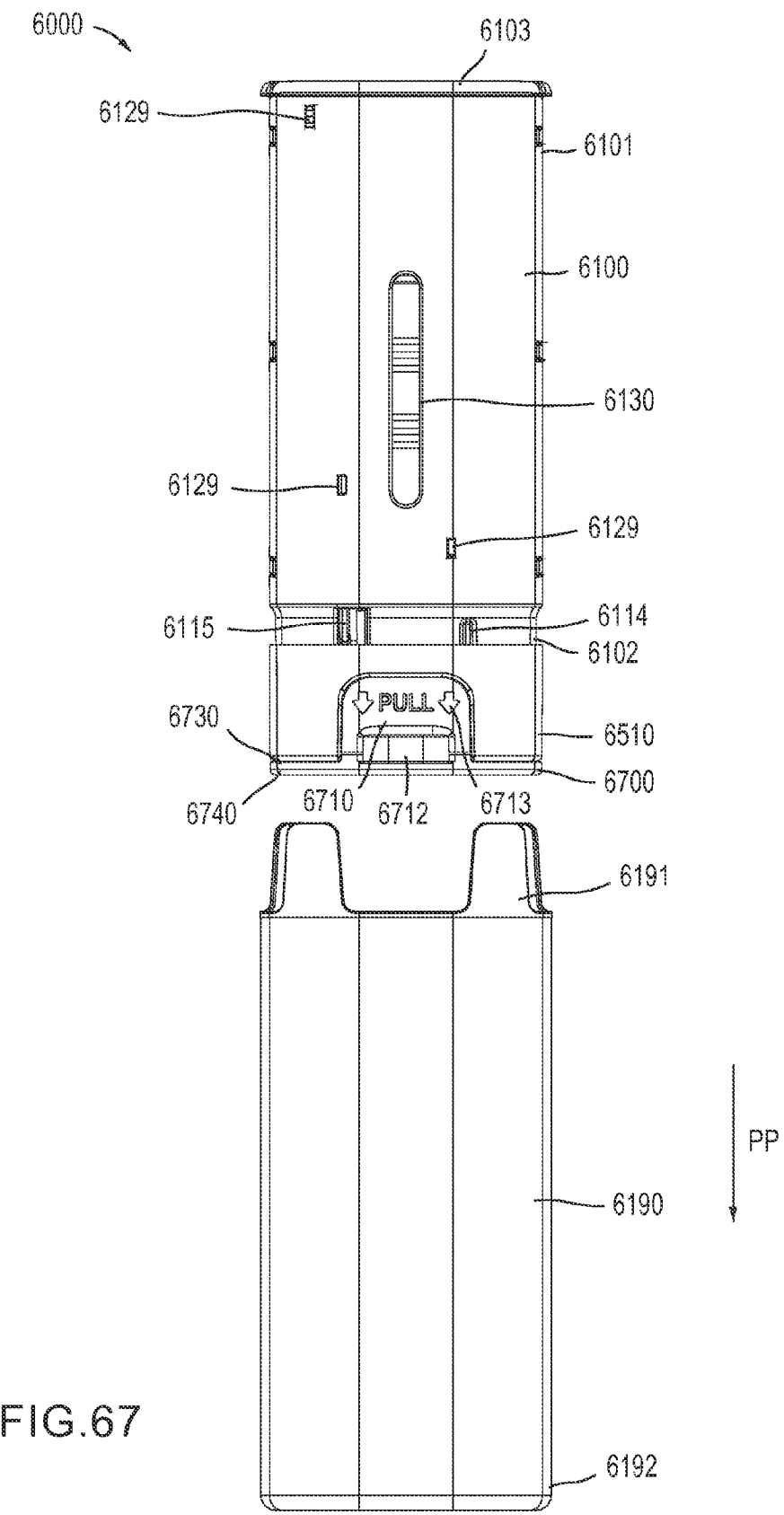
FIG. 67 is a back view of the medical injector illustrated in FIG. 18 in a second configuration.

As shown in FIG. 67, the medical injector 6000 is first enabled by moving the medicament delivery device 6000 from the first configuration to the second configuration by moving the cover 6190 from a first position to a second position. The cover 6190 is moved from the first position to the second position by moving it with respect to the housing 6100 in the direction shown by the arrow PP in FIG. 67. When the cover 6190 is moved with respect to the housing 6100 in the direction PP, the battery isolation protrusion 6197 is removed from the area between the battery clip 6910 and the second surface 6966 of the battery assembly 6962. In this manner, the battery assembly 6962 is operatively coupled to the electronic circuit system 6900 when the cover 6190 is removed, thereby providing power to the electronic circuit system 6900. Similarly stated, this arrangement allows the electronic circuit system 6900 to be actuated when the cover 6190 is removed.

When power is provided, as described above, the electronic circuit system 6900 can output one or more predetermined electronic outputs. For example, in some embodiments, the electronic circuit system 6900 can output an electronic signal associated with recorded speech to the audible output device 6956. Such an electronic signal can be, for example, associated with a .WAV file that contains a recorded instruction, instructing the user in the operation of the medical injector 6000. Such an instruction can state, for example, "Remove the safety tab near the base of the auto-injector." The electronic circuit system 6900 can simultaneously output an electronic signal to one and/or both of the LEDs 6958A, 6958B thereby causing one and/or both of the LEDs 6958A, 6958B to flash a particular color. In this manner, the electronic circuit system 6900 can provide both audible and visual instructions to assist the user in the initial operation of the medical injector 6000.

In other embodiments, the electronic circuit system 6900 can output an electronic output associated with a description and/or status of the medical injector 6000 and/or the medicament contained therein. For example, in some embodiments, the electronic circuit system 6900 can output an audible message indicating the symptoms for which the medicament should be administered, the expiration date of the medicament, the dosage of the medicament or the like.

In yet other embodiments, the electronic circuit system 6900 can output a wireless signal to a cell phone, computer, compliance tracking device, emergency dispatch system or the like. For example, in some embodiments, the electronic circuit system 6900 can output an wireless signal to a compliance tracking device, which receives the signal and monitors the activity (e.g., the arming of, the use of or the like) of the medical injector 6000.

In some embodiments, the medical injector 6000 can be repeatedly moved between the first configuration and the second configuration when the cover 6190 is moved repeatedly between the first position and the second position, respectively. Said another way, in some embodiments, the cover 6190 can be removed and replaced about the housing 6100 any number of times. When the cover 6190 is moved from the second position to the first position, the battery isolation protrusion 6197 is inserted between the battery clip 6910 and the second surface 6966 of the battery assembly 6962, deactivating the electronic circuit system 6900. When the cover is moved from the first position to the second position a second time, the electronic circuit system 6900 is once again activated. In other embodiments, the cover 6190 is configured to be removed from the housing only one time and the electronic circuit system 6900 is therefore configured output a single electronic output in response thereto, which, for example, can warn the user about the compromised sterility of the needle 6216.

Figure 68:
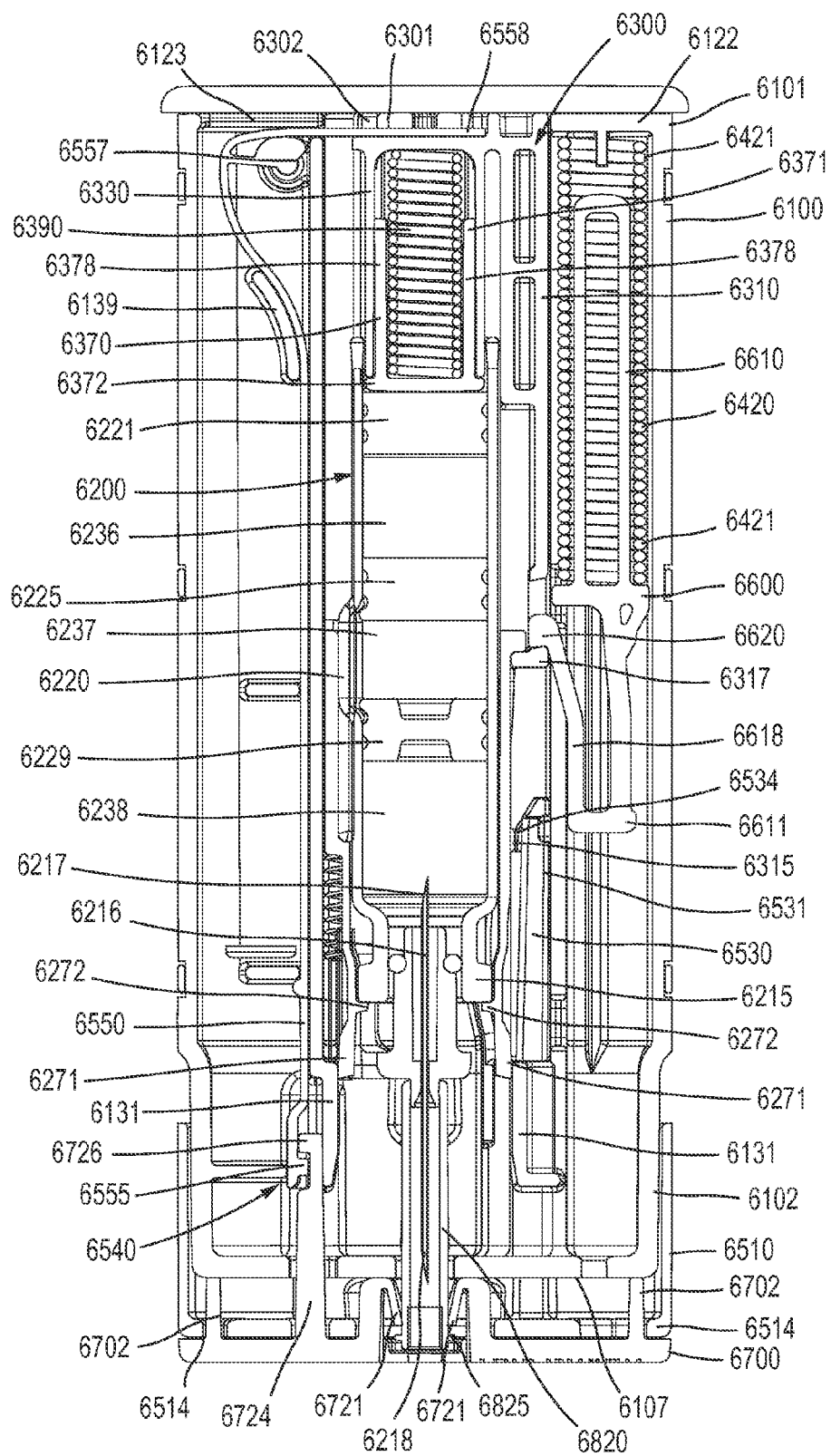
FIG. 68 is a front cross-sectional view of the medical injector illustrated in FIG. 18 in the second configuration.

After the cover 6190 is removed from the housing 6100, the medical injector 6000 is in the second configuration. As shown in FIG. 68, the medical injector 6000 is in a locked or pre-actuated position while in the second configuration. Thus, the safety lock protrusions 6702 of the safety lock 6700 are disposed within the safety lock protrusion openings 6514 of the base, and in contact with the distal surface 6107 of the housing 6100. With the safety lock 6700 coupled to the housing 6100 and/or the base 6510, the mixing actuator member 6550 is in a first position and/or configuration. As described above, the lock surface 6560 of the retention portion 6558 included in the mixing actuator member 6550 exerts a reaction force on the retention protrusions 6379 of the mixing piston 6370 (e.g., the second movable member 6370). In this manner, the mixing spring 6390 is maintained in the compressed configuration and the mixing piston 6370 remains in a first position, relative to the piston portion 6330 of the first movable member 6301. Therefore, the medicament container assembly 6200 remains in a first configuration (e.g., a pre-mixed configuration). In this configuration, the diluent volume 6236 is separated and/or fluidically isolated from the dry medicament volume 6237. Similarly, the dry medicament volume 6237 is substantially separated from the void volume 6238. The proximal end portion 6217 of the needle 6216 is disposed within the void volume 6238, and is therefore substantially isolated from the medicament. Furthermore, the distal end portion 6218 of the needle 6216 is disposed within the needle sheath 6820 such that a user is protected from a sharp point defined by the distal end of the needle 6216, and the sterility of the needle 6216 is maintained.

The medical injector 6000 can be moved from the second configuration (FIGS. 67 and 68) to a third configuration (FIGS. 69-72) by moving the safety lock 6700 from a first position to a second position. The safety lock 6700 is moved from a first position to a second position by moving the safety lock 6700 with respect to the housing 6100 in the direction shown by the arrow QQ in FIG. 69. When the safety lock 6700 is moved from the first position to the second position, the safety lock protrusions 6702 are no longer in contact with the distal surface 6107 of the housing 6100, and are removed from safety lock protrusion openings 6514 of the base, thereby enabling the medicament delivery mechanism 6300. Additionally, when the safety lock 6700 is removed from and/or moved relative to the housing 6100, the actuator 6724 of the safety lock 6700 also moves in the direction QQ to actuate the mixing actuator member 6550. More specifically, as described above (e.g., with respect to FIGS. 31, 62 and 64) the protrusion 6726 of the actuator 6724 is in contact with the engagement surface 6554 of the catch 6553; therefore, when the actuator 6724 is moved in the direction QQ, the protrusion 6726 exerts a first force $F_1$ on the engagement surface 6554 of the catch 6553 to move at least the distal end portion 6552 of the mixing actuator member 6550 in the direction QQ.

With the distal end portion 6552 of the mixing actuator member 6550 moved in the direction QQ, the protrusion 6555 of the mixing actuator member 6550 moves with relation to the first actuation portion 6926 of the electronic circuit system 6900, thereby moving the first switch 6972 from a first state (e.g., a state of electrical continuity) to a second state (e.g., a state of electrical discontinuity). When the protrusion 6555 moves the first switch 6972 of the electronic circuit system 6900 to the second state, the electronic circuit system 6900 can output one or more predetermined electronic outputs. For example, the protrusion 6555 can irreversibly move the first switch 6972 to the second state such that a processor (not shown) can output an electronic signal associated with recorded speech to the audible output device 6956. Such an electronic signal can be, for example, associated with a recorded message notifying the user of the status of the medical injector 6000. Such a status message can state, for example, "The needle guard has been removed and the mixing operation is no ongoing." The electronic circuit system 6900 can also simultaneously output an electronic signal to one and/or both of the LEDs 6958A, 6958B, thereby causing one and/or both of the LEDs 6958A, 6958B to start flashing, stop flashing, change color, or the like.

In some embodiments, the first actuation portion 6926 and the protrusion 6555 can be configured such that the protrusion 6555 must move a predetermined distance before the protrusion 6555 engages the boundary 6929 of the opening 6928. For example, in some embodiments, the protrusion 6555 must move approximately 0.62 inches before the protrusion 6555 engages the boundary 6929 of the opening 6928. In this manner, the safety lock 6700 can be moved slightly without irreversibly moving the first switch 6972 of the electronic circuit system 6900 to the second state. Accordingly, this arrangement will permit the user to inadvertently and/or accidentally move the safety lock 6700 without actuating the electronic circuit system 6900.

In some embodiments, the electronic circuit system 6900 can be configured to output the status message for a predetermined time period, such as, for example, five seconds. After the predetermined time period has elapsed, the electronic circuit system 6900 can output an audible message further instructing the user in the operation of the medical injector 6000. Such an instruction can state, for example, "The mixing operation is now complete. Place the base of the auto-injector against the patient's thigh. To complete the injection, press the base firmly against the patient's thigh." In some embodiments, the electronic circuit system 6900 can simultaneously output an electronic signal to one and/or both of the LEDs 6958A, 6958B, thereby causing one and/or both of the LEDs 6958A, 6958B to flash a particular color. In this manner, the electronic circuit system 6900 can provide both audible and/or visual instructions to assist the user in the placement and actuation of the medical injector 6000. In some embodiments, the electronic circuit system 6900 can be configured to repeat the instructions after a predetermined time period has elapsed.

In other embodiments, the output associated with the completion of the mixing operation (or any other operations described herein) need not be based on an elapsed time. For example, as described above, some such embodiments, the electronic circuit system 6900 can produce an output when the mixing event has ended based at least in part upon the location of a plunger within the medicament container.

As described above, in other embodiments, the medical injector 6000 can have a network interface device (not shown) configured to operatively connect the electronic circuit system 6900 to a remote device (not shown) and/or a communications network (not shown). In this manner, the electronic circuit system 6900 can send a wireless signal notifying a remote device that the safety lock 6700 of the medical injector 6000 has been removed and that the medical injector 6000 has been armed. In other embodiments, the electronic circuit system 6900 can send a wireless signal (e.g., a wireless 911 call) notifying an emergency responder that the medical injector 6000 has been armed.

The actuation of the mixing actuator member 6550 also actuates the mixing piston 6370. As described above, the protrusion 6726 of the actuator 6724 exerts the first force $F_1$ on the engagement surface 6554 of the catch 6553 such that at least a portion of the first force $F_1$ moves the mixing actuator member 6550 in the direction QQ. The mixing actuator guide 6119, the lower retention protrusions 6138, the upper retention protrusion 6139, and the upper mixing actuator plate 6123 of the first housing member 6110 (see e.g., FIG. 25) engage portions of the mixing actuator member 6550 to facilitate a desired motion, bending, flexing, or reconfiguration of at least a portion of the mixing actuator member 6550. This arrangement allows at least a portion of the mixing actuator member 6550 to pivot about the pivot protrusions 6557 disposed within the pivot protrusion apertures 6125 and 6155 of the housing, as shown by the arrow QQ' in FIG. 69. Furthermore, the upper retention protrusion 6139 defines a curved shape configured to engage the curved portion 6556 of the mixing actuator member 6550. Thus, the housing 6100 and/or the upper retention protrusion 6139 define a channel and/or track within which and/or against which a portion of the mixing actuator member 6550 can move, flex, and/or bend in a non-linear manner.

The arrangement of the portion of the mixing actuator member 6550 that defines the curved path 6556, the stiffening arm 6564, and the upper mixing actuator plate 6123 facilitate a transferring of a portion of the first force $F_1$ in the direction QQ into a second force $F_2$ in the direction RR, as shown in FIG. 70. Similarly stated, mixing actuator member 6550 is configured such that at least a portion of the first force $F_1$ exerted on the catch 6553 by the protrusion 6726 of the safety lock 6700 moves the retention portion 6558 in the direction RR. In some embodiments, the position of the pivot protrusions 6557, relative to the rest of the mixing actuator member 6550 and the stiffening arm 6564 are such that the transferring of the first force $F_1$ includes amplifying the first force $F_1$. More specifically, the length of the stiffening arm 6564 defines a first moment arm and the distance defined between the pivot protrusions 6557 and the retention portion 6558 defines a second moment arm, substantially smaller than the first moment arm. In this manner, a torque produced from the rotation about the pivot protrusions 6557 results in the amplification of the first force $F_1$ by the ratio of the length of the first moment arm to the length of the second moment arm.

By way of example, in some embodiments, the length of the first moment arm (e.g., the length of the stiffening arm 6564) can be four times as long as the length of the second moment arm (e.g., the length defined between the pivot protrusions 6557 and the retention portion 6558). Therefore, as a first force is applied in the direction QQ, the pivot motion of the mixing actuator member 6550 about the pivot protrusions 6557 results in a second force in the direction RR that is four times greater than the first force. Furthermore, this arrangement reduces the lateral translation of the retention portion 6558 (e.g., the translation of the portion of the mixing actuator member 6550 in the direction QQ is greater than the translation of the retention portion 6558 in the direction RR. In this manner, in some embodiments, the retention portion 6558 can be configured move in the direction RR with the second force $F_2$, resulting in a relatively fast movement of the retention portion 6558.

As shown in FIG. 70, the lateral motion of the retention portion 6558 disengages the lock surface 6560 from the retention protrusions 6379 of the mixing piston 6370. More specifically, with reference to FIG. 70, the retention portion 6558 is moved within the retention portion channel 6306 in the direction RR such that the retention protrusions 6379 disposed to the left of the alignment protrusion 6305 are at least momentarily positioned in alignment with the notches 6559 and the retention protrusions 6379 disposed to the right of the alignment protrusions 6305 are at least momentarily positioned adjacent to an end of the retention portion 6558. In this manner, the lock surface 6560 no longer exerts the reaction force on the distal surface of the retention protrusions 6379 to maintain the mixing spring 6390 in the first configuration (e.g., the compressed configuration). Therefore, when the retention portion 6558 moves laterally, the mixing spring 6390 expands to the second configuration and exerts a force $F_3$ to move the mixing piston 6370 in the distal direction, as indicated by arrow SS in FIG. 71.

Figure 71:
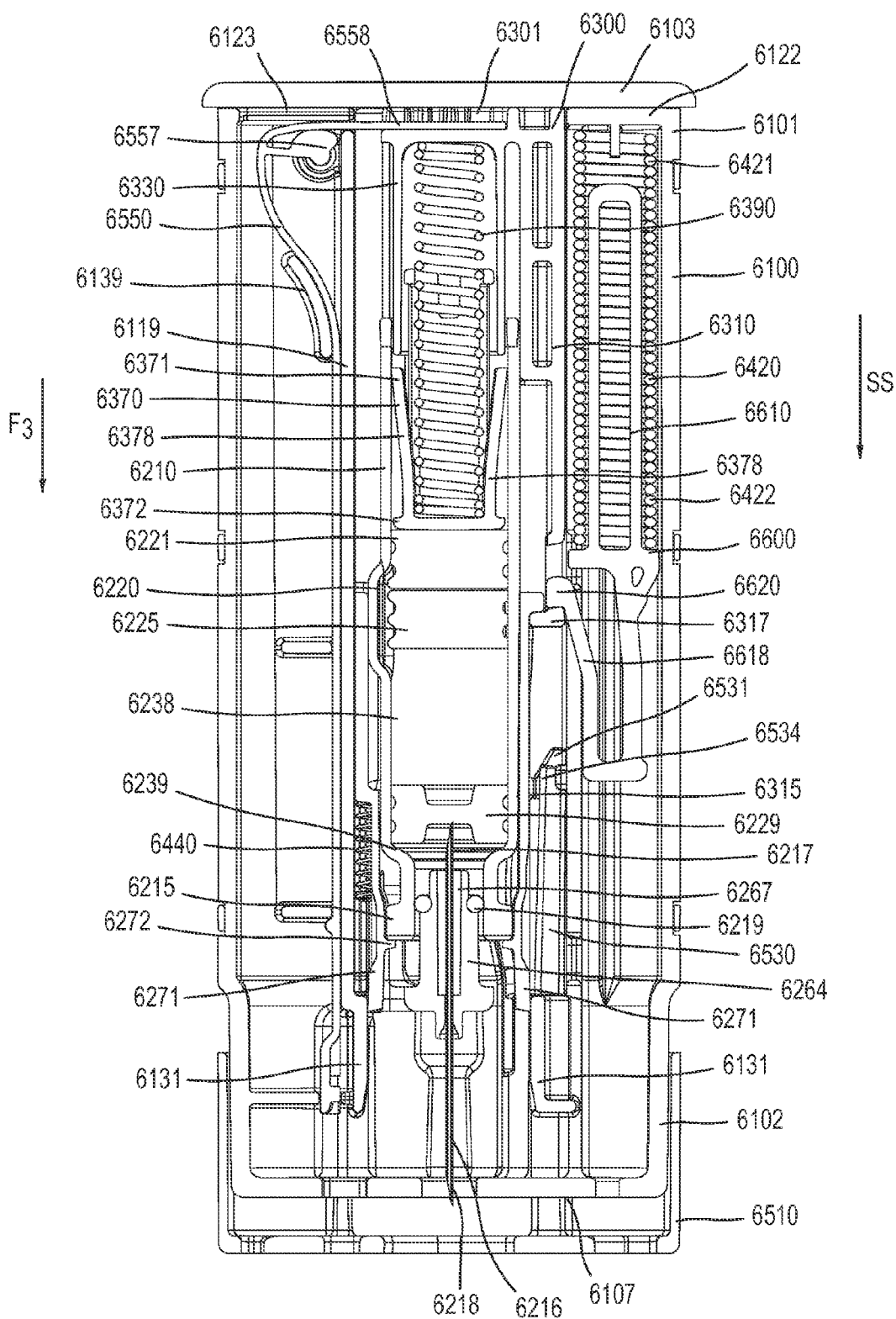
FIG. 71 is a front cross-sectional view of the medical injector illustrated in FIG. 18 in the third configuration.

With the mixing spring 6390 in the second configuration (e.g., the expanded configuration), much of the proximal end portion 6371 of the mixing piston 6370 is disposed outside of the opening 6333 defined by the piston portion 6330 of the first movable member 6301. Similarly stated, the proximal end portion 6371 of the mixing piston 6370 is disposed in a distal position relative to the distal end 6334 of the piston portion 6330 of the first movable member 6301. As described above, with the mixing piston 6370 outside of the piston portion 6330, the tabs 6378 (i.e., retention members or portions) included in the walls 6376 of the mixing piston 6370 expand to an undeformed position, as shown in FIG. 71. In this manner, the tabs 6378 can engage the distal end 6334 of the piston portion 6330 after the first movable member 6301 is moved to a second position, as described in further detail herein. More particularly, as shown in FIG. 73, the tabs 6378 (i.e., retention members or portions) are configured to engage the distal end 6334 of the piston portion 6330 to limit movement of the mixing piston 6370 relative to the first movable member 6301 during the needle insertion and/or injection operations.

Figure 72:
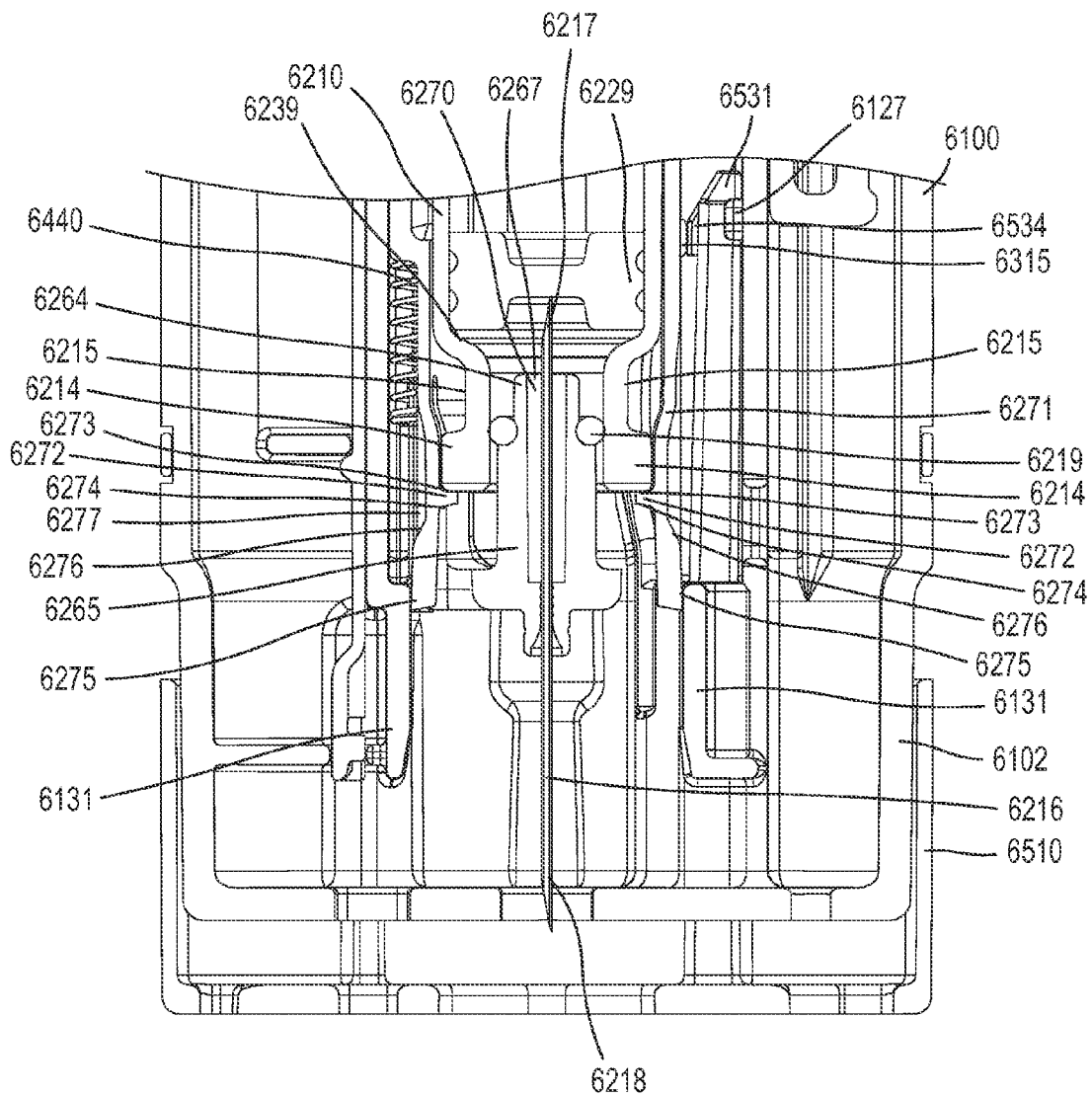
FIG. 72 is an enlarged view of a portion of the front cross-section illustrated in FIG. 71.

The distal movement of the mixing piston 6370 begins the mixing event, as shown in FIGS. 71 and 72. More specifically, the distal surface 6375 of the mixing piston 6370 engages the proximal surface 6222 of the first elastomeric member 6221 and transfers a portion of the force $F_3$ exerted by the mixing spring 6390 to move at least the first elastomeric member 6221 in the distal direction. The arrangement of the elastomeric members within the medicament container 6210 is such that the portion of the force $F_3$ exerted on the first elastomeric member 6221 moves the first elastomeric member 6221, the second elastomeric member 6225, and the third elastomeric member 6229 in the distal direction. Expanding further, the constituents in the diluent volume 6236, the dry medicament volume 6237, and the void volume 6238 are such that when the force $F_3$ is applied, the volume of the void volume 6238 is reduced. For example, in some embodiments, at a portion of a gas within the void volume 6238 is evacuated from the void volume 6238. In some embodiments, the gas can exit the void volume 6238 via the distal end portion 6213 of the medicament container 6210. In some embodiments, the gas can exit the void volume 6238 via the needle 6216. In this manner, the third elastomeric member 6229 is moved in the distal direction to contact a distal shoulder 6239 of the medicament container 6210. As shown in FIG. 72, the distal shoulder 6239 engages the distal surface 6231 of the third elastomeric member 6229 to stop the distal movement of the third elastomeric member 6229 such that the proximal end portion 6217 of the needle 6216 does not substantially puncture through the thickness T of the third elastomeric member 6229.

Concurrently, the application of the force $F_3$ results in the distal movement of the first elastomeric member 6221 and the second elastomeric member 6225. Therefore, as shown in FIG. 71, the diluent volume 6236 and the dry medicament volume 6237 are placed in fluid communication via the bypass 6220 such that the diluent within the diluent volume 6236 is transferred to the dry medicament volume 6237. In this manner, the diluent can mix with the lyophilized medicament disposed within the dry medicament volume 6237 to reconstitute the medicament for injection.

After the mixing event, the medical injector 6000 can be moved from the third configuration (FIG. 69-72) to a fourth configuration (FIGS. 73 and 74) by moving the base 6510 from a first position to a second position. Similarly stated, the medical injector 6000 can be actuated by the system actuator assembly 6500 by moving the base 6510 proximally relative to the housing 6100. The base 6510 is moved from its first position to its second position by placing the medical injector 6000 against the body of the patient and moving the base 6510 with respect to the housing 6100 in the direction shown by the arrow TT in FIG. 73.

When the base 6510 is moved from the first position to the second position, the system actuator assembly 6500 actuates the medicament delivery mechanism 6300, thereby placing the medical injector 6000 in its fourth configuration (i.e., the needle insertion configuration), as shown in FIGS. 73 and 74. More specifically, the proximal movement of the system actuator assembly 6500 and/or the base 6510 moves the release member 6530 in the proximal direction within the housing 6100, thereby allowing the first latch protrusion 6315 to be disengaged from the system lock surface 6534 of the proximal end portion 6533 of the release member 6530. Similarly stated, when the system actuator assembly 6500 is moved in the proximal direction, the system lock surface 6534 disengages the first latch protrusion 6315. Moreover, when the system lock surface 6534 moves in the proximal direction relative to the first latch protrusion 6315, the first latch protrusion 6315 moves and/or deforms substantially laterally into the channel 6533 defined by the release member 6530.

When the first latch protrusion 6315 is disposed within the channel 6533, the force applied by the system lock surface 6534 of the base 6510 to maintain the first latch protrusion 6315 within the latch member notch 6120 is removed and the first latch protrusion 6315 is allowed to disengage the latch member notch 6120. Therefore, the engagement surface 6109 of the latch member notch 6120 no longer applies the reaction force to the first latch protrusion 6315; thus, the spring 6420 is allowed to expand. As described above, the proximal end portion 6421 of the spring 6420 is in contact with the upper spring plate 6122 of the first housing member 6110 such that the spring 6420 expands in the direction shown be the arrow UU in FIG. 73. With the distal end portion 6422 of the spring 6420 in contact with the spring seat 6615 of the transfer member 6600, a force $F_4$ produced by the expansion of the spring 6420 is applied to the transfer member 6600, which moves the transfer member 6600 in the direction shown by the arrow UU. In this manner, the latch 6620 of the transfer member 6600 transfers at least a portion of the force $F_4$ to the second latch protrusion 6317 of the latch portion 6310 of the first movable member 6301 such that the portion of the force moves the medicament delivery mechanism 6300 in the distal direction, shown by the arrow UU in FIG. 73. Thus, the first movable member 6301 and the transfer member 6600 move together distally within the housing 6100.

When the medicament delivery mechanism 6300 is moving distally, the piston portion 6330 of the first movable member 6301 applies a portion of the force $F_4$ to the medicament container 6210. More specifically, the distal end 6334 of the piston portion 6330 engages the latches 6378 of the mixing portion 6370. With the latches 6378 in the extended position (described above), the piston portion 6330 can transfer a portion of the force $F_4$ to the mixing piston 6370 such that the mixing piston 6370 further transfers a portion of the force $F_4$ to the first elastomeric member 6221. With the first elastomeric member 6221, the second elastomeric member 6225, and the third elastomeric member 6229 in their respective second positions, the portion of the force $F_4$ transferred to the first elastomeric member 6221 moves the medicament container assembly 6200 within the housing 6100 to a third configuration. Expanding further, the mixed medicament contained within the mixed volume 6237 is such that the medicament is a substantially incompressible liquid; thus the portion of the force $F_4$ acts to move the medicament container assembly 6200 in the distal direction rather than moving the first elastomeric member 6221, the second elastomeric member 6225, and/or the third elastomeric member 6229 within the medicament container 6210.

As described above, the portion of the force $F_4$ exerted by the piston portion 6330 and/or the mixing piston 6370 moves the medicament container assembly 6200 in the distal direction. As shown in FIG. 72, when the medicament container assembly 6200 is in the first position (e.g., prior to being moved by the portion of the force $F_4$), an engagement surface 6275 of the needle insertion tabs 6271 included in the carrier 6260 are in contact with the carrier engagement surface 6131 included in the first housing member 6110. In this configuration, the flanged end 6214 of the medicament container 6210 is disposed on a proximal surface 6273 of the container shoulder 6272. Therefore, when the portion of the force $F_4$ is exerted on the first elastomeric member 6221, the force is transferred through the medicament container 6210 to the proximal surface 6273 of the container shoulder 6272. Thus, a portion of the force $F_4$ is exerted on the container shoulder 6272 to move the carrier 6260 in the distal direction (FIGS. 73 and 74).

As described above, when the carrier 6260 and/or medicament container assembly 6200 moves to the second position, the protrusion 6279 of the electronic engagement portion 6278 actuates the electronic circuit 6900 to trigger a predetermined output or sequence of outputs. When the protrusion 6279 is moved in the distal direction relative to the opening 6945, the second switch 6973 is moved from a first state (e.g., a state of electrical continuity) to a second state (e.g., a state of electrical discontinuity). When the protrusion 6279 moves the second switch 6973 of the electronic circuit system 6900 to the second state, the electronic circuit system 6900 can output one or more predetermined electronic outputs.

For example, in some embodiments, the electronic circuit system 6900 can output an electronic signal associated with recorded speech to the audible output device 6956. Such an electronic signal can be, for example, associated with an audible countdown timer, instructing the user on the duration of the injection procedure. Said another way, if it takes, for example, ten seconds to complete an injection, an audible countdown timer can count from ten to zero ensuring that the user maintains the medical injector 6000 in place for the full ten seconds. In other embodiments, the electronic signal can be, for example, associated with a recorded message notifying the user that the injection is complete, instructing the user on post-injection disposal and safety procedures, instructing the user on post-injection medical treatment or the like. Such a status message can state, for example, "The injection is now complete. Please seek further medical attention from a doctor." The electronic circuit system 6900 can also simultaneously output an electronic signal to one and/or both LEDs 6958A, 6958B, thereby causing one and/or both LEDs 6958A, 6958B to stop flashing, change color or the like, to provide a visual indication that the injection is complete. In other embodiments, the electronic circuit system 6900 can send a wireless signal notifying a remote device that the injection is complete. In this manner, a patient's compliance can be monitored.

As shown in FIG. 74, the carrier 6260 moves to a second position within the housing 6100 during the needle insertion operation. With the carrier 6260 in the second position, a distal surface 6296 of the carrier 6260 contacts the housing 6100, thereby limiting the distal movement of the carrier 6260. Furthermore, with the carrier 6260 in the second position, the carrier engagement surface 6131 is disposed within a recesses 6277 defined by the needle insertion tabs 6271. With the carrier engagement surface 6131 disposed within the recesses 6277, the needle insertion tabs 6271 return to an undeformed configuration, as described above. In the undeformed configuration, the needle insertion tabs 6271 extend such that the flanged end 6214 is no longer in contact with the container shoulders 6272. Thus, the portion of the force $F_4$ applied to the first elastomeric member 6221 moves the medicament container 6210 in the distal direction, relative to the carrier 6260.

When the medicament container 6210 moves in the distal direction relative to the carrier 6260, the medicament container 6210 moves distally about the needle hub 6264 such that the upper portion 6267 of the needle hub 6264 is disposed within the distal counter bore 6234 of the third elastomeric member 6229. In this manner, the proximal end portion 6217 of the needle 6216 punctures through the thickness T of the third elastomeric member 6229 and the medical injector 6000 can be placed in a fifth configuration (i.e., the medicament delivery configuration).

Figure 75:
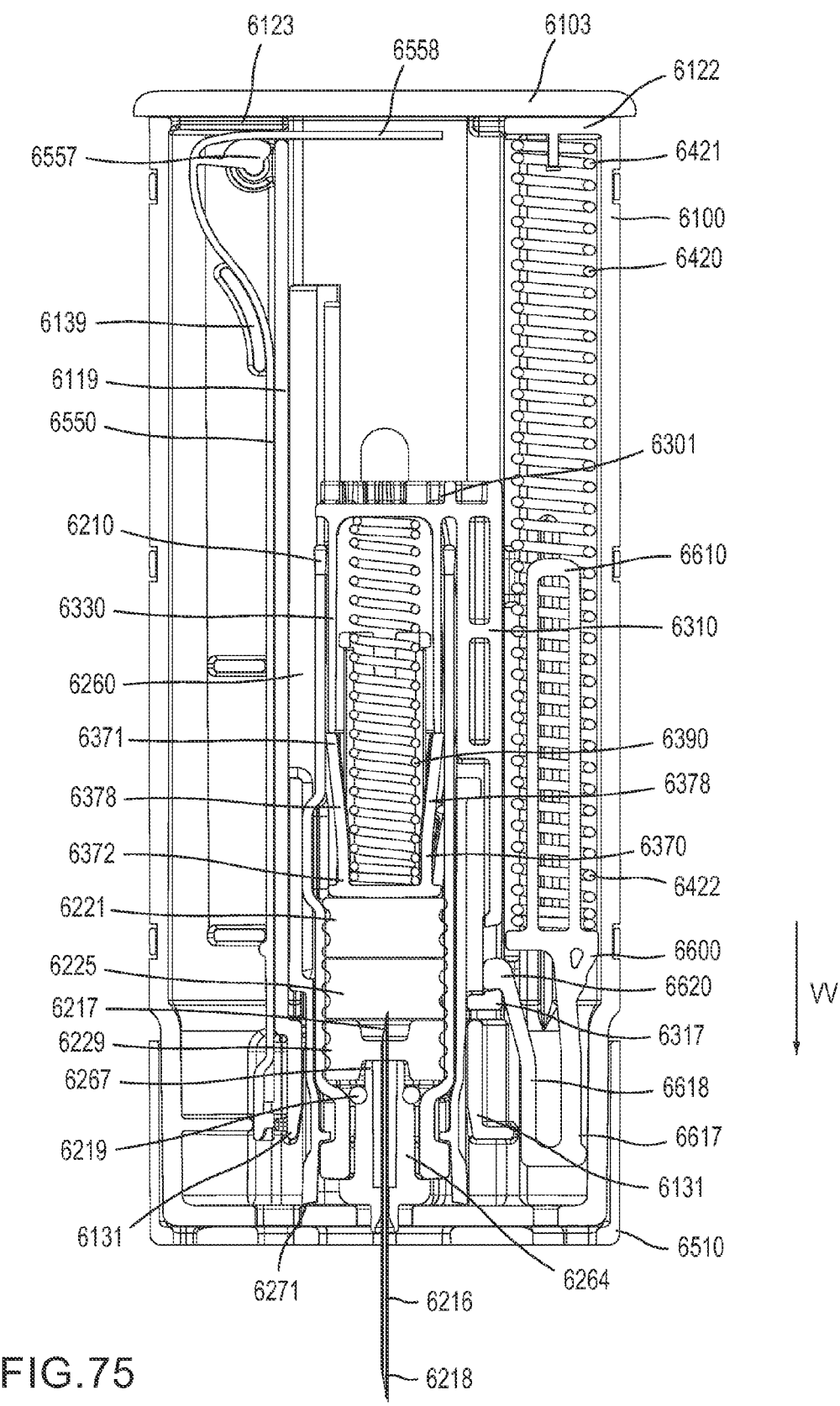
FIG. 75 is a front cross-sectional view of the medical injector illustrated in FIG. 18 in a fifth configuration (i.e., the injection configuration).

The medical injector 6000 is placed in the fifth configuration when the proximal end portion 6217 of the needle 6216 is disposed within the mixing volume 6237 and a portion of the force $F_4$ is exerted on the first elastomeric member 6221, as shown in FIG. 75. With the medicament container 6210 and the carrier 6260 in the second position within the housing 6100 (e.g., moved in the distal direction), the portion of the force $F_4$ exerted on the first elastomeric member 6221 can move the first elastomeric member 6221 and the second elastomeric member 6225 from the second position to a third position within the medicament container 6210. More specifically, the mixing piston 6370 and/or piston portion 6330 exerts the portion of the force $F_4$ on the proximal surface 6222 of the first elastomeric member 6221 as indicated by arrow VV in FIG. 75 to move the first elastomeric member 6221 and the second elastomeric member 6225 to the third position. In this manner, the medicament disposed within the dry medicament volume 6237 (e.g., the volume defined between the distal surface 6227 of the second elastomeric member 6225 and the proximal surface 6230 of the third elastomeric member 6229) is transferred to the needle 6216 and injected into the body of the patient.

When the spring 6420 fully expands, the medicament delivery mechanism 6300 moves in the distal direction to fully inject the medicament within the medicament container 6210. Additionally, when the spring 6420 is fully expanded and/or when the medicament delivery mechanism 6300 has moved a desired distance within the housing 6100, the guide protrusion 6624 of the transfer member 6600 engages the lower notch 6121 of the housing 6100 (see e.g., FIG. 25) to place the transfer member 6600 in the second configuration. Expanding further, the guide protrusion 6624 is aligned with the lower notch 6121 such that the guide protrusion 6624 moves through the lower notch 6121 to move the transfer member 6600 to the second position. As described above, when the guide protrusion 6624 moves through the lower notch 6121, the bendable portion 6622 of the transfer member 6600 bends (e.g., returns to an undeformed position), thereby placing the transfer member 6600 in its second configuration, as shown in FIG. 76. In this manner, the latch 6620 can be disengaged from the second latch protrusion 6317. Similarly stated, the spring 6420 and/or the transfer member 6600 are decoupled from the medicament delivery mechanism 6300. With the latch arm 6618 disengaged from the latch portion 6310, the medical injector 6000 can be moved from the fifth configuration to the sixth configuration (i.e., the retraction configuration).

With the transfer member 6600 disengaged from the medicament delivery mechanism 6300, the medicament container assembly 6200 and the medicament delivery mechanism 6300 are configured to move within the housing 6100 in the direction shown by the arrow WW in FIG. 76 in response to a force exerted by the retraction member 6440 (e.g., the retraction spring). Similarly stated, with the medicament delivery mechanism 6300 disengaged from the transfer member 6600 and/or the spring 6420, the force $F_4$ is no longer applied to the medicament delivery mechanism 6300. In this manner, the retraction member 6440 is configured to expand in the direction of the arrow WW to apply a retraction force to the medicament container assembly 6200. Similarly stated, with the portion of the force $F_4$ configured to compress the retraction spring 6440 removed, the retraction member 6440 expands, returning to its uncompressed (i.e., non-deformed) configuration.

During the retraction operation, the retraction spring 6440 exerts a retraction force on the retraction spring surface 6284 to move the carrier 6260 in the direction WW. The proximal movement of the carrier 6260 (e.g., the retraction) places the carrier engagement surface 6131 in contact with an angled surface 6276 of the needle insertion tabs 6271. In this manner, the angled surface 6276 is configured to slide relative to the carrier engagement surface 6131 as the carrier 6260 moves in the proximal direction in response to the retraction force exerted by the retraction member 6440. As the carrier 6260 continues to move in the proximal direction the engagement surface 6275 is placed into contact with the carrier engagement surface 6131 such that the needle insertion tabs 6271 are placed in the deformed configuration (e.g., non-extended configuration). Therefore, the container shoulders 6272 move closer together to maintain the flanged end 6214 of the medicament container 6210 between a distal surface 6274 of the container shoulder 6272 and a proximal surface 6297 of the container-mounting portion 6263. In this manner, the medicament container 6210 is coupled to the carrier 6260 and a portion of the retraction force moves the medicament container 6210 in the proximal direction. This motion, removes the needle 6216 from the target location of the patient and retracts the needle into the housing 6100, as shown in FIG. 76.

While specific components are discussed above with respect to the medical injector 6000, in other embodiments, any of the medicament delivery devices and/or medical injectors described herein can include components that are modified and/or removed from those shown and described above with respect to the medical injector 6000. Similarly stated, in other embodiments, a medical injector can include different, more or fewer components than are shown in the medical injector 6000 without substantially changing the mixing and/or medicament injection event. For example, FIGS. 77-105 show a medical injector 7000, according to an embodiment.

Figure 77:
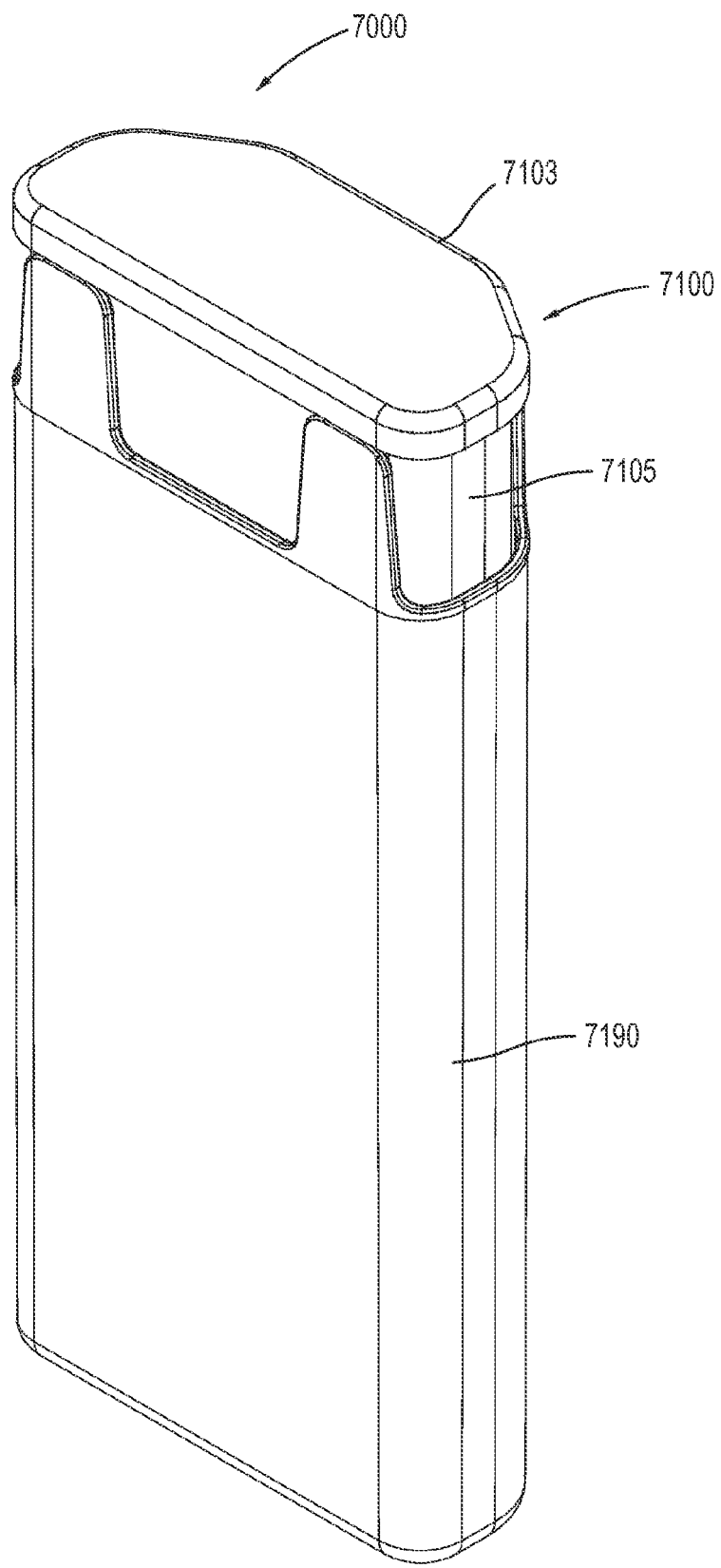
FIG. 77 is a front perspective view of a medical injector according to an embodiment, in a first configuration.
Figure 78:
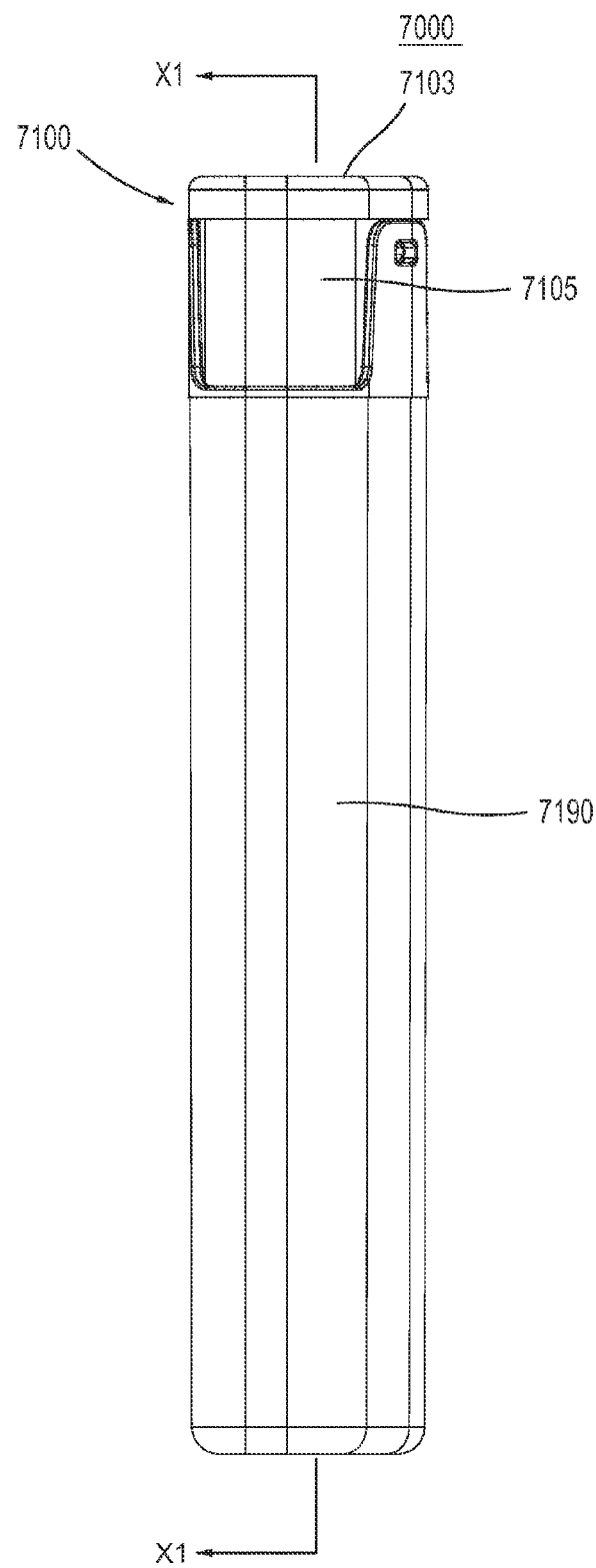
FIG. 78 is a side view of the medical injector illustrated in FIG. 77.
Figure 79:
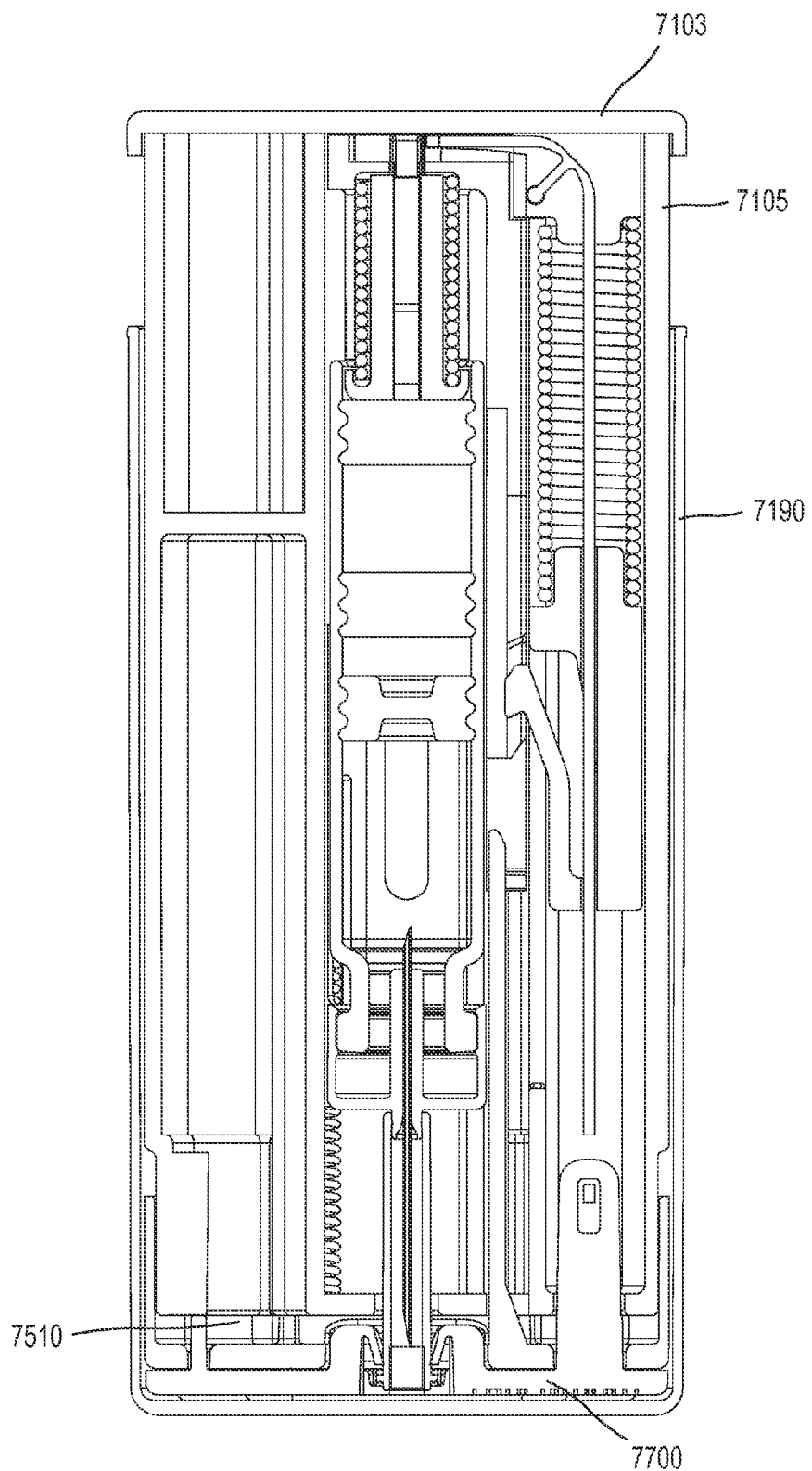
FIG. 79 is a cross-sectional view taken along line X1-X1 of the medical injector illustrated in FIG. 78.

FIG. 77 is a perspective view, FIG. 78 is a side view, and FIG. 79 is a cross-sectional view taken along line X1-X1, of an injector 7000 in a first configuration. The injector 7000 includes a housing 7100 including a body 7105 and a proximal cap 7103. The injector 7000 includes a case 7190 and a safety lock 7700 (shown in FIG. 80). The case 7190 and the safety lock 7700 can be configured to prevent damage to the injector 7000, to prevent the accidental actuation of the injector, to identify the contents of the injector 7000, and/or to initiate an electronic output during operation of the injector, as described in further detail herein.

Figure 80:
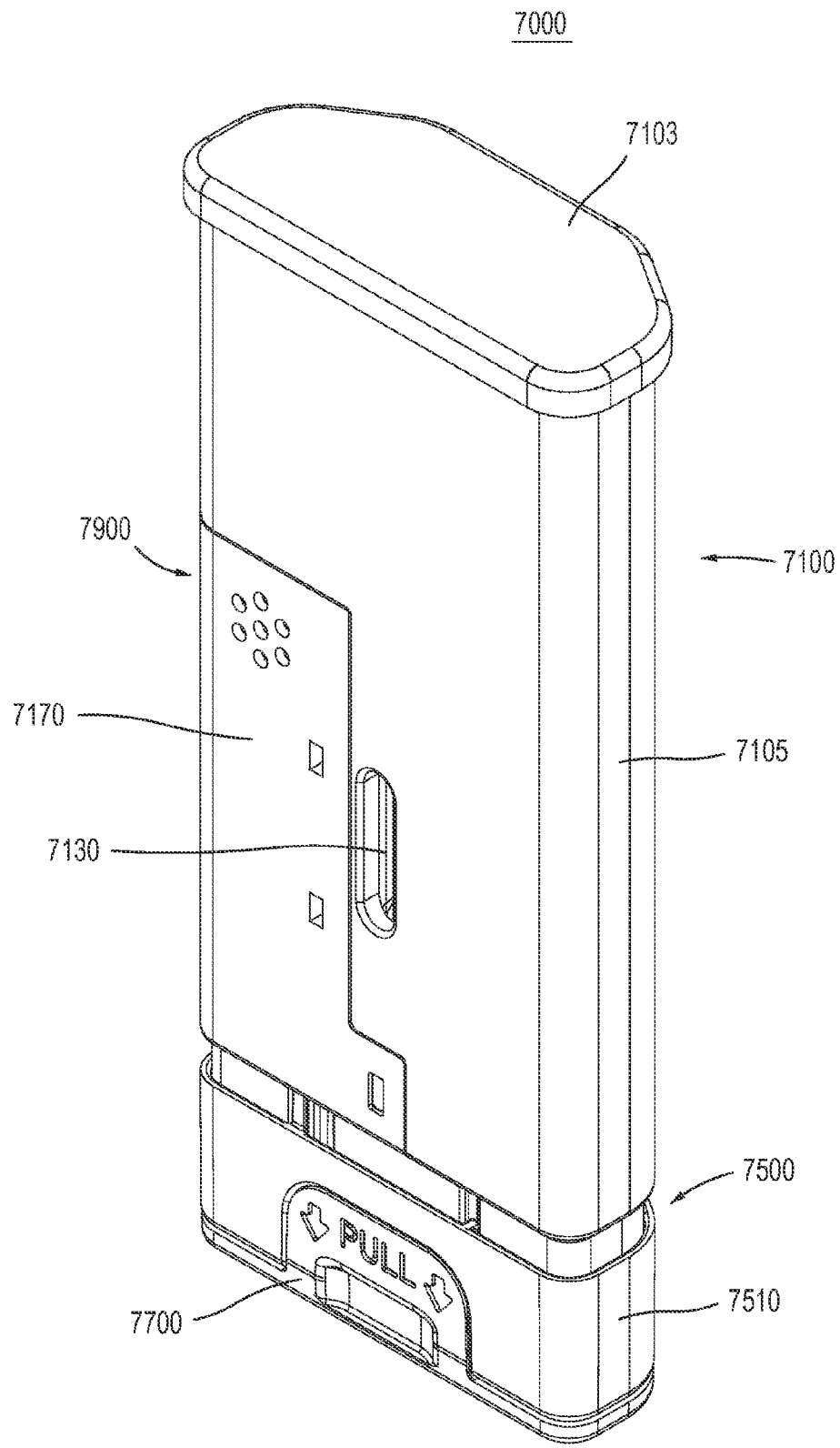
FIG. 80 is a front perspective view of the medical injector illustrated in FIG. 77 in a second configuration.
Figure 81:
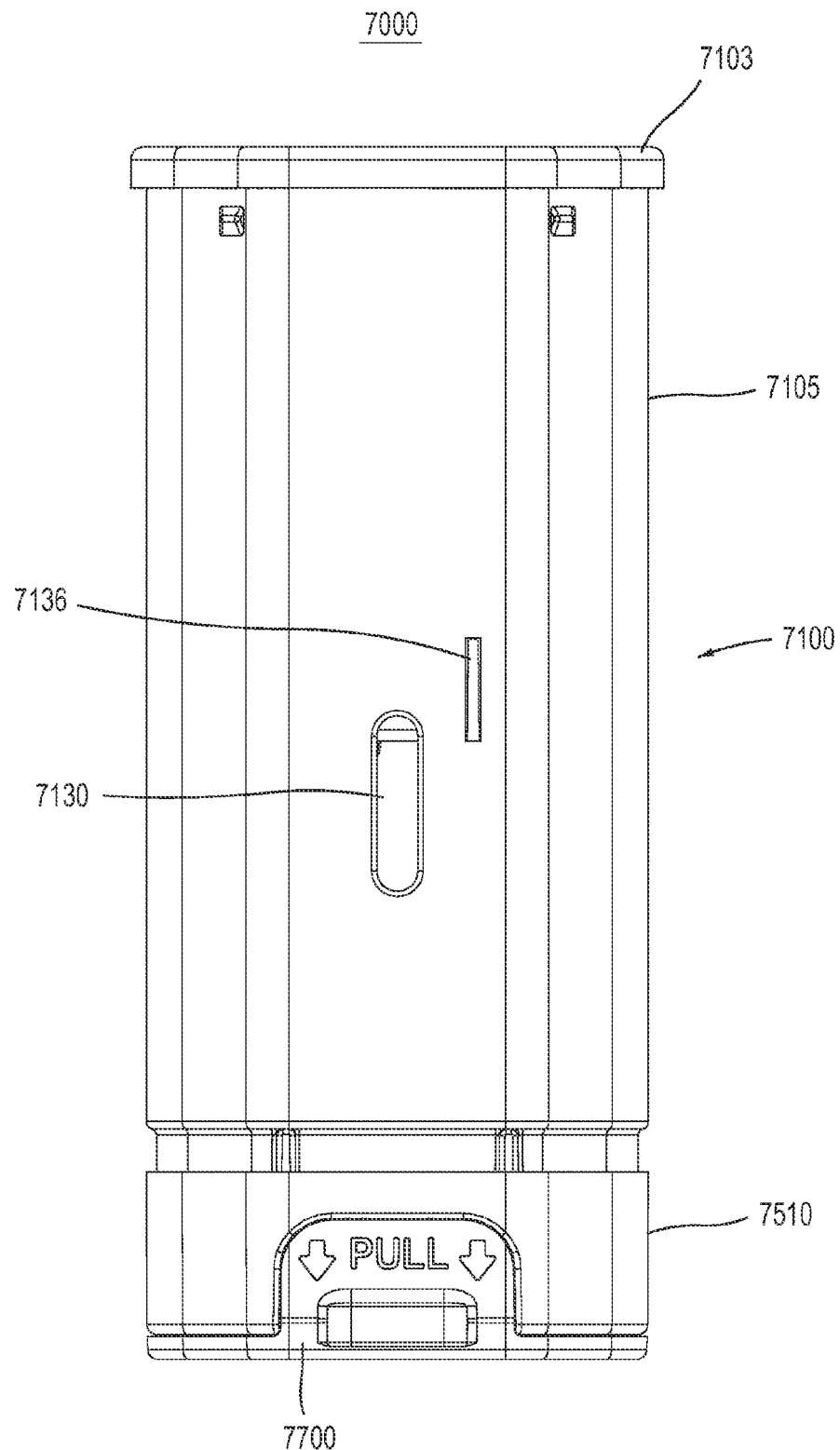
FIG. 81 is a rear view of the medical injector illustrated in FIG. 77 in the second configuration.
Figure 82:
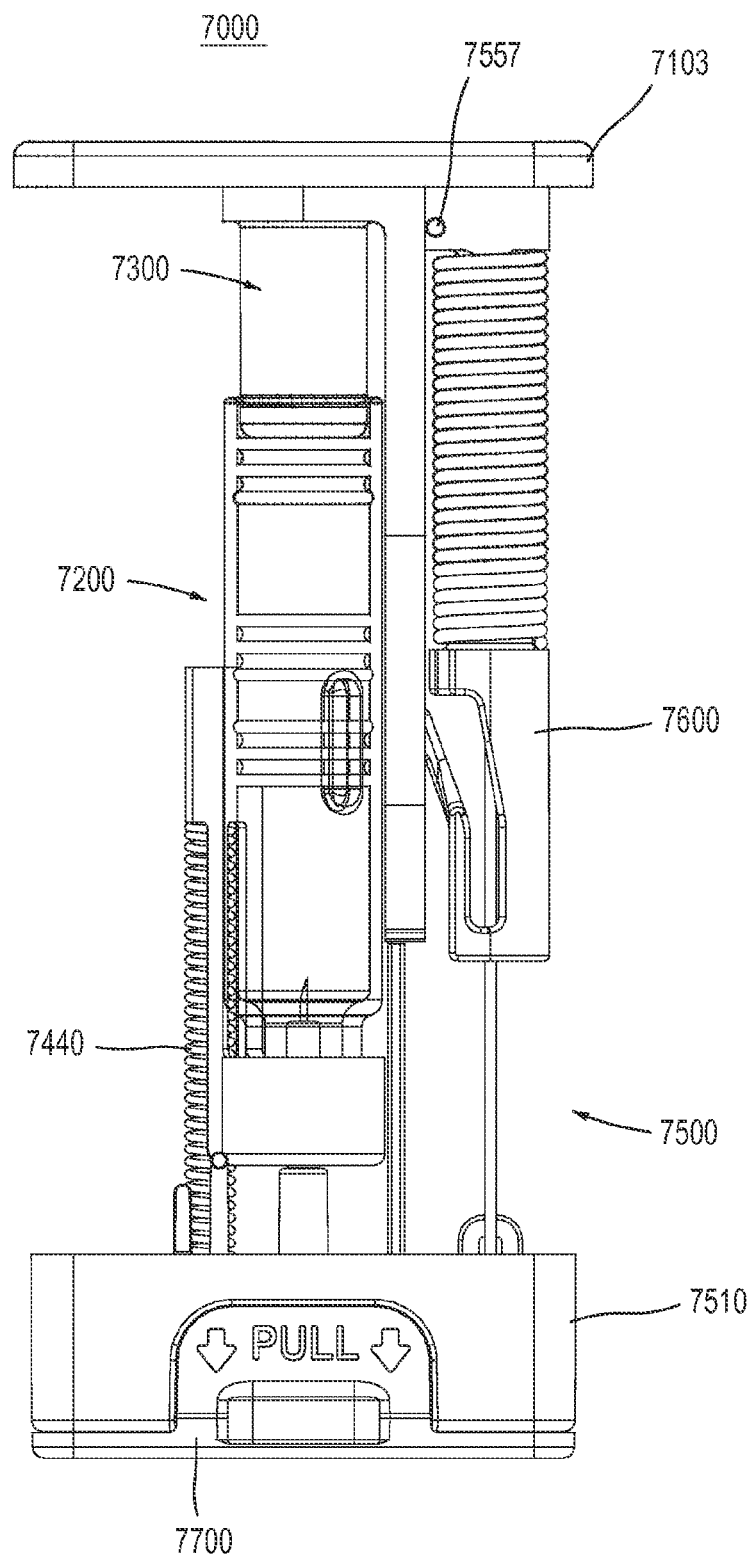
FIG. 82 is a front view of a portion of the medical injector illustrated in FIG. 77 in the second configuration.
Figure 94:
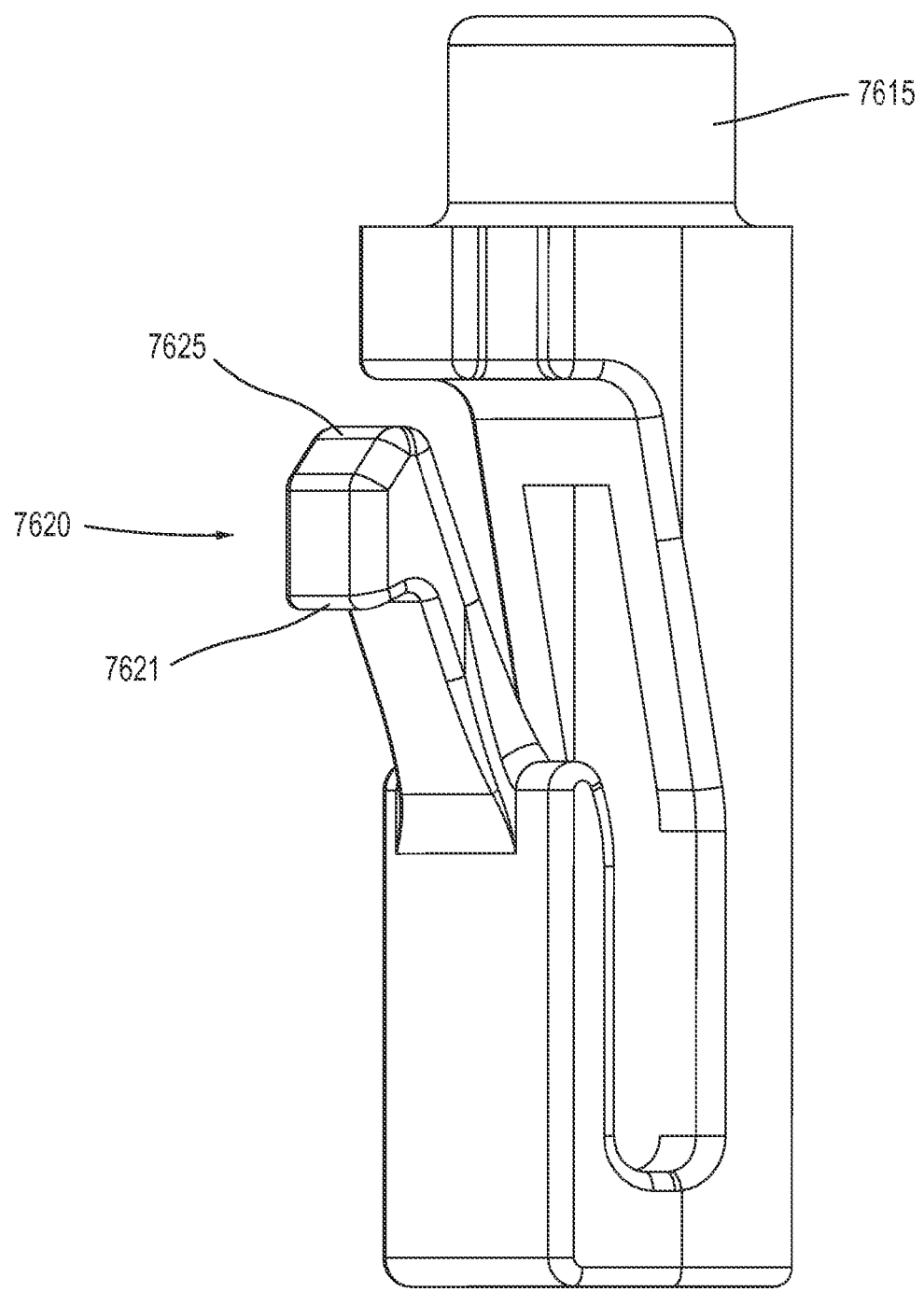
FIG. 94 is a perspective view of the transfer member illustrated in FIG. 90.
Figure 95:
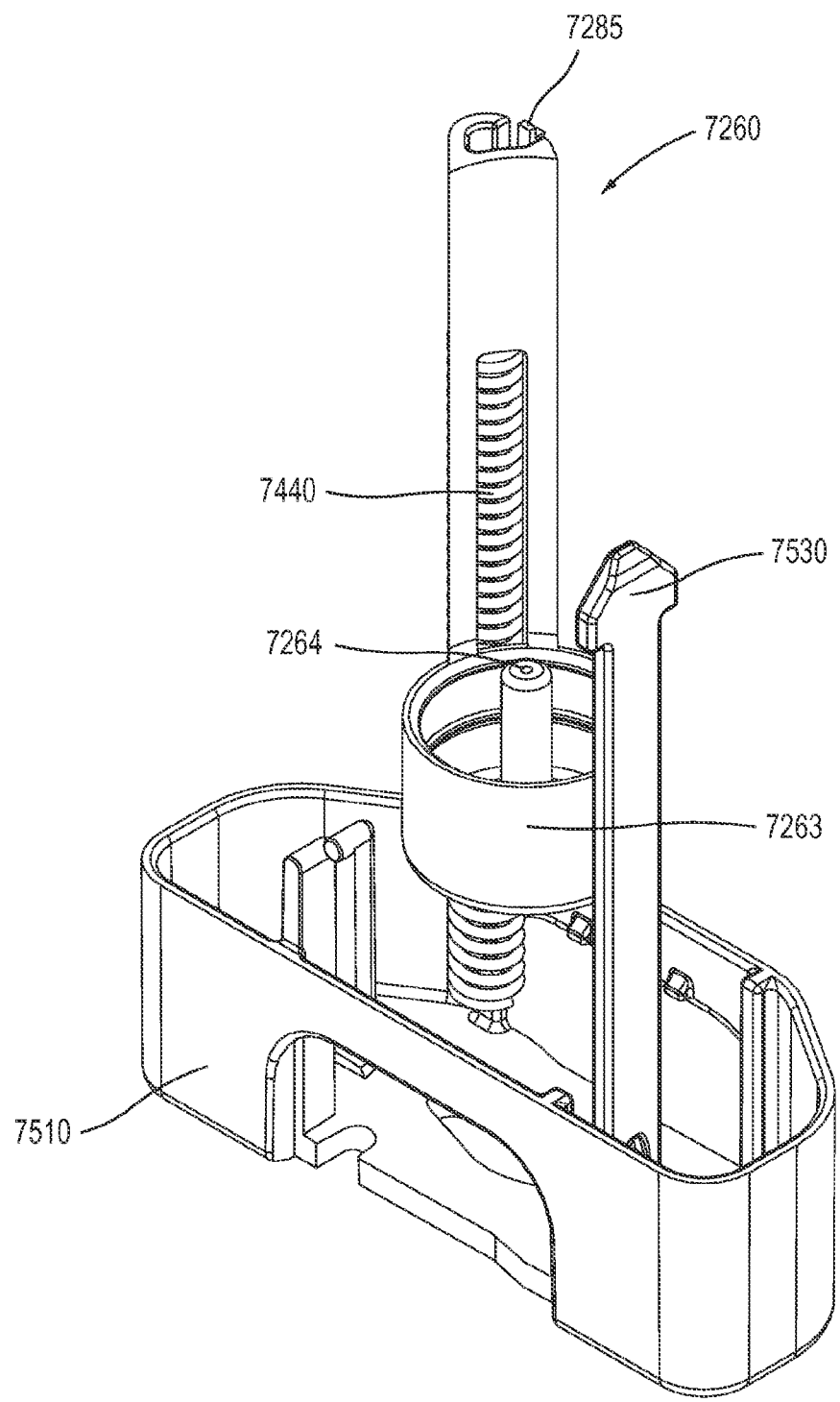
FIG. 95 is a perspective view of a portion of the medical injector of FIG. 77 illustrating a retraction member.

FIG. 80 is a rear perspective view, and FIG. 81 is a rear view, of the injector 7000 in a second configuration (e.g., with the case 7190 removed). FIG. 82 is a front view of the injector 7000, shown without the body 7105 to more clearly show the components disposed within the housing 7100, as described below. The injector 7000 includes a system actuator assembly 7500 having components (including the base 7510) configured to initiate an injection and/or mixing of a medicament contained within the injector 7000. The injector 7000 includes an electronic assembly 7900 (as shown in FIGS. 96-99) configured to provide at least one electronic output associated with injection and/or mixing. The housing 7100 can include openings configured to provide an indication of a status to a user of the injector 7000 and/or to interact with the internal components of injector 7000, specifically, the housing 7100 includes a status window 7130 and a catch 7136. The injector 7000 includes a medicament container assembly 7200 (as shown in FIGS. 82-86), a medicament delivery mechanism 7300 (as shown in FIGS. 86-93), a transfer member 7600 (as shown in FIGS. 93 and 94), and a retraction member 7440 (as shown in FIG. 95).

Figure 83:
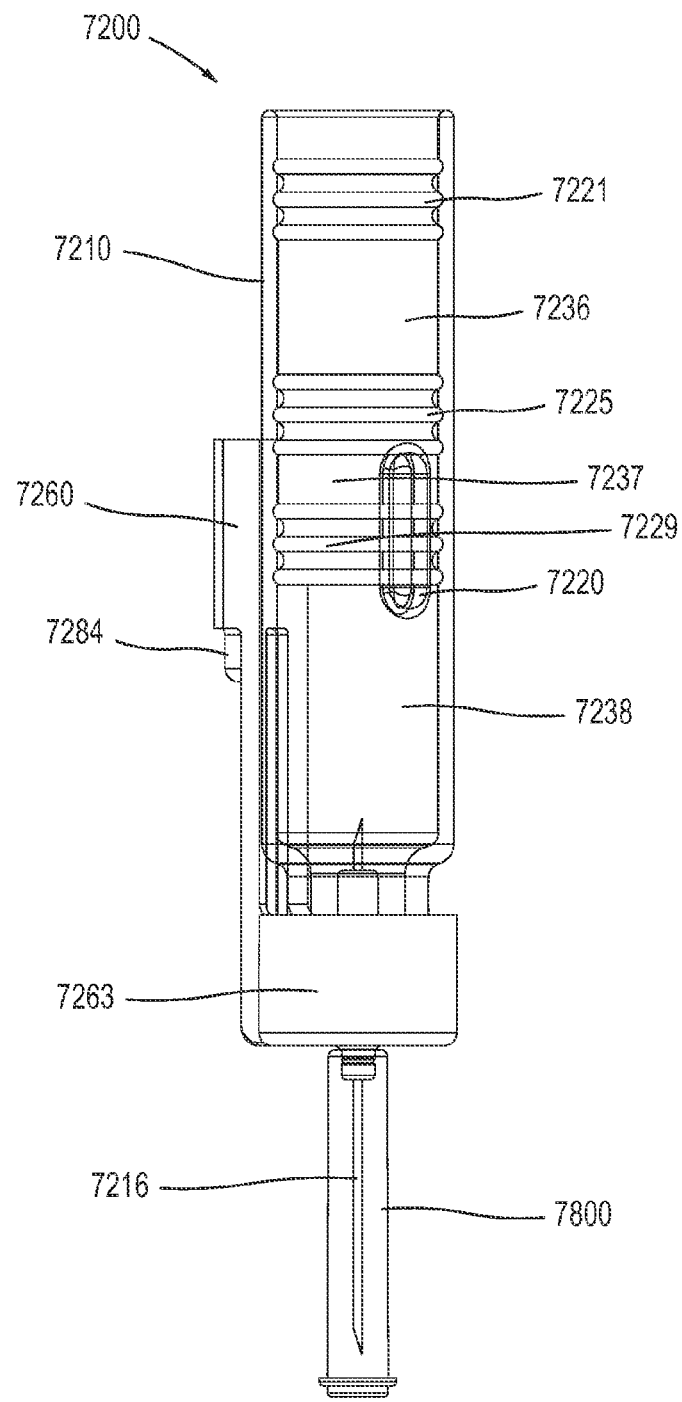
FIG. 83 is a front view of a medicament container assembly of the medical injector illustrated in FIG. 77.
Figure 84:
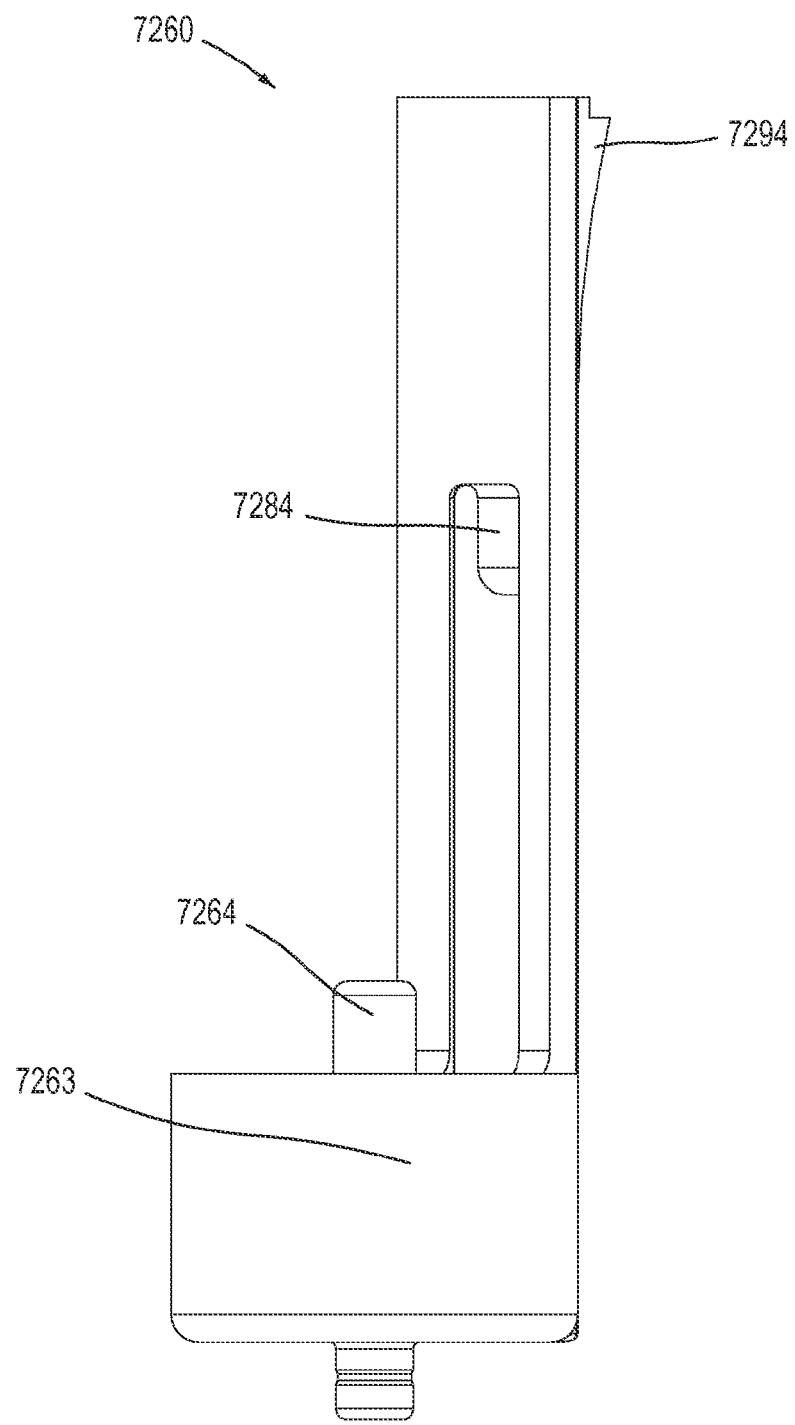
FIG. 84 is a side view of a portion of the medicament container assembly illustrated in FIG. 83.
Figure 85:
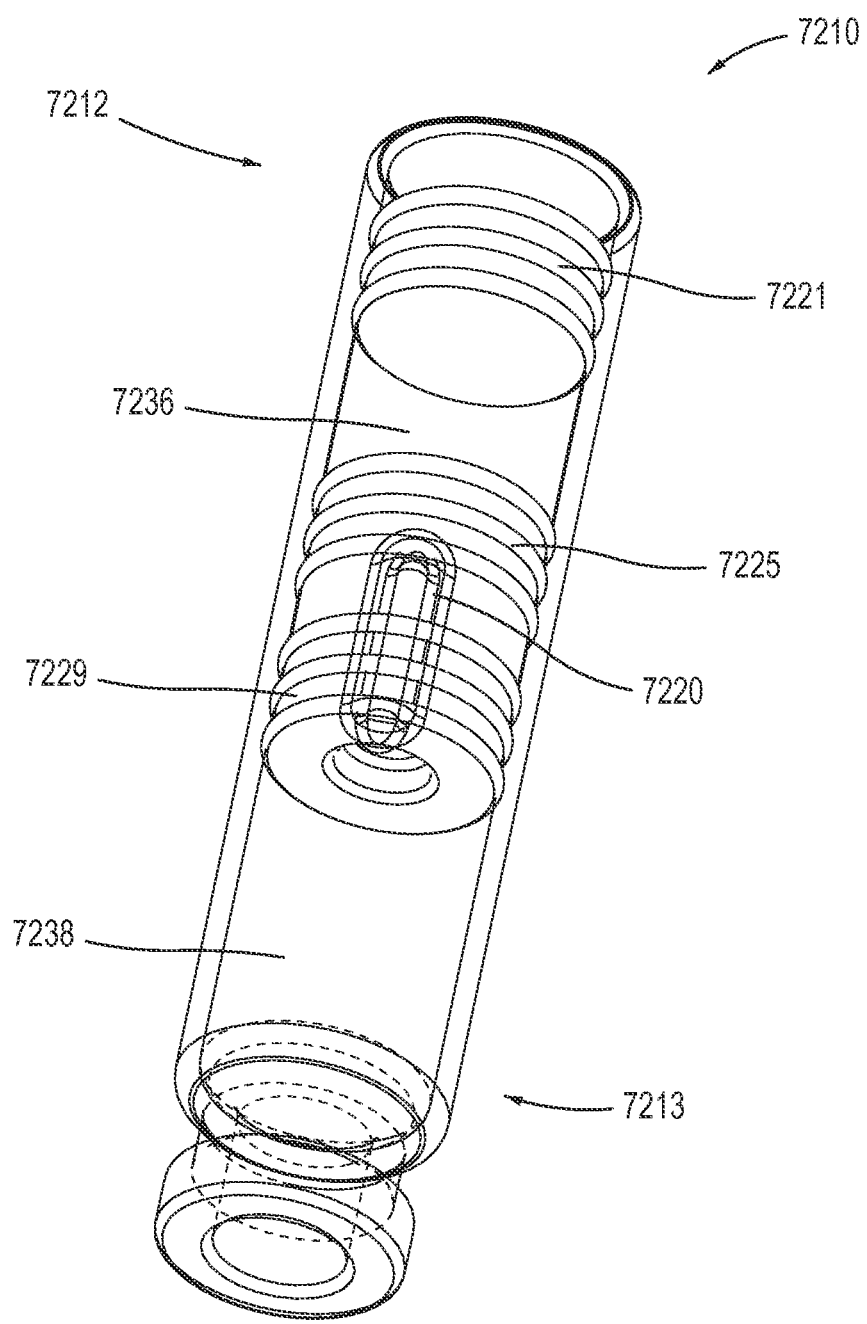
FIG. 85 is a perspective view of a portion of the medicament container assembly illustrated in FIG. 83.
Figure 90:
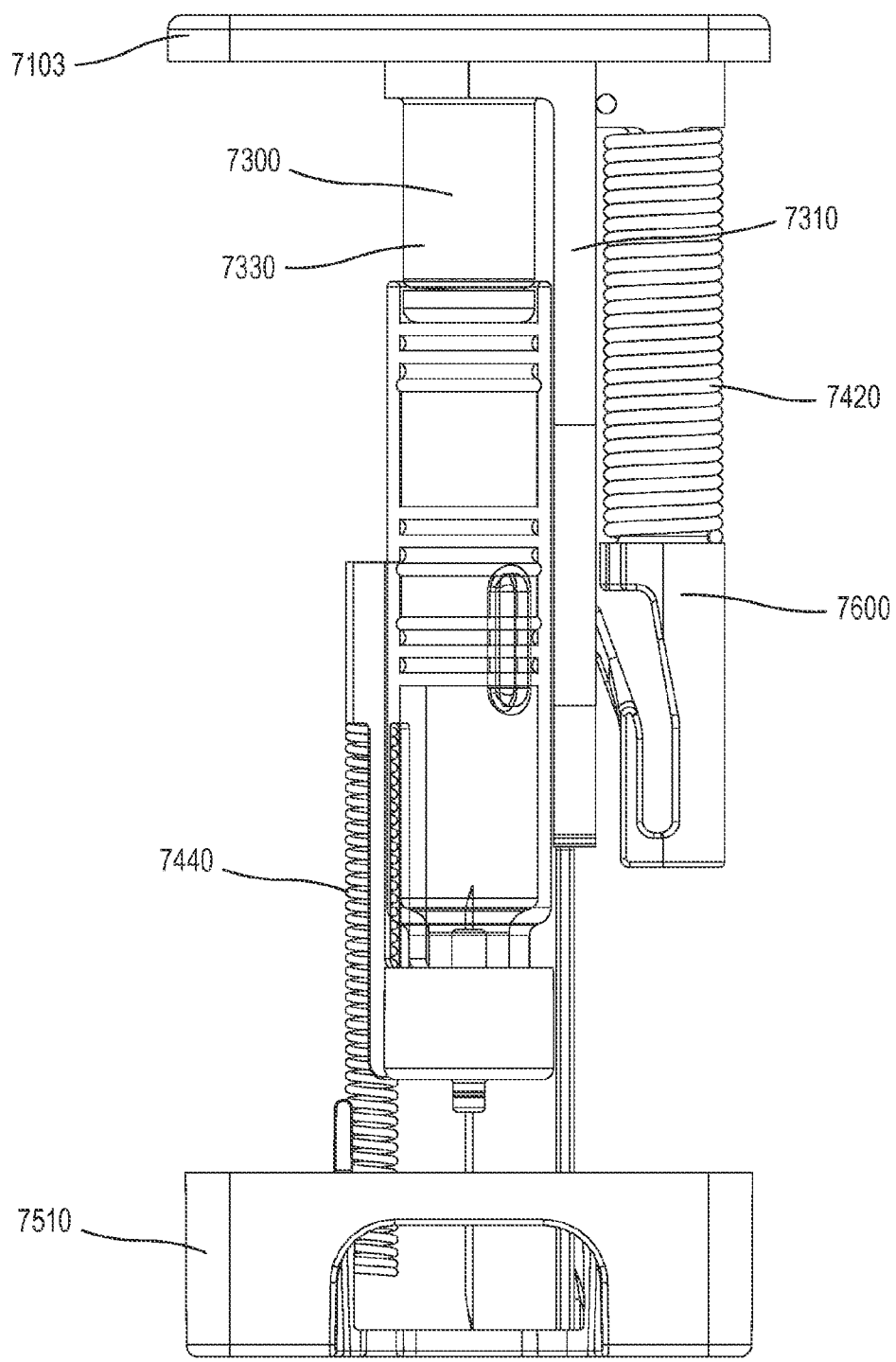
FIG. 90 is a front view of medicament delivery mechanism included in the medical injector illustrated in FIG. 77.

FIGS. 83-85 show components of the medicament container assembly 7200 of the injector 7000. The medicament container assembly 7200 includes components configured to store a medicament, segregate stored medicament components, and mix medicament components. The medicament container assembly 7200 includes a carrier 7260 and a medicament container 7210. The carrier 7260 includes a retraction member protrusion 7284, a container mounting portion 7263, a needle hub 7264, and a latch 7294. The retraction member protrusion 7284 receives a proximal end portion of the retraction member 7440 (as shown in FIG. 90), such that the retraction member 7440 can move the carrier 7260 in the proximal direction. The container mounting portion 7293 receives a distal end portion 7213 of the medicament container 7210. The needle hub 7264 can receive, hold, and/or contain at least a portion of a needle 7216 and can be configured to receive a needle guard 7800. A plug (similar to the plug 6827 shown and described above) can be disposed within the needle guard 7800. In some embodiments, the needle 7216 penetrates the plug during injection. In other embodiments, the needle guard 7800 can be coupled to the safety lock 7700 such that the needle guard 7800 is removed from the needle 7216 when the safety lock 7700 is removed from the housing 7100. The latch 7294 presses against and/or is disposed within the catch 7136 of the housing (shown in FIG. 81) to prevent and/or limit proximal movement of the medicament container 7210 when the injector 7000 is in the first configuration, the second configuration, a third configuration (e.g., the mixing configuration), and a fourth configuration (e.g., the needle insertion configuration).

The medicament container 7210 includes a first elastomeric member 7221, a second elastomeric member 7225, and a third elastomeric member 7229. The first elastomeric member 7221, the second elastomeric member 7225, and the third elastomeric member 7229 are placed within the medicament container 7210 during the fill process, as described below, to define a diluents volume 7236, a mixing volume 7237, and a void volume 7238. Said another way, the diluents volume 7236 is the volume within the medicament container 7210 between a distal surface of first elastomeric member 7221 and a proximal surface of second elastomeric member 7225, the mixing volume 7237 is the volume within medicament container 7210 between a distal surface of second elastomeric member 7225 and a proximal surface of third elastomeric member 7229, and the void volume 7238 is the volume within the medicament container 7210 distal to the distal surface of the third elastomeric member 7229.

The medicament container 7210 includes a bypass 7220, a proximal end portion 7212, and a distal end portion 7213. The bypass 7220 can be a singular channel bypass or can define multiple channels. Although the bypass 7220 is shown as an external bypass, alternatively, in some embodiments, the bypass 7220 can be internal (e.g., defined by an internal structure of the container) and/or defined by the second elastomeric member 7225. Said another way, in some embodiments the bypass can be configured such that the outer diameter of the medicament container 7210 is substantially constant. As shown in FIGS. 83 and 85, the diluents volume 7236, the mixing volume 7237, and the void volume 7238 are defined by the relative positions of the first elastomeric member 7221, the second elastomeric member 7225, and the third elastomeric member 7229. The diluents volume 7236 can contain medicament diluents, such as, for example, water; the mixing volume 7237 can contain a lyophilized medicament. The second elastomeric member 7225 and a sidewall of the medicament container 7210 can collectively produce a fluid tight seal between the diluents volume 7236 and the mixing volume 7237 to prevent premature mixing of the diluents and the lyophilized medicament.

Figure 86:
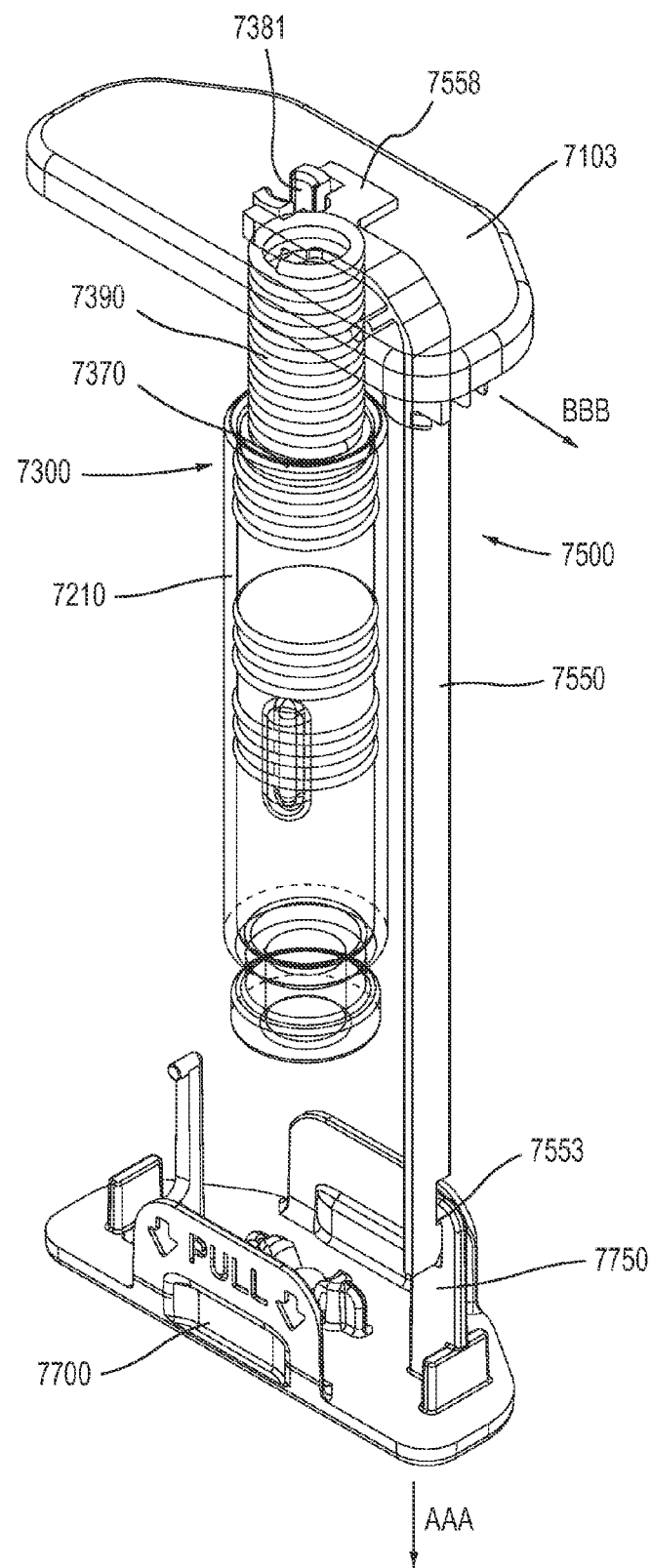
FIG. 86 is a front perspective view of a portion of the medical injector illustrated in FIG. 77.
Figure 101:
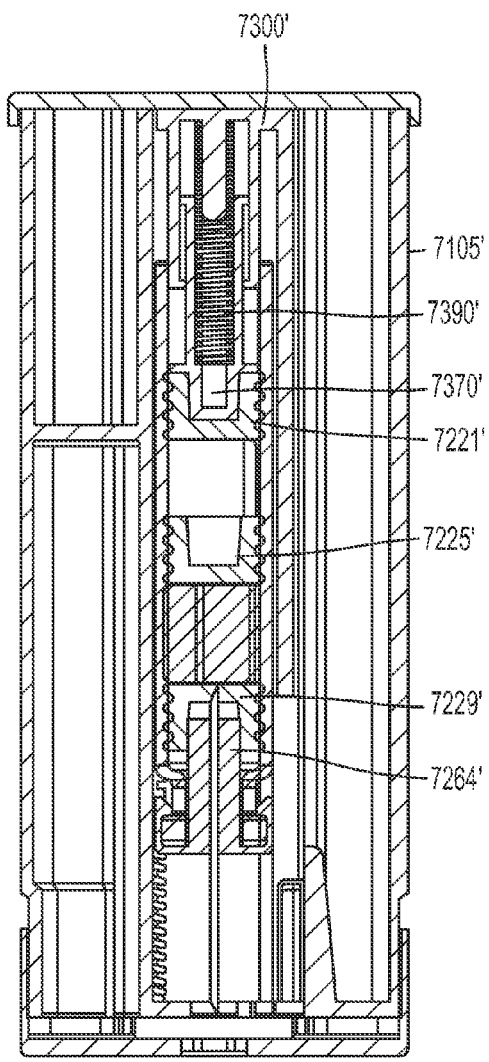

The proximal end 7212 of the medicament container 7210 receives a second movable member 7370 (i.e., a mixing piston, as shown in FIG. 86). In use, when the system actuator assembly 7500 is actuated, the second movable member 7370 moves in the distal direction within the proximal end portion 7212 of the medicament container 7210, which moves the first elastomeric member 7221 in the in the distal direction (see e.g., FIGS. 101 and 102). The distal movement of the first elastomeric member 7221 causes the diluents in diluents volume 7236 to move the second elastomeric member 7225 in the distal direction (see e.g., FIG. 101). In some embodiments, the movement can be substantially simultaneous (e.g. when the diluent is an incompressible fluid). As shown in FIG. 101, distal movement of the second elastomeric member 7225 can cause the substantially dry, solid and/or lyophilized medicament in mixing volume 7237 to move the third elastomeric member 7229 in the distal direction. When the first elastomeric member 7221, the second elastomeric member 7225, and the third elastomeric member 7229, move in the in the distal direction, the volume and location of the diluents volume 7236, the mixing volume 7237, and the void volume 7238, can change. By way of example, when the first elastomeric member 7221, second elastomeric member 7225, and third elastomeric member 7229, move in the in the distal direction, the volume of the diluents volume 7236 and the mixing volume 7237 can initially remain substantially unchanged while the volume of the void volume 7238 can be reduced (see e.g., FIG. 101). When the proximal end of the second elastomeric member 7225 moves in the distal direction past the proximal end portion of the bypass 7220, the diluents volume 7236 can be placed in fluid communication with mixing volume 7237. Thus, continued distal movement of first elastomeric member 7221 can cause the diluents in diluents volume 7236 to flow into mixing volume 7237 via the bypass 7220 and can cause the diluents and the substantially dry, solid and/or lyophilized medicament to mix in the mixing volume 7238, forming a reconstituted medicament within the mixing volume 7237. In some embodiments, when the diluents volume 7236 and the mixing volume 7237 are in fluid communication, the movement of the second elastomeric member 7225 can slow or stop.

Figures 102, 103:
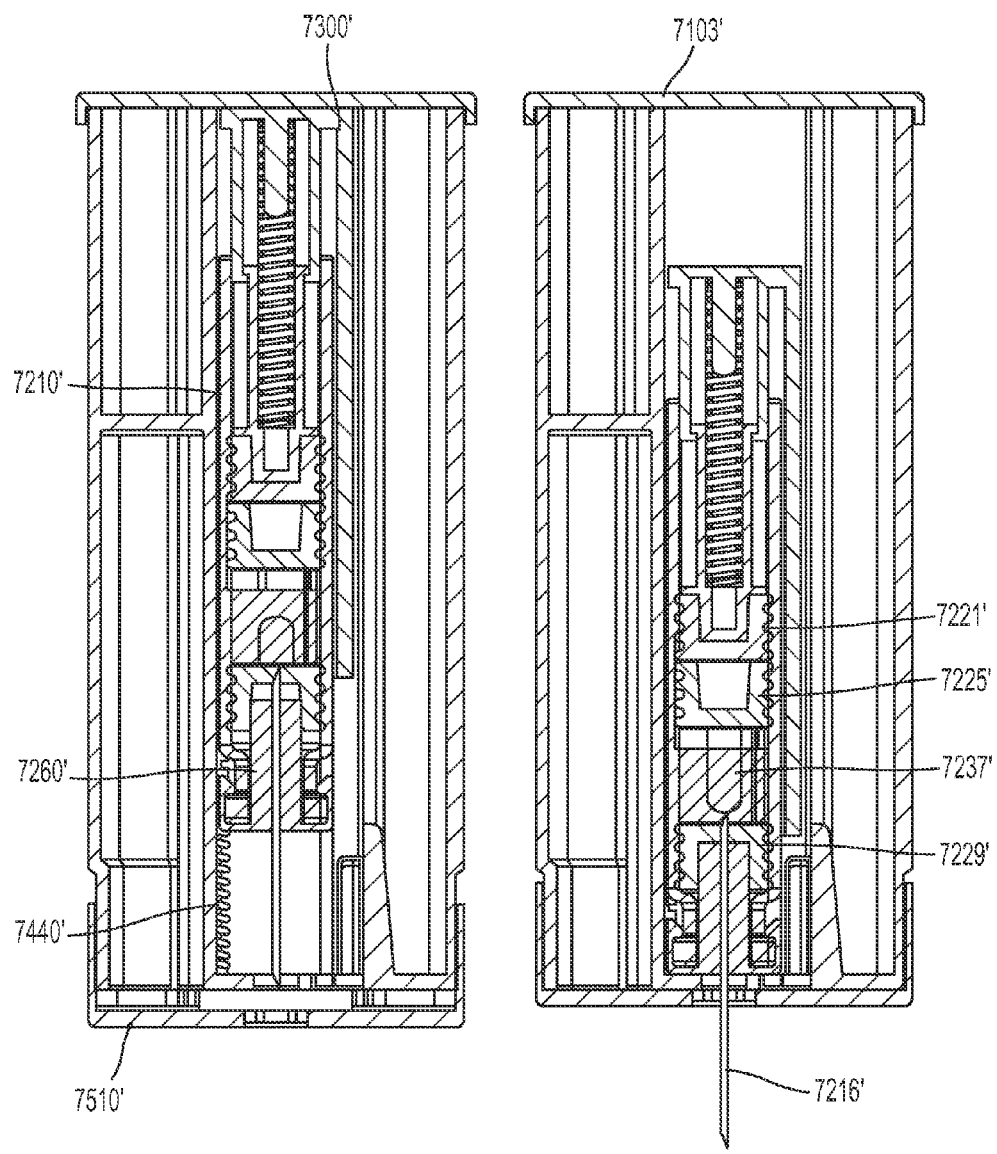

As shown and described below with respect to FIG. 102, when the diluents flows into the mixing volume 7237, the volume of the diluents volume 7236 can be reduced, the volume of the mixing volume 7238 can increase, and the volume of the void volume 7238 can be reduced. In some embodiments, when the volume of the void volume 7238 is decreased, air within the void volume 7238 can escape via the needle 7216. The first elastomeric member 7221 can contact the second elastomeric member 7225 and can continue to move in the distal direction as shown in FIG. 102. The distal movement of the first elastomeric member 7221 and the second elastomeric members 7225 can cause the medicament to move the third elastomeric member 7229 in the distal direction, thereby forcing air within the void volume 7238 to escape from medicament container 7210.

In some embodiments, the distal movement of third elastomeric member 7229 during the mixing operation can cause the third elastomeric member 7229 to contact needle 7216. Furthermore, in some embodiments, the distal movement of third elastomeric member 7229 can cause the third elastomeric member 7229 to contact needle 7216 such that the needle 7216 penetrates through only a portion of the third elastomeric member 7229, thus preventing fluid communication between the needle 7216 and the mixing volume 7237 (and the medicament therein) until injection. In this manner, the needle 7216 remains fluidly isolated from the mixing volume 7237 until after the needle insertion event as described below. After completion of the mixing event and/or the insertion event, continued movement of the third elastomeric member 7229 within the medicament container 7210 can cause the needle 7216 to substantially penetrate through the third elastomeric member 7229 and allow the needle 7216 to be placed in fluid communication with mixing volume 7237 and the medicament.

As shown in FIG. 85, in some embodiments, a distal surface of the third elastomeric member 7229 includes a counter bore to allow the third elastomeric member 7229 to move about needle hub 7264 during the mixing operation, as shown in FIGS. 101-103. This configuration effectively reduces the thickness of the portion of the third elastomeric member 7229 through which the needle 7216 penetrates. In some embodiments, the distal surface and a proximal surface of the third elastomeric member 7229 can include a counter bore to reduce the thickness of the portion of the third elastomeric member 7229 through which the needle 7216 penetrates, as described above with respect to FIGS. 73 and 74. In some embodiments, this arrangement can also be used to increase the volume of the mixing volume 7237. In some embodiments, the proximal and/or distal sides of any of the elastomeric members 7221, 7225, or 7229, can be shaped to increase or decrease the volumes of the diluents volume 7236, the mixing volume 7237, and/or the void volume 7238, respectively. Thus, the flow of a fluid to or from the diluents volume 7236, the mixing volume 7237, and/or the void volume 7238 and/or the mixing of medicament formulations within the mixing volume 7237 can be controlled.

Figure 89:
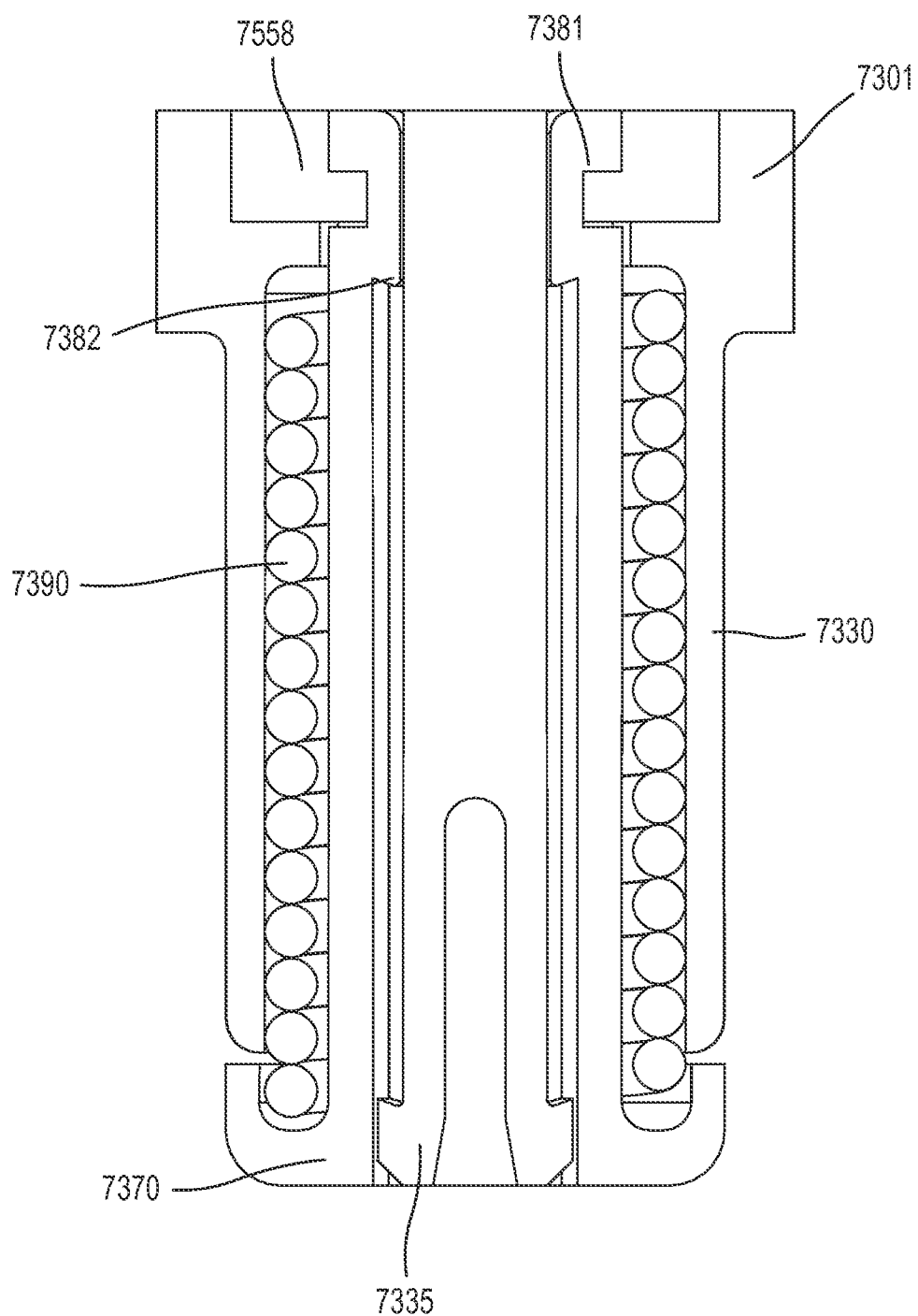
FIG. 89 is a cross-sectional view of a portion of the movable assembly illustrated in FIG. 86.

FIGS. 86-90 depict portions of the injector 7000 including the medicament delivery mechanism 7300 and the transfer member 7600. The injector 7000 includes components configured to store, transport, and mix medicaments such as the safety lock 7700, the proximal cap 7103, medicament container assembly 7200, and the medicament delivery mechanism 7300. The medicament delivery mechanism 7300 can be activated by portions of the system actuator assembly 7500 and includes a first movable member 7301, the second movable member 7370 and a mixing spring 7390. When the injector 7000 is in the first and second configurations, the second movable member 7370 and the mixing spring 7390 are disposed within a piston portion 7330 of the first movable member 7301 (as shown in FIG. 89). A mixing activator member 7550 is operatively coupled to the safety lock 7700 via a hook portion 7553. The mixing activator member 7550 includes a pivot protrusion 7557 operatively coupled to proximal cap 7103 (see e.g., FIG. 82) that allows the mixing activator member 7550 to pivot about the pivot protrusion 7557.

Figure 87:
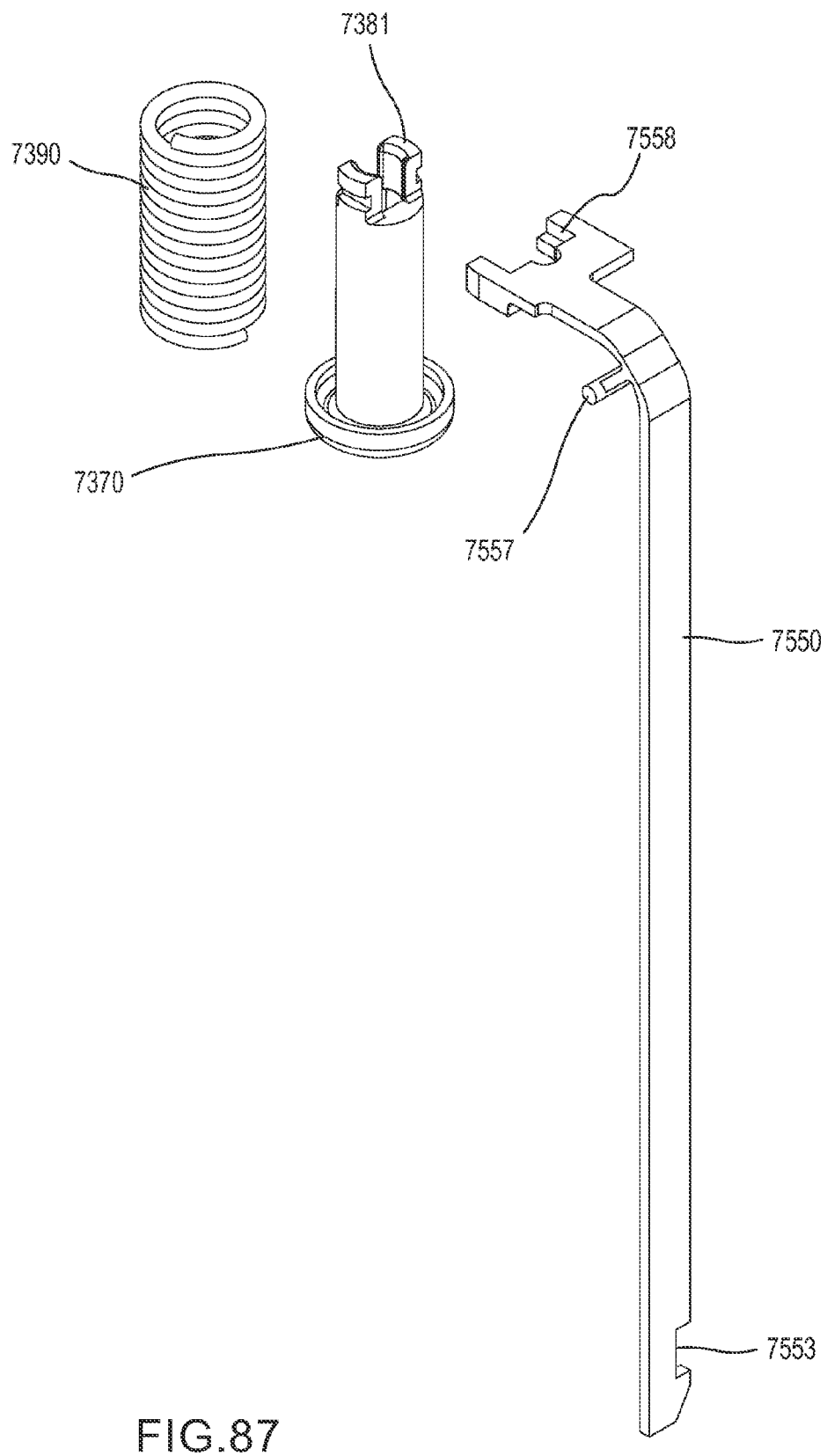
FIG. 87 is a perspective exploded view of a portion of the movable assembly and the system actuator assembly illustrated in FIG. 86.
Figure 88:
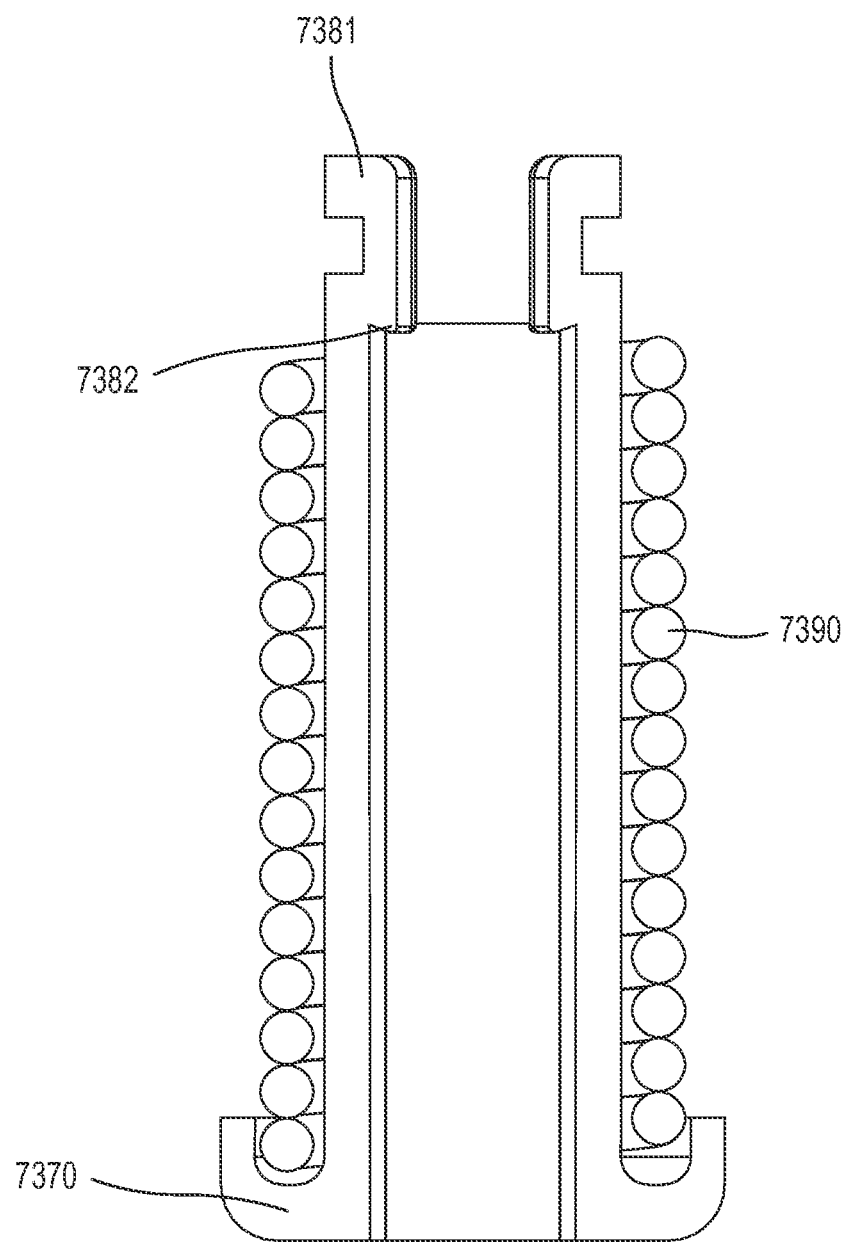
FIG. 88 is a cross-sectional view of a portion of the movable assembly illustrated in FIG. 86.

As shown in FIGS. 86, 87 and 89, the mixing activator member 7550 includes a retention portion 7558 that is operatively engaged with an external retention portion 7381 of the second movable member 7370 when the injector 7000 is in the first configuration (e.g., before actuation of the second movable member 7370). The second movable member 7370 includes an internal retention shoulder 7382 that engages a portion of the first movable member 7301 upon completion of the mixing operation. More particularly, the internal retention shoulder 7182 engages a mixing retainer 7335 included in the piston portion 7330 of the first movable member 7301 (shown in FIG. 89) to stop the distal movement of second movable member 7370 upon completion of the mixing event. The mixing spring 7390 is configured exert a force to move the second movable member 7370 in the distal direction when moving from a compressed configuration (e.g., when the injector is in the first configuration) to an uncompressed configuration (e.g., when the injector is in the second configuration) in the distal direction such that the second movable member 7370 contacts the first elastomeric member 7221.

The medicament delivery mechanism 7300 is configured such that when the safety lock 7700 is removed from the injector 7000, a force acting in the distal direction (as shown by the arrow AAA in FIG. 86) is applied to the hook portion 7553 prior to the hook portion 7553 being disengaged from a retention portion 7750 of the safety lock 7700. The distal force causes the mixing activator member 7550 to freely rotate about pivot protrusion 7557 thereby moving the retention portion 7558 in the direction of the arrow BBB shown in FIG. 86. When the retention portion 7558 is disengaged from the external retention portion 7381, the mixing spring 7390 moves from the compressed configuration to the uncompressed configuration and exerts a force on the second movable member 7370, thereby moving the second movable member 7370 in the distal direction. The distal movement of the second movable member 7370 causes the external retention portion 7381 to act against the retention portion 7558 of the mixing activator member 7550, causing the mixing activator member 7550 to further rotate. The mixing activator member 7550 rotates such that the external retention portion 7381 of the second movable member 7370 is no longer operatively coupled to the retention portion 7558 of the mixing activator member 7550, and the mixing spring 7390 moves the second movable member 7370 into contact with the first elastomeric member 7221. Continued movement of the second movable member 7370 moves the first elastomeric member 7221, the second elastomeric member 7225 and/or the third elastomeric member 7229, as described above.

The first movable member 7301 includes the piston portion 7330 and a latch portion 7310. The piston portion 7330 is operatively coupled to the injection spring 7420 via the transfer member 7600. In this manner, expansion of the injection spring 7420 moves transfer member 7600 in the distal direction, thereby moving the piston portion 7330 in the distal direction to move the medicament container 7210.

Figure 91:
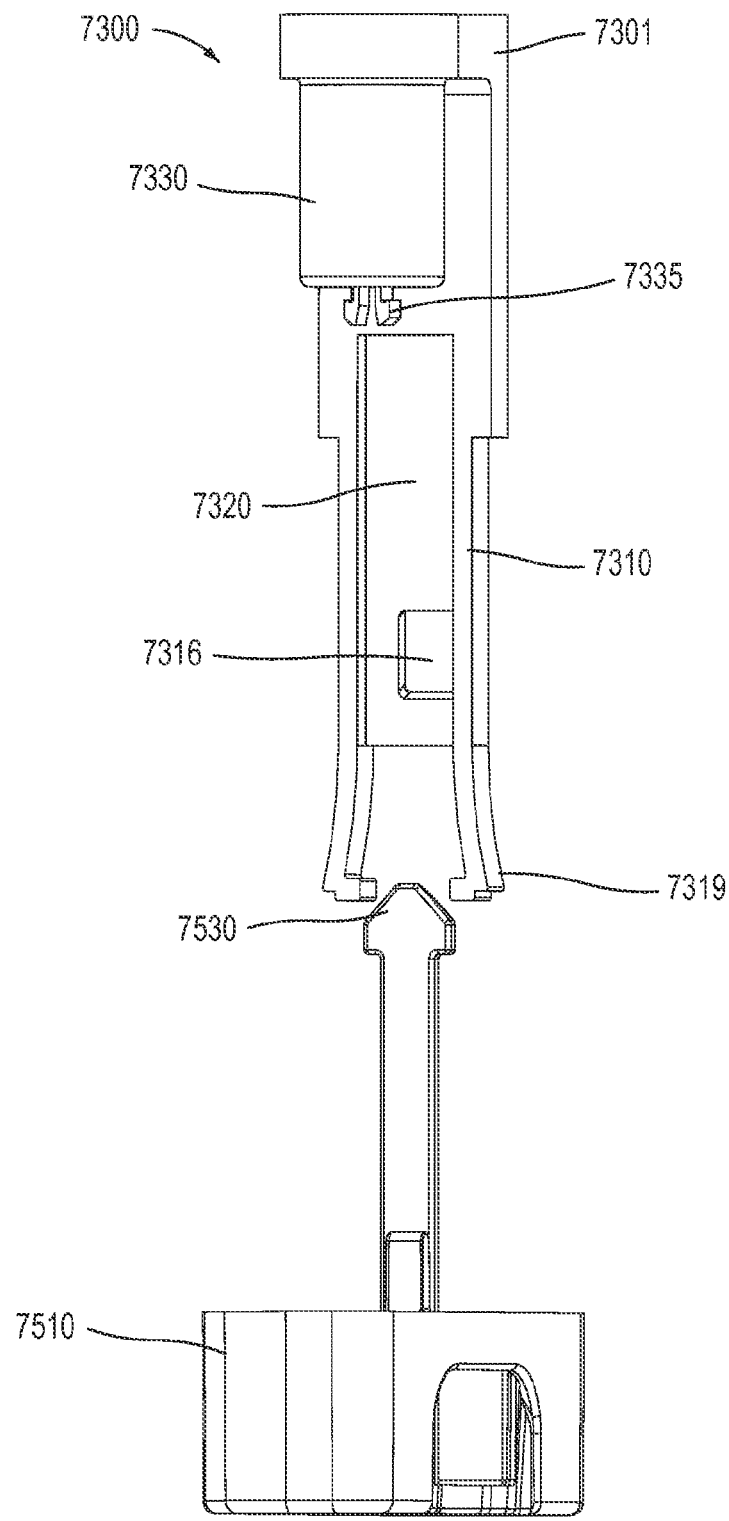
FIG. 91 is front perspective view of a portion of the medical delivery mechanism illustrated in FIG. 90.
Figure 92:
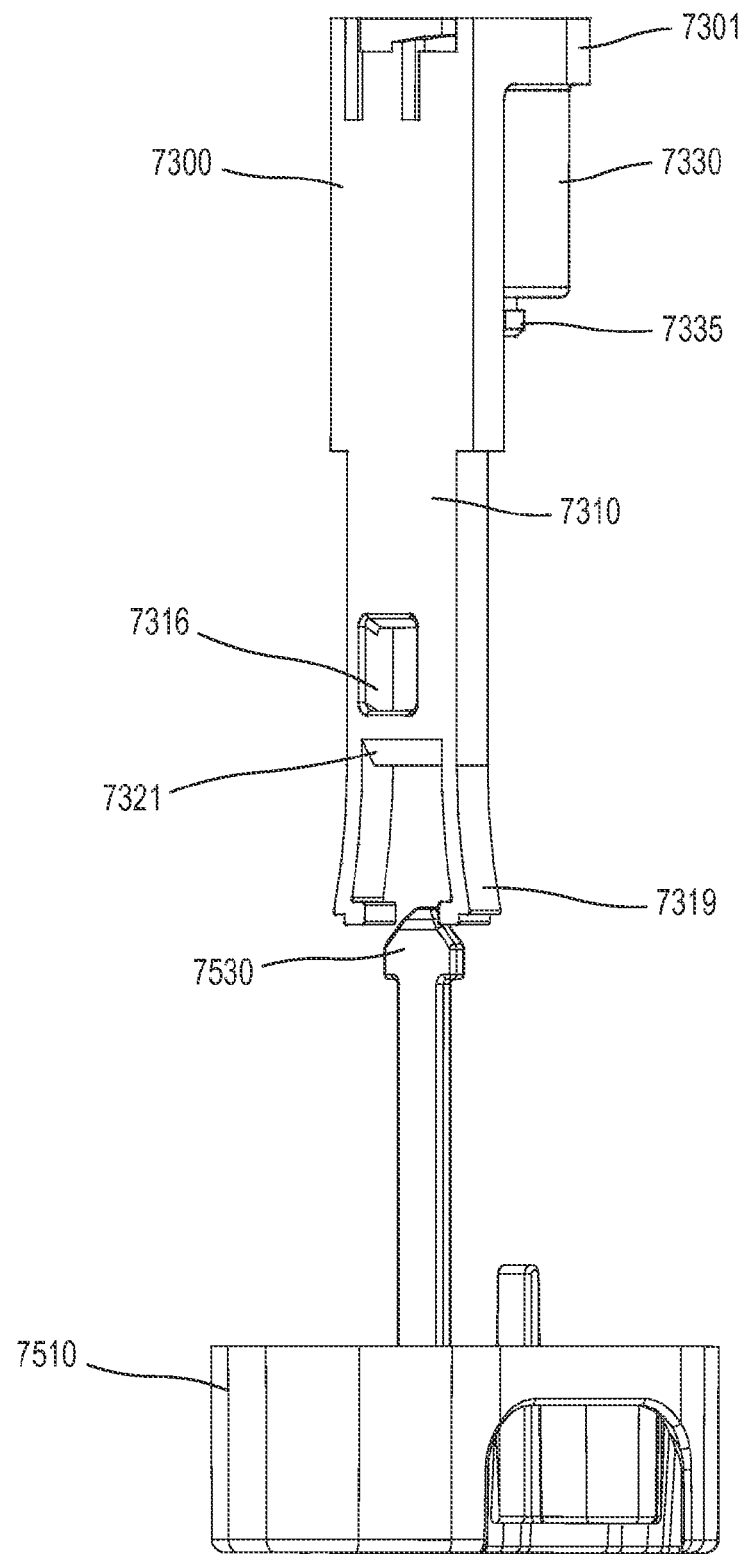
FIG. 92 is rear perspective view of the portion of the medical delivery mechanism illustrated in FIG. 90.
Figure 93:
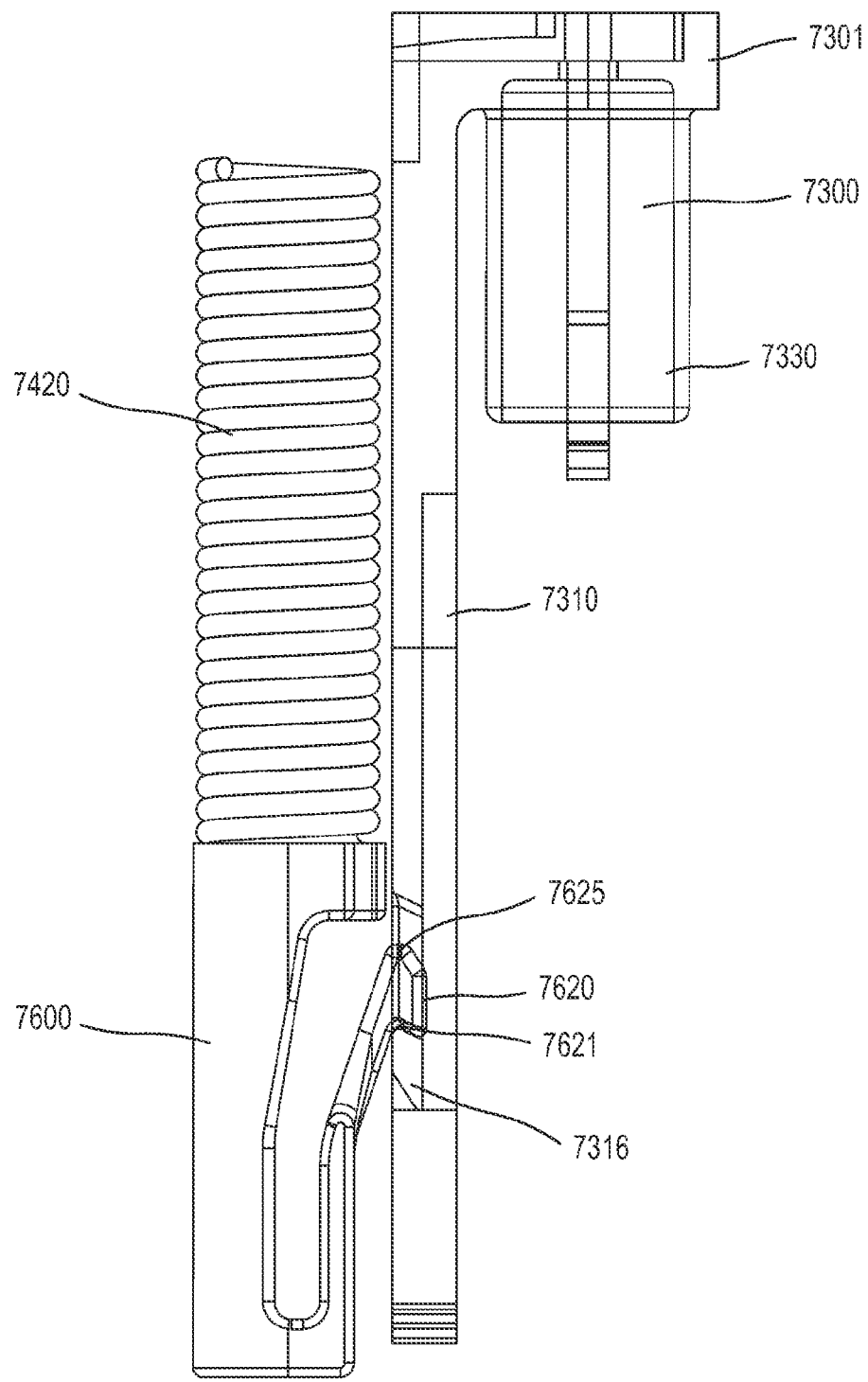
FIG. 93 is a side view of the portion of the medicament delivery mechanism illustrated in FIG. 90.

As shown in FIGS. 91-93, the latch portion 7310 of the first movable member 7301 includes a release portion 7319 and a ramp 7321 and defines a channel 7320 and an opening 7316. The injection spring 7420 can move between a compressed configuration and an uncompressed configuration to exert an insertion force against the proximal cap 7103 and the transfer member 7600. When the injector 7000 is in the first, second and third configuration (i.e., prior to actuation of the insertion spring 7420), the release portion 7319 rests on and/or engages a rod 7530 of the base 7510 (as shown in FIGS. 91 and 92). The release portion 7319, the base 7510, and the injection spring 7420 are collectively configured such that injection spring 7420 cannot produce enough force to deform the release portion 7319 to move the release portion 7319 in the distal direction over the rod 7530. The release portion 7319, however, is configured (e.g., flexible) such that pushing the base 7510 in the proximal direction deforms the release portion 7319, thereby allowing the rod 7530 to move in the proximal direction through release portion 7319. The channel 7320 allows the first movable member 7301 to move about the rod 7530 during injection and retraction. The opening 7316 receives a latch 7620 of the transfer member 7600.

With the movement of the rod 7530 past the release portion 7319, the insertion spring 7420 is released from the compressed configuration (e.g., allowed to expand). The arrangement of the proximal cap 7103 is such that the proximal cap 7103 exerts a reaction force equal to and in an opposite direction of the portion of the insertion force exerted on the proximal cap 7103 by the insertion spring 7420. In this manner, the distal end portion of the insertion spring 7420 is configured to extend in the distal direction. Thus, the expansion of the insertion spring 7420 can move the transfer member 7600 and therefore the first movable member 7301 in the distal direction. The mixing retainer 7335 can be configured to engage the internal retention shoulder 7382 of the second movable member 7370 to limit the distal movement of the second movable member 7370, as described above. In some embodiments, the second movable member 7370 can include a retention portion configured to limit movement of the second movable member 7370 relative to the first movable member 7301 in a proximal direction (i.e., to limit and/or prevent retraction of the second movable member 7370 back into the piston portion 7330).

FIG. 93 depicts the first movable member 7301, the transfer member 7600, and the injection spring 7420 (the first movable member 7301 is shown translucent to better show the interaction between the transfer member 7600 and the latch portion 7310 of the first movable member 7301). The latch 7620 of the transfer member 7600 includes a top surface 7625, and a bottom surface 7621 configured to engage the distal end portion of the sidewall defining the opening 7316. The transfer member 7600 also includes an injection spring seat 7615.

FIG. 95 depicts the retraction member 7440 and other components that interact with retraction member 7440 to retract the needle 7216 back into the housing 7100 after injection of the medicament. The retraction member 7440 is seated about the retraction member protrusion 7284 of the carrier 7260 and can be seated about a spring seat (not shown) on the base 7510 and/or a sidewall of the housing 7100. The retraction member 7440 can be disposed substantially uncompressed (i.e., substantially expanded) between the retraction member protrusion 7284 and the base 7510 and/or the sidewall of the housing 7100. In some embodiments, the retraction member 7440 can be disposed partially compressed between the retraction member protrusion 7284 and the base 7510. In those embodiments in which the retraction member 7440 is disposed in an at least partially compressed state, the latch 7294 interacts and/or engages with the catch 7136 of the housing 7100 to limit the proximal movement of the carrier 7260. In this manner, the force exerted on the carrier 7260 by the retraction member 7440 is not transferred to the medicament container 7210, the medicament delivery mechanism 7300, the system actuator assembly 7500, and/or the transfer member 7600. When the carrier 7260 moves in the distal direction during injection, the retraction member 7440 is compressed between the base 7510 and the carrier 7260. In this manner, as described in more detail below, the retraction spring 7440 exerts a proximal (or retraction) force on the carrier 7260 upon completion of the injection operation.

Figure 96:
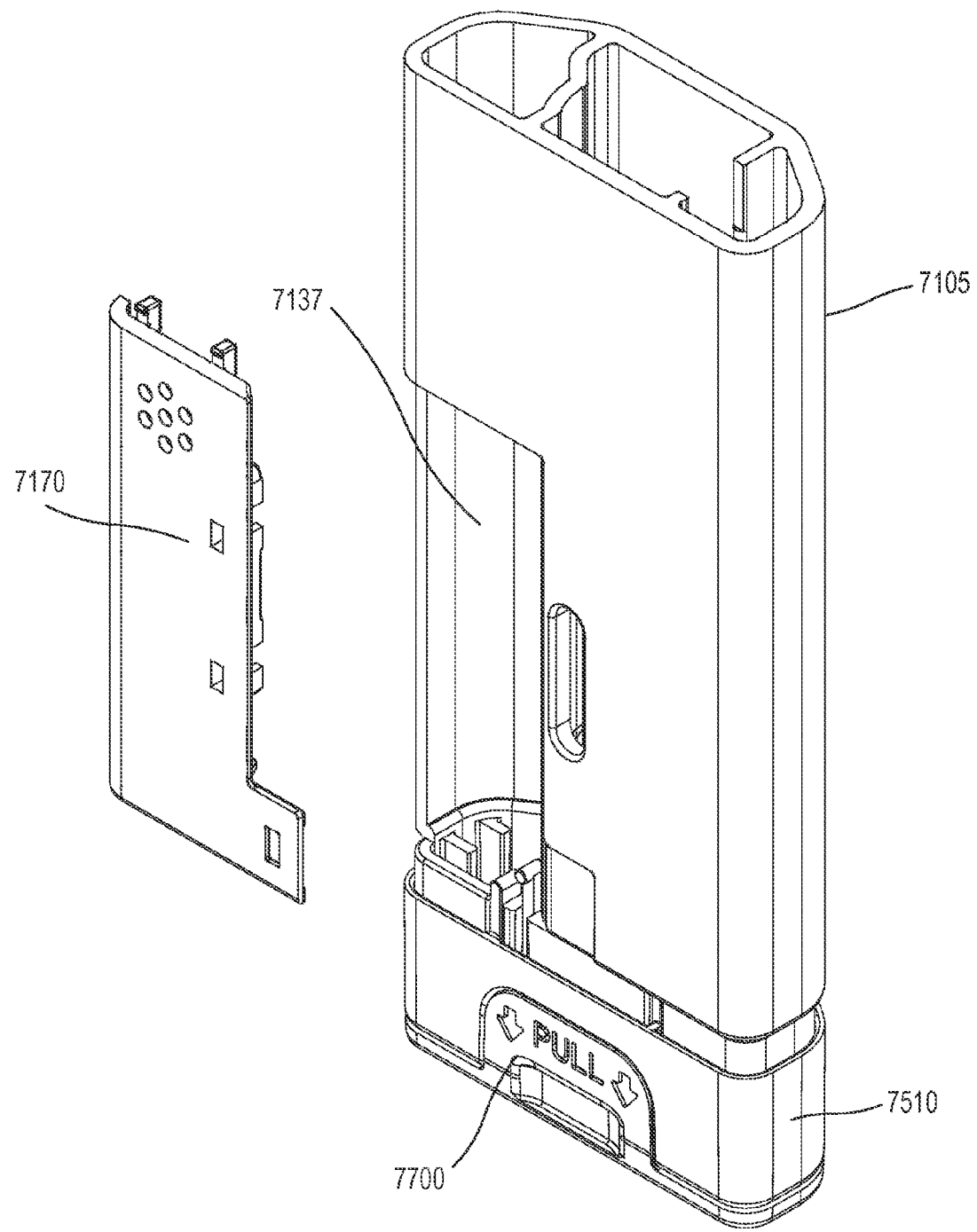
FIG. 96 is a perspective view of a portion of an electronic assembly of the medical injector illustrated in FIG. 77.
Figure 97:
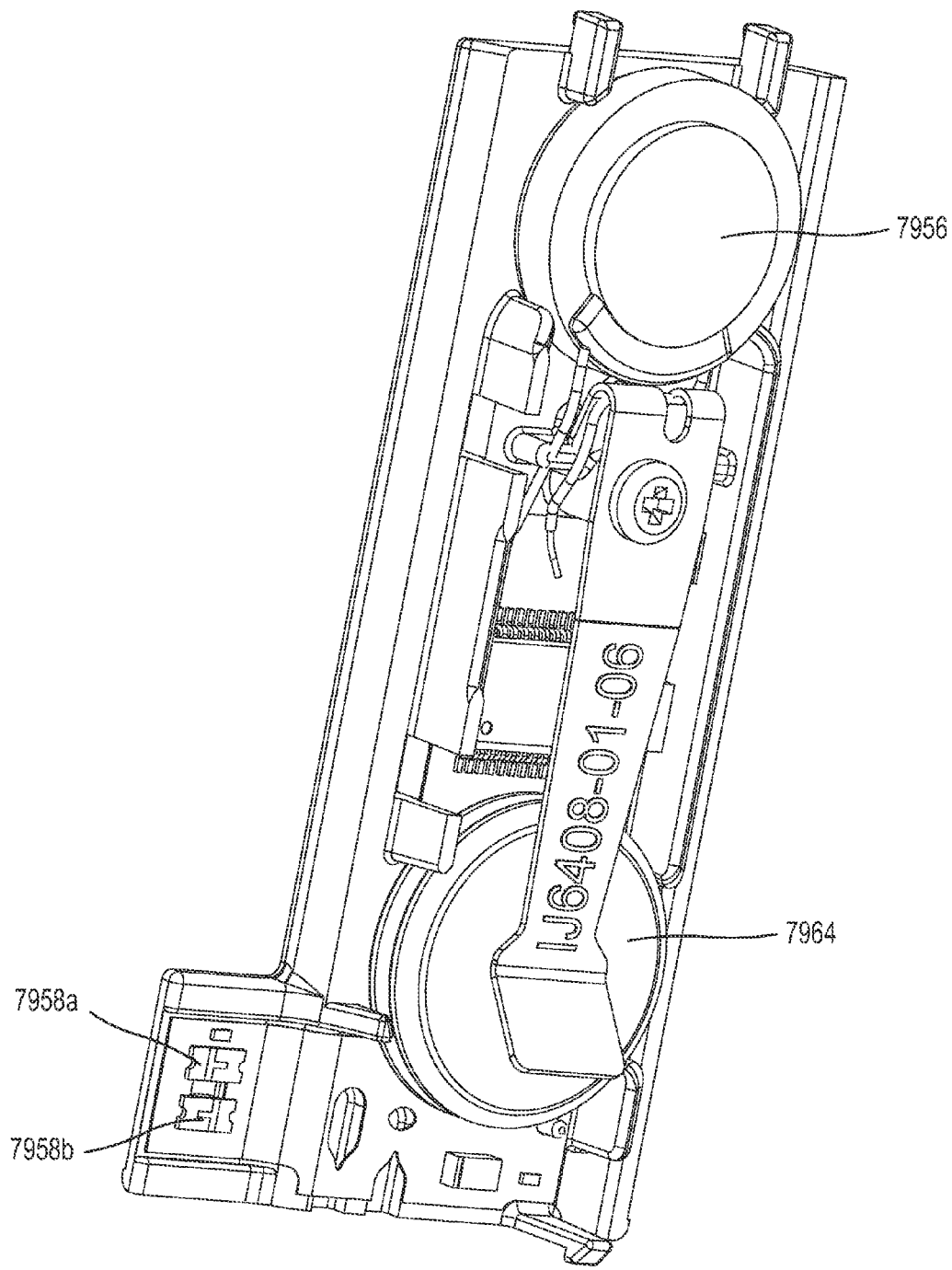
FIG. 97 is a rear perspective view of a portion of the electronic assembly of the injector shown in FIG. 77.
Figure 98:
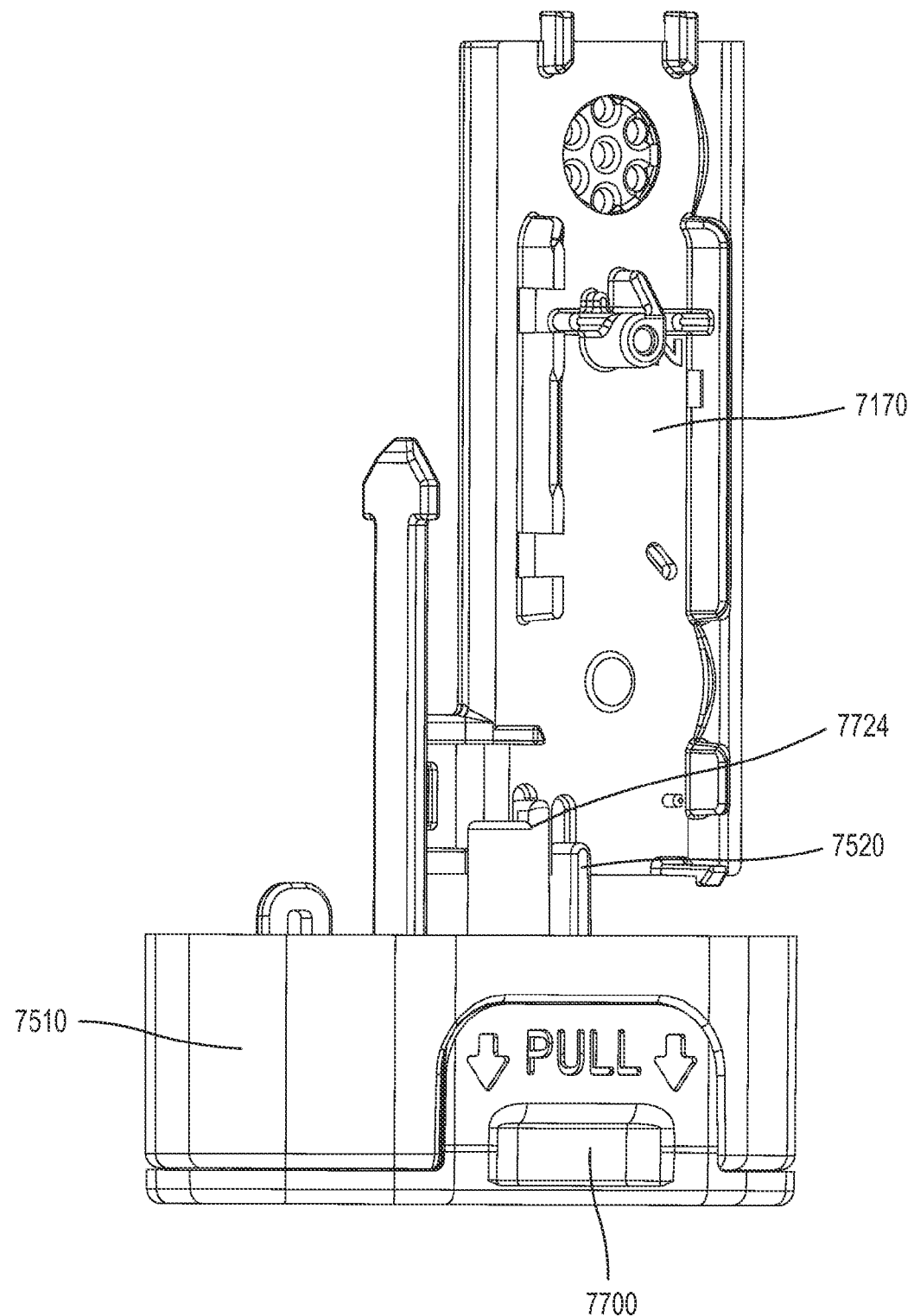
FIG. 98 is a rear perspective view of a portion of the electronic assembly and the base included in the medical injector illustrated in FIG. 77.
Figure 99:
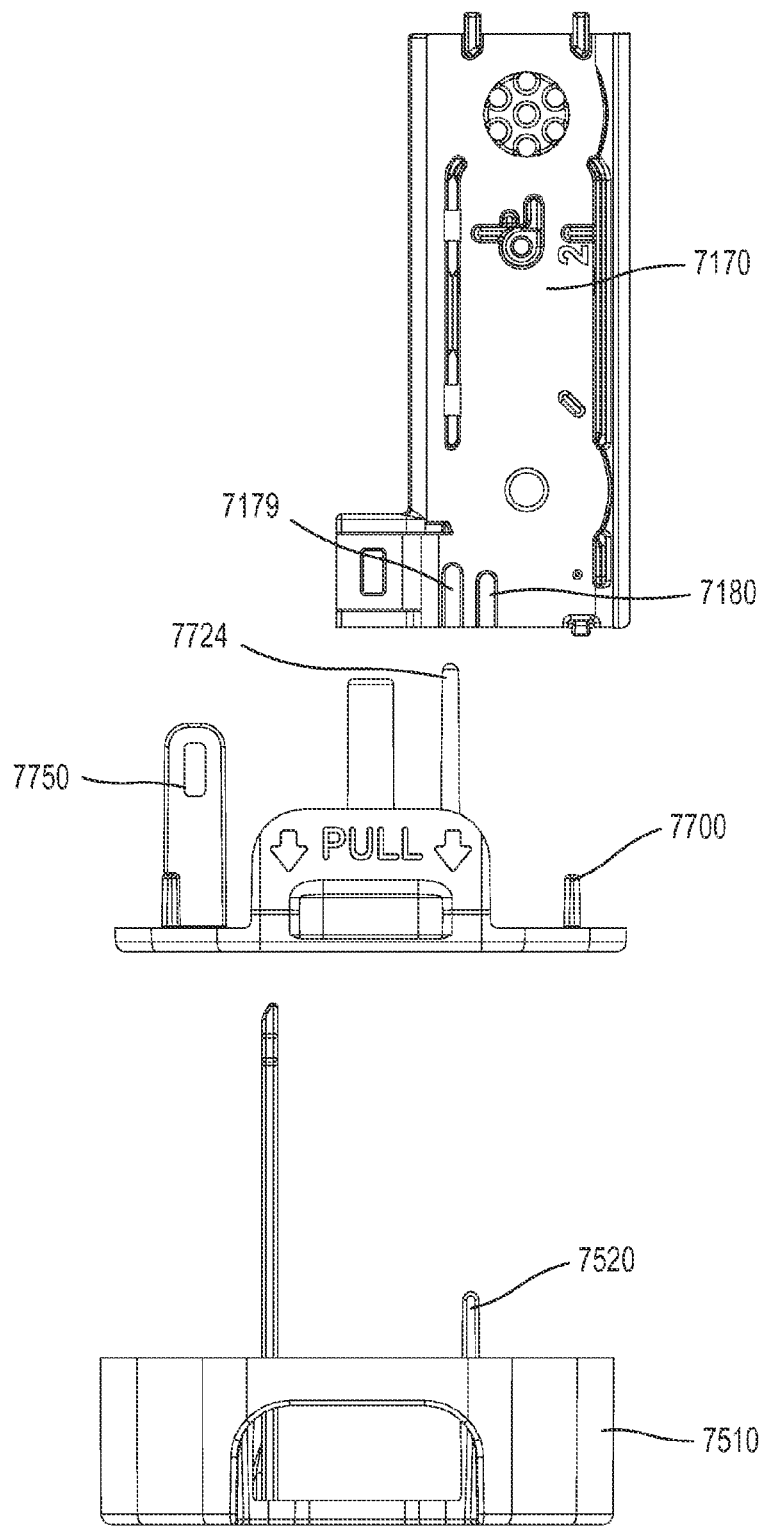
FIG. 99 is a rear exploded view of a portion of the electronic assembly, the base, and the safety lock included in the medical injector illustrated in FIG. 77.

FIGS. 96-99 depict the electronic assembly 7900, and other components of the injector 7000 that interact with the electronic assembly 7900. The electronic assembly 7900 includes any suitable electronic components operatively coupled to produce and/or output an electronic output and/or to perform the functions described herein. The electronic assembly 7900 can be similar to the electronic circuit systems described in U.S. Pat. No. 7,731,686, entitled "Devices, Systems and Methods for Medicament Delivery," filed Jan. 9, 2007, and/or U.S. Patent Application Publication Number 2008/0269689, entitled "Medicament Delivery Device Having an Electronic Circuit System," filed May 12, 2009, both of which are incorporated herein by reference in their entirety. As shown in FIG. 96, the housing 7100 of the injector 7000 defines a volume 7137 configured to receive an electronic circuit housing 7170. The electronic assembly 7900 can include an audio output device 7956, (e.g. a speaker), a battery assembly 7964, and at least one visual output device 7958 (e.g., an LED light). As shown in FIG. 99, the electronic circuit housing 7170 defines a first actuation groove 7179 and a second actuation groove 7180. The safety lock 7700 includes first switch actuator 7724 disposed within the first actuation groove 7179 such that removal of the safety lock 7700 from the injector 7000 engages a first switch of the electronic assembly 7900 to initiate an electronic output of the electronic assembly 7900. The base 7510 includes second switch actuator 7520 disposed within second switch actuation groove 7180 such that actuation of the base 7510 engages a second switch of the electronic assembly 7900 to initiate an electronic output of the electronic assembly 7900.

The operation of the injector 7000 can be described as follows with reference to an injector 7000' shown in FIGS. 100-105. The injector 7000' is similar to, and can have similar components as the injector 7000. Accordingly, similar components can perform similar functions. By way of example, the first elastomeric member 2217' of the injector 7000 can be similar in configuration to the first elastomeric member 7221 of the injector 7000. Furthermore, any component described in relation to injector 7000, can be included in injector 7000'. By way of example, the injector 7000' can have an electronic assembly 7900 (not shown in FIGS. 100-105). Thus, the following description of the injector 7000' includes references to components described above with regards to injector 7000.

Figure 100:
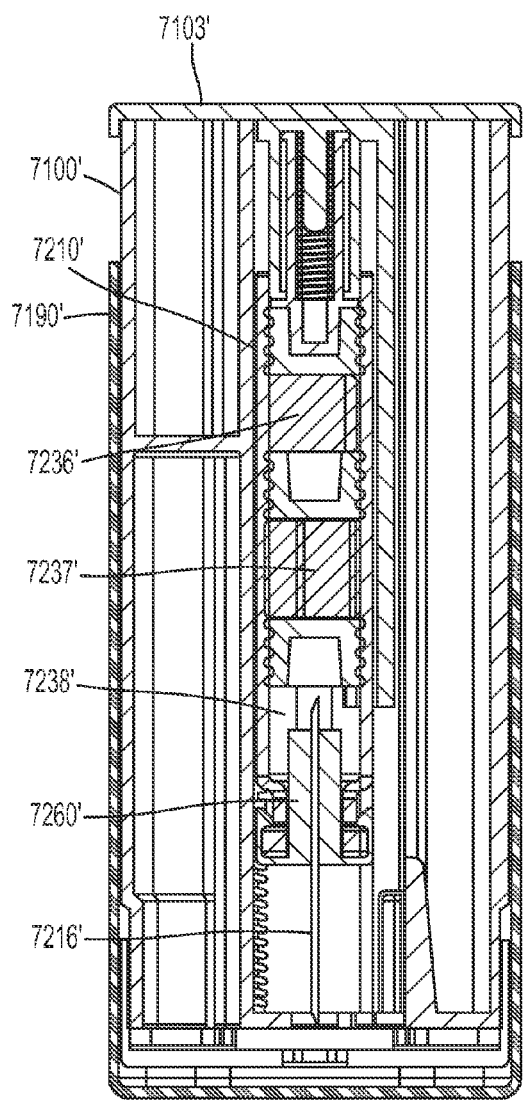
FIGS. 100-105 are cross-sectional views illustrating the operation of a medical injector according to an embodiment.

FIG. 100 depicts injector 7000' with the case 7190' disposed about the housing 7100 (e.g., the first configuration). As depicted in FIG. 101, the case 7190' can be removed from the injector 7000'(e.g., the second configuration). Removing the case 7190' can actuate the electronic assembly 7900 to produce an electronic output, such as, for example, an output indicating the status of injector 7000' or providing instructions for operation. Removing the case 7190' can actuate the electronic assembly 7900 by engaging a portion of the electronic assembly 7900, placing the battery assembly 7964 in electronic communication with a processor, or the like.

The safety lock 7700' can be removed from the injector 7000' to place the injector 7000' in a third configuration (e.g., the initiation of the mixing operation). Removing the safety lock 7700 can cause the first switch actuator 7724 to activate a first switch to produce a second electronic output and/or continue producing the current electronic output. Removing the safety lock 7700 also initiates the mixing operation (e.g., the third configuration). Specifically, removing the safety lock 7700 causes the retention portion 7558 to disengage from the release portion 7553 of the mixing activator member 7550 and can allow the mixing activator member 7550 to rotate freely about the pivot protrusion 7557. As described above with reference to medicament delivery mechanism 7300, force from the mixing spring 7390' acts on the second movable member 7370' and causes the second movable member 7370' to move in the distal direction. The distal movement of the second movable member 7370' causes the external retention portion 7381 to act against the retention portion 7558 of the mixing activator member 7550 causing the mixing activator member 7550 to rotate. The mixing activator member 7550 rotates such that the external retention portion 7381 of the second movable member 7370' is disengaged from the retention portion 7558 of the mixing activator member 7550, thereby allowing the mixing spring 7390' to move the second movable member 7370' into the medicament container 7210' and subsequently into contact with the first elastomeric member 7221'.

The distal movement the second movable member 7370' within the medicament container 7210' moves the first elastomeric member 7221', the second elastomeric member 7225', and/or the third elastomeric member 7229' within the medicament container 7210', as described above, and as shown in FIGS. 101 and 102. In this manner, actuation of the medicament delivery mechanism 7300 produces the mixing operation as described above.

As described above, the distal movement of the third elastomeric member 7229' during the mixing operation causes the third elastomeric member 7229' to contact the needle 7216', such that the needle 7216' penetrates through a portion of the third elastomeric member 7229', as shown in FIGS. 101 and 102. When the second movable member 7370' has moved a predetermined distance within the medicament container 7210, the internal retention shoulder 7382 contacts the mixing retainer 7335 of the first movable member 7301' to stop the distal movement of the second movable member 7370'. In some embodiments, this arrangement can prevent the needle 7216' from being placed in fluid communication with the mixing volume 7237 and/or the medicament. At this point, mixing of the medicament is substantially completed and the injector 7000' is in the fourth configuration (see e.g., FIG. 102). In some embodiments, however, the needle 7216' can penetrate through the third elastomeric member 7229' before the internal retention shoulder 7382 stops the distal movement of the second movable member 370' and can allow the needle 7216' to be in fluid communication with the mixing volume 7237' and the medicament.

During the mixing operation, the electronic assembly 7900 can output a countdown timer to alert the user to refrain from activating the insertion spring 7420 of the injector 7000' until the mixing is complete and/or can instruct the user to activate the injector 7000' after the mixing is complete. The electronic assembly 7900 can provide the user with instructions for activating the injector 7000', such as, for example, identifying where to inject the medicament and/or how to begin injection (e.g., by pressing the base 7510' against the body).

The user can move the base 7510' (and any of the other bases shown and described herein) using any suitable motion and/or operation. For example, in some embodiments, the user can grasp the sides of the housing 7110' and push against the proximal portion thereof. Moving the base 7510' in the proximal direction can start the insertion and injection process (e.g., a fifth configuration and sixth configuration, respectively). When the base 7510' is moved in the proximal direction, movement of the rod 7530 deforms the release portion 7319 such that the rod 7530 moves in the proximal direction within the channel 7320 of the first movable member 7301'. The injection spring 7420 acts against the proximal cap 7103 and the transfer member 7600, as described above, to cause the transfer member 7600 to move in the distal direction. The latch 7620 of the transfer member 7600 acts within the opening 7316 and moves the first movable member 7301' in the distal direction. The medicament delivery mechanism 7300', the carrier 7260', and the medicament container 7210' can move substantially together, as shown in FIG. 103, to insert the needle 7216'. This operation also causes retraction spring 7440 to compress. A distal end portion of the carrier 7260' contacts the base 7510' and/or the housing 7100 to stop movement of the carrier 7260 (e.g., the sixth configuration as shown in FIG. 103).

Figures 104, 105:
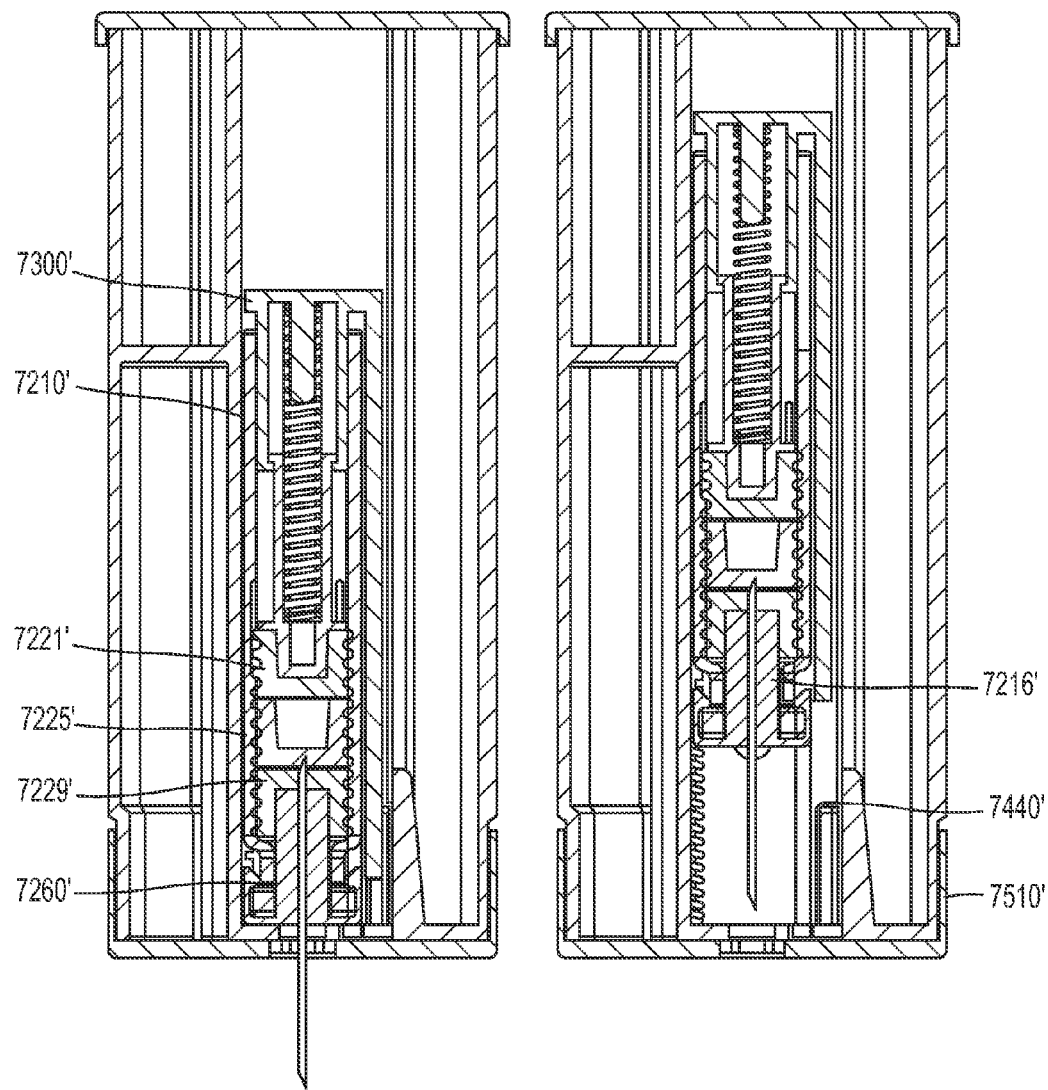

Upon completion of the needle insertion operation, the injection spring 7420 continues to move the transfer member 7600, the first movable member 7301', the mixing spring 7390' and the second movable member 7370' in the distal direction. Said in another way, the medicament delivery mechanism 7300' moves relative to the carrier 7260'. The second movable member 7370' causes the first elastomeric member 7221' and the second elastomeric member 7225' to move in the distal direction and causes the medicament within the mixing volume 7237' to move the third elastomeric member 7229' in the distal direction. The third elastomeric member 7229' moves in the distal direction such that the needle 7216' penetrates through the third elastomeric member 7229' thus placing the needle 7216' in fluid communication with the mixing volume 7237' and the medicament (see, e.g. FIG. 103). The third elastomeric member 7229' contacts the distal end portion 7213 of the medicament container 7210' to stop its distal movement. Continued movement of the first elastomeric member 7221' and the second elastomeric member 7229' causes medicament within the mixing volume 7237' to flow into needle 7216' and out of injector 7000'. The first elastomeric member 7221' and the second elastomeric member 7225' continue to move in the distal direction and into contact with the third elastomeric member 7229', thereby stopping the flow of medicament from the mixing volume 237' through the needle 7216' and out of the injector 7000' (e.g., a seventh configuration as shown in FIG. 104).

Upon completion of the injection operation, the disengagement rod (not shown) of the base 7510' contacts the ramp 7321 of the first movable member 7301' and causes the latch 7620 of the transfer member 7600 to move out of the opening 7316 of the first movable member 7301'. Said another way, upon completion of the insertion, the transfer member 7600 is disengaged from the first movable member 7301', thereby removing the force of the injection spring 7420 from the medicament delivery mechanism 7300'. The retraction member 7440, which has been compressed by the injection operation between the retraction member protrusion 7284 and the base 7510', expands and moves the carrier 7260' and the needle 7216' in the proximal direction within the injector 7000' (e.g., an eighth configuration as shown in FIG. 105). Although described as being a portion of the base 7510', in other embodiments, the disengagement rod can be coupled to any suitable portion of the injector, such as for example, the housing 7100'. Moreover, in some embodiments, the retraction member 7440' can expand fully. In some embodiments the carrier 7260' can move in the proximal direction and the latch 7294 can contact the catch 7136 of body 7100 to stop the proximal movement of the carrier 7260 and the needle 7216.

Other embodiments can include any suitable mechanism for disengaging the transfer member 7600 from the medicament delivery mechanism 7300'. For example, in some embodiments, when the transfer member 7600 and the medicament delivery mechanism 7300' reach the distal end portion of the housing 7100, a disengagement member (not shown) of the base 7510' can limit the travel of the medicament delivery mechanism 7300' at a predetermined distance from the base 7510' (e.g., towards the end of the travel of the medicament delivery mechanism 7300'). Thus, when the base 7510' is pulled away from the injection site, the force of the injection spring 7420' can push the base 7510' and/or the medicament delivery mechanism 7300' in the distal direction. This movement can allow the latch 7620 of the transfer member 7600 to align with a slot (not shown) in a retention member (not shown) of the housing 7100', thereby allowing the latch 7620 to become disengaged from the first movable member 7301'. After the latch 7620 is disengaged, retraction can occur, as described above. In this manner, because the base 7510' remains stationary while the injector 7000' is pressed firmly against the patient (e.g., the base cannot move in the distal direction), the retraction operation is prevented until the pressure is released (i.e., until the base 7510' is removed). This can provide time for the entire dose to be delivered through the needle 7216' before retraction occurs.

Although the injector 7000 is shown and described as having a second movable member 7370 that is separate (e.g., has a separate spring, can be separately actuated, etc.) from the first movable member 7301, in other embodiments, a second movable member and a first movable member can share common components and/or can be actuated by a single energy storage member. For example, FIGS. 106-111 depict an injector 8000. Certain components within the injector 8000 can be similar to and have similar functions as the corresponding components in the injector 7000. By way of example, the first elastomeric member 8221 of the injector 8000 can be similar in configuration to the first elastomeric member 7221 of the injector 7000. The injector 8000 differs from injector 7000, however, in that injector 8000 does not include a separately actuated mixing assembly (e.g., the second movable member 7370 and/or the mixing spring 7590 included in the injector 7000).

The injector 8000 includes a housing 8100, a proximal cap 8103, a case 8190, a base 8510, a medicament container 8210, and a first, second, and third elastomeric member 8221, 8225, 8229, respectively, that define a diluents volume 8236, a mixing volume 8237, and a void volume 8238, as described above. The injector 8000 also includes a needle 8216, and a movable member 8300. As described below, the movable member 8300 effectuates both the mixing and the injection of the medicament.

Figures 106, 107:
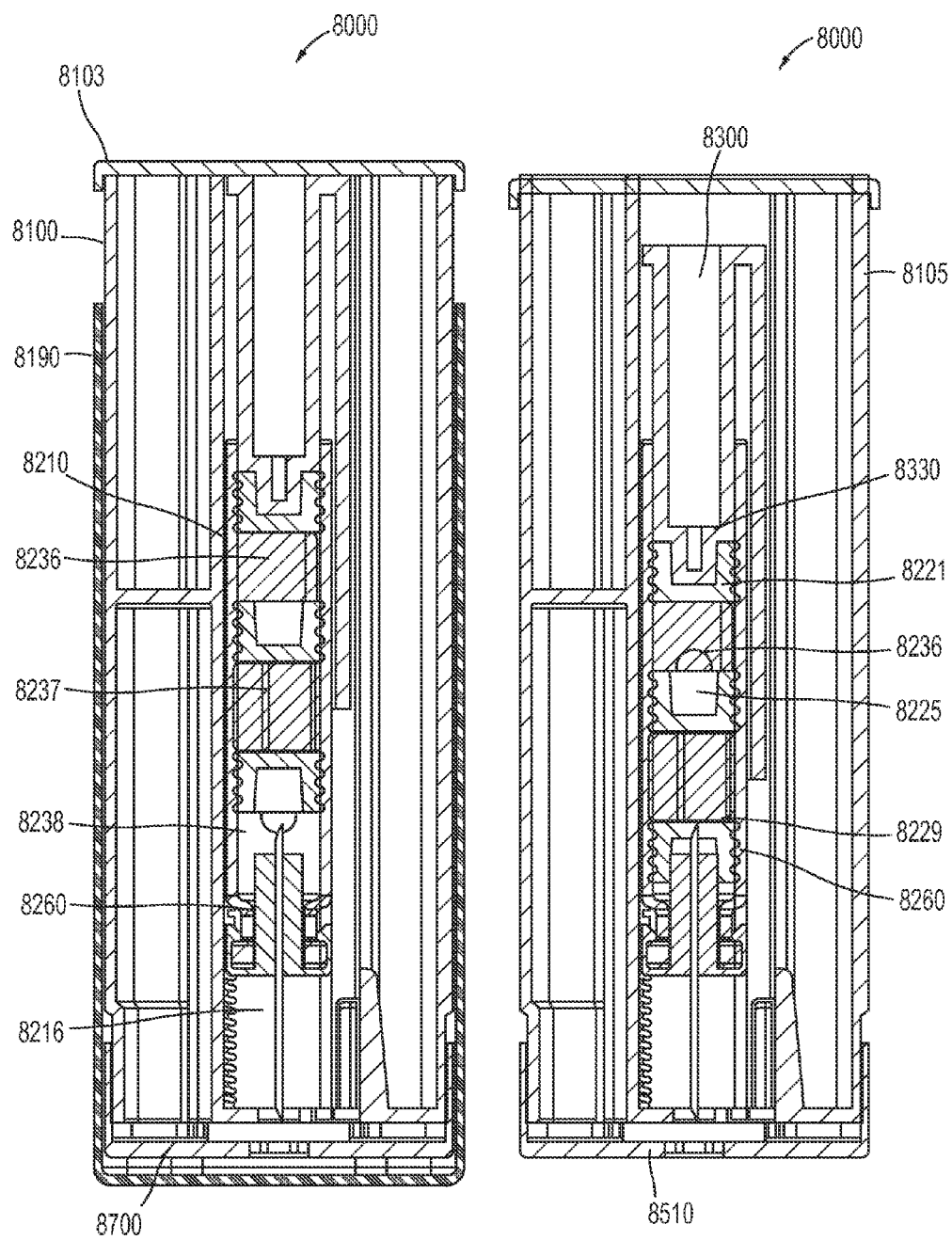

FIG. 106 depicts the injector 8000 with the case 8190 disposed about the housing 8100 (e.g., a first configuration). As depicted in FIG. 8102, the case 8190 can be removed from the injector 8000 to place the injector 8000 in a second configuration. Removing the case 8190 can actuate an electronic assembly (not shown in FIGS. 106-111) to produce an electronic output, such as, for example, an output indicating the status of the injector 8000 or providing instructions for operation. Removing the case 8190 can actuate the electronic assembly by engaging a portion of the electronic assembly, placing a battery assembly in electronic communication with a processor, or the like, as described above.

A safety lock 8700 can be removed from injector 8000 to place the injector 8000 in a third configuration (e.g., initiation of the mixing operation). Removing safety lock 8700 can cause an actuator (similar to the first switch actuator 7724) to activate a first switch, to produce a second electronic output and/or continue producing a current electronic output. Removing the safety lock 8700 exposes the base 8510 of the injector 8000.

The base 8510 can be moved in the proximal direction thereby causing an injection spring (not shown in FIGS. 106-111) to act against the proximal cap 8103 (e.g., a distal end portion of the injection spring moves in the distal direction), which moves the movable member 8300 in the distal direction as described above with reference to injector 7000. The initial movement of the movable member 8300 starts the mixing operation (e.g., the third configuration, see FIG. 107). More specifically, the base 8510 can be moved in the proximal direction and can cause a release rod to deform a release portion to actuate the injection assembly, in a similar manner as described above. The injection spring can act against the proximal cap 8103 and a transfer member (e.g., similar to the transfer member 7600) to move the transfer member, in the distal direction, and therefore the movable member 8300. The distal movement of the movable member 8300 causes a piston portion 8330 of the movable member 8300 to contact the first elastomeric member 8221 and to move the first elastomeric member 8221 in the distal direction.

The distal movement of the first elastomeric member 8221 moves the second elastomeric member 8225 and/or the third elastomeric member 8229 within the medicament container 8210, as described above, and as shown in FIGS. 107 and 108. In this manner, actuation of the injection spring produces the mixing operation.

As described above, the distal movement of third elastomeric member 8229 during the mixing operation causes the third elastomeric member 8229 to contact needle 8216, such that the needle 8216 penetrates through a portion of the third elastomeric member 8229. At this point, mixing of the medicament is substantially complete and the injector 8000 is in a fourth configuration (see e.g., FIG. 108). In some embodiments, however, the needle 8216 can penetrate through the third elastomeric member 8229 thereby allowing the needle 8216 to be in fluid communication with the mixing volume 8237 and the medicament.

Continued movement of the movable member 8300 starts the insertion and injection processes (e.g., a fifth configuration). The movable member 8300, the carrier 8260, and the medicament container 8210 can move substantially together, and can cause the retraction member 8440 to compress. In this manner, the needle 8216 is inserted as shown in FIG. 109. A distal end portion of the carrier 8260 contacts the base 8510 and/or the housing 8100 to stop the distal movement of the carrier 8260 and the medicament container 8210 (e.g., a sixth configuration, see FIG. 109).

Figure 110:
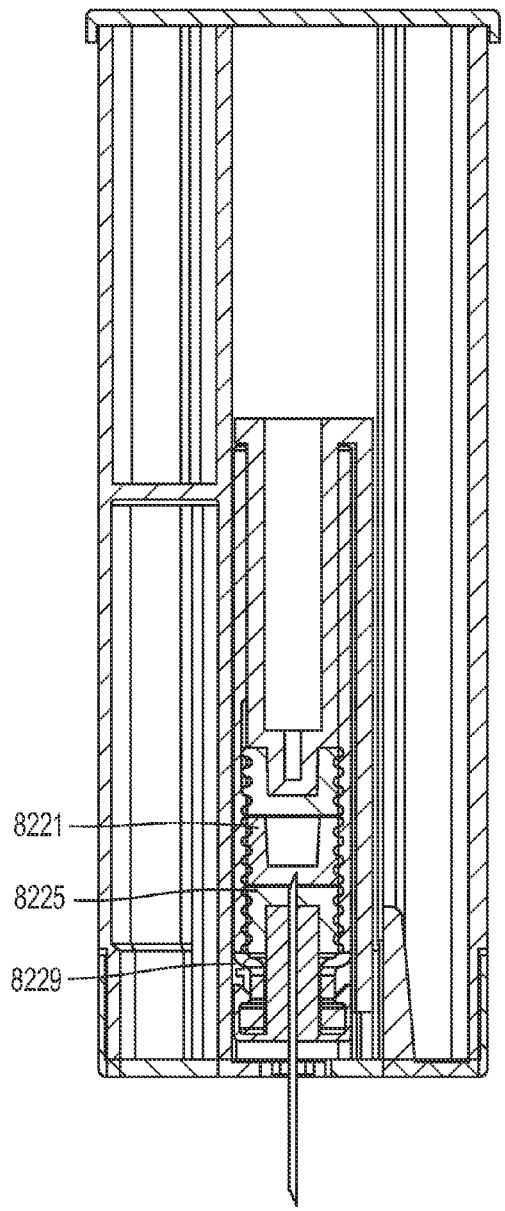
Figure 111:
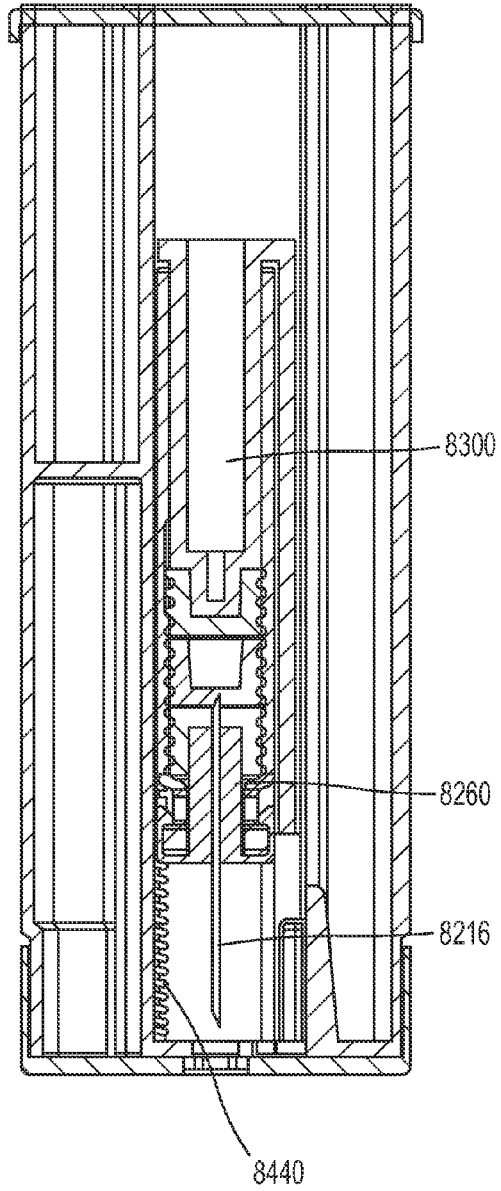

Upon completion of the needle insertion operation, the injection spring continues to move the movable member 8300 in the distal direction. Said in another way, the movable member 8300 moves relative to carrier 8260 and within the medicament container 8210, as shown in FIGS. 109-110. The piston portion 8330 of the movable member 8300 moves the first elastomeric member 8221 and the second elastomeric member 8225 in the distal direction, thereby causing the medicament within the mixing volume 8237 to move the third elastomeric member 8229 in the distal direction. The third elastomeric member 8229 moves in the distal direction such that the needle 8216 penetrates through the third elastomeric member 8229 thus placing the needle 8216 in fluid communication with the mixing volume 8237 and the medicament (see, e.g. FIG. 109). The third elastomeric member 8229 contacts the distal end portion 8213 of the medicament container 8210 to stop its distal movement. Continued movement of the first elastomeric member 8221 and the second elastomeric member 8229 causes the medicament within the mixing volume 8237 to flow into the needle 8216 and out of the injector 8000. The first elastomeric member 8221 and the second elastomeric member 8225 can continue to move in the distal direction and into contact with the third elastomeric member 8229, thereby stopping the flow of medicament from the mixing volume 8237 through the needle 8216 and out of the injector 8000 (e.g., a seventh configuration, see FIG. 110).

Upon completion of the injection operation, the movable member 8300 disengages from the injection spring. The movable member 8300 can disengage from the injection spring by any suitable mechanism. For example, in some embodiments the injector 8000 can include a transfer member similar to the transfer member 7600 described above. After the movable member 8300 is disengaged from the injection spring, the retraction member 8440, which has been compressed by the injection operation between the movable member 8300 and the base 8510, can expand and can move the carrier 8260 and the needle 8216 in the proximal direction within injector 8000 (e.g., an eighth configuration, see FIG. 111). In some embodiments, retraction member 8440 can expand fully.

Although the injector 7000 is shown as described as having a first elastomeric member, a second elastomeric member, and a third elastomeric member within the medicament container. In other embodiments, the injector 7000 can include only a first elastomeric member and a second elastomeric member within the medicament container. For example, FIGS. 112-117 depict an injector 9000 that does not include a third elastomeric member within the medicament container. Other components within injector 9000, however, can be similar to and have similar functions as the components corresponding in the injector 7000 and the injector 8000. By way of example, first elastomeric member 9221 of the injector 9000 can be similar in configuration to first elastomeric member 7221 of the injector 7000.

The injector 9000 includes a housing 9100, a proximal cap 9103, a case 9190, a base 9510, a medicament container 9210, a first elastomeric member 9221 and a second elastomeric member 9225 that define a diluents volume 9236 and a mixing volume 9237, a needle 9216, and a movable member 9300. In some embodiments, the movable member 9300 can effectuate both the mixing and the injection of the medicament.

Figure 112:
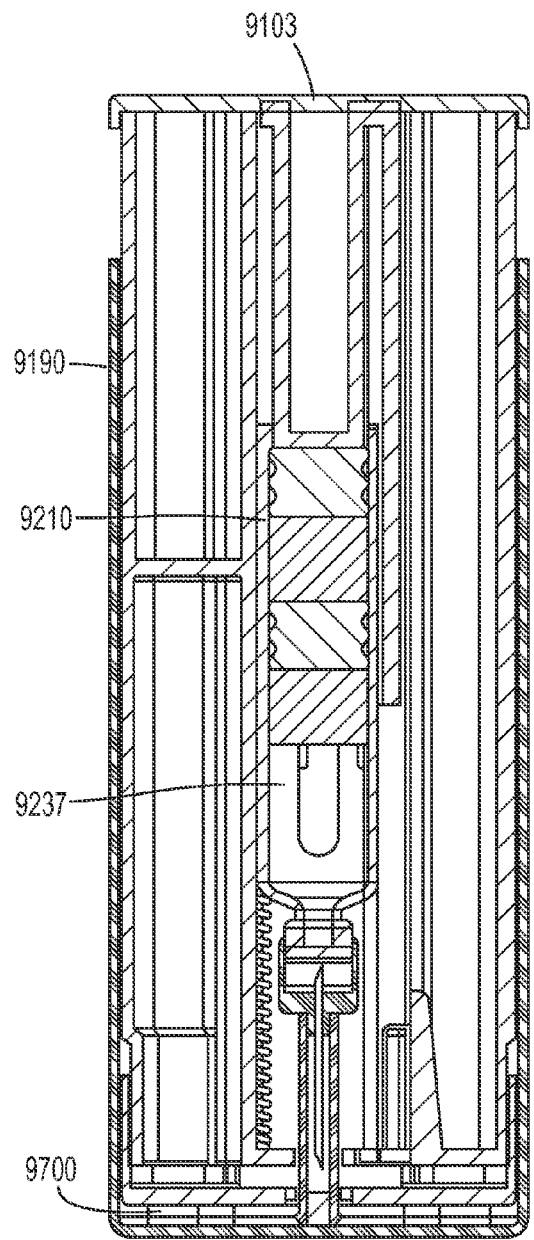
FIGS. 112-117 are cross-sectional views illustrating the operation of a medical injector according to an embodiment.
Figure 113:
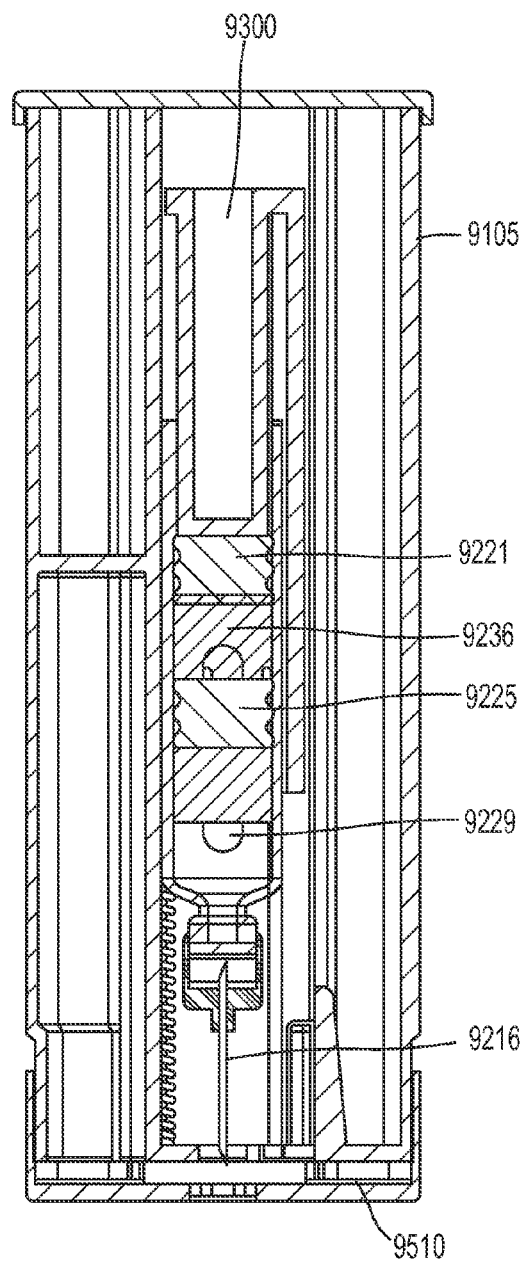
Figures 114, 115:
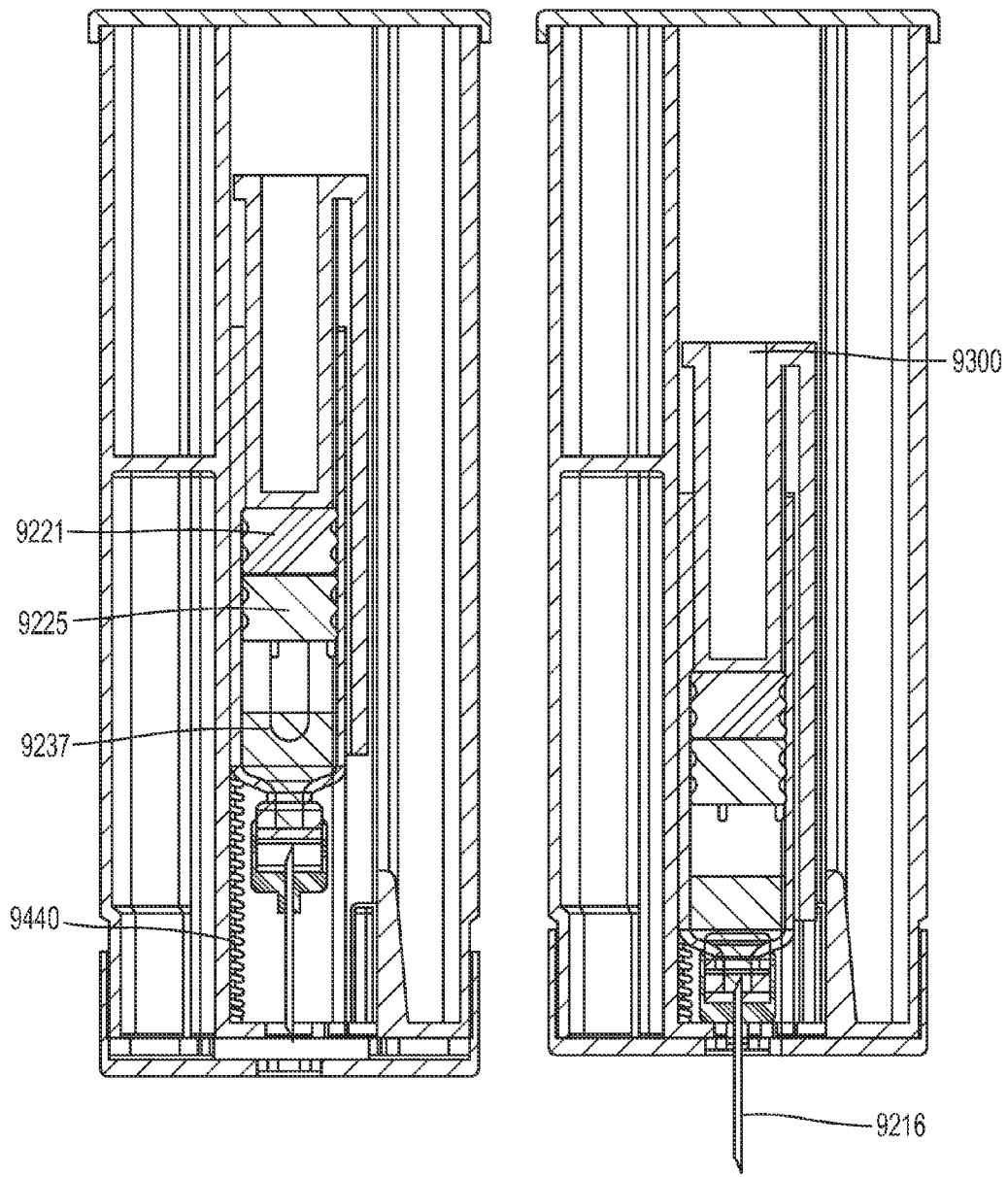
Figure 116:
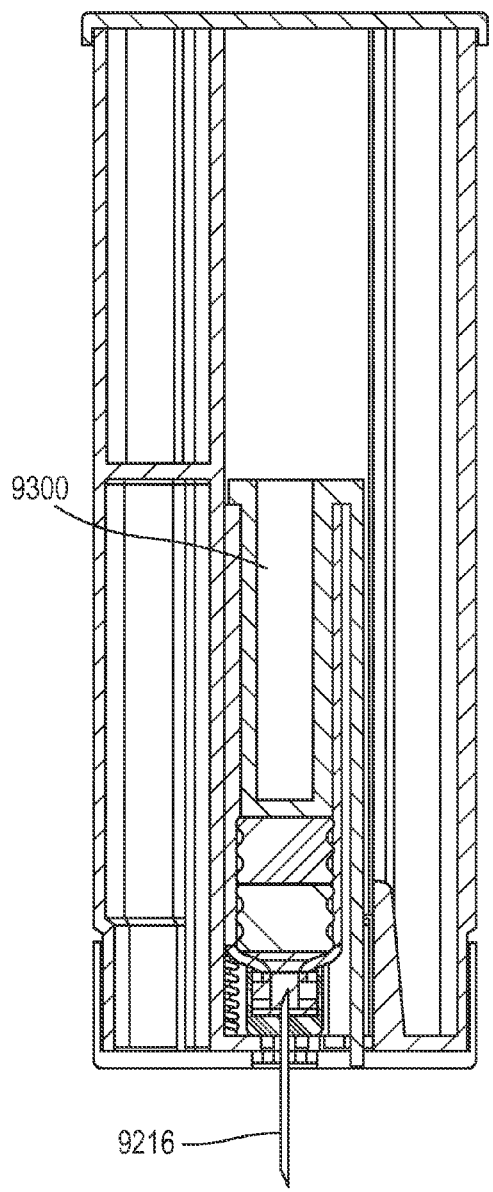
Figure 117:
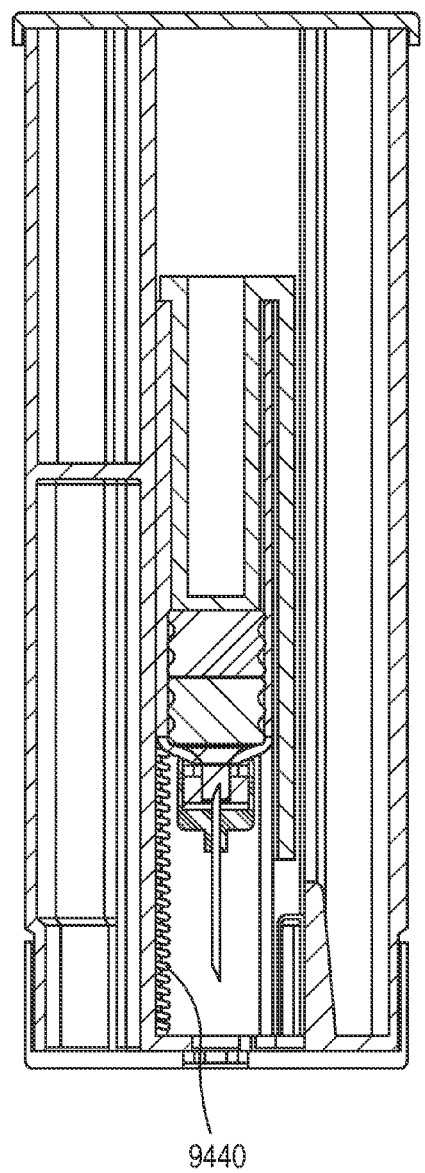

FIG. 112 depicts the injector 9000 with the case 9190 disposed about the housing 9100 (e.g., a first configuration). As depicted in FIG. 113, the case 9190 can be removed from the injector 9000 to place the injector 9000 in a second configuration. Removing the case 9190 can actuate an electronic assembly (not shown in FIGS. 112-117) to produce an electronic output, such as, for example, an output indicating the status of the injector 9000 or providing instructions for operation. Removing the case 9190 can actuate the electronic assembly by engaging a portion of the electronic assembly, placing a battery assembly in electronic communication with a processor, or the like.

The safety lock 9700 can be removed from the injector 9000 to place the injector 9000 in a third configuration (e.g., initiation of the mixing operation). Removing the safety lock 9700 can cause a first switch actuator 9724 to activate a first switch of the electronic assembly to produce a second electronic output and/or continue producing a current electronic output.

Removing the safety lock 9700 exposes the base 9510 of injector 9000. The base 9510 can be moved in the proximal direction thereby causing an injection spring to act against the proximal cap 9103, which moves the movable member 9300 in the distal direction. The initial movement of the movable member 9300 starts the mixing operation as described above with reference to the injector 8000 (e.g., the third configuration, see FIG. 113). More specifically, the base 9510 can be moved in the proximal direction and can cause a release rod to deform release portion to actuate the injection assembly, in a similar manner as described above. An injection spring acts against the proximal cap 9103 and a transfer mechanism (e.g., similar to the transfer member 7600), and causes the injection latch, and therefore the piston portion 9330, to move in the distal direction. The distal movement of the movable member 9300 causes a piston portion 9330 of the movable member 9300 to contact the first elastomeric member 9221. The distal movement of the first elastomeric member 9221 within the medicament container 9210 can move the second elastomeric member 9225 within the medicament container 9210 as described above, and as shown in FIGS. 113 and 9114. In this manner, actuation of the injection spring produces the mixing operation, as described above.

As the diluent flows into the mixing volume 9237, the volume of the diluents volume 9236 can be reduced, and the volume of the mixing volume 9237 can remain substantially the same. The first elastomeric member 9221 can contact the second elastomeric member 9225 and can continue to move in the distal direction. In this manner, mixing of the medicament can be substantially complete (e.g., a fourth configuration). The distal movement of the first elastomeric member 9221 and the second elastomeric member 9225 can cause the volume of the mixing volume 9237 to be reduced and can cause any air within the mixing volume 9237 to vent out of the injector 9000.

The injector 9000, and any other injectors described herein (including the injector 7000 and 7000'), can use any suitable mechanism for venting the air within the mixing volume 9237. For example, in some embodiments, the mixing mechanism can include a "two-step" mixing actuator. The initial actuation (or first step) of the mixing mechanism results in the mixing operation, as described above. In such embodiments, the injector can include a protrusion or other member to limit the further movement of the spring. When mixing of the medicament is substantially complete, a user can orient the injector 9000 upwards, and can press a "vent" button, which actuates a release mechanism to allow the spring to expand further. Continued pressure exerted by the spring, can cause the container to move, such that the needle 9216 pierces a crimp seal. In this manner, air within the mixing volume 9237 can escape via needle 9216. In some embodiments, the continued pressure exerted by the spring can increase the turbulence of the diluent flowing within the medicament container, thereby enhancing the mixing operation.

In a three-plunger design (e.g., injectors 7000, 7000' and 8000), upon pressing the "vent" button, continued distal movement of the first elastomeric member 7221', the second elastomeric member 7225' and the third elastomeric member 225' within the medicament container 7210 causes the needle 7216 to pierce the third elastomeric member 7225'. In this manner, air within the mixing volume 7237' can escape via needle 7216.

After venting, the user can push an injection button (not shown) and can allow a mixing spring (not shown) to continue to push the elastomeric members toward the distal end of the medicament container 7210 and can begin the injection process as described below.

Continued movement of the movable member 9300 starts the injection process (e.g., a fifth configuration). The movable member 9300, the carrier 9260, and the medicament container 9210 can move substantially together, and can cause retraction member 9440 to compress. In this manner, needle 9216 is inserted. A distal end portion of carrier 9260 can contact the base 9510 and/or the housing 9100 to stop the distal movement of the carrier 9260 and the medicament container 9210 (e.g., a sixth configuration).

The injection spring can continue to move the injection latch and movable member 9300. Said in another way, the movable member 9300 can begin to move relative to the carrier 9260. A piston portion 9330 of the movable member 9300 can cause the first elastomeric member 9221 and the second elastomeric member 9225 to move in the distal direction, causing medicament within the mixing volume 9237 to flow into the needle 9216 out of the injector 9000. The first elastomeric member 9221 and the second elastomeric member 9225 can continue to move in the distal direction into contact with the distal end portion 9213 of the medicament container 9210. At this point, the flow of medicament from the mixing volume 9237 through the needle 9216 and out of the injector 9000 is stopped (a seventh configuration).

As the transfer member and the movable member 9300 near the base 9510, the transfer member can be decoupled from the movable member 9300 by any suitable mechanism, thereby removing the force of the injection spring (not shown) from movable member 9300. The retraction member 9440, which has been compressed by the injection operation between the retraction member protrusion 9284 and the base 9510, can expand and can move the carrier 9260 and the needle 9216 in the proximal direction within the injector 9000 (e.g., an eighth configuration). In some embodiments, the retraction member 9440 can expand fully. In some embodiments, the carrier 9260 can move in the proximal direction and a latch included in the carrier 260 can contact a catch of the housing 9100 to stop the proximal movement of the carrier 9260 and the needle 9216.

Although the injector 7000 is shown and described as having a mixing activator member 7550 that is partially disposed within the injection spring 7420, in other embodiments, a mixing activator release member and an injection spring (and/or injection assembly) can be disposed on opposing sides within an injector. Said another way, a mixing activator release member may not be disposed within the injection spring. For example, FIGS. 118-133 depict an injector 10000. Certain components within the injector 10000 can be similar to and have similar functions as the corresponding components in the injector 10000. By way of example, first elastomeric member 10221 of the injector 10000 can be similar in configuration to first elastomeric member 7221 of the injector 7000. The injector 10000 at least differs from injector 7000, however, in that a mixing activator member 10550 of the injector 10000 is not disposed within an injection spring 10420.

Figure 118:
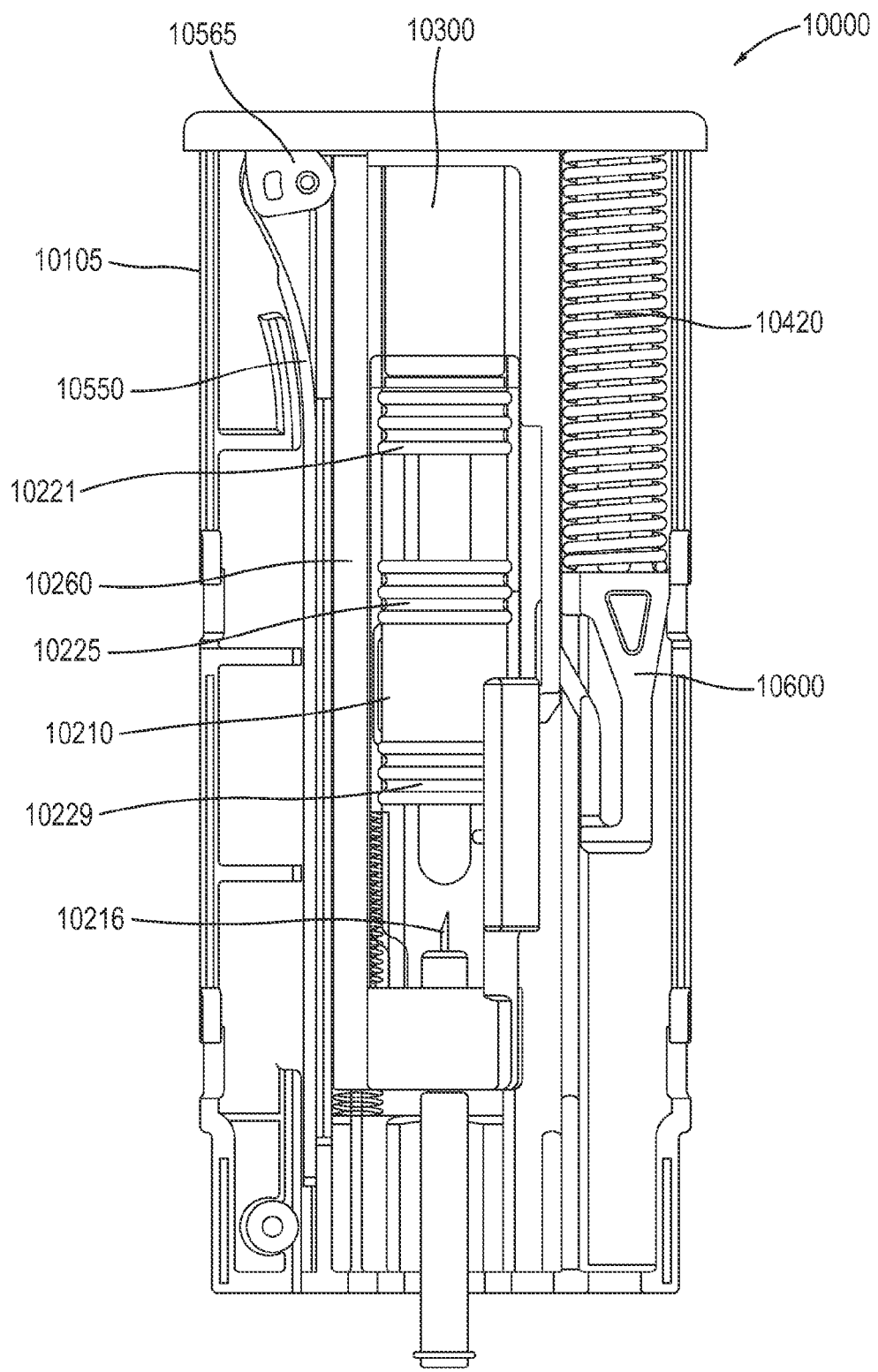
FIG. 118 is a front view of a portion of a medical injector in a first configuration, according to an embodiment.
Figure 119:
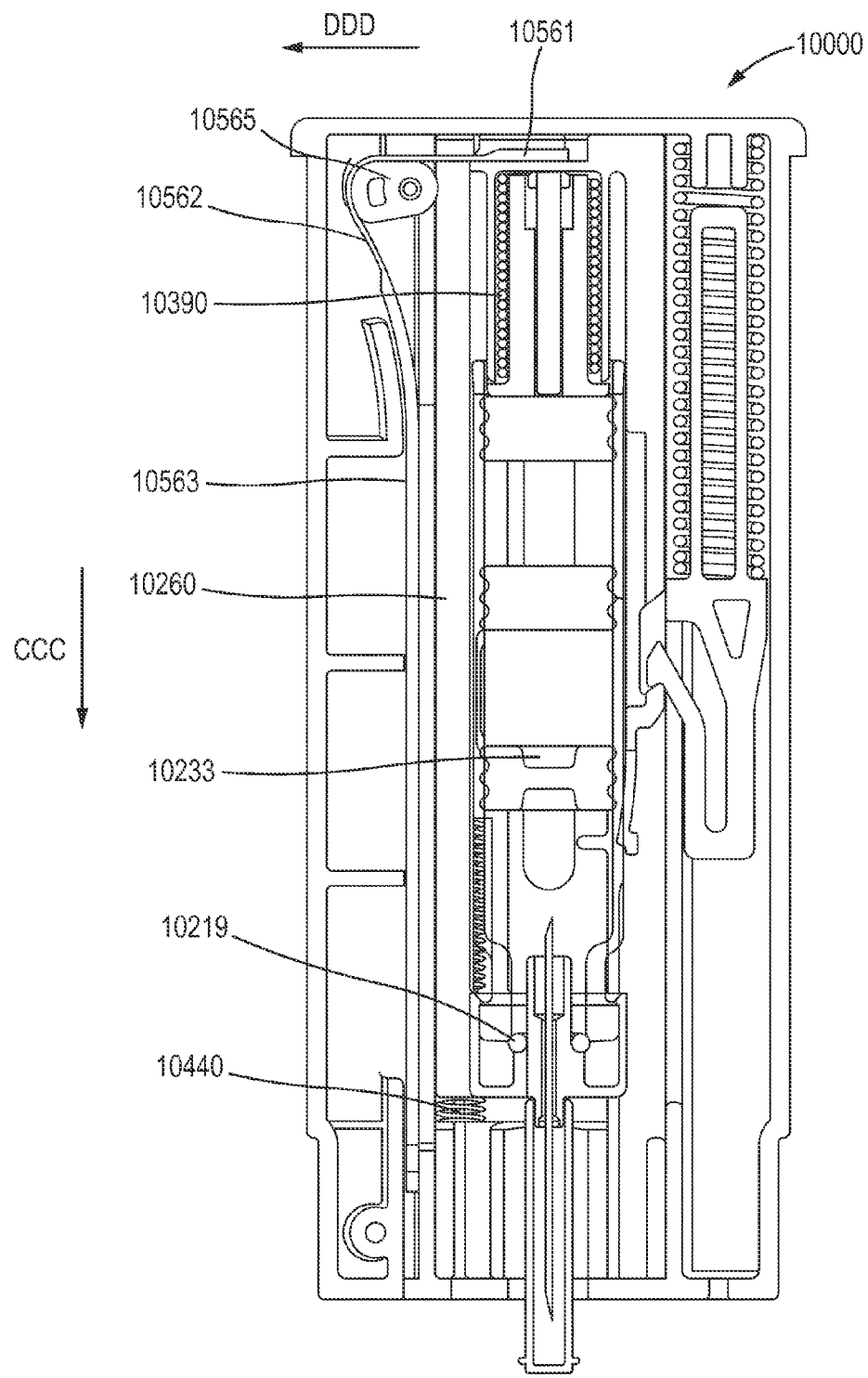
FIG. 119 is a front cross-sectional view of the portion of the medical injector illustrated in FIG. 118 in the first configuration.
Figure 120:
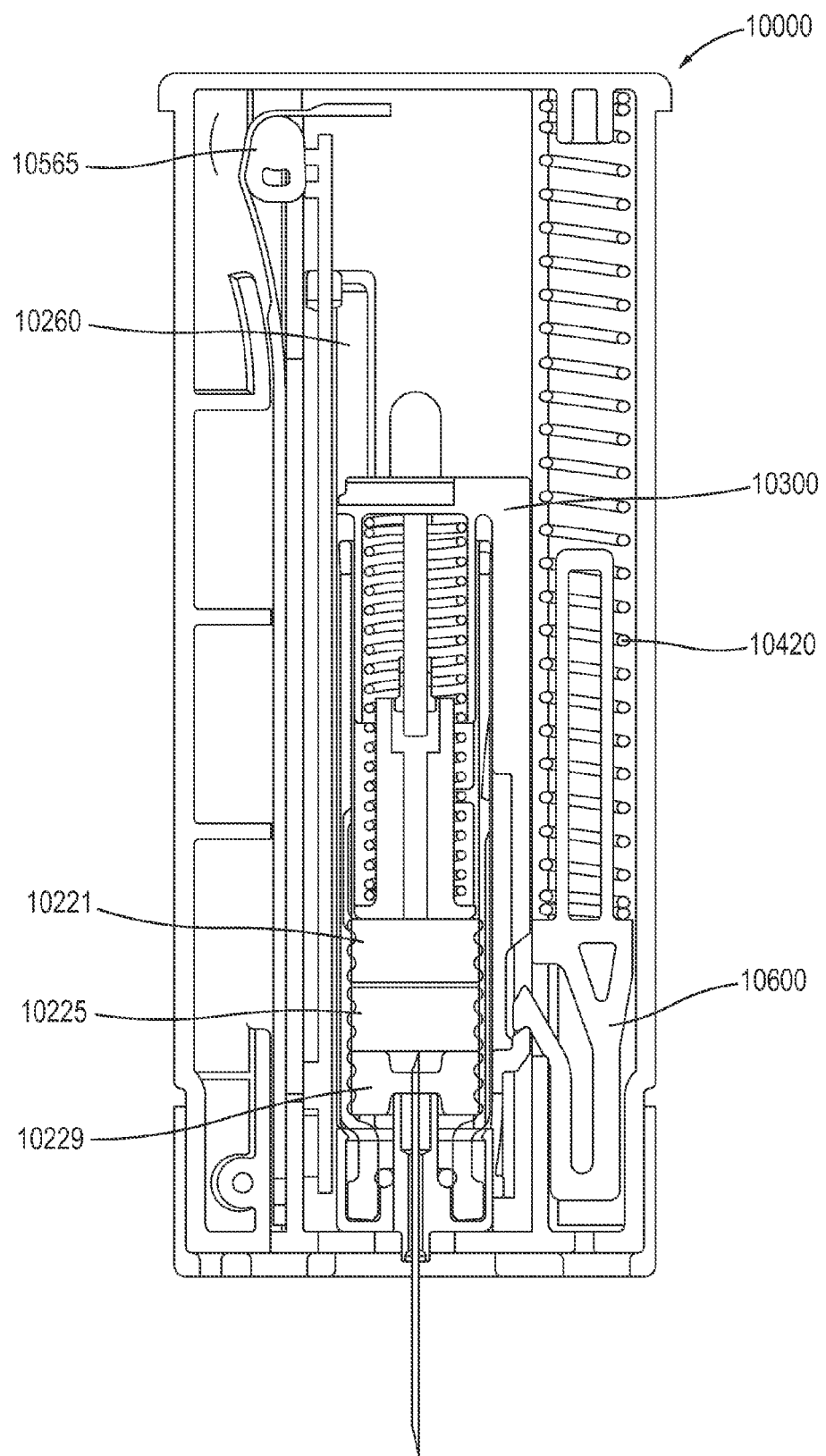
FIG. 120 is a front cross-sectional view of a portion of the medical injector illustrated in FIG. 118 in a second configuration.
Figure 121:
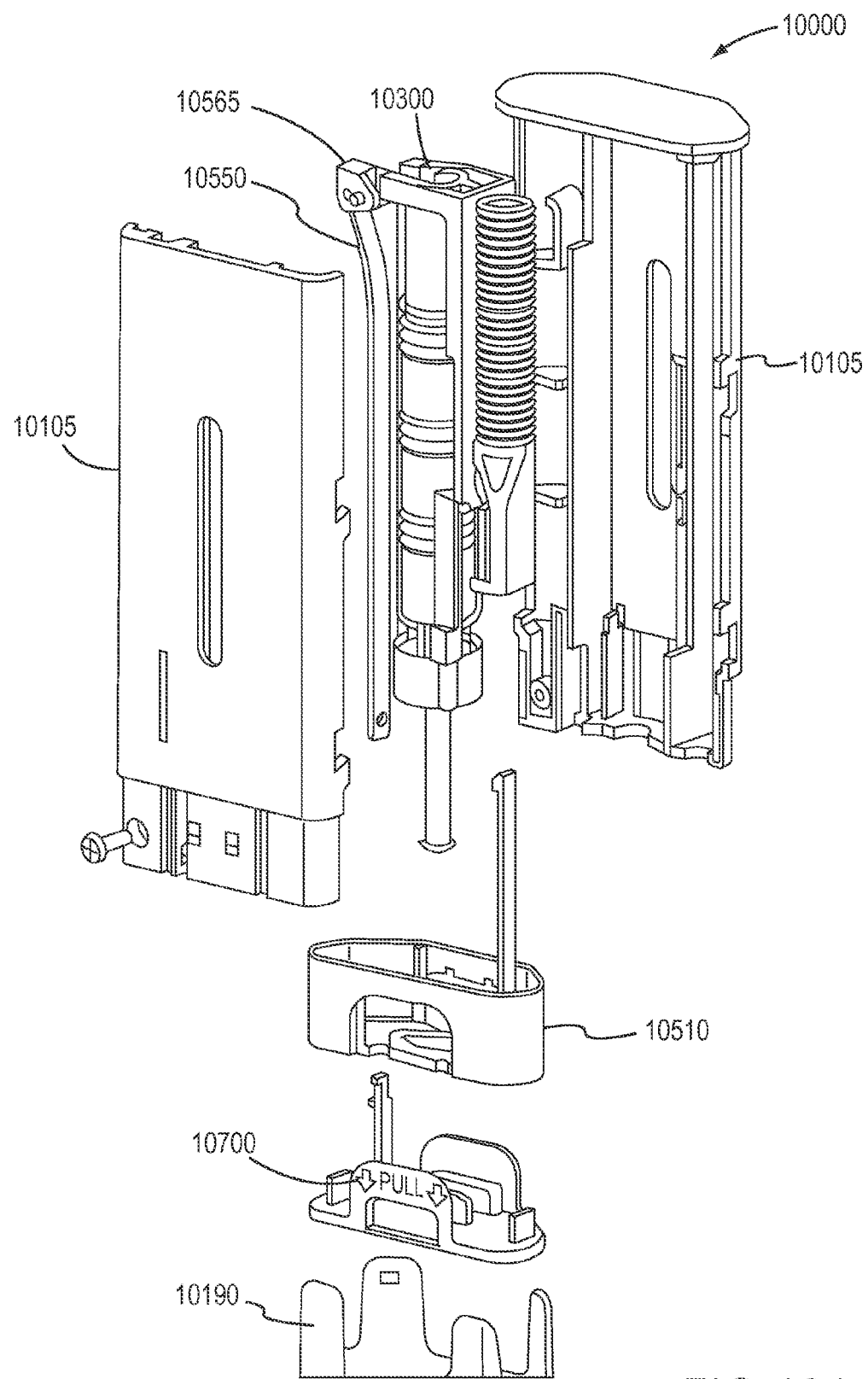
FIG. 121 is an exploded perspective view of a portion of the medical injector illustrated in FIG. 118.
Figure 133:
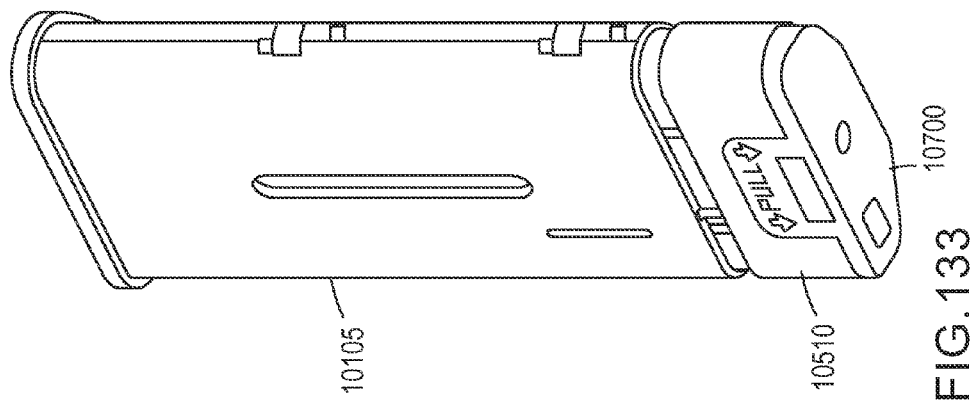
FIG. 133 is a perspective view of the medical injector illustrated in FIG. 118 in the first configuration.
Figure 132:
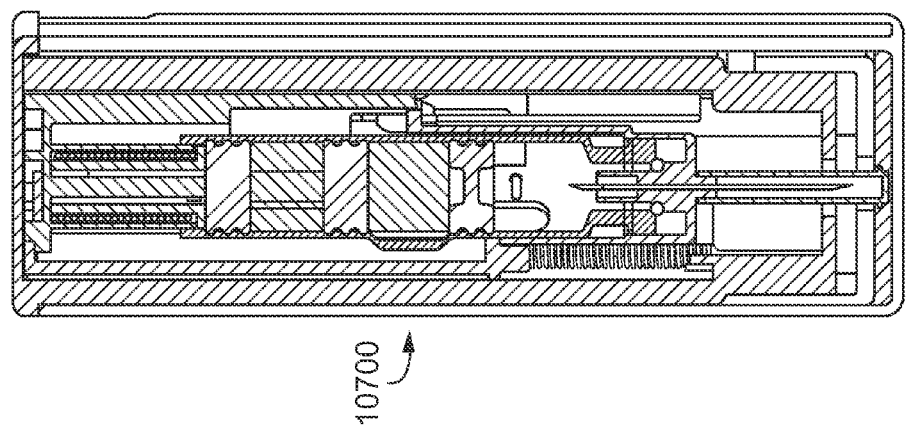
FIG. 132 is a cross-sectional view of the medical injector illustrated in FIG. 131 taken along the line W2-W2.

FIG. 118 is a front view of the injector 10000 in a second configuration, FIG. 119 is a cross-sectional view of the injector 10000 in the second configuration, FIG. 120 is a cross-sectional view of the injector 10000 in the seventh configuration, and FIG. 121 is an exploded perspective view of the injector 10000. FIG. 122-FIG. 130 depict the operation of the injector 10000. FIG. 131 depicts a top view of the injector 10000, and FIG. 132 depicts a cross-sectional view the injector 10000 taken along line W2-W2. FIG. 133 depicts a view of the injector 10000 in the second configuration. The injector 10000 includes a body 10105, a carrier 10260, a medicament container 10210, a first elastomeric member 10221, a second elastomeric member 10225, a third elastomeric member 10229, a mixing activator member 10550, a mixing latch guide 10565, a mixing spring 10390, a medicament delivery mechanism 10300, an injection spring 10420, an transfer member 10600, an energy-absorbing member 10219, and a retraction member 10440. As shown in FIGS. 118-121, the mixing activator member 10550 includes a first thickness 10561, a second thickness 10562, and third thickness 10563. In this manner, the rigidity of the mixing activator member 10550 can vary spatially. Said another way, the mixing activator member 10550 can be less rigid at certain points (e.g., the second thickness 10562) to allow the mixing activator member 10550 to deform and/or bend more easily during the operation of the injector 10000, e.g. about the mixing latch guide 10565. In some embodiments, however, mixing activator member 10550 can be a substantially uniform thickness. In some embodiments, mixing activator member 10550 can include more or fewer than three thicknesses. In some embodiments, other injectors shown in described herein can include a mixing latch with varying thicknesses as described above. The mixing latch guide 10565 can act as a cam for the mixing activator member 10550 during movement of the mixing activator member 10550. In this manner, a vertical portion of the mixing activator member 10550 can move twice as far in the direction CCC as a horizontal portion of the mixing activator member 10550 moves in the direction DDD. Said another way, the mixing latch guide 10565 imparts a mechanical advantage on the mixing activator member 10550. In other embodiments, the mixing latch guide 10565 can be configured such that the vertical portion of the mixing activator member 10550 can move a shorter distance in the direction CCC than the horizontal portion of the mixing activator member 10550 moves in the direction DDD.

The injector 10000 also includes the energy-absorbing member 10219. The energy-absorbing member 10219 can absorb, deflect and/or redirect energy, and/or otherwise reduce the energy transferred into certain components of the injector 10000 during operation. More specifically, the energy-absorbing member 10219 can reduce the energy transferred to the medicament container during operation. In this manner, a medicament container including fragile materials can be less likely to deform and/or otherwise break during injection.

Figures 126, 127:
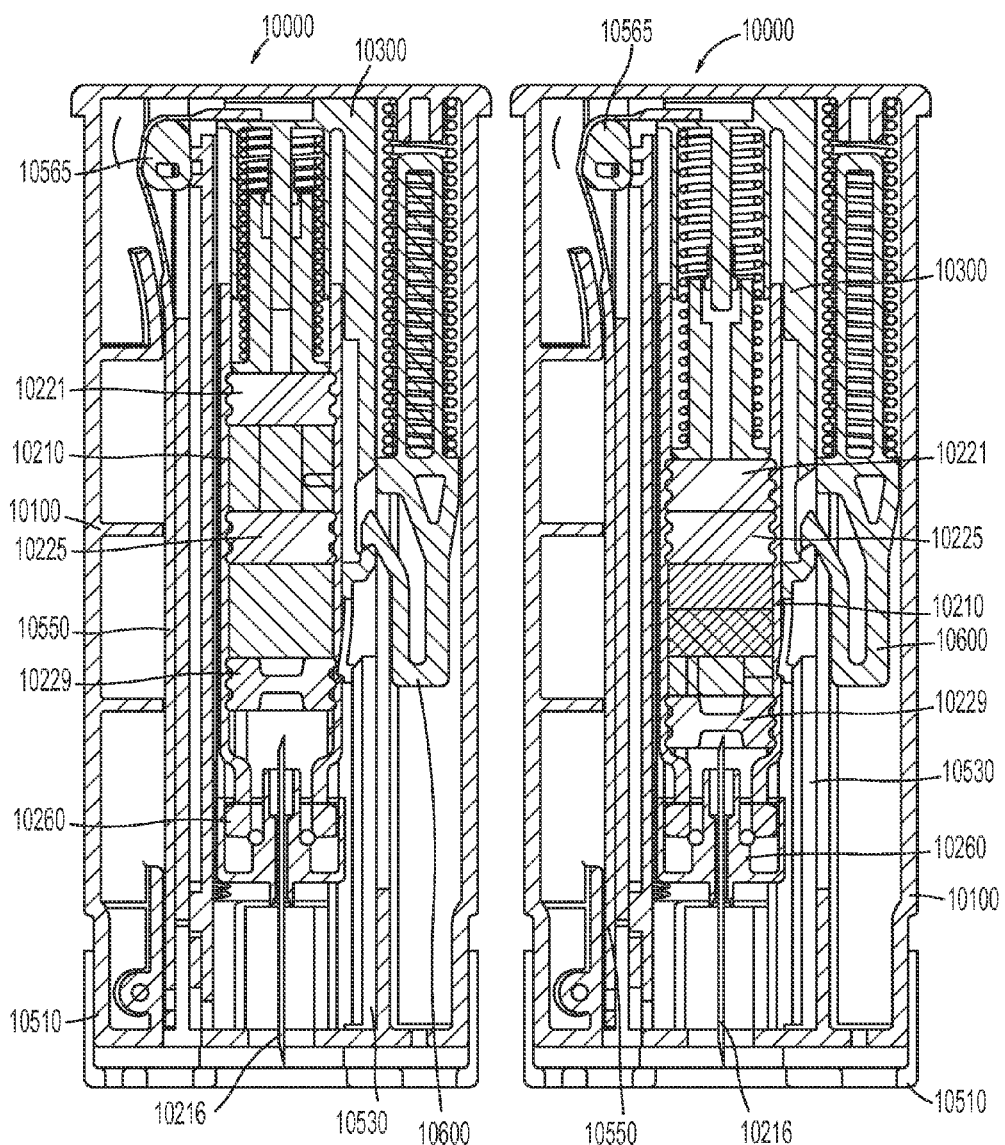
FIGS. 126-130 are cross-sectional views illustrating the operation of the medical injector illustrated in FIG. 118.
Figures 128, 129:
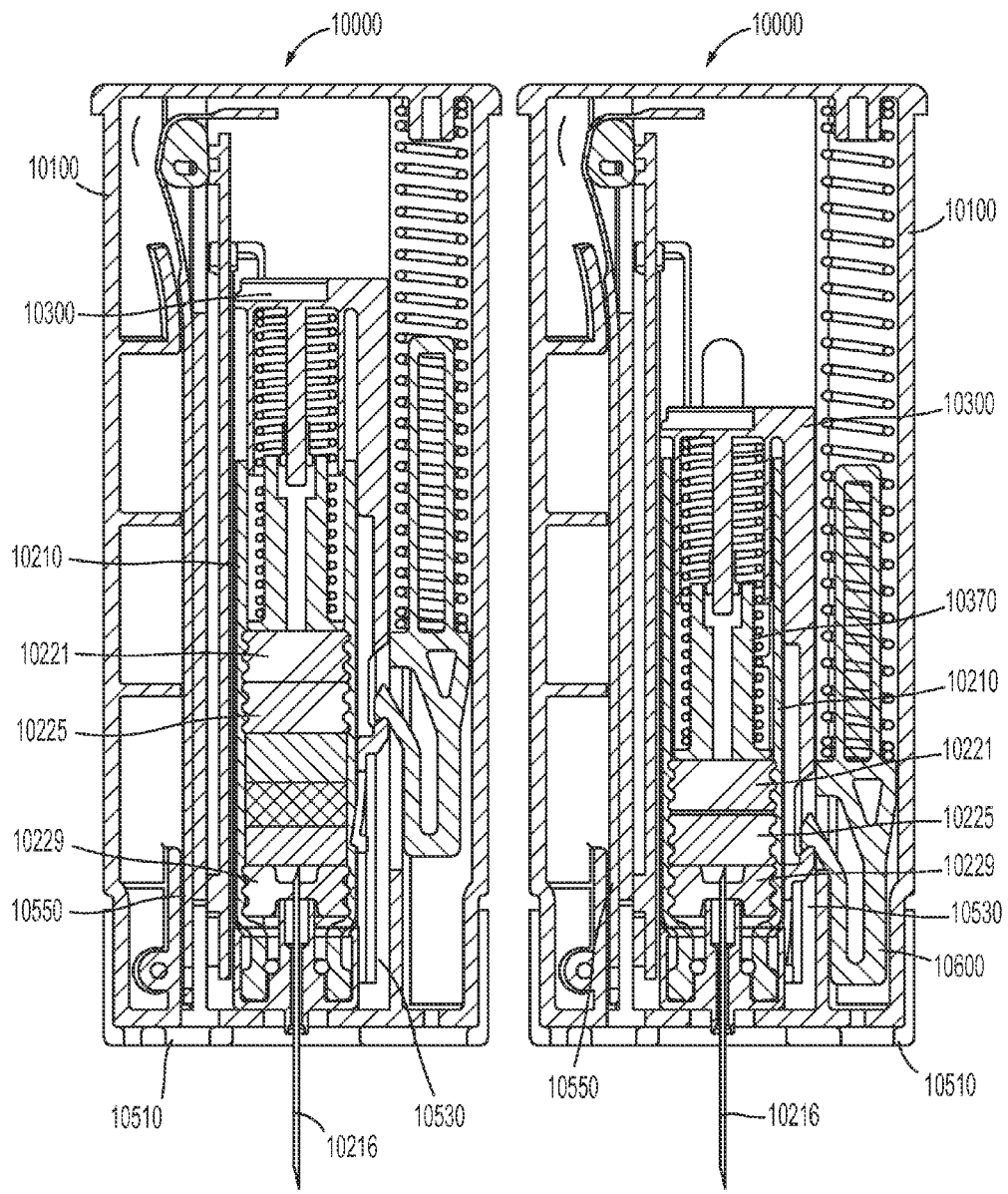
Figure 130:
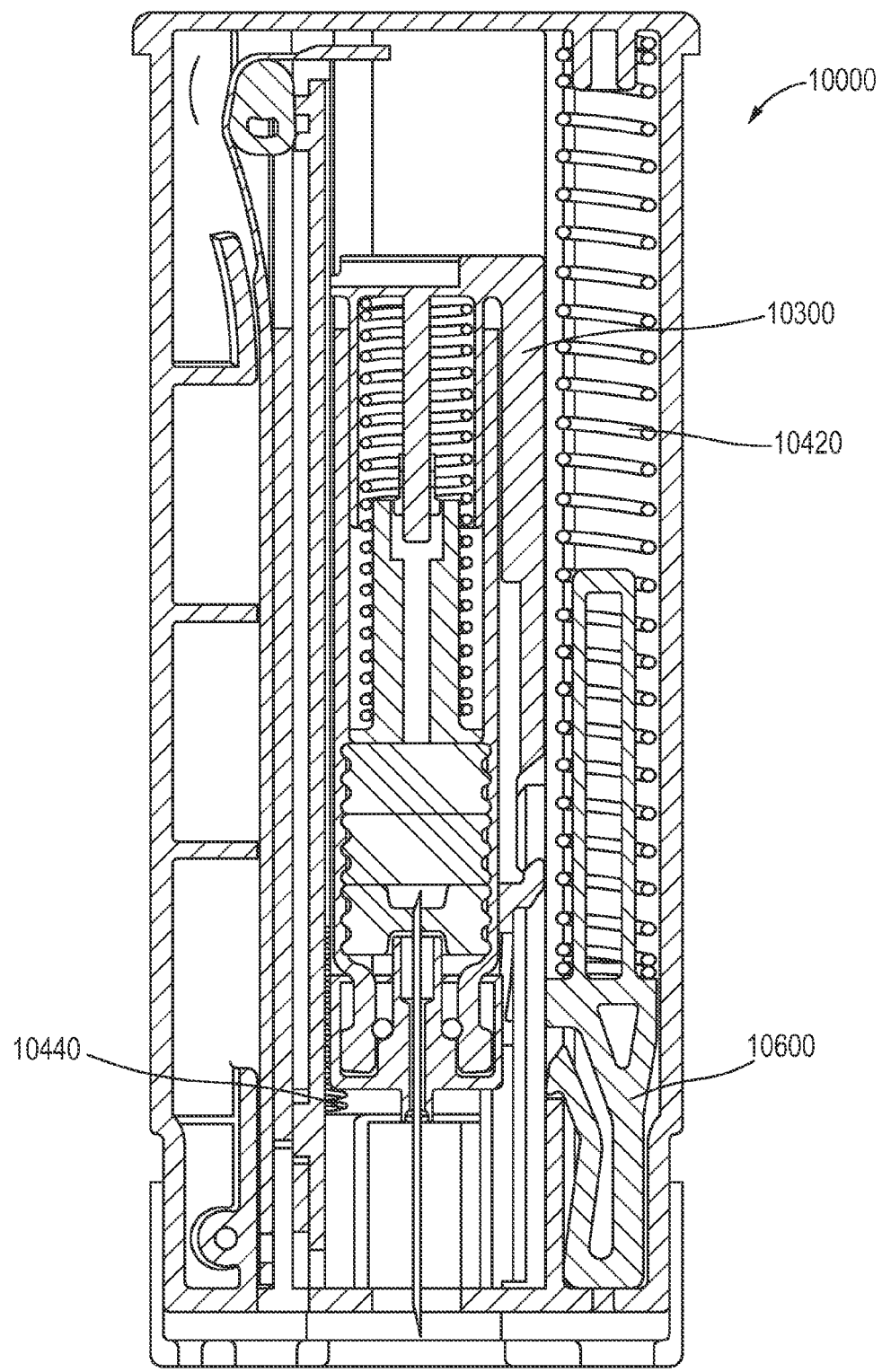
Figure 131:
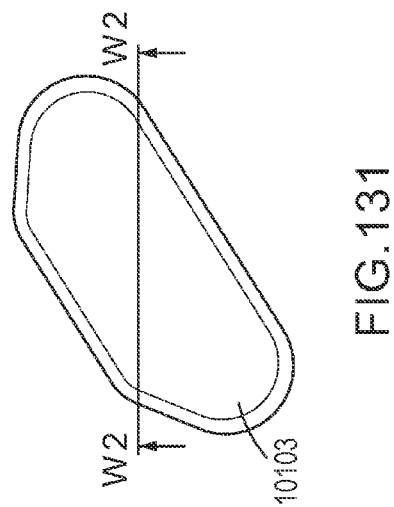
FIG. 131 is a top view of the medical injector illustrated in FIG. 118.

FIG. 122-FIG. 130 depict the operation of the injector 10000. The operation of injector 10000 can be similar to the operation of the injector 7000 and the injector 7000' as described above. FIG. 122 is a top view of the injector 10000, FIG. 123 is a bottom view of the injector 10000, FIG. 124 is a cross-sectional view of the injector 10000 in the first configuration (i.e. prior to removal of a case 10190), and FIG. 125 is a cross-sectional view of the injector 10000 taken along line W1-W1. FIG. 126 is a cross-sectional view of the injector 10000 in the third configuration (e.g., mixing start). FIG. 127 is a cross-sectional view of the injector 10000 in the fourth configuration (e.g., mixing end). FIG. 128 is a cross-sectional view of the injector 10000 at the end of the fifth configuration (e.g., insertion) and the beginning of the sixth configuration (e.g., injection start). FIG. 129 is a cross-sectional view of the injector 10000 in the seventh configuration (e.g., injection end). FIG. 130 is a cross-sectional view of the injector 10000 in the eighth configuration (e.g. retraction). As shown in FIG. 130, after the injection process ends, the latch 10620 is decoupled from the medicament delivery mechanism 10300. In this manner, the retraction member 10440 does not have to overcome the force of the injection spring 10420.

Figure 134:
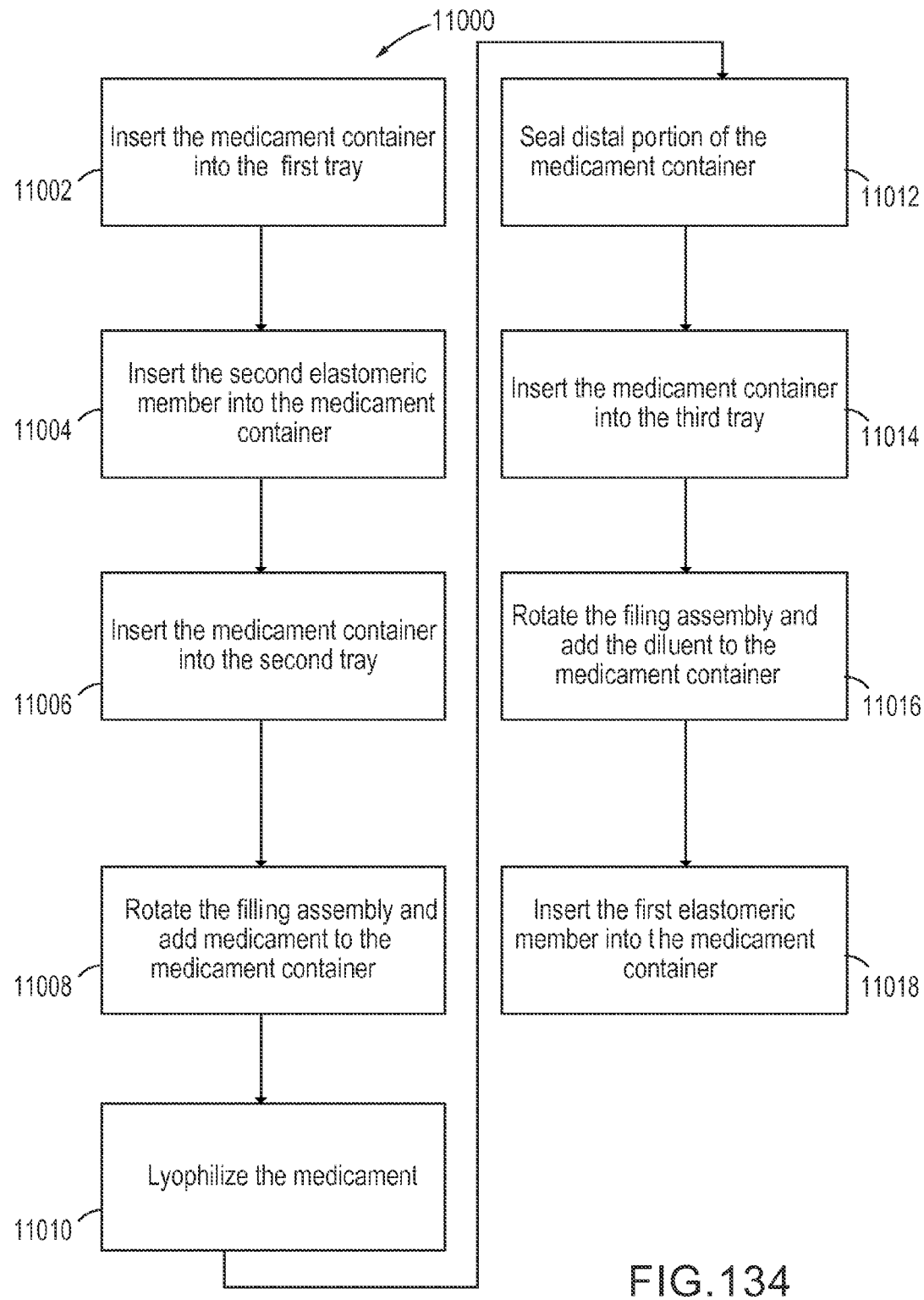
FIG. 134 is a flow chart illustrating a method of filling a medicament container according to an embodiment.
Figure 135:
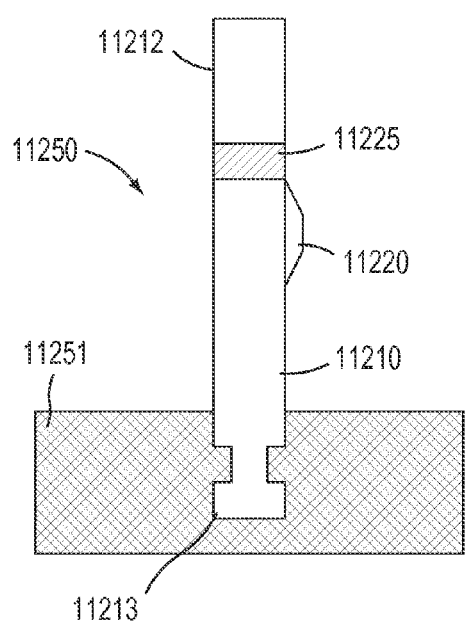
FIGS. 135-142 are schematic illustrations of an embodiment of a filling assembly operating according to the method illustrated in FIG. 134.
Figure 136:
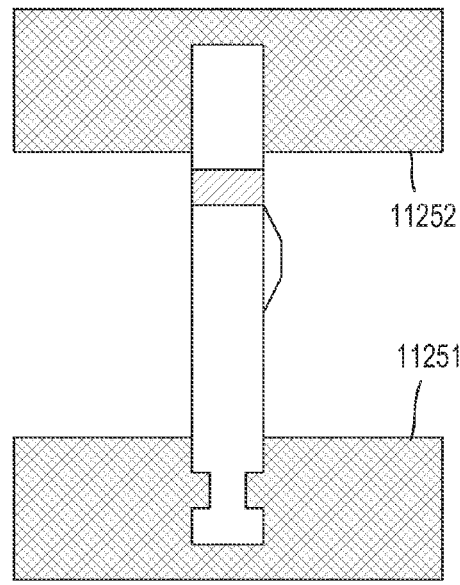

FIG. 134 is a flow chart illustrating, and FIGS. 135-142 are schematic illustrations depicting, a method 11000 and a filling assembly 11250 according to an embodiment. The method 11000 relates to the filling of medicament constituents in a medicament container 11210. The filling assembly 11250 includes a first tray 11251, a second tray 11252, a third tray 11253 (shown in FIG. 140), and the medicament container 11210. The medicament container 11210 can be similar to medicament container 11210, and upon completion of the fill/finish operation includes a first elastomeric member 11221, a second elastomeric member 11225, a bypass 11220, a distal end portion 11213, a proximal end portion 11212, and a crimp seal 242. The method 11000 includes inserting a portion of the distal end portion 11212 of the medicament container 11210 into the first tray 11251 (at 11002). The method 11000 includes inserting the second elastomeric member 11225 within the medicament container 11210 and moving the second elastomeric member 11225 toward the distal end portion 11212 of the medicament container 11210 (at 11004, see e.g., FIG. 135). In some embodiments, the second elastomeric 11225 can be moved in the distal direction such that at least a proximal surface of the second elastomeric member 11225 is proximal to the bypass 11220. The method 11000 includes placing the second tray 11252 over a portion of the proximal end portion 11213 of the medicament container 11210 (at 11006, see e.g., FIG. 136). Said another way, a portion of the proximal end portion 11213 of the medicament container 11210 is inserted into the second tray 11252.

Figure 137:
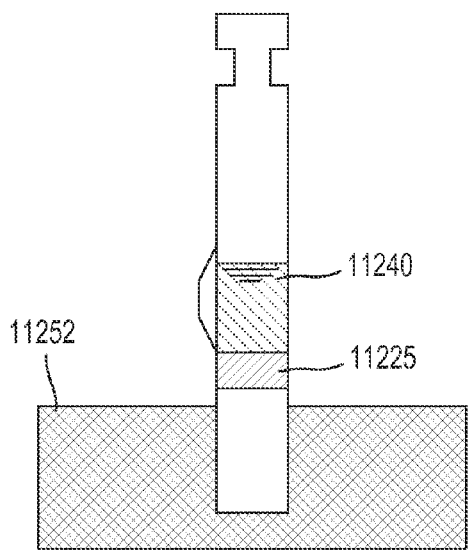
Figure 138:
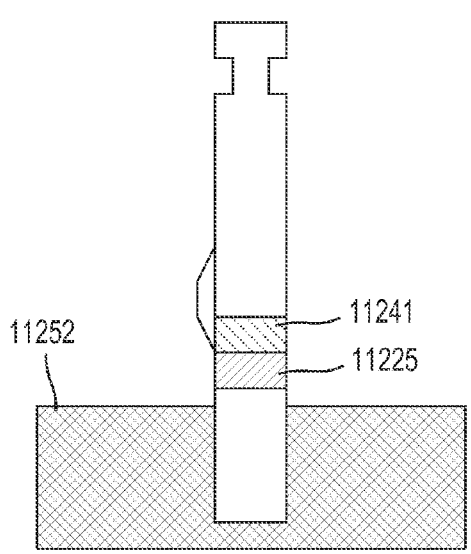
Figure 139:
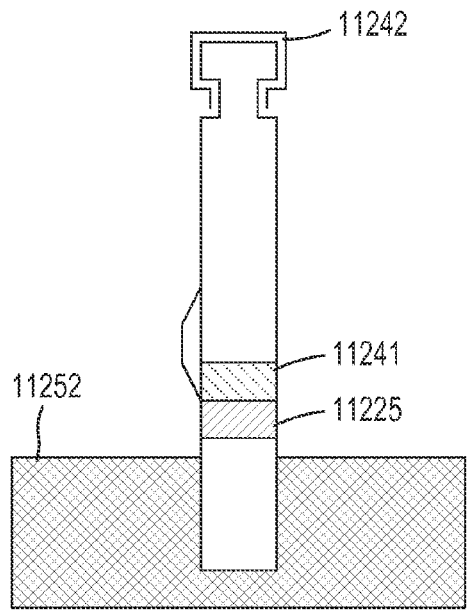
Figure 140:
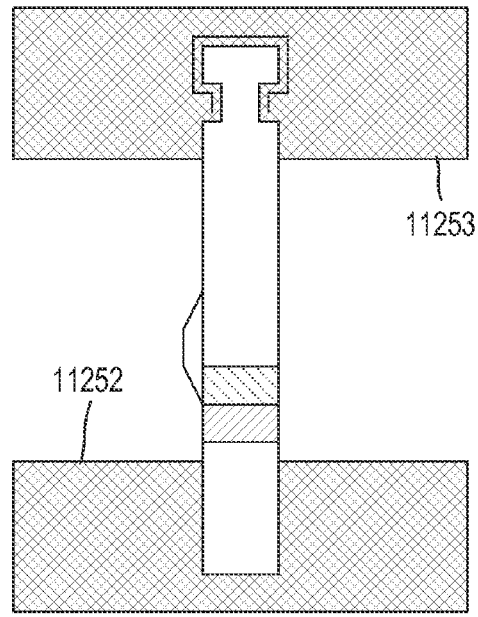
Figure 141:
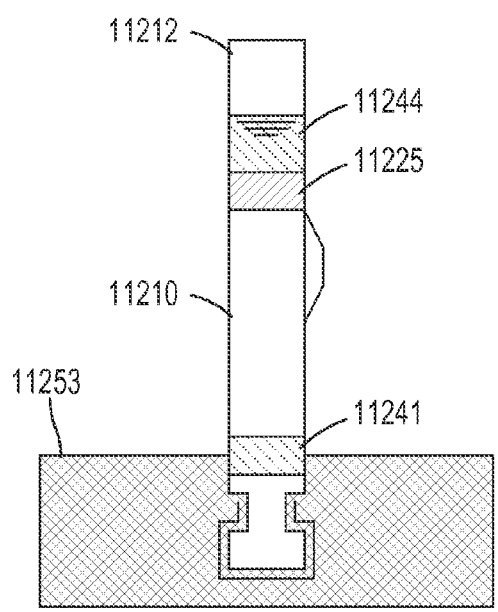
Figure 142:
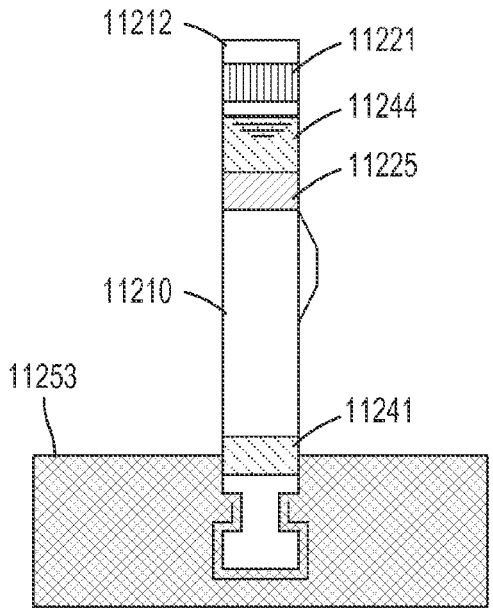

The method 11000 includes rotating the filling assembly 11250, removing the first tray 11251, and adding a medicament 11240 via the distal end portion 11213 of the medicament container 11210 (at 11008, see e.g., FIG. 137). The filling assembly 11250 is inserted into a lyophilizing machine (not shown), and the medicament 11240 is lyophilized (the lyophilized medicament is designated as 11241) (at 11010, see e.g., FIG. 138). In some embodiments, the lyophilized medicament 11241 can be added to the medicament container 11210 at operation 11006. The method 11000 includes sealing the distal end portion 11213 of the medicament container 11210 with a crimp seal 11242 (at 11012, see e.g., FIG. 139). The method 11000 includes placing the third tray 11253 over a portion of the distal end portion 11213 of the medicament container 11210 (at 11014, see e.g., FIG. 140). Said another way, a portion of the distal end portion 11213 of the medicament container 11210 is inserted into the third tray 11253. In some embodiment, the first tray 11251 can be used in place of the third tray 11253 at operation 11014. The method 11000 includes rotating the filling assembly 11250, removing the second tray 11252, and adding a diluent 11244 via the proximal end portion 11212 of the medicament container 11210 (at 11016, see e.g., FIG. 141). The method 11000 includes inserting the first elastomeric member 11221 within the medicament container 11210 and moving the first elastomeric member 11221 toward the distal end portion 11213 of the medicament container 11210 (at 11018, see e.g., FIG. 142).

Figure 143:
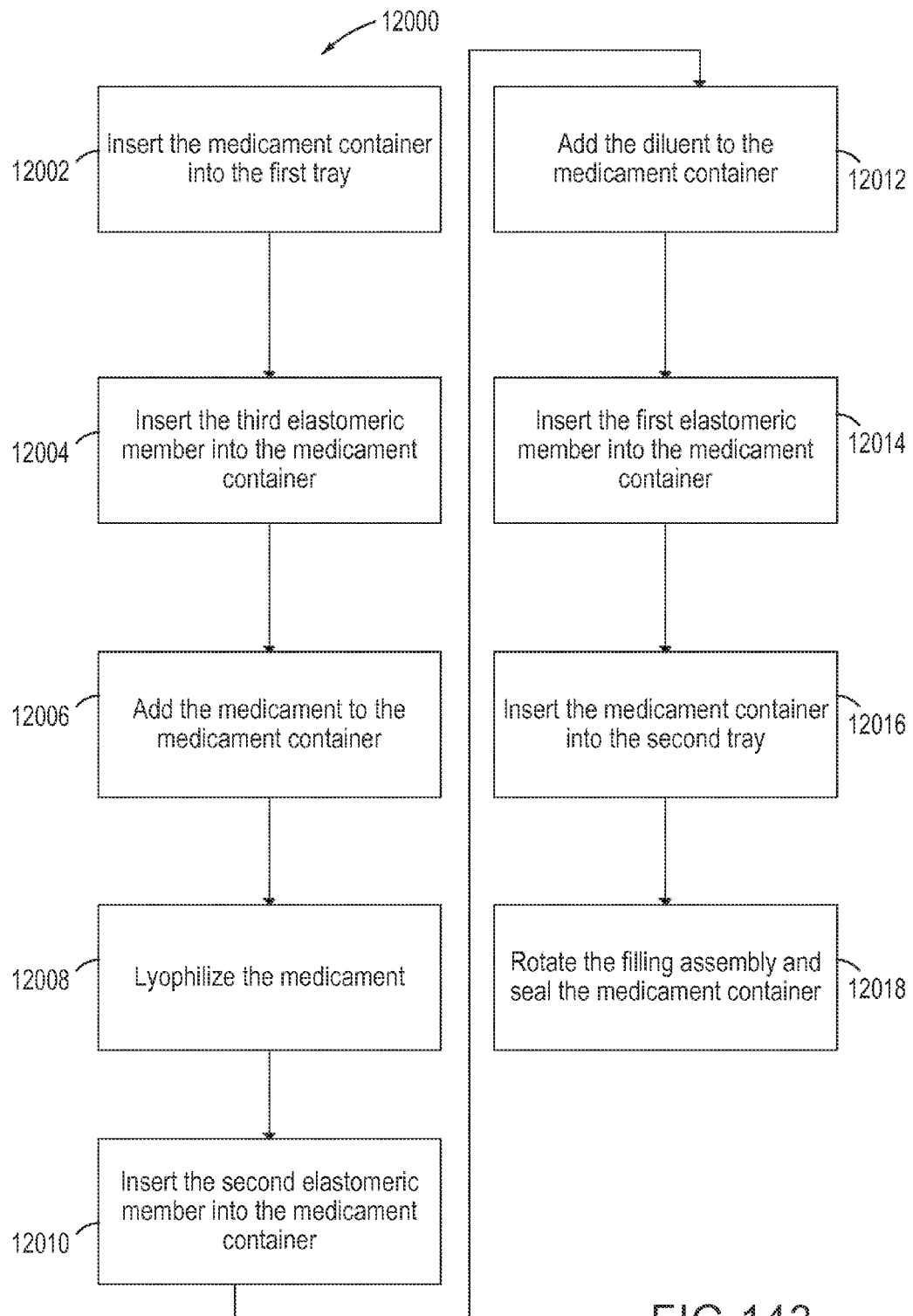
FIG. 143 is a flow chart illustrating a method of filling a medicament container according to an embodiment.
Figure 144:
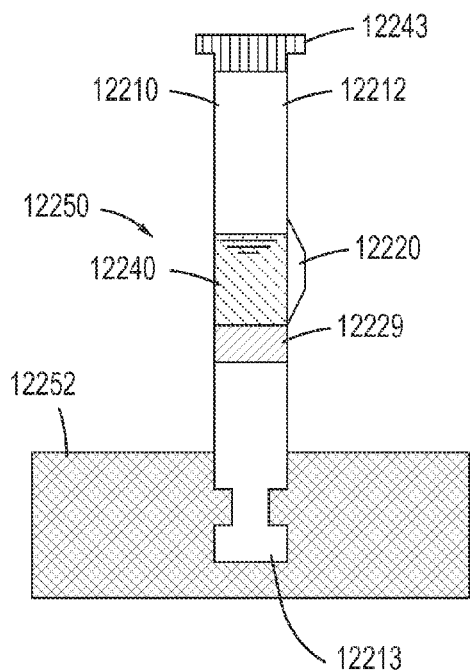
FIGS. 144-150 are schematic illustrations of an embodiment of a filling assembly operating according to the method illustrated in FIG. 143.
Figure 145:
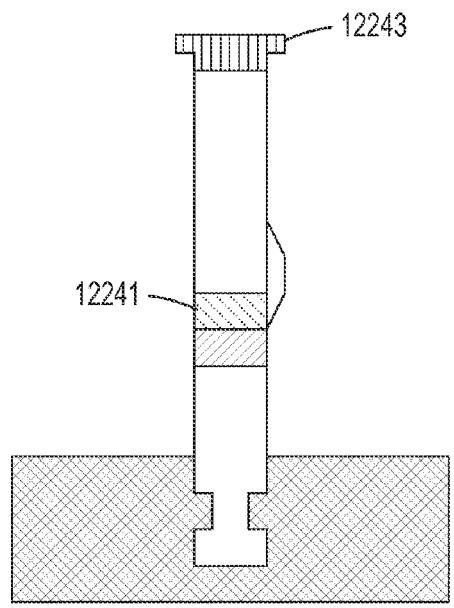
Figure 146:
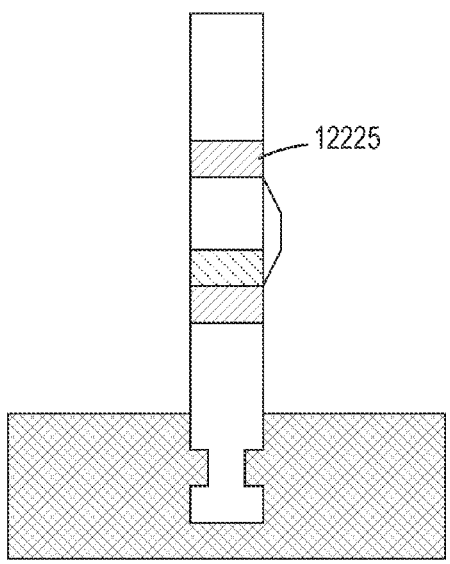
Figure 147:
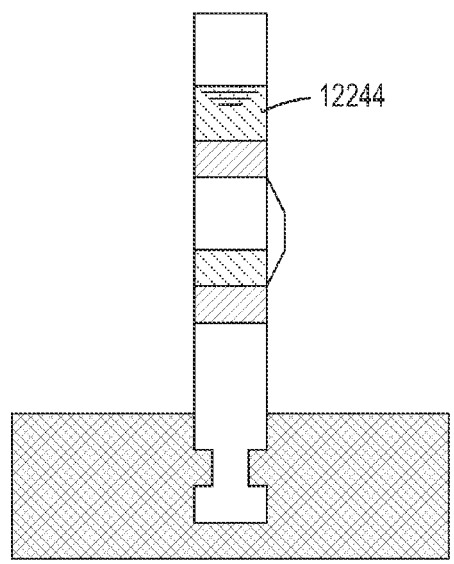
Figure 148:
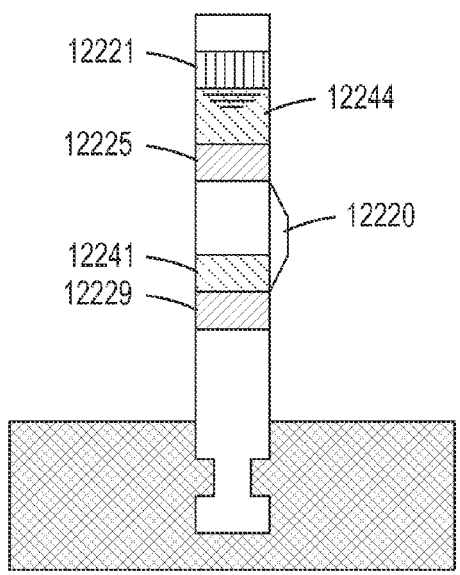

FIG. 143 is a flow chart illustrating, and FIGS. 144-150 depict a method 12000 and a filling assembly 12250 according to an embodiment. The method 12000 relates to the filling of medicament constituents in a medicament container 12210. All or portions of the method 12000 can be performed by any suitable filling system, such as, for example, a filling system 13000 depicted in FIG. 151. The filling assembly 12250 includes a first tray 12251, a second tray 12252, and the medicament container 12210. The medicament container 12210 can be similar to medicament container 12210 and includes a first elastomeric member 12221, a second elastomeric member 12225, a temporary elastomeric member 12243, a third elastomeric member 12229, a bypass 12220, a distal end portion 12213, a proximal end portion 12212, and, optionally, a crimp seal 12242.

Figure 151:
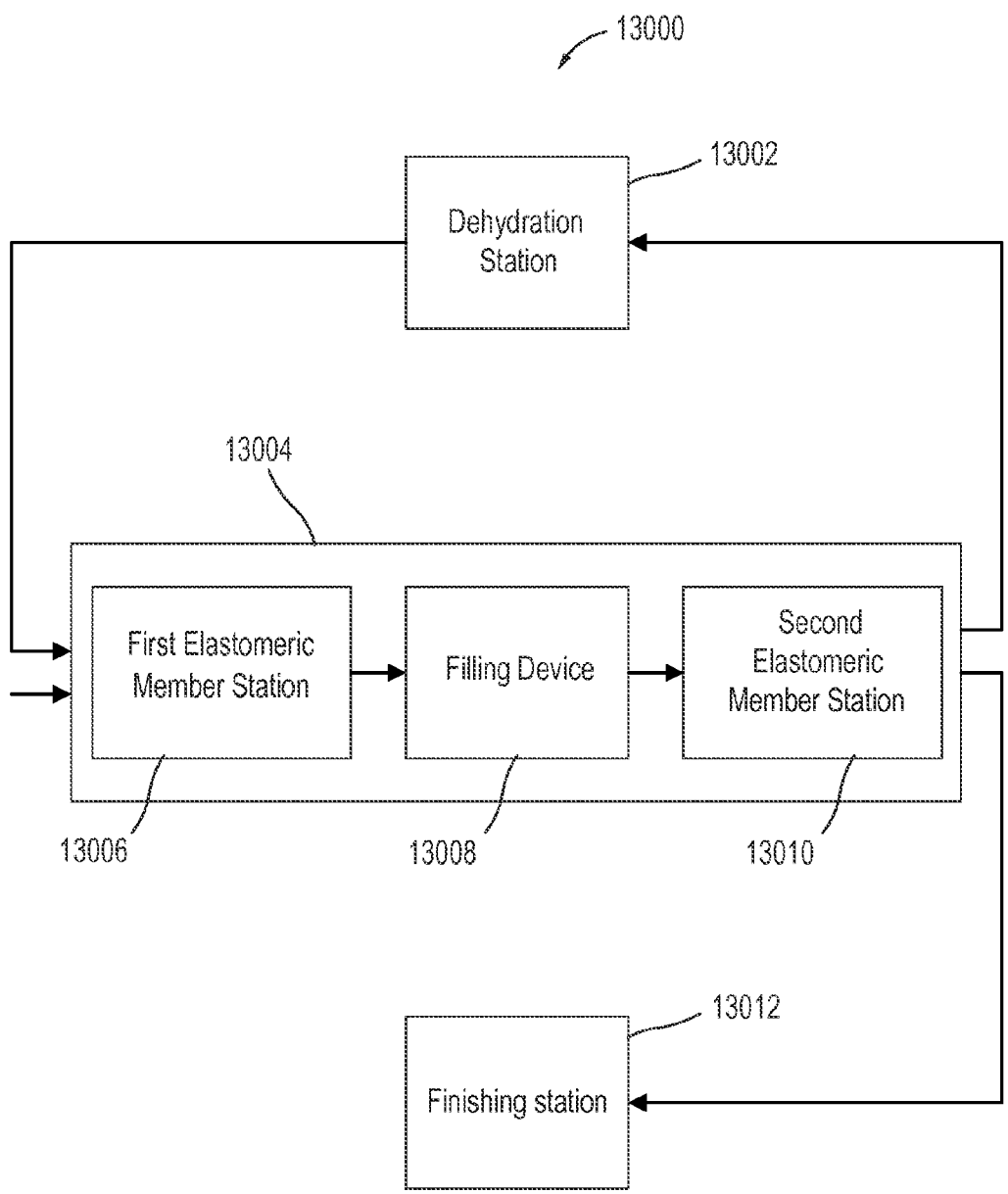
FIG. 151 is a system block diagram of a filling system according to an embodiment.

The filling system 13000 includes a filling station 13004, a dehydration (or lyophilization) station 13002, and a finishing station 13012. The filling station 13004 includes a first elastomeric member station 13006 configured to insert the third elastomeric member 12229 and/or the second elastomeric member 12225 into the medicament container 12210, a filling device 13008 configured to add medicament and/or diluents to the medicament container 12210, and a second elastomeric member station 13010 configured to insert the first elastomeric member 12221 and/or the temporary elastomeric member 12243 into the medicament container 12210. In some embodiments, the filling station 13004 can include more or fewer elastomeric member stations, e.g., an elastomeric member station for each of the first elastomeric member 12221, the second elastomeric member 12225, the third elastomeric member 12229, and/or the temporary elastomeric member 12243. In some embodiments, the filling station 13004 can include more or fewer filling devices, e.g., a filling device for each of the medicament and/or the diluents. While FIG. 151 depicts the first elastomeric member station 13006, the filling device 13008, and the second elastomeric member station 13010 as being grouped within the filling station 13004, in some embodiments these components of the filling station 13004 can be in other configurations, e.g., over multiple filling stations 13004. The dehydration station 13002 can be configured to lyophilize medicament within the medicament container 12210, and finishing station 13012 can be configured to prepare the medicament container 12210 for further assembly and/or packaging.

The method 12000 includes inserting a portion of the distal end portion 12213 of the medicament container 12210 into the first tray 12251 (at 12002). The method 12000 can include moving the medicament container 12210 into the filling station 13004 and can include moving the medicament container 12210 into the first elastomeric member station 13006. The method 12000 includes inserting the third elastomeric member 12229 within the medicament container 12210 and moving the third elastomeric member 12229 toward the distal end portion 12213 of the medicament container 12210 (at 12004, see e.g., FIG. 144). In some embodiments, the third elastomeric member 12229 can be moved in the distal direction such that at least a distal surface of the third elastomeric member 12229 is distal to a distal edge of the bypass 12220.

The method 12000 can include moving the medicament container 12210 into the filling device 13008. The method 12000 includes adding a medicament 12240 via the proximal end portion 12212 of the medicament container 12210 (at 12006, see e.g., FIG. 144). The method 12000 can include moving the medicament container 12210 into the second elastomeric member station 13010. The method 12000 includes adding a temporary elastomeric member 12243 to seal the medicament container 12210 upon completion of the lyophilization process, as described below.

The method 12000 can include moving the medicament container 12210 into the dehydration station 13002. The method 12000 includes lyophilizing the medicament 12240 (the lyophilized medicament is designated 12241 at 12008, see e.g., FIG. 145). During the lyophilization process, the temporary elastomeric member 12243 can allow the volume within the medicament container 12210 that contains the medicament 12240 to be in fluid communication with an area outside of the medicament container 12210. Said another way, the temporary elastomeric member 12243 can allow the volume within the medicament container 12210 that contains the medicament 12240 to "breath" during the lyophilization process. After the medicament 12240 is lyophilized, the method optionally includes manipulating the temporary elastomeric member 12243 to fluidically isolate the volume within the medicament container 12210 that contains the lyophilized medicament 12241, thereby preventing the lyophilized medicament 12241 from absorbing any moisture from the ambient air. In some embodiments, the method can include compressing the temporary elastomeric member 12243 within the medicament container to obstruct or close channels defined therein.

Although the method 12000 is shown as including an operation of lyophilizing a medicament within the medicament container, in other embodiments, the lyophilized medicament can be added to the medicament container 12210 at operation 12006.

The method 12000 can include returning the medicament container 12210 to the filling station 13004, and can include moving the medicament container into the first elastomeric member station 13006. In this manner, portions of the filling station 13004, which were used to insert the third elastomeric member 12229 and/or fill the medicament container 12210 with the medicament 12240 can also be used to insert the second elastomeric member 12225 and/or fill the medicament container 12210 with diluents 12244, as described below. This arrangement conserves fill station resources and space. In other embodiments, however, the method 12000 can include moving the medicament container 12210 into a third elastomeric member station (not shown).

The method 12000 includes removing the temporary elastomeric member 12243 from the medicament container 12210. The method 12000 then includes inserting the second elastomeric member 12225 within the medicament container 12210 and moving the second elastomeric member 12225 toward the distal end portion 12212 of the medicament container 12210 (at 12010, see e.g., FIG. 146). In some embodiments, the second elastomeric 12225 can be moved in the distal direction such that at least a proximal surface of the second elastomeric member 12225 is proximal a proximal edge of the bypass 12220. The method 12000 can include moving the medicament container 12210 into the filing device 13008. In some embodiment, the method 12000 can include moving the medicament container 12210 into a second filling device (not shown). The method 12000 includes adding a diluent 12244 via the proximal end portion 12212 of the medicament container 12210 (at 12012, see e.g., FIG. 147).

The method 12000 can include moving the medicament container 12210 into the second elastomeric member station 13010. In some embodiments the method 12000 can include moving the medicament container 12210 into a fourth elastomeric member station (not shown). The method 12000 includes inserting the first elastomeric member 12221 within the medicament container 12210 and moving the first elastomeric member 12221 toward the distal end portion 12213 of the medicament container 12210 (at 12014, e see e.g., FIG. 148).

Figure 149:
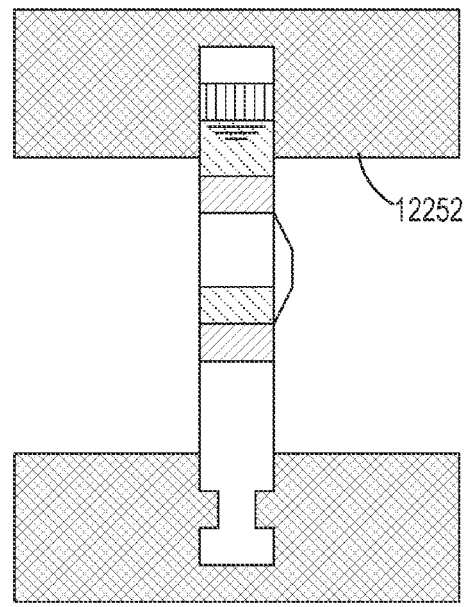
Figure 150:
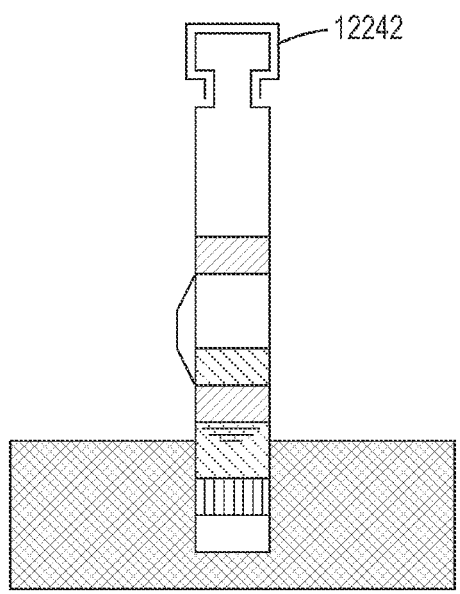

The method 12000 includes placing the second tray 12252 over a portion of the proximal end portion 12213 of the medicament container 12210 (at 12016, see e.g., FIG. 149). Said another way, a portion of the proximal end portion 12213 of the medicament container 12210 is inserted into the second tray 12252. The method 12000 includes removing the first tray 12251 and sealing the distal end portion 12212 of the medicament container 12210 with the crimp seal 12242 (at 12018, see e.g., FIG. 150). In some embodiments, (e.g., embodiments with three elastomeric members) the medicament container need not include a seal 12242. In such embodiments, the third elastomeric member 12229 can seal the lyophilized medicament 12241 within the medicament container 12210, and in this manner, the method 12000 can exclude steps 12016 and 12018.

Although shown as including the first tray 12251 and the second tray 12252, in some embodiments, filling assembly 12250 and the method 12000 may not include the first tray 12251 and/or the second tray 12252 for all or a portion of the method 12000, e.g., the medicament container 12210 can be removed from the first tray 12251 and/or the second tray 12252 for all or a portion of the method 12000. Similarly, although shown as including the first tray 11251, the second tray 11252, and the third tray 11253, in some embodiments, filling assembly 11250 and the method 11000 may not include the first tray 11251, the second tray 11252 and/or the third tray 11253 for all or a portion of the method 11000, e.g., the medicament container 11210 can be removed from the first tray 11251, the second tray 11252 and/or the third tray 11253 for all or a portion of the method 11000.

Although shown as including a crimp seal, in other embodiments, a medicament container being filled and finished to include three elastomeric members may not include a crimp seal. In such embodiments, the distal-most elastomeric member can function to seal the distal end of the medicament container.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Although many of the medicament delivery devices are shown and described herein as being medical injectors having a medicament container divided into two portions (see e.g., the medical injector 6000), in other embodiments, any of the components, methods and/or formulations described herein can be used in any suitable medicament delivery device, such as, for example, an auto-injector, a pen injector, an inhaler, a nasal delivery system or the like. In some embodiments, the medicament delivery device can include a medicament container having any number of plungers and/or defining any number of volumes therein.

Although the components and methods described herein are shown and described as being included in device that include a medicament, in other embodiments, any of the components and/or methods described herein can be used in either an actual medicament delivery device or a simulated medicament delivery device. A simulated medicament delivery device can, for example, correspond to an actual medicament delivery device and can be used, for example, to train a user in the operation of the corresponding actual medicament delivery device. A simulated medicament delivery device or trainer can be similar to the simulated medicament delivery devices or trainers described in U.S. Patent Publication Number 2008/0059133, entitled "Medical Injector Simulation Device," filed Feb. 27, 2007, which is incorporated herein by reference in its entirety.

In such embodiments, the simulated medicament delivery device can simulate the actual medicament delivery device in any number of ways. For example, in some embodiments, the simulated medicament delivery device can have a shape corresponding to a shape of the actual medicament delivery device, a size corresponding to a size of the actual medicament delivery device and/or a weight corresponding to a weight of the actual medicament delivery device. Moreover, in some embodiments, the simulated medicament delivery device can include components that correspond to the components of the actual medicament delivery device. In this manner, the simulated medicament delivery device can simulate the look, feel and sounds of the actual medicament delivery device. For example, in some embodiments, the simulated medicament delivery device can include external components (e.g., a housing, a needle guard, a sterile cover, a safety lock or the like) that correspond to external components of the actual medicament delivery device. In some embodiments, the simulated medicament delivery device can include internal components (e.g., an actuation mechanism, a compressed gas source, a medicament container or the like) that correspond to internal components of the actual medicament delivery device.

In some embodiments, however, the simulated medicament delivery device can be devoid of a medicament and/or those components that cause the medicament to be delivered (e.g., a needle, a nozzle or the like). In this manner, the simulated medicament delivery device can be used to train a user in the use of the actual medicament delivery device without exposing the user to a needle and/or a medicament. Moreover, the simulated medicament delivery device can have features to identify it as a training device to prevent a user from mistakenly believing that the simulated medicament delivery device can be used to deliver a medicament. For example, in some embodiments, the simulated medicament delivery device can be of a different color than a corresponding actual medicament delivery device. Similarly, in some embodiments, the simulated medicament delivery device can include a label clearly identifying it as a training device.

Although the mixing actuator member 6550 is shown and described above as being actuated by the safety lock 6700, in other embodiments, a mixing actuator can be actuated by any suitable mechanism. For example, in some embodiments, a mixing actuator member can be actuated by the needle sheath. In such embodiments, the mixing actuator member can be coupled to the needle sheath such that as the needle sheath is moved in the distal direction the needle sheath moves the mixing actuator in the distal direction. In other embodiments, the mixing actuator can be operably coupled to the needle sheath (e.g., via an intervening structure). In other embodiments, the mixing actuator member can be monolithically formed with the needle sheath and/or the safety lock.

Although the needle hub 6264 is shown and described as being configured to receive and be coupled to the needle 6216, in other embodiments, a device can include a container hub that is devoid of a needle. For example, in some embodiments, the medical injector 6000 can be a needleless injector and the hub can define a pathway and/or otherwise be coupled to a delivery member through which the medicament is conveyed upon actuation.

In some embodiments, the audible sound produced by any of the devices shown and described herein can be produced in conjunction with one or more visual outputs. For example, in some embodiments, a medicament delivery device can include a video screen (e.g., an LCD screen) upon which messages, videos and/or other instructions can be shown during use of the device. In some embodiments, the device can include a touch screen such that, in addition to the feedback from the movement of various components of the device (e.g., the carrier) as described herein, the electronic circuit system can receive input directly from the user.

Although the electronic circuit system 6900 is shown and described above as being actuated by the removal of the cover 6190, the movement of the mixing actuator member 6550 and/or the movement of the base 6510, in other embodiments, the electronic circuit system of any of the devices shown herein can be actuated by any suitable mechanism. In some embodiments, for example, a medicament delivery device can include a movable battery clip, an on/off switch or the like that can be manipulated by the user to actuate the electronic circuit system. In some embodiments, for example, a medical injector need not have a cover similar to the cover 6190, but can be manually actuated by a "start" button depressed by the user.

Although the carrier 7260 is shown and described above as receiving a portion of the medicament container 7210, in other embodiments, a carrier can substantially surround the medicament container 7210. For example, in some embodiments, a carrier can include a first portion and a second portion coupled by a hinge, such that the carrier can be configured between a first (opened) configuration and a second (closed) configuration. In this manner, the carrier can substantially receive the medicament container 7210 when in the open configuration and be moved to substantially surround the medicament container 7210 when placed in the closed configuration.

Although the medicament container assembly 6200 is described above as being configured to accommodate an o-ring or other suitable damping member to reduce the forces exerted on the medicament container 6210 during insertion and/or injection, in other embodiments, any suitable mechanisms or structures for reducing the energy, impulse and/or forces applied to the carrier and/or the medicament container can be employed. For example, in some embodiments, a carrier can include a deformable portion (e.g., a "crush rib") configured to deform when contacting the housing during an insertion event. In this manner, the deformable portion can absorb at least a portion of the energy and/or force generated during the impact, thereby reducing the magnitude of the energy, impulse and/or force applied to the medicament container. Similarly, in some embodiments, a portion of a medicament delivery mechanism 6300 can include a crush rib or an impact portion configured to plastically and/or elastically deform to absorb and/or dampen the forces from the needle insertion operation.

Any of the medicament containers described herein can be any container suitable for storing the compositions disclosed herein. In some embodiments, the medicament container can be a pre-filled syringe, a pre-filled cartridge, a vial, an ampule or the like. In some embodiments, for example, any of the devices shown and described herein can include components and/or mechanisms to accommodate a pre-filled syringe, similar to the embodiments shown and described in U.S. patent application Ser. No. 13/357,935, entitled "Medicament Delivery Devices for Administration of Medicament within a Prefilled Syringe," filed on the same date herewith, which is incorporated herein by reference in its entirety. In other embodiments, the medicament container 1400 can be a container having a flexible wall, such as, for example, a bladder.

Any of the devices and/or medicament containers shown and described herein can be constructed from any suitable material. Such materials include glass, plastic (including thermoplastics such as cyclic olefin copolymers), or any other material used in the manufacture of prefilled syringes containing medications.

Any of the devices and/or medicament containers shown and described herein can include any suitable medicament or therapeutic agent. For example, although the medical injectors described above are shown and described is including a multi-chamber medicament container (e.g., medicament container 6210) that includes a substantially dry medicament (e.g., contained within the dry medicament volume 6237) and a diluent (e.g., contained within the diluent volume 6237), in other embodiments, any of the medicament delivery devices disclosed herein can include a multi-chamber container that is filled with any suitable substances. For example, in some embodiments, any of the medicament delivery devices disclosed herein can include a medicament container (e.g., a cartridge) that separately stores and mixes, upon actuation, two liquid substances. For example in some embodiments, any of the devices shown and described herein can include a medicament container filled with (in separate chambers) epinephrine and at least one antihistamine (e.g., epinephrine and diphenhydramine, epinephrine and hydroxyzine, epinephrine and cetirizine); an antipsychotic medicament and a benzodiazepine (e.g. haloperidol and diazepam, haloperidol and midazolam, haloperidol and lorazepam); insulin and a GLP-1 analog or incretin mimetic (e.g. insulin and exenatide, insulin and lixisenatide); an NSAID and an opiode (e.g., ketorolac and buprenorphine). Other suitable compositions that can be included in any of the medicament containers and/or devices described herein include pralidoxime chloride and atropine; obidoxime chloride and atropine; epinephrine and atropine; methotrexate and etanercept; methotrexate and adalimumab; and methotrexate and certolizumab.

Glucagon Formulation

In some embodiments, a composition can include glucagon and/or any pharmaceutically acceptable constituents for use in the medicament delivery devices disclosed herein. In some embodiments, the glucagon formulation can be prepared and/or filled according to any of the methods described herein (e.g., method 11000). A composition according to an embodiment can be formulated such that the target concentration of glucagon in the solution, either before lyophilization (see e.g., operation 11010 shown and described above with reference to FIG. 134) and/or after being reconstituted upon actuation of the device, is approximately 1 mg/mL. In other embodiments, the target concentration of glucagon in the solution, either before lyophilization and/or after being reconstituted, can be be approximately 2 mg/mL, approximately 1.5 mg/mL, approximately 0.5 mg/mL (e.g., a pediatric dose) or approximately 0.25 mg/mL. In other embodiments a composition can be formulated such that the target concentration of glucagon in the solution, either before lyophilization and/or after being reconstituted upon actuation of the device, is between approximately 0.25 mg/mL and 2 mg/mL, between approximately 0.5 mg/mL and 1 mg/mL, or between approximately 0.8 mg/mL and 1.2 mg/mL.

In certain embodiments, the concentration (either before lyophilization or upon reconstitution) of glucagon in a glucagon formulation is about 1 mg/mL and the total solute concentration is about 50 mg/mL. For example, in some embodiments, a composition can include glucagon and any suitable bulking agents to increase the total solute concentration in the glucagon formulation. In this manner, the glucagon formulation can be more effectively lyophilized and/or reconstituted. For example, in some embodiments, as described below, certain bulking agents can be used to improve the stability, solubility and/or efficacy of the composition when reconstituted in any of the devices shown and described herein. In some embodiments, certain bulking agents can be used to produce a visual indicia when the composition is reconstituted (e.g., such agents can allow the reconstituted medicament to be more easily detected by the user).

In some embodiments, a composition can include a peptide, such as, for example, glucagon and a carbohydrate. In this manner, the stability of the peptide (e.g., glucagon) can be increased during lyophilization and subsequent storage. In particular, the stability of peptides, such as glucagon, can be increased in an amorphous (i.e. non-crystalline) environment. It is believed that carbohydrates undergoing dehydration create a solid-state environment that is amorphous and exhibits high viscosity when maintained below the glass transition temperature. In addition, carbohydrates contain multiple hydroxyl groups that may form hydrogen bonds with polar groups on a protein or peptide surface in an amorphous solid-state environment. Without being bound by any particular mechanism, when water is removed during lyophilization, such carbohydrates may maintain the hydrogen bonds and preserve the native-like solid state of the polypeptide structure. In certain embodiments, therefore, the glucagon formulations include other excipients, such as, but not limited to carbohydrates. Suitable carbohydrates include, but are not limited to, lactose, trehalose, mannitol, and combinations thereof.

Additionally, the solubility of glucagon increases below a pH of 4. In certain embodiments, the glucagon formulations, prior to lyophilization and/or after reconstitution, have a pH of less than about pH 5.0, including less than about pH 4.5, less than about pH 4.0, less than about pH 3.5, less than about pH 3.0, less than about pH 2.5, less than about pH 2.0. In other embodiments of the invention, the glucagon formulations, prior to lyophilization and/or after reconstitution, have a pH range of about pH 1.5 to about pH 5.0, inclusive of all ranges and subranges therebetween, e.g., about pH 2.0 to about pH 4.5, about pH 2.0 to about pH 4.0, about pH 2.0 to about pH 3.5, about pH 2.0 to about pH 3.0, about pH 2.0 to about pH 2.5, about pH 2.5 to about pH 4.5, about pH 2.5 to about pH 4.0, about pH 2.5 to about pH 3.5, about pH 2.5 to about pH 3.0, about pH 3.0 to about pH 4.5, about pH 3.0 to about pH 4.0, about pH 3.0 to about pH 3.5, about pH 3.5 to about pH 4.5, and about pH 3.5 to about pH 4.0. In certain embodiments, the pH of the glucagon formulation is adjusted prior to lyophilization by the addition of a suitable acid, such as hydrochloric acid or citric acid.

The lyophilized formulations of the present invention may be reconstituted by any suitable diluent or combination of diluent, including, but not limited to, water, sterile water, glycerin, or hydrochloric acid.

As described above, in some embodiments, a glucagon formulation can include any suitable bulking agents and/or excipients. Table 1 lists the formulations investigated for lyophilization. The formulations set for the below include a concentration of glucagon in the solution, either before lyophilization and/or after being reconstituted, of approximately 1 mg/mL.

TABLE 1

| Formulation | Excipients and Concentration | Medicament |
|---|---|---|
| 1 | Lactose - 49 mg/mL | 1 mg/mL glucagon |
| 2 | Trehalose - 40 mg/mL<br>Mannitol - 20 mg/mL | 1 mg/mL glucagon |
| 3 | Trehalose - 40 mg/mL<br>Mannitol - 20 mg/mL<br>Citric acid - 1.8 mg/mL<br>Sodium citrate - 0.35 mg/mL | 1 mg/mL glucagon |
| 4 | Glycine - 20 mg/mL | 1 mg/mL glucagon |
| 5 | Mannitol - 40 mg/mL<br>Ascorbic acid - 5 mg/mL | 1 mg/mL glucagon |

Formulation 1 included lactose, which is a known animal-derived excipient. Lactose, which is used in the commercially available glucagon formulations, is a reducing sugar that may destabilize glucagon. Accordingly, Formulations 2 through 5 are lactose-free formulations. Formulation 2 utilized trehalose and mannitol as carbohydrate bulking agents. Formulation 3 included a buffer system of citric acid and sodium citrate, in addition to the carbohydrate bulking agents. Formulation 4 was carbohydrate free, containing only glycine as the bulking agent. Formulation 5 utilized only mannitol as a bulking agent and included ascorbic acid. All formulations except Formulation 3 employed hydrochloric acid to reduce the solution pH to approximately 3 before lyophilization.

Trehalose, however, is a non-reducing sugar, and without being bound by any particular mechanism, may potentially increase the stability of glucagon, prior to lyophilization, during lyophilization, in storage, and/or after reconstitution. In addition to the improved properties of Formulation 3, the absence of any animal-based excipients, such as lactose, make it particularly appealing from a regulatory standpoint, as the FDA has strict guidelines regarding animal-based excipients.

All five formulations listed in Table 1 were successfully reconstituted with water and resulted in solutions suitable for use in the multi-chambered container closure system of the present invention.

In some embodiments, the medicament contained within any of the medicament containers shown herein can be a vaccine, such as, for example, an influenza A vaccine, an influenza B vaccine, an influenza A (H1N1) vaccine, a hepatitis A vaccine, a hepatitis B vaccine, a haemophilus influenza Type B (HiB) vaccine, a measles vaccine, a mumps vaccine, a rubella vaccine, a polio vaccine, a human papilloma virus (HPV) vaccine, a tetanus vaccine, a diphtheria vaccine, a pertussis vaccine, a bubonic plague vaccine, a yellow fever vaccine, a cholera vaccine, a malaria vaccine, a smallpox vaccine, a pneumococcal vaccine, a rotavirus vaccine, a varicella vaccine and/or a meningococcus vaccine. In other embodiments, the medicament contained within any of the medicament containers shown herein can be epinephrine. In other embodiments, the medicament contained within any of the medicament containers shown herein can be naloxone, including any of the naloxone formulations described in U.S. patent application Ser. No. 13/036,720, entitled "Medicament Delivery Device for Administration of Opioid Antagonists Including Formulation for Naloxone," filed on Feb. 28, 2011.

In other embodiments, the medicament contained within any of the medicament containers shown herein can include insulin, glucagon, human growth hormone (HGH), erythropoiesis-stimulating agents (ESA), DeMab, Interferon and other chronic therapies, or the like. Such formulations can be produced using a general lyophilization process with glucagon (of recombinant origin) using bulking agents, stabilizers, buffers, acidifying agents or other excipients comprising of, but not limited to, one or more of the following combinations: lactose, hydrochloric acid; glucose, histidine, hydrochloric acid; trehalose, mannitol, citrate; trehalose, mannitol, hydrochloric acid; trehalose, glycine, hydrochloric acid; Mannitol, ascorbic acid; and Glycine, hydrochloric acid.

In other embodiments any of the injectors described herein can be filled with and/or used to inject medicament formulations, including lyophilized biologics and/or biopharmaceuticals, such as, for example, canakinumab, certolizumab, golimumab, and/or interleukins, for the treatment of crypyrin associated periodic syndromes, hereditary andioedema, and other auto-immune diseases. In yet other embodiments any of the injectors described herein can be filled with and/or used to inject intranasal biologics, such as glucagon or human growth hormone, formulated for use in an auto injector, for the treatment of musculoskeletal diseases, growth disorders, diabetes & treatment related disorders.

In other embodiments, any of the injectors described herein can be filled with and/or used to inject an anti-thrombotics, such as LMWH, ULMWH, Xa Inhibitors, biotinylated idraparinux, etc., for either the acute management and/or surgical prophylaxis of deep vein thrombosis and/or pulmonary embolism or for the management of other conditions which may require anticoagulation to prevent thromboembolism, such as its use in cardiovascular diseases including atrial fibrillation and ischemic stroke. In another example, in some embodiments an injector according to an embodiment can be filled with and/or used to inject formulations for the treatment of asthma and/or chronic obstructive pulmonary disease.

In other embodiments, any of the injectors described herein can be filled with and/or used to inject recombinant hyaluronidase.

In other embodiments, any of the injectors described herein can be filled with and/or used to inject depot medroxyprogesterone acetate for the treatment of infertility.

In other embodiments, any of the injectors described herein can be filled with and/or used to inject environmental, food, and household allergen formulations for the treatment of allergic disease, specifically for use in immunotherapy.

In still other embodiments, the medicament contained within any of the medicament containers shown herein can be a placebo substance (i.e., a substance with no active ingredients), such as water.

The medicament containers and/or medicament delivery devices disclosed herein can contain any suitable amount of any medicament. For example, in some embodiments, a medicament delivery device as shown herein can be a single-dose device containing an amount medicament to be delivered of approximately 0.4 mg, 0.8 mg, 1 mg, 1.6 mg or 2 mg. As described above, the fill volume can be such that the ratio of the delivery volume to the fill volume is any suitable value (e.g., 0.4, 0.6 or the like). In some embodiments, an electronic circuit system can include a "configuration switch" (similar to any of the switches shown and described above, such as the switch 6972) that, when actuated during the assembly of the delivery device, can select an electronic output corresponding to the dose contained within the medicament container.

Although the electronic circuit system 6900 is shown and described above as having two irreversible switches (e.g., switch 6972 and switch 6973), in other embodiments, an electronic circuit system can have any number of switches. Such switches can be either reversible or irreversible.

Although the electronic circuit system 6900 is shown and described above as producing an electronic output in response to the actuation of two switches (e.g., switch 6972 and switch 6973), in other embodiments, an electronic circuit system can produce an electronic output in response to any suitable input, command or prompt. Suitable input for prompting an output can include, for example, an audible input by the user (e.g., the user's response to a voice prompt produced by the electronic circuit system), an input from a "start button" depressed by the user, an input from a sensor (e.g., a proximity sensor, a temperature sensor or the like), movement of (e.g., shaking) of the medicament delivery device, or the like. In some embodiments, an electronic circuit system can include a microphone and/or a voice recognition module to detect a user's vocal input.

Although medical devices having two LEDs and an audio output device have been shown, in other embodiments the medical device might have any number of LEDs and/or audio output devices. Additionally, other types of output devices, such as haptic output devices, can be used. In some embodiments, outputs from an electronic circuit system can include, for example, an audible or visual output related to the composition of the medicament (e.g., an indication of the expiration date, the symptoms requiring treatment with the medicament or the like), the use of the medicament delivery device, and/or post-administration procedures (e.g., a prompt to call 911, instructions for the disposal of the device or the like).

In some embodiments, the electronic circuit system 6900 of the types shown and described herein can be used in either an actual medicament delivery device or a simulated medicament delivery device. A simulated medicament delivery device can, for example, correspond to an actual medicament delivery device and can be used, for example, to train a user in the operation of the corresponding actual medicament delivery device.

The simulated medicament delivery device can simulate the actual medicament delivery device in any number of ways. For example, in some embodiments, the simulated medicament delivery device can have a shape corresponding to a shape of the actual medicament delivery device, a size corresponding to a size of the actual medicament delivery device and/or a weight corresponding to a weight of the actual medicament delivery device. Moreover, in some embodiments, the simulated medicament delivery device can include components that correspond to the components of the actual medicament delivery device. In this manner, the simulated medicament delivery device can simulate the look, feel and sounds of the actual medicament delivery device. For example, in some embodiments, the simulated medicament delivery device can include external components (e.g., a housing, a needle guard, a sterile cover, a safety lock or the like) that correspond to external components of the actual medicament delivery device. In some embodiments, the simulated medicament delivery device can include internal components (e.g., an actuation mechanism, a compressed gas source, a medicament container or the like) that correspond to internal components of the actual medicament delivery device.

In some embodiments, however, the simulated medicament delivery device can be devoid of a medicament and/or those components that cause the medicament to be delivered (e.g., a needle, a nozzle or the like). In this manner, the simulated medicament delivery device can be used to train a user in the use of the actual medicament delivery device without exposing the user to a needle and/or a medicament. Moreover, the simulated medicament delivery device can have features to identify it as a training device to prevent a user from mistakenly believing that the simulated medicament delivery device can be used to deliver a medicament. For example, in some embodiments, the simulated medicament delivery device can be of a different color than a corresponding actual medicament delivery device. Similarly, in some embodiments, the simulated medicament delivery device can include a label clearly identifying it as a training device.

Although various embodiments have been described as having particular features and/or combinations of components, other embodiments are possible having a combination of any features and/or components from any of embodiments where appropriate. For example, any of the devices shown and described herein can include an electronic circuit system as described herein. For example, although the medicament delivery device 10000 shown in FIGS. 118-133 is not shown as including an electronic circuit system, in other embodiments, a medicament delivery device similar to the device 10000 can include an electronic circuit system similar to the electronic circuit system 6900 shown and described above.

What is claimed is:

1. An apparatus, comprising:
   a housing;
   a medicament container assembly at least partially disposed within the housing, the medicament container assembly including a first elastomeric member and a second elastomeric member, the first elastomeric member defining, at least in part, a first volume, the second elastomeric member defining, at least in part, a second volume; and
   a movable assembly including a first movable member and a second movable member, the second movable member configured to move within the medicament container assembly in a distal direction relative to the first movable member to change the movable assembly from a first configuration to a second configuration, a distal end portion of the second movable member configured to move at least the second elastomeric member in the distal direction within the medicament container assembly when the movable assembly changes from the first configuration to the second configuration,
   the first movable member configured to move the first elastomeric member in the distal direction within the medicament container assembly to expel at least a portion of the contents of the first volume and the second volume,
   the second movable member including a retention portion, the retention portion being retracted when the movable assembly is in the first configuration and being extended when the movable assembly is in the second configuration, the retention portion configured to limit movement of the second movable member in a proximal direction relative to the medicament container assembly when the movable assembly is in the second configuration.

2. The apparatus of claim 1, wherein:
   the first volume contains a first substance, and the second volume contains a second substance.

3. The apparatus of claim 2, wherein the second substance is selected from the group consisting of adalimumab, atropine, buprenorphine, certolizumab, cetirizine, diazepam, diphenhydramine, epinephrine, etanercept, exenatide, glucagon, haloperidol, hydroxyzine, insulin, ketorolac, lixisenatide, lorazepam, methotrexate, midazolam, obidoxime chloride, pralidoxime chloride, and combinations thereof.

4. The apparatus of claim 2, wherein the second substance is a substantially dry glucagon formulation, wherein the formulation further comprises a carbohydrate.

5. The apparatus of claim 1, wherein the movable assembly is configured to move the medicament container assembly within the housing after the movable assembly is in the second configuration.

6. The apparatus of claim 1, wherein:
   a length of the movable assembly increases when the second movable member moves relative to the first movable member.

7. The apparatus of claim 1, wherein:
   a proximal end portion of the second movable member is disposed outside of a proximal end portion of the first movable member when the movable assembly is in the first configuration, the proximal end portion of the second movable member is disposed outside of a distal end portion of the first movable member when the movable assembly is in the second configuration.

8. The apparatus of claim 1, wherein:
   a portion of the second movable member configured to be slidably disposed within a piston portion of the first movable member.

9. The apparatus of claim 1, wherein:
   the retention portion is configured to limit movement of the second movable member relative to the first movable member when the retention portion is engaged with a release member.

10. The apparatus of claim 1, wherein:
    the retention portion is a first retention portion,
    the second movable member includes a second retention portion, the second retention portion configured to limit movement of the second movable member relative to the first movable member when the movable assembly is in the first configuration.

11. The apparatus of claim 1, wherein:
    the retention portion is a first retention portion,
    the first movable member includes a second retention portion configured to engage a portion of the housing to maintain a movable assembly in the first position within the housing.

12. The apparatus of claim 1, wherein:
    a portion of the second movable member is disposed within the first movable member when the movable assembly is in the first configuration, the portion of the second movable member is disposed outside of the first movable member when the movable assembly is in the second configuration.

13. The apparatus of claim 1, wherein the movable assembly includes an energy storage member configured to produce a force to move the second movable member relative to the first movable member.

14. The apparatus of claim 1, wherein:
    a portion of the second movable member is disposed within the first movable member; and
    the movable assembly includes a spring disposed within the first movable member and the second movable member, the spring configured to produce a force to move the second movable member relative to the first movable member.

15. The apparatus of claim 1, wherein:
the movable assembly includes a first energy storage member configured to produce a first force to move the second movable member relative to the first movable member; and
the first movable member is configured to be operably coupled to a second energy storage member configured to produce a second force to move the movable assembly from the first position to the second position.

16. The apparatus of claim 1, wherein a portion of the movable assembly is configured to actuate an electronic circuit system.

17. The apparatus of claim 1, wherein the medicament container assembly defines at least one channel configured to place the first volume in fluid communication with the second volume as the movable assembly moves from the first configuration to the second configuration.

18. An apparatus, comprising:
a housing;
a medicament container at least partially disposed within the housing, the medicament container including a first elastomeric member and a second elastomeric member, the first elastomeric member defining, at least in part, a first volume, the second elastomeric member defining, at least in part, a second volume; and
a movable assembly configured to move at least the second elastomeric member in a distal direction a first distance within the medicament container when the movable assembly moves from a first configuration to a second configuration such that a first substance within the first volume is mixed with a second substance within the second volume, a length of the movable assembly increasing when the movable assembly moves from the first configuration to the second configuration,
the movable assembly configured to move at least the first elastomeric member a second distance within the medicament container when at least a portion of the movable assembly moves within the housing after the movable assembly has been moved to the second configuration to expel at least a portion of the contents of the first volume and the second volume,
the movable assembly includes a first movable member and a second movable member, the second movable member configured to move relative to the first movable member to change the movable assembly from the first configuration to the second configuration,
the movable assembly includes a retention portion configured to limit movement of the second movable member when the movable assembly is in the second configuration.

19. The apparatus of claim 18, wherein:
the movable assembly is configured to move the medicament container from a first medicament container position to a second medicament container position when the movable assembly moves within the housing.

20. The apparatus of claim 18, wherein:
the movable assembly configured to move the medicament container from a first medicament container position to a second medicament container position when the movable assembly moves from a first position within the housing to a second position within the housing,
the movable assembly configured to move at least the first elastomeric member the second distance when the movable assembly moves from the second position within the housing to a third position within the housing.

21. The apparatus of claim 18, wherein:
the first volume contains a first substance, and the second volume contains a second substance.

22. The apparatus of claim 18, wherein a piston portion of the first movable member is configured to move within the medicament container to move at least the first elastomeric member the second distance, a portion of the second movable member configured to be slidably disposed within the piston portion of the first movable member, the portion of the second movable member configured to move within the first movable member to change the movable assembly from the first configuration to the second configuration.

23. The apparatus of claim 18, wherein the movable assembly includes an energy storage member configured to produce a force to change the movable assembly from the first configuration to the second configuration.

24. The apparatus of claim 18, wherein:
the movable assembly includes a first energy storage member configured to produce a first force to change the movable assembly from the first configuration to the second configuration; and
the movable assembly is configured to be operably coupled to a second energy storage member configured to produce a second force to move the movable assembly within the housing to move the first elastomeric member the second distance within the medicament container.

25. The apparatus of claim 18, wherein the movable assembly includes a spring configured to urge the movable assembly toward the second configuration, the apparatus further comprising:
a release member configured to maintain the spring in a compressed configuration when the release member is engaged with the movable assembly.

26. The apparatus of claim 18, wherein the medicament container defines at least one channel configured to place the first volume in fluid communication with the second volume as the movable assembly moves from the first configuration to the second configuration.

27. The apparatus of claim 18, wherein:
the retention portion being retracted when the movable assembly is in the first configuration, the retention portion being extended when the movable assembly is in the second configuration.

28. The apparatus of claim 18, wherein:
the retention portion being in a retracted position when the movable assembly is in the first configuration, the retention portion being in an extended position when the movable assembly is in the second configuration, the retention portion biased in the extended position.

29. An apparatus, comprising:
a housing including an aperture;
a medicament container at least partially disposed within the housing, the medicament container including a first elastomeric member and a second elastomeric member, the first elastomeric member defining, at least in part, a first volume, the second elastomeric member defining, at least in part, a second volume;
a movable member configured to move at least the first elastomeric member within the medicament container;
a release member having a pivot portion pivotably couple to the housing via the aperture, a first end portion and a second end portion, the second end portion configured to move between a first position and a second position, the second end portion of the release member configured to limit movement of the movable member when the second end portion is in the first position, the release member configured such that when the first end portion is moved in a first direction, the second end portion moves in a second direction from the first position to the second position, the second direction different than the first direction;

a needle configured to be placed in fluid communication with the medicament container; and a needle cover assembly covering at least a portion of the needle when the needle cover assembly is coupled to the housing, the first end portion of the release member coupled to a portion of the needle cover assembly such that when the needle cover assembly is removed from the housing, the first end portion is moved in the first direction.

30. The apparatus of claim 29, wherein the second end portion is engaged with a portion of the movable member when the second end portion is in the first position, the second end portion is spaced apart from the movable member when the second end portion is in the second position.

31. The apparatus of claim 29, wherein the release member is configured to amplify a force applied to the first end portion when the force is transferred to the second end portion.

32. The apparatus of claim 29, wherein the first end portion of release member spaced apart from the pivot portion by a first distance, the second end portion of the release member spaced apart from the pivot portion by a second distance, the second distance different than the first distance.

33. The apparatus of claim 29, wherein the release member includes a pivot protrusion configured to be disposed within the aperture, at least a portion of the release member configured to rotate about the pivot protrusion when the second end portion is moved from the first position to the second position.

34. The apparatus of claim 29, wherein the pivot portion is configured to deform when the first end portion is moved in the first direction.

35. The apparatus of claim 29, wherein the second direction is substantially normal to the first direction.

36. The apparatus of claim 29, wherein the first end portion is configured to actuate an electronic circuit system when the first end portion is moved in the first direction.

37. The apparatus of claim 29, wherein:

the first volume contains a first substance, and the second volume contains a second substance; and the movable member is a mixing piston configured to move the first elastomeric member to mix the first substance and the second substance.

38. The apparatus of claim 37, further comprising:

an energy storage member configured to produce a force to convey the first substance and the second substance from the medicament container;

an actuation member configured to actuate the energy storage member when the actuation member is moved; and a safety lock movably coupled to the housing, the safety lock configured to engage a portion of the actuation member to limit movement of the actuation member, the first end portion of the release member coupled to the safety lock such that when the safety lock is moved relative to the housing, the first end portion is moved in the first direction.

\* \* \* \* \*